United States Patent
Smith et al.

(10) Patent No.: US 10,548,982 B2
(45) Date of Patent: Feb. 4, 2020

(54) REVERSIBLE COVALENT LINKAGE OF FUNCTIONAL MOLECULES

(71) Applicant: UCL BUSINESS PLC, London (GB)

(72) Inventors: Mark Smith, London (GB); Stephen Caddick, London (GB); James Baker, London (GB); Vijay Chudasama, London (GB)

(73) Assignee: UCL BUSINESS LTD, London (GB)

( * ) Notice: Subject to any disclaimer, the term of this patent is extended or adjusted under 35 U.S.C. 154(b) by 0 days.

(21) Appl. No.: 16/198,134

(22) Filed: Nov. 21, 2018

(65) Prior Publication Data

US 2019/0142950 A1    May 16, 2019

Related U.S. Application Data

(63) Continuation of application No. 15/045,906, filed on Feb. 17, 2016, now Pat. No. 10,174,094, which is a continuation of application No. 13/389,625, filed as application No. PCT/GB2010/001499 on Aug. 9, 2010, now Pat. No. 9,295,729.

(30) Foreign Application Priority Data

Aug. 10, 2009 (GB) ................................ 0913965
Aug. 10, 2009 (GB) ................................ 0913967.6
Aug. 14, 2009 (GB) ................................ 0914321.5

(51) Int. Cl.
| | |
|---|---|
| A61K 47/60 | (2017.01) |
| A61K 47/62 | (2017.01) |
| A61K 47/54 | (2017.01) |
| C07K 14/655 | (2006.01) |
| C07D 207/14 | (2006.01) |
| C07D 207/456 | (2006.01) |
| C07D 209/52 | (2006.01) |
| G01N 33/58 | (2006.01) |
| A61K 49/00 | (2006.01) |
| A61K 47/55 | (2017.01) |
| C07D 207/416 | (2006.01) |
| C07K 14/435 | (2006.01) |

(52) U.S. Cl.
CPC .......... *A61K 47/545* (2017.08); *A61K 47/551* (2017.08); *A61K 47/60* (2017.08); *A61K 47/62* (2017.08); *A61K 49/0017* (2013.01); *C07D 207/416* (2013.01); *C07D 207/456* (2013.01); *C07D 209/52* (2013.01); *C07K 14/435* (2013.01); *C07K 14/655* (2013.01); *G01N 33/58* (2013.01); *Y02P 20/55* (2015.11)

(58) Field of Classification Search
CPC ........ A61K 47/60; A61K 47/62; A61K 47/54; C07K 14/655; C07D 207/14; C07D 207/456; C07D 209/52; G01N 33/58
See application file for complete search history.

(56) References Cited

U.S. PATENT DOCUMENTS

| | | | |
|---|---|---|---|
| 2,861,093 | A | 11/1958 | McConnell et al. |
| 4,680,272 | A | 7/1987 | Smith |
| 5,414,074 | A | 5/1995 | Koreeda et al. |
| 5,519,142 | A | 5/1996 | Hoess et al. |
| 7,144,743 | B2 | 12/2006 | Boschetti |
| 7,504,430 | B2 | 3/2009 | Michejda et al. |
| 9,295,729 | B2 | 3/2016 | Smith et al. |
| 2004/0082079 | A1 | 4/2004 | Besenbruch |
| 2005/0255322 | A1 | 11/2005 | Choi et al. |
| 2006/0122096 | A1 | 6/2006 | Rozema et al. |
| 2007/0248950 | A1 | 10/2007 | Reppy et al. |
| 2009/0074885 | A1 | 3/2009 | Monahan et al. |
| 2015/0037360 | A1 | 2/2015 | Smith |
| 2016/0176942 | A1 | 6/2016 | Smith |

FOREIGN PATENT DOCUMENTS

| | | |
|---|---|---|
| BE | 725964 | 5/1969 |
| CA | 667583 A | 7/1963 |
| DE | 2032709 | 1/1972 |
| DE | 3513715 A1 | 10/1986 |
| DE | 19843873 A1 | 3/2000 |
| GB | 1544686 | 4/1979 |
| JP | 49116085 A | 11/1974 |
| JP | 63145282 A | 6/1988 |
| JP | 2009-504784 | 2/2009 |
| JP | 2011-530506 | 12/2011 |
| JP | 2011-530507 | 12/2011 |
| JP | 2011-530509 | 12/2011 |
| WO | 1994-9410156 | 5/1994 |
| WO | 9937649 A1 | 7/1999 |
| WO | 016286 A1 | 2/2003 |

(Continued)

OTHER PUBLICATIONS

Nishiwaki et al., 1981, caplus an 1981:65531.*

(Continued)

*Primary Examiner* — Sun Jae Yoo
(74) *Attorney, Agent, or Firm* — Dorf & Nelson LLP; Scott D. Locke, Esq.

(57) ABSTRACT

The present invention relates to the use of a compound containing a moiety of formula (I) as a reagent for linking a compound of formula $R_1$—H which comprises a first functional moiety of formula $F_1$ to a second functional moiety of formula $F_2$

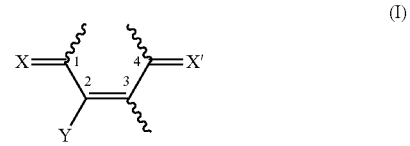

(I)

wherein X, X', Y, $R_1$, $F_1$ and $F_2$ are as defined herein. The present invention also provides related processes and products. The present invention is useful for creating functional conjugate compounds, and specifically conjugates in which at least one of the constituent molecules carries a thiol group.

10 Claims, 7 Drawing Sheets

Specification includes a Sequence Listing.

(56) References Cited

FOREIGN PATENT DOCUMENTS

| WO | 2005-081972 | 9/2005 |
| WO | 022494 A2 | 2/2007 |
| WO | 2009-027679 | 3/2009 |
| WO | 2010016935 A2 | 2/2010 |
| WO | 2010016938 A2 | 2/2010 |
| WO | 2010016944 A2 | 2/2010 |
| WO | 2011-018611 A1 | 2/2011 |
| WO | 2011-018612 A2 | 2/2011 |
| WO | 2011-018613 A1 | 2/2011 |

OTHER PUBLICATIONS

Wolf et al., 1961, caplus an 1961:76180.*
Woolins-et-al., Sulfur Inorganic Chemistry, 2006, Encyclopedia of Inorganic Chemistry, John Wiley & Sons Ltd, pp. 1-36.*
Li et al., 1988, Chinese Science Bulletin, 43(13), 1085-1089.*
Sun, Li et al., Researches on a Novel Method for Fluorination of Halopyridazine Derivatives in Ionic Liquid, Chinese Journal of Chemistry, 2007, 25, 1005-1007.
Galoyan, G, et al., Reactions of heterocyclic compounds containing enolizing carbonyl group V. Reaction of promo- and dibromomaleic hydrazides and their sulfo esters with amines Armyanskii Khimicheskii Zhurnal ,German National Library of Science and Technology\50TIB\51, 1970, vol. 23, No. 9, 837-43.
De Araujo-Junior, Joao X., et al., Synthesis of regiospecifically polysubstituted pyridazinones, Science Direct, Tetrahedron Letters 48 (2007) 7818-7820.
Allan Robin D., et al., Studies on pryidazine azide cyclisation reactions, Organic Biomolecular Chemistry, 2004, 2, 1782-1788.
Takaya, Masahiro, et al., Studies on Pyridazinone Derivatives. Analgesic-Antiinflammatory Activiies of 3(2H)-Pyridazinone Derivatives., Yakugaku Zasshi 114(2), 94-110 (1994).
Jelen, Boris, et al., Directed Regiospecificity of 1,3-Dipolar Cycloaddition of 2-Diazopropane to 4- and 5- substitued Pyridazin-3(2H)-ones, Journal of Heterocyclic Chemistry, 28, 369 (1991).
Hisao Satoh, et al., Synthesis of Monochloromaleic Hydrazide Derivatives, Synthesis of Methylthio-and Phenylthiomaleic Hydrazide and their N-methyl and O-acyl Derivatives, Bulletin Tokyo Medical College, No. 11 (1985) 1-12.
Balan, Sibu et al., Site-Specific PEGylation of Protein Disulfide Bonds Using a Three-Carbon Bridge, Bioconjugate Chem. 2007, 18, 61-76.
Retro-Diels-Alder Reaction: Possible Involvement in the Metabolic Activation of 7-Oxabicyclo [2.2.1] hepta-2(3),5(6)-diene-2,3-dicarboxylates and a Phosphonate Analog, Chem. Res. Toxicol., 1996, vol. 9, 241-246.
Antibody-Mediated Fluorescence Enhancement Based on Shifting the Intramolecular Dimer= Monomer Equilibrium of Fluorescent Dyes, Anal. Chem., 1994, vol. 66, 1500-1506.
Derivative-chemistry-Wikipedia, 201 8, https://en.wikipedia.org/wiki/Derivative_(chemistry).
Klingsberg, 1965,caplus an 1965:15321.
Bhongle et al., 1984, caplus an 1984:630270.
Panaeva et al., 1994, caplus an 1994:582409.
Chun et al., 2008, caplus an 2008:1267640.
Biological Response, 2018, http://dictionary.reverso.net/english-definition/biological%20response.
Cytotoxic, https://en.wikipedia.org/wiki/Cytotoxicity, 2018.
Hong et al., Thiol-selective fluorogenic probes for labelling and release, J. Am. Chem. Soc., 2009, 131(29), pp. 9986-9994.
Kar et al., PM-20, a novel inhibitor of Cdc25A, induces extracellular signal-regulated kinase½ phosphorylation and inhibits hepatocellular carcinoma growth in vitro and in vivo, Mol. Cancer Ther., 2006, 5(6), pp. 1511-1519.
Lorey et al., Transcellular proteolysis demonstrated by novel cell surface-associated substrates of dipeptidyl peptidase IV (CD26), Journal of Biological Chemistry, 277(36), 2002 pp. 33170-33177 and Journal of Biological Chemistry, Additions and corrections, 277(43) 2002 p. 41294.
Cooney et al., Inhibition of L-asparagine synthetase by mucochloric and mucobromic acids, Enzyme, 21(6), 1976, pp. 524-439.
Smith et al., Protein modification, bioconjugation, and disulfide bridging using bromomaleimides, Journal of the American Chemical Society, 132(6), 2010, pp. 1960-1965.
Tedaldi et al., Bromomaleimides: new reagents for the selective and reversible modification of cysteine, Chemical Communications, 43, 2009 pp. 6583-6585.
Augustin et al., Synthese von N-dichlormaleoyl-aminosäuren und peptide, Journal Für Praktische Chemie, 327(5), 1985 pp. 857-864.
Al-Holly et al., Synthesis of glucosylthiomaleimides, Pharmazie 34, H.10, 1979 pp. 645-646.
Lynch et al., Reactions of dichloromaleimides with alcohols, phenols and thiols, J. Het. Chem. 9(5), 1972 pp. 1027-1032.
Fonseca et al., A novel synthesis of arcyriaflavin-A, Tetrahedron Letters, 36(15), 1995 pp. 2689-2692.
Konecny, Synthesis and biological properties of dithiocarbamic acid esters XI.* Pesticidal activity of N-(alkyl or aryl)-3,4-bis(N',N'-dialkylthiocarbamoylthio)maleimides, Chem. Zvesti, 38(4), 1984 pp. 523-530.
Uttamchandani et al., Small molecule microarrays: recent advances and applications, Current Opinion in Chemical Biology 2005, 9, pp. 4-13.
Marchand et al., Activatable quantum dots for mouse non-invasive fluorescence imaging, Proceedings of SPIE, 6626, 2007 pp. E1-E9.
Li et al., Site-specific binding of quinines to proteins through thiol addition and addition-elimination reactions, J. Am. Chem. Soc. 2005, 127 pp. 6140-6141.
Gaina et al., Poly(urethane-urea) varnishes containing tributyltin groups, J. Inorg. Organomet. Polym. 2009, 19 pp. 157-165.
Iepishkina et al., Maleimidophenylmethacrylates and their derivatives as polystyrene thermal stabilizers, Mol. Cryst. Liq. Cryst., 486, 2008 pp. 340-347.
White et al., Step-growth polymers from bismaleimides, synthesis and reactions of some new polyimides, Polymer Preprints (American Chemical Society Division of Polymer Chemistry), 1985, 26(1) pp. 132-133.
Sava et al., Synthesis and characterization of poly(maleimide-ethers) from the reaction of bischloromaleimides with 4,4'-(hexafluoroisopropylidene)diphenol, J.M.S.-Pure Appl. Chem. A34(4), 1997 pp. 725-733.
Lebetkin et al., Disposition of 3-chloro-4-(dichloromethyl)-5-hydroxy-2(5H)-furanone (MX) in B6C3F1 mice and F344 rats, Journal of Toxicology and Environmental Health, Part A, 65, 2002 pp. 2101-2118.
Yoneyama, Antagonistic mechanism of sulfhydryl compounds on cellocidin activity, Journal of Antibiotics, 31(10), 1978 pp. 1065-1066.
Hirota et al., Role of dehydropeptidase-I in the metabolism of glutathione and its conjugates in the rat kidney, Research Communications in Chemical Pathology and Pharmacology, 56(2), 1987, pp. 235-242.
Li et al., De novo design, synthesis and characterization of quinoproteins, Chem. Eur. J. 2006, 12 pp. 7236-7245.
Shaunak et al., Site-specific PEGylation of native disulfide bonds in therapeutic proteins, Nature Chemical Biology 2(6), 2006 pp. 312-313.
Zloh et al., Identification and insertion of 3-carbon bridges in protein disulfide bonds: a computational approach, Nature Protocols 2(5), 2007 pp. 1070-1083.
Davis et al., Chemical modification of proteins at cysteine: opportunities in chemistry and biology, Chem. Asian J. 2009, 4 pp. 630-640.
Blätther et al., New hereterobifunctional protein cross-linking reagent that forms an acid-labile link, Biochemistry 1985, 25 pp. 1517-1524.
Haas et al., Targeting of doxorubicin to the urinary bladder of the rat shows increased cytotoxicity in the bladder urine combined with an absence of renal toxicity, Journal of Drug Targeting 2002, 10(1) pp. 81-89.

(56) References Cited

OTHER PUBLICATIONS

Dyba et al., Small molecule toxins targeting tumor receptors, Current Pharmaceutical Design 2004, 10 pp. 2311-2334.
Kirby and Lancaster, Structure and efficiency in intramolecular and enzymic catalysis. Catalysis of amide hydrolysis by the carboxy-group of substituted maleamic acids, J. Chem. Soc. Perkin Trans. 2, 1972 pp. 1206-1214.
Glüsenkamp et al., Rapid hydrolysis of amides under physiological conditions: influence of the microenvironment on the stability of the amide bond, Bioorganic & Medicinal Chemistry Letters 8, 1998 pp. 285-288.
Rozema et al., Endosomolysis by masking of a membrane-active agent (EMMA) for cytoplasmic release of macromolecules, Bioconjugate Chem. 2003, 14 pp. 51-57.
Rozema et al., Dynamic polyconjugates for targeted in vivo delivery of siRNA to hepatocytes, Proc. Natl. Acad. Sci. USA, 2007, 104 pp. 12982-12987.
Packard et al., Site-directed labelling of a monoclonal antibody: targeting to a disulfide bond, Biochemistry 1986, 25 pp. 3548-3552.
International Search Report, PCT/GB 2010/ 001504, dated Jan. 5, 2011.
Search Report, GB0913965.0, dated Dec. 1, 2009.
Search Report, GB0913967.6, dated Dec. 11, 2009.
Search Report, GB0914321.5, dated Dec. 10, 2009.
International Search Report, PCT/GB 2010/ 001499, dated Jan. 5, 2011.
International Search Report, PCT/GB 2010/ 001500, dated Feb. 21, 2011.
Chem. Res. Toxicol., 1996, vol. 9, 241-246.
Anal. Chem., 1994, vol. 66, 1500-1506.
Japanese Patent Office, Notice of Reasons for Refusal, Japanese Application No. 524273/2012, dated Oct. 17, 2014.
European Search Report, Application No. 12189317.6, The Hague, dated Feb. 8, 2013.
Baloniak et al., IPSO and CINE Substitution of Bromine in the 4-Bromo- and 5-Bromopyridazine-3,6-Dione Derivatives. Part I. Reactions with Sodium Thiolates, Department of Organic Chemistry, School of Medicine, 60-780 Poznan, Polish Journal of Chemistry, 65, 1085-1090 (1991).
Baloniak et al., IPSO and CINE Substitution of Bromine in the 4-Bromo- and 5-Bromopyridazine-3,6-Dione Derivatives. Part II. Reactions with Thiols, Department of Organic Chemistry, School of Medicine, 60-780 Poznan, Polish Journal of Chemistry, 66, 935-941 (1992).
Condorelli, P. et al., Sintesi di 2,3-diazafenotiazine- Notα II N-metil-derivati della 1,4-diosso-1,2,3,4-tetraidro 2 3-diazafenotiazina, Catania, Istituto di Chimica Farmacautica & Tossicologica dell'Universita, 242-251.
Search Report, Chinese State Intellectual Property Office, Serial No. 2010800416534, dated Jan. 24, 2014.
Satoh, Hisao et al., Synthesis of Monochloromaleic Hydrazide Derivatives, Synthesis of Methylthio- and Phenylthiomaleic Hydrazide and their N-methyl and O-acyl Derivatives, Bull. Tokyo Med. Coll., No. 11 (1985) pp. 1-12.
Tonegawa, Masami et al., Synthesis of Monochloromaleic Hydrazide Derivatives 2, Substitution of Methanethiol for Chlorine, Bull. Tokyo Med. Coll., No. 14 (1988) pp. 1-11.
Japanese Patent Office, Notice of Reasons for Refusal, Application No. Japanese Patent Application No. 524272/2012, dated Jul. 18, 2014. (Office Action and Translation).

\* cited by examiner

SEQUENCE LISTING

```
<160> NUMBER OF SEQ ID NOS: 1

<210> SEQ ID NO 1
<211> LENGTH: 123
<212> TYPE: PRT
<213> ORGANISM: Artificial Sequence
<220> FEATURE:
<223> OTHER INFORMATION: Synthetic

<400> SEQUENCE: 1

Met Gly Ile Glu Met Lys Pro His Pro Trp Phe Phe Gly Lys Ile Pro
1               5                   10                  15

Arg Ala Lys Ala Glu Glu Met Leu Ser Lys Gln Arg His Asp Gly Ala
            20                  25                  30

Phe Leu Ile Arg Glu Ser Glu Ser Ala Pro Gly Asp Phe Ser Leu Ser
        35                  40                  45

Val Lys Phe Gly Asn Asp Val Gln His Phe Lys Val Cys Arg Asp Gly
    50                  55                  60

Ala Gly Lys Tyr Phe Leu Trp Val Val Lys Phe Asn Ser Leu Asn Glu
65                  70                  75                  80

Leu Val Asp Tyr His Arg Ser Thr Ser Val Ser Arg Asn Gln Gln Ile
                85                  90                  95
```

```
Phe Leu Arg Asp Ile Glu Gln Val Pro Gln Gln Pro Thr Tyr Val Gln
            100                 105                 110
Ala Gly Ser Arg Ser His His His His His His
            115                 120
```

REVERSIBLE COVALENT LINKAGE OF FUNCTIONAL MOLECULES

CROSS-REFERENCE TO RELATED APPLICATIONS

This application is a continuation of U.S. patent application Ser. No. 15/045,906, filed Feb. 17, 2016, which is a continuation of U.S. patent application Ser. No. 13/389,625, filed Apr. 6, 2012, issued which issued on Mar. 29, 2016 as U.S. Pat. No. 9,295,729, which pursuant to 35 U.S.C. § 371 is a National Stage Application of PCT/GB2010/001499, filed Aug. 9, 2010, which claims priority to GB 0913967.6, filed Aug. 10, 2009, GB 0913965.0, filed Aug. 10, 2009 and GB 0914321.5, filed Aug. 14, 2009. The entire contents of each of the aforementioned applications are incorporated herein by reference as if set forth in their entirety.

INTRODUCTION

It is well known that it can be desirable to link together two or more molecules, which each have specific functional properties. In this way, it becomes possible to generate new molecules, known as conjugates, which have the combined characteristics of their components. This technique provides an attractive means for modifying the existing properties of functionally useful molecules, or adding entirely new functional aspects to such molecules, in a controlled and broadly applicable manner.

The possibility of conjugating together two or more functional compounds has stimulated particularly strong interest in the biotechnological field. Conjugation of biomolecules such as proteins or biologically active molecules such as drugs to a secondary functional compound has been used in a vast range of applications, including detection techniques, proteomics studies, purification methods and the diagnosis and treatment of disease. Such is the ubiquity of these methodologies that standard text books devoted entirely to this topic are now available. One such textbook is "Bioconjugate Techniques" (Greg T. Hermanson, Academic Press Inc., 1996), the content of which is herein incorporated by reference in its entirety.

Methods for joining together diverse functional compounds typically focus on the use of relatively small cross-linker molecules. A linking reagent of this type contains at least two functional groups. Each of these functional groups is capable of reacting with a functional molecule in order to generate a final, cross-linked conjugate molecule.

A very wide variety of functional groups for cross-linker reagents have been developed to react with specific target functional groups present on the functional molecules that are to be joined together. For example, cross-linkers containing activated ester groups such as the N-hydroxysuccinimide esters have long been used to react with functional moieties containing reactive amine groups, such as proteins. Hydrazide-containing cross-linkers (for example, adipic acid dihydrazide) have been used for functionalising carboxyl-containing functional molecules such as glycoproteins.

Cross-linking of one functional molecule to another can also be achieved by targeting a reactive thiol group in a functional molecule. This approach can be particularly attractive where the functional molecule in question is a peptide or a protein. One reason for this is that thiol-containing cysteine residues typically have low natural abundance in proteins, thus opening up the possibility of highly selective modification procedures. Standard site-directed mutagenesis techniques also allow for the easy insertion of a cysteine residue at a specific location in a protein, so generating a reactive thiol group, which can then be modified by a functional moiety via a suitable cross-linker.

Various compounds have been used as linking reagents capable of reacting with a thiol group. These reagents include 1,2-dicarbonyl ethene derivatives, α-halo carbonyl compounds and thiosulfonates. Of these, 1,2-dicarbonyl ethene derivatives, such as maleimides, are generally recognised to be the most selective reagents for reaction with a thiol, in particular with a cysteine moiety. The thiol group in a thiol-containing functional molecule ("R—SH") reacts with maleimide to produce a thioether linkage as follows:

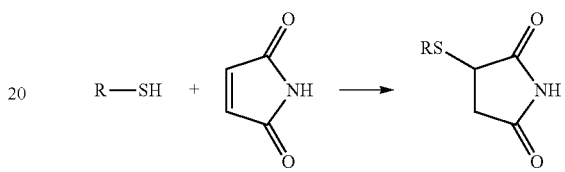

The reactive amide moiety in the maleimide is available to react with a further functional compound, to yield a conjugate in which the thiol-containing functional molecule is attached to a further functional moiety. Maleimide reagents are therefore useful for conjugating cysteine-containing proteins to various secondary molecules (for example, a fluorophore, biotin, a polyethylene glycol or a carbohydrate). These secondary molecules are often joined to the maleimide ring by way of a chemically inert linker species.

Unfortunately, however, this approach to conjugate generation has several disadvantages. For example, chemical manipulation of the reaction product is typically possible only at the amide moiety. This means that it can be difficult to add more than one further functional group to the thiol-containing compound with a single maleimide linker. Furthermore, the thioether bond formed between the thiol-containing functional molecule and the maleimide cross-linker is irreversible. Accordingly, the derivitisation effected via the cross-linker is permanent and it is not possible to regenerate the native thiol-containing reagent.

The irreversibility of the known derivisation reaction between a thiol-containing reagent and a maleimide-containing cross-linker can place severe limitations on its practical utility in areas such as protein purification, quantitative proteomic analysis, probing binding sites, enabling structural studies and in drug delivery. For example, in a purification method involving generation of a conjugate between a thiol-containing protein and an affinity tag (such as biotin), it would not be possible to regenerate the native protein after purification by detachment from the maleimide. An inability to regenerate thiol-containing reagents can also be a serious problem when carrying out procedures involving proteins that are difficult to express, such as many GPCRs (G-protein coupled receptors). The irreversibility of the cross-linking process also precludes the exploitation of bioconjugate methodology in areas where lability of the bond between the cross-linker and the protein is important (for example, where the cross-linking entity is designed to block the activity of an enzyme for only a limited, and preferably controllable, period).

The present invention is based on the surprising finding that it is advantageous to incorporate an electrophilic leaving group onto the C=C double bond of a known 1,2-dicarbonyl ethene cross-linking reagent. That chemical modification enables a thiol-containing functional moiety such as a peptide or a protein to link to the cross-linking reagent while retaining the C=C double bond. This has the following advantages:

- The reaction between the cross-linker and the thiol compound can often be carried out rapidly and with high yield using only a substantially stoichiometric amount of cross-linker.
- The thioether bond between the cross-linker and the thiol-containing molecule is readily reversible, and in particular can be cleaved in a controlled manner at a time chosen by the skilled worker.
- The retention of the double bond in the compound obtained after linking the thiol-containing functional moiety to the cross-linker constitutes a reaction site for linking to further functional compounds. It can therefore be easier to add extra functional moieties to the conjugate.

The new cross-linking methodology is readily applicable across the full spectrum of known methods involving conjugation of functional moieties, which are now routinely carried out in the art.

U.S. Pat. No. 4,680,272 describes the use of halogenated maleimides and derivatives thereof as a fluorescent "stain" for detecting proteins having amine or thiol groups. U.S. Pat. No. 4,680,272 does not, however, disclose the use of 1,2-dicarbonyl ethene cross-linking reagents having an electrophilic leaving group on the C=C double bond for constructing conjugate molecules, nor that the bond formed between a thiol compound and such a cross-linker is readily reversible and can often be carried out at high yield using a substantially stoichiometric amount of cross-linker.

Hong et al. (J. Am. Chem. Soc., 2009, 131 (29), pp 9986-9994) describes a new class of fluorogenic probes for thiols based on a 7-oxanorbornadiene framework. In one specific experiment described in this paper, a 7-oxanorbornadiene reagent carrying a dansyl fluorogenic moiety was reacted with bovine serum albumin. The resulting product underwent a retro-Diels-Alder reaction to generate a product comprising a maleimide cross-linking moiety which carried the bovine serum albumin at one carbon atom of the C=C double bond and a hydrogen atom at the other carbon atom of the C=C double bond. Hong et al. does not, however, describe the use of 1,2-dicarbonyl ethenes carrying an electrophilic leaving group as reagents for constructing a conjugate molecule.

U.S. Pat. No. 7,504,430 B2 and Kar et al. (Mol. Cancer Ther 2006; 5(6) June 2006 pp 1511-1519) describe a process for making maleimide-containing pharmaceutical compounds where a 3,4-dibromomaleimide derivative is reacted with small, optionally substituted mercaptoalkyl compounds. These documents do not, however, describe processes for constructing conjugate molecules comprising at least two functional moieties as defined herein, nor that the bond formed between a thiol compound and a cross-linker according to the present invention is readily reversible and can often be carried out at high yield using a substantially stoichiometric amount of cross-linker.

SUMMARY OF THE INVENTION

The present invention provides (1) use of a compound containing a moiety of formula (I) as a reagent for linking a compound of formula $R_1$—H which comprises a first functional moiety of formula $F_1$ to a second functional moiety of formula $F_2$

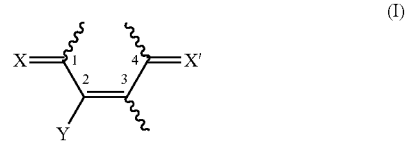

(I)

wherein:
X and X' are the same or different and each represents oxygen, sulfur or a group of formula =NQ, in which Q is hydrogen, hydroxyl, $C_{1-6}$ alkyl or phenyl;
Y is an electrophilic leaving group;
$R_1$ is a group of formula —$F_1$ or -L-$F_1$, wherein L is a linker group, and $R_1$—H comprises at least a first SH group; and
the first functional moiety and the second functional moiety are the same or different and are each selected from a detectable moiety, an enzymatically active moiety, an affinity tag, a hapten, an immunogenic carrier, an antibody or antibody fragment, an antigen, a ligand, a biologically active moiety, a liposome, a polymeric moiety, an amino acid, a peptide, a protein, a cell, a carbohydrate, a DNA and an RNA;
wherein the group $R_1$ becomes attached to the moiety of formula (I) via nucleophilic attack of the first SH group in the compound of formula $R_1$—H at the 2-position of the moiety of formula (I), such that the group Y at the 2-position is replaced by the group $R_1$.

The present invention also provides (2) a process for producing a conjugate, which process comprises
(i) reacting a compound containing a moiety of formula (I) with a compound of formula $R_1$—H, thus producing a compound containing a moiety of formula (II)

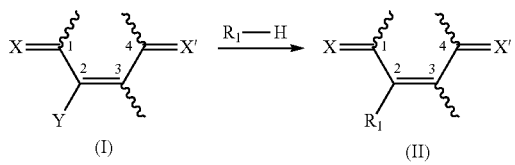

(ii) subsequently linking a moiety of formula $F_2$ to said moiety of formula (II);
wherein step (i) involves attaching the group $R_1$ via nucleophilic attack of the first SH group in the compound of formula $R_1$—H at the 2-position of the moiety of formula (I), such that the group Y at the 2-position is replaced by the group $R_1$,
and wherein X, X', Y, $R_1$, $F_2$ and the compound containing a moiety of formula (I) are all as defined in (1) above.

The present invention further provides (3) a process for producing a conjugate, which process comprises reacting a compound of formula $R_1$—H with a compound comprising (a) a moiety of formula (I) and (b) at least one moiety of formula $F_2$ linked thereto, wherein:
the moiety of formula (I) and $F_2$ are each as defined in (1) above;
$R_1$ is as defined in (1) above; and
the process involves attaching the group $R_1$ via nucleophilic attack of the first SH group in the compound of formula $R_1$—H at the 2-position of the moiety of formula (I), such that the group Y at the 2-position is replaced by the group $R_1$.

Still further, present invention provides (4) a process which comprises
(i) providing a compound comprising a moiety of formula (II); and
(ii) cleaving the bond between the group $R_1$ and the carbon atom at the 2-position of the moiety of formula (II);
wherein:
  $R_1$ is as defined in (1) above; and
  the moiety of formula (II) is as defined in (2) above.

As will be evident to a skilled chemist, all of these uses and processes are linked by the finding that it is advantageous to incorporate an electrophilic leaving group onto the C=C double bond of a known dicarbonyl ethene cross-linking reagent. Further, many of the intermediates and products involved in these uses and processes are believed to novel. The present invention therefore also provides the following embodiments (5) to (9).

The present invention provides (5) a compound of formula (IIa)

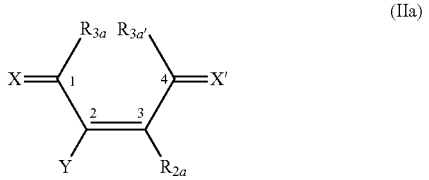

wherein:
either:
  $R_{3a}$ represents a group of formula $R_3$ or a group of formula $F_2$ or $-L(F_2)_m(Z)_{n-m}$ and $R_{3a}'$ independently represents a group of formula $R_3'$ or a group of formula $F_2$ or $-L(F_2)_m(Z)_{n-m}$; or
  $R_{3a}$ and $R_{3a}'$ together form a group of formula —O— or $-N(R_{33a'})$, wherein $R_{33a'}$ represents a group of formula $R_{33'}$ or a group of formula $F_2$ or $-L(F_2)_m(Z)_{n-m}$; or
  $R_{3a}$ and $R_{3a}'$ together form a group of formula $-N(R_{33a'})-N(R_{33a'})-$, wherein each $R_{33a'}$ is the same or different and represents a group of formula $R_{33'}$ or a group of formula $F_2$ or $-L(F_2)_m(Z)_{n-m}$;
  $R_{2a}$ represents a group of formula $R_2$ or a group of formula $F_2$ or $-L(F_2)_m(Z)_{n-m}$;
m is an integer having a value of from zero to n;
the compound of formula (IIa) comprises at least one group of formula $F_2$;
$F_2$ is as defined in (1) above;
X and X' are the same or different and each represents oxygen, sulfur or a group of formula =NQ, in which Q is hydrogen, hydroxyl, $C_{1-6}$ alkyl or phenyl;
either:
  $R_3$ and $R_3'$ are the same or different and each represents a hydrogen atom or a group of formula E, Nu, $-L(Z)_n$ or IG; or
  $R_3$ and $R_3'$ together form a group of formula $-N(R_{33'})$, wherein $R_{33'}$ represents a hydrogen atom or a group of formula Y, Nu, $-L(Z)_n$ or IG;
$R_2$ represents a hydrogen atom or a group of formula Y, Nu, $-L(Z)_n$ or IG;
each group of formula E and Y is the same or different and represents an electrophilic leaving group;

each group of formula Nu is the same or different and represents a nucleophile selected from —OH, —SH, —NH$_2$ and
—NH($C_{1-6}$ alkyl);
each group of formula L is the same or different and represents a linker group;
each group of formula Z is the same or different and represents a reactive group attached to a group of formula L which is capable of reacting with a compound containing a second functional moiety as defined in claim 1 such that said second functional moiety becomes linked to said group of formula L;
n is 1, 2 or 3; and
each group of formula IG is the same or different and represents a moiety which is a $C_{1-20}$ alkyl group, a $C_{2-20}$ alkenyl group or a $C_{2-20}$ alkynyl group, which is unsubstituted or substituted by one or more substituents selected from halogen atoms and sulfonic acid groups, and in which (a) 0, 1 or 2 carbon atoms are replaced by groups selected from $C_{6-10}$ arylene, 5- to 10-membered heteroarylene, $C_{3-7}$ carbocyclylene and 5- to 10-membered heterocyclylene groups, and (b) 0, 1 or 2 —CH$_2$— groups are replaced by groups selected from —O—, —S—, —S—S—, —C(O)— and —N($C_{1-6}$ alkyl)- groups, wherein:
(i) said arylene, heteroarylene, carbocyclylene and heterocyclylene groups are unsubstituted or substituted by one or more substituents selected from halogen atoms and $C_{1-6}$ alkyl, $C_{1-6}$ alkoxy, $C_{1-6}$ alkylthiol, —N($C_{1-6}$ alkyl)($C_{1-6}$ alkyl), nitro and sulfonic acid groups; and
(ii) 0, 1 or 2 carbon atoms in said carbocyclylene and heterocyclylene groups are replaced by —C(O)— groups.

Also provided by the present invention is (6) a compound of formula (IIb)

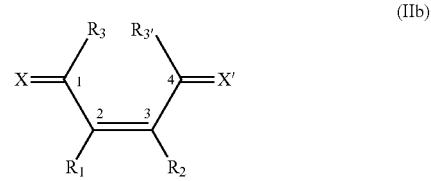

wherein:
$R_1$ is as defined in (1) above;
X and X' are the same or different and each represents oxygen, sulfur or a group of formula =NQ, in which Q is hydrogen, hydroxyl, $C_{1-6}$ alkyl or phenyl;
either:
  $R_3$ and $R_3'$ are the same or different and each represents a hydrogen atom or a group of formula E, Nu, $-L(Z)_n$ or IG; or
  $R_3$ and $R_3'$ together form a group of formula —O— or $-N(R_{33'})$, wherein $R_{33'}$ represents a hydrogen atom or a group of formula Y, Nu, $-L(Z)_n$ or IG; or
  $R_3$ and $R_3'$ together form a group of formula $-N(R_{33'})-N(R_{33'})-$, wherein each $R_{33'}$ is the same or different and represents a hydrogen atom or a group of formula Y, Nu, $-L(Z)_n$ or IG;
$R_2$ represents a hydrogen atom or a group of formula Y, Nu, $-L(Z)_n$ or IG;
each group of formula E and Y is the same or different and represents an electrophilic leaving group;

each group of formula Nu is the same or different and represents a nucleophile selected from —OH, —SH, —$NH_2$ and —$NH(C_{1-6}$ alkyl);

each group of formula L is the same or different and represents a linker group;

each group of formula Z is the same or different and represents a reactive group attached to a group of formula L which is capable of reacting with a compound containing a second functional moiety as defined in claim 1 such that said second functional moiety becomes linked to said group of formula L;

n is 1, 2 or 3; and each group of formula IG is the same or different and represents a moiety which is a $C_{1-20}$ alkyl group, a $C_{2-20}$ alkenyl group or a $C_{2-20}$ alkynyl group, which is unsubstituted or substituted by one or more substituents selected from halogen atoms and sulfonic acid groups, and in which (a) 0, 1 or 2 carbon atoms are replaced by groups selected from $C_{6-10}$ arylene, 5- to 10-membered heteroarylene, $C_{3-7}$ carbocyclylene and 5- to 10-membered heterocyclylene groups, and (b) 0, 1 or 2 —$CH_2$— groups are replaced by groups selected from —O—, —S—, —S—S—, —C(O)— and —$N(C_{1-6}$ alkyl)- groups, wherein:

(i) said arylene, heteroarylene, carbocyclylene and heterocyclylene groups are unsubstituted or substituted by one or more substituents selected from halogen atoms and $C_{1-6}$ alkyl, $C_{1-6}$ alkoxy, $C_{1-6}$ alkylthiol, —$N(C_{1-6}$ alkyl)($C_{1-6}$ alkyl), nitro and sulfonic acid groups; and (ii) 0, 1 or 2 carbon atoms in said carbocyclylene and heterocyclylene groups are replaced by —C(O)— groups;

provided that $R_3$ and $R_3'$ do not together form a group of formula —$N(R_{33'})$.

The present invention further provides (7) a compound of formula (III)

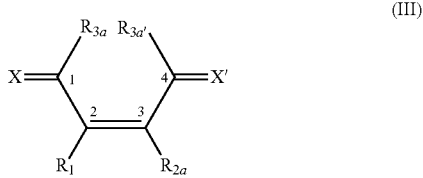

(III)

wherein:
either:
$R_{3a}$ represents a group of formula $R_3$ or a group of formula $F_2$ or -$L(F_2)_m(Z)_{n-m}$ and $R_{3a}'$ independently represents a group of formula $R_3'$ or a group of formula $F_2$ or -$L(F_2)_m(Z)_{n-m}$; or $R_{3a}$ and $R_{3a}'$ together form a group of formula —O— or —$N(R_{33a'})$, wherein $R_{33a'}$ represents a group of formula $R_{33'}$ or a group of formula $F_2$ or -$L(F_2)_m(Z)_{n-m}$; or $R_{3a}$ and $R_{3a}'$ together form a group of formula —$N(R_{33a'})$—$N(R_{33a'})$—, wherein each $R_{33a'}$ is the same or different and represents a group of formula $R_{33'}$ or a group of formula $F_2$ or -$L(F_2)_m(Z)_{n-m}$;

$R_{2a}$ represents a group of formula $R_2$ or a group of formula $F_2$ or -$L(F_2)_m(Z)_{n-m}$;

m is an integer having a value of from zero to n;

$R_1$ is as defined in (1) above;
$F_2$ is as defined in (1) above;
X and X' are the same or different and each represents oxygen, sulfur or a group of formula =NQ, in which Q is hydrogen, hydroxyl, $C_{1-6}$ alkyl or phenyl;

either:
$R_3$ and $R_3'$ are the same or different and each represents a hydrogen atom or a group of formula E, Nu, -$L(Z)_n$ or IG; or $R_3$ and $R_3'$ together form a group of formula —O— or —$N(R_{33'})$, wherein $R_{33'}$ represents a hydrogen atom or a group of formula Y, Nu, -$L(Z)_n$ or IG; or $R_3$ and $R_3'$ together form a group of formula —$N(R_{33'})$—$N(R_{33'})$—, wherein each $R_{33'}$ is the same or different and represents a hydrogen atom or a group of formula Y, Nu, -$L(Z)_n$ or IG;

$R_2$ represents a hydrogen atom or a group of formula Y, Nu, -$L(Z)_n$ or IG;

each group of formula E and Y is the same or different and represents an electrophilic leaving group;

each group of formula Nu is the same or different and represents a nucleophile selected from —OH, —SH, —$NH_2$ and —$NH(C_{1-6}$ alkyl);

each group of formula L is the same or different and represents a linker group;

each group of formula Z is the same or different and represents a reactive group attached to a group of formula L which is capable of reacting with a compound containing a second functional moiety as defined in claim 1 such that said second functional moiety becomes linked to said group of formula L;

n is 1, 2 or 3; and each group of formula IG is the same or different and represents a moiety which is a $C_{1-20}$ alkyl group, a $C_{2-20}$ alkenyl group or a $C_{2-20}$ alkynyl group, which is unsubstituted or substituted by one or more substituents selected from halogen atoms and sulfonic acid groups, and in which (a) 0, 1 or 2 carbon atoms are replaced by groups selected from $C_{6-10}$ arylene, 5- to 10-membered heteroarylene, $C_{3-7}$ carbocyclylene and 5- to 10-membered heterocyclylene groups, and (b) 0, 1 or 2 —$CH_2$— groups are replaced by groups selected from —O—, —S—, —S—S—, —C(O)— and —$N(C_{1-6}$ alkyl)- groups, wherein:

(i) said arylene, heteroarylene, carbocyclylene and heterocyclylene groups are unsubstituted or substituted by one or more substituents selected from halogen atoms and $C_{1-6}$ alkyl, $C_{1-6}$ alkoxy, $C_{1-6}$ alkylthiol, —$N(C_{1-6}$ alkyl)($C_{1-6}$ alkyl), nitro and sulfonic acid groups; and (ii) 0, 1 or 2 carbon atoms in said carbocyclylene and heterocyclylene groups are replaced by —C(O)— groups;

which comprises at least one group of formula $F_2$ and in which $R_{2a}$ is not a hydrogen atom.

Still further, the present invention provides (8) a compound of formula (IIIa)

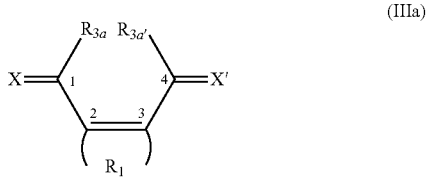

(IIIa)

wherein:
either:
R$_{3a}$ represents a group of formula R$_3$ or a group of formula F$_2$ or -L(F$_2$)$_m$(Z)$_{n-m}$ and R$_{3a}$' independently represents a group of formula R$_3$' or a group of formula F$_2$ or -L(F$_2$)$_m$(Z)$_{n-m}$; or R$_{3a}$ and R$_{3a}$' together form a group of formula —O— or —N(R$_{33a'}$), wherein R$_{33a'}$ represents a group of formula R$_{33'}$ or a group of formula F$_2$ or -L(F$_2$)$_m$(Z)$_{n-m}$; or R$_{3a}$ and R$_{3a}$' together form a group of formula —N(R$_{33a'}$)—N(R$_{33a'}$)—, wherein each R$_{33a'}$ is the same or different and represents a group of formula R$_{33'}$ or a group of formula F$_2$ or -L(F$_2$)$_m$(Z)$_{n-m}$;

m is an integer having a value of from zero to n;

R$_1$ is as defined in (1) above, and wherein R$_1$ comprises at least a first thiol group and a second thiol group, said first thiol group being attached to the 2-position in the compound of formula and second thiol group being attached to the 3-position in the compound of formula (IIIa);

F$_2$ is as defined in (1) above;

X and X' are the same or different and each represents oxygen, sulfur or a group of formula =NQ, in which Q is hydrogen, hydroxyl, C$_{1-6}$ alkyl or phenyl;

either:
R$_3$ and R$_3$' are the same or different and each represents a hydrogen atom or a group of formula E, Nu, -L(Z)$_n$ or IG; or R$_3$ and R$_3$' together form a group of formula —O— or —N(R$_{33'}$), wherein R$_{33'}$ represents a hydrogen atom or a group of formula Y, Nu, -L(Z)$_n$ or IG; or R$_3$ and R$_3$' together form a group of formula —N(R$_{33'}$)—N(R$_{33'}$)—, wherein each R$_{33'}$ is the same or different and represents a hydrogen atom or a group of formula Y, Nu, -L(Z)$_n$ or IG;

R$_2$ represents a hydrogen atom or a group of formula Y, Nu, -L(Z)$_n$ or IG;

each group of formula E and Y is the same or different and represents an electrophilic leaving group;

each group of formula Nu is the same or different and represents a nucleophile selected from —OH, —SH, —NH$_2$ and —NH(C$_{1-6}$ alkyl);

each group of formula L is the same or different and represents a linker group;

each group of formula Z is the same or different and represents a reactive group attached to a group of formula L which is capable of reacting with a compound containing a second functional moiety as defined in claim 1 such that said second functional moiety becomes linked to said group of formula L;

n is 1, 2 or 3; and each group of formula IG is the same or different and represents a moiety which is a C$_{1-20}$ alkyl group, a C$_{2-20}$ alkenyl group or a C$_{2-20}$ alkynyl group, which is unsubstituted or substituted by one or more substituents selected from halogen atoms and sulfonic acid groups, and in which (a) 0, 1 or 2 carbon atoms are replaced by groups selected from C$_{6-10}$ arylene, 5- to 10-membered heteroarylene, C$_{3-7}$ carbocyclylene and 5- to 10-membered heterocyclylene groups, and (b) 0, 1 or 2 —CH$_2$— groups are replaced by groups selected from —O—, —S—, —S—S—, —C(O)— and —N(C$_{1-6}$ alkyl)- groups, wherein:

(i) said arylene, heteroarylene, carbocyclylene and heterocyclylene groups are unsubstituted or substituted by one or more substituents selected from halogen atoms and C$_{1-6}$ alkyl, C$_{1-6}$ alkoxy, C$_{1-6}$ alkylthiol, —N(C$_{1-6}$ alkyl)(C$_{1-6}$ alkyl), nitro and sulfonic acid groups; and (ii) 0, 1 or 2 carbon atoms in said carbocyclylene and heterocyclylene groups are replaced by —C(O)— groups.

The present invention provides (9) a compound of formula (IVa) or (IVb)

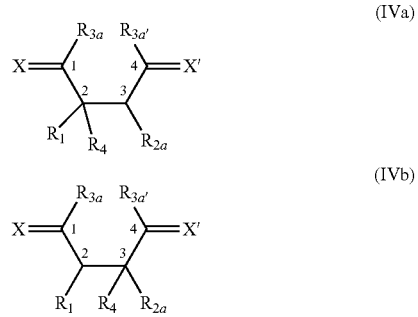

wherein
R$_1$ is as defined in (1) above;

X and X' are the same or different and each represents oxygen, sulfur or a group of formula =NQ, in which Q is hydrogen, hydroxyl, C$_{1-6}$ alkyl or phenyl;

either:
R$_{3a}$ represents a group of formula R$_3$ or a group of formula F$_2$ or -L(F$_2$)$_m$(Z)$_{n-m}$ and R$_{3a}$' independently represents a group of formula R$_3$' or a group of formula F$_2$ or -L(F$_2$)$_m$(Z)$_{n-m}$; or R$_{3a}$ and R$_{3a}$' together form a group of formula —O— or —N(R$_{33a'}$), wherein R$_{33a'}$ represents a group of formula R$_{33'}$ or a group of formula F$_2$ or -L(F$_2$)$_m$(Z)$_{n-m}$; or R$_{3a}$ and R$_{3a}$' together form a group of formula —N(R$_{33a'}$)—N(R$_{33a'}$)—, wherein each R$_{33a'}$ is the same or different and represents a group of formula R$_{33'}$ or a group of formula F$_2$ or -L(F$_2$)$_m$(Z)$_{n-m}$;

R$_{2a}$ represents a group of formula R$_2$ or a group of formula F$_2$ or -L(F$_2$)$_m$(Z)$_{n-m}$;

m is an integer having a value of from zero to n;

either:
R$_3$ and R$_3$' are the same or different and each represents a hydrogen atom or a group of formula E, Nu, -L(Z)$_n$ or IG; or R$_3$ and R$_3$' together form a group of formula —O— or —N(R$_{33'}$), wherein R$_{33'}$ represents a hydrogen atom or a group of formula Y, Nu, -L(Z)$_n$ or IG; or R$_3$ and R$_3$' together form a group of formula —N(R$_{33'}$)—N(R$_{33'}$)—, wherein each R$_{33'}$ is the same or different and represents a hydrogen atom or a group of formula Y, Nu, -L(Z)$_n$ or IG;

R$_2$ represents a hydrogen atom or a group of formula Y, Nu, -L(Z)$_n$ or IG;

each group of formula E and Y is the same or different and represents an electrophilic leaving group;

each group of formula Nu is the same or different and represents a nucleophile selected from —OH, —SH, —NH$_2$ and —NH(C$_{1-6}$ alkyl);

each group of formula L is the same or different and represents a linker group;

each group of formula Z is the same or different and represents a reactive group attached to a group of formula L which is capable of reacting with a compound containing a second functional moiety as defined in claim 1 such that said second functional moiety becomes linked to said group of formula L;

n is 1, 2 or 3;

each group of formula IG is the same or different and represents a moiety which is a $C_{1-20}$ alkyl group, a $C_{2-20}$ alkenyl group or a $C_{2-20}$ alkynyl group, which is unsubstituted or substituted by one or more substituents selected from halogen atoms and sulfonic acid groups, and in which (a) 0, 1 or 2 carbon atoms are replaced by groups selected from $C_{6-10}$ arylene, 5- to 10-membered heteroarylene, $C_{3-7}$ carbocyclylene and 5- to 10-membered heterocyclylene groups, and (b) 0, 1 or 2 —$CH_2$— groups are replaced by groups selected from —O—, —S—, —S—S—, —C(O)— and —N($C_{1-6}$ alkyl)- groups, wherein:

(i) said arylene, heteroarylene, carbocyclylene and heterocyclylene groups are unsubstituted or substituted by one or more substituents selected from halogen atoms and $C_{1-6}$ alkyl, $C_{1-6}$ alkoxy, $C_{1-6}$ alkylthiol, —N($C_{1-6}$ alkyl)($C_{1-6}$ alkyl), nitro and sulfonic acid groups; and (ii) 0, 1 or 2 carbon atoms in said carbocyclylene and heterocyclylene groups are replaced by —C(O)— groups;

$R_4$ is a halogen atom, a hydroxyl, $C_{1-6}$ alkoxy, thiol, $C_{1-6}$ alkylthio or $C_{1-6}$ alkylcarbonyloxy group, or a group of formula $F_2$;

at least one of the groups $R_{2a}$ and $R_4$ comprises a group of formula $F_2$; and $F_2$ is as defined in (1) above.

The present invention also provides (10) a process for producing a compound of formula (IVa) or (IVb) as defined in (9) above, which comprises (i) providing a compound of formula (III); and

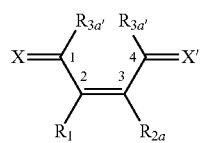

(III)

(ii) reacting the compound of formula (III) with a compound of formula $R_4$—H, wherein $R_4$ is as defined in (9) above;

wherein:

either:

$R_{3a}$ represents a group of formula $R_3$ or a group of formula $F_2$ or -L($F_2$)$_m$(Z)$_{n-m}$ and $R_{3a}$' independently represents a group of formula $R_3$' or a group of formula $F_2$ or -L($F_2$)$_m$(Z)$_{n-m}$; or $R_{3a}$ and $R_{3a}$' together form a group of formula —O— or —N($R_{33a'}$), wherein $R_{33a'}$ represents a group of formula $R_{33'}$ or a group of formula $F_2$ or -L($F_2$)$_m$(Z)$_{n-m}$; or $R_{3a}$ and $R_{3a}$' together form a group of formula —N($R_{33a'}$)—N($R_{33a'}$)—, wherein each $R_{33a'}$ is the same or different and represents a group of formula $R_{33'}$ or a group of formula $F_2$ or -L($F_2$)$_m$(Z)$_{n-m}$;

$R_{2a}$ represents a group of formula $R_2$ or a group of formula $F_2$ or -L($F_2$)$_m$(Z)$_{n-m}$;

m is an integer having a value of from zero to n;

$R_1$ is as defined in (1) above;

$F_2$ is as defined in (1) above;

X and X' are the same or different and each represents oxygen, sulfur or a group of formula =NQ, in which Q is hydrogen, hydroxyl, $C_{1-6}$ alkyl or phenyl;

either:

$R_3$ and $R_3$' are the same or different and each represents a hydrogen atom or a group of formula E, Nu, -L(Z)$_n$ or IG; or $R_3$ and $R_3$' together form a group of formula —O— or —N($R_{33'}$), wherein $R_{33'}$ represents a hydrogen atom or a group of formula Y, Nu, -L(Z)$_n$ or IG; or $R_3$ and $R_3$' together form a group of formula —N($R_{33'}$)—N($R_{33'}$)—, wherein each $R_{33'}$ is the same or different and represents a hydrogen atom or a group of formula Y, Nu, -L(Z)$_n$ or IG;

$R_2$ represents a hydrogen atom or a group of formula Y, Nu, -L(Z)$_n$ or IG;

each group of formula E and Y is the same or different and represents an electrophilic leaving group;

each group of formula Nu is the same or different and represents a nucleophile selected from —OH, —SH, —$NH_2$ and —NH($C_{1-6}$ alkyl);

each group of formula L is the same or different and represents a linker group;

each group of formula Z is the same or different and represents a reactive group attached to a group of formula L which is capable of reacting with a compound containing a second functional moiety as defined in claim 1 such that said second functional moiety becomes linked to said group of formula L;

n is 1, 2 or 3; and each group of formula IG is the same or different and represents a moiety which is a $C_{1-20}$ alkyl group, a $C_{2-20}$ alkenyl group or a $C_{2-20}$ alkynyl group, which is unsubstituted or substituted by one or more substituents selected from halogen atoms and sulfonic acid groups, and in which (a) 0, 1 or 2 carbon atoms are replaced by groups selected from $C_{6-10}$ arylene, 5- to 10-membered heteroarylene, $C_{3-7}$ carbocyclylene and 5- to 10-membered heterocyclylene groups, and (b) 0, 1 or 2 —$CH_2$— groups are replaced by groups selected from —O—, —S—, —S—S—, —C(O)— and —N($C_{1-6}$ alkyl)- groups, wherein:

(i) said arylene, heteroarylene, carbocyclylene and heterocyclylene groups are unsubstituted or substituted by one or more substituents selected from halogen atoms and $C_{1-6}$ alkyl, $C_{1-6}$ alkoxy, $C_{1-6}$ alkylthiol, —N($C_{1-6}$ alkyl)($C_{1-6}$ alkyl), nitro and sulfonic acid groups; and (ii) 0, 1 or 2 carbon atoms in said carbocyclylene and heterocyclylene groups are replaced by —C(O)— groups.

The present invention further provides (11) a process for detecting a compound of formula $R_1$—H in a sample, which comprises incubating said sample with a compound comprising (a) a moiety of formula (I) and (b) a compound of formula $F_2$ linked thereto, under conditions allowing for detection of said compound of formula $R_1$—H in said sample, wherein:

the compound comprising (a) a moiety of formula (I) and (b) a compound of formula $F_2$ linked thereto is as defined in (3) above; and the compound of formula $F_2$ is a detectable moiety, which is capable of producing a signal which can be modified by the group of formula $R_1$.

Still further, the present invention provides (12) a process for detecting whether a substance is present in a sample, which process comprises:

providing a compound as defined in any one of (7), (8) and (9) above, provided that the compound as defined in (8) comprises at least one group of formula $F_2$, wherein one of said first functional moiety and said second functional moiety is a functional moiety that is capable of generating a detectable signal and the other of said first functional moiety and said second functional moiety is a functional moiety that is capable of interacting with said substance;

incubating said sample with said compound; and monitoring for a signal under conditions allowing for generation of a detectable signal from said functional moiety that is capable of generating a detectable signal.

The invention also provides (13) a process for identifying whether a substance interacts with a functional moiety of formula $R_1$, which process comprises:

producing a conjugate comprising (a) said functional moiety of formula $R_1$ and (b) a detectable moiety which is capable of producing a signal which can be modified by said substance, by carrying out a process according to either of (2) and (3) above;

incubating said conjugate with said substance;

obtaining a signal from said detectable moiety; and comparing said signal with a control signal obtainable when said conjugate has not been contacted with the substance, thus determining whether the substance interacts with the conjugate.

Furthermore, the present invention provides (14) a compound as defined in any one of (7), (8) and (9) above for use in a method of treatment of the human or animal body by surgery or therapy or a diagnostic method practised on the human or animal body, provided that the compound as defined in (8) comprises at least one group of formula $F_2$.

The invention also provides a compound containing a moiety of formula (VI) and a functional moiety linked thereto

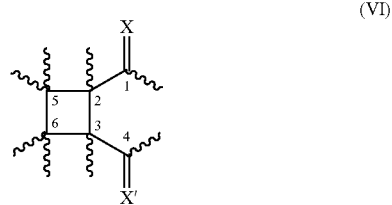

(VI)

wherein:

X and X' are the same or different and each represents oxygen, sulfur or a group of formula =NQ, in which Q is hydrogen, hydroxyl, $C_{1-6}$ alkyl or phenyl; and said functional moiety is selected from a detectable moiety, an enzymatically active moiety, an affinity tag, a hapten, an immunogenic carrier, an antibody or antibody fragment, an antigen, a ligand, a biologically active moiety, a liposome, a polymeric moiety, an amino acid, a peptide, a protein, a cell, a carbohydrate, a DNA and an RNA.

DETAILED DESCRIPTION OF THE INVENTION

Figure 1:
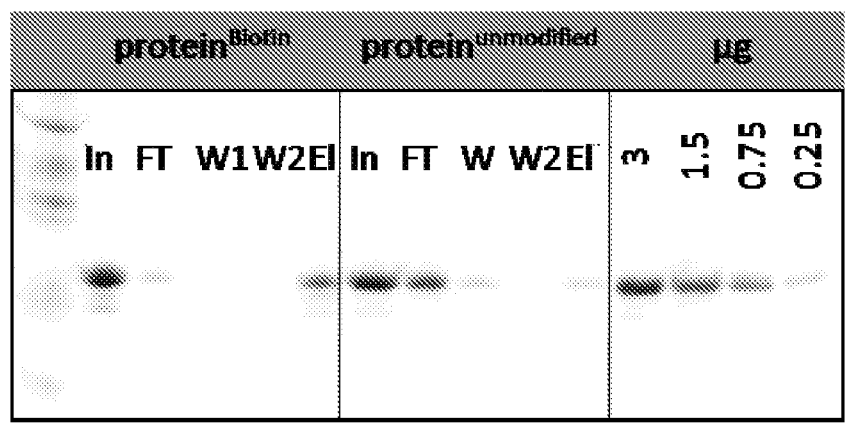
FIG. 1 shows the results of the protocol described in Example 31 wherein protein/biotin-PEG-bromomaleimide adduct and unmodified model protein solutions (In) were added to neutravidin-coated agarose beads, centrifuged, the flow-through (FT) collected, the beads washed with PBS and both wash fractions collected (W1 and W2), protein released from the beads by incubation in PBS containing β-mercaptoethanol, the sample centrifuged and the eluant (El) containing cleaved protein collected.

As used herein, the term "functional moiety" means a moiety which forms part of a conjugate and which is one of a detectable moiety, an enzymatically active moiety, an affinity tag, a hapten, an immunogenic carrier, an antibody or antibody fragment, an antigen, a ligand, a biologically active moiety, a liposome, a polymeric moiety, an amino acid, a peptide, a protein, a cell, a carbohydrate, a DNA and an RNA.

As will be readily understood by those of skill in the art, a functional moiety comprised within a compound (for example, within a conjugate molecule) is obtainable by attaching a corresponding "functional compound" thereto. When a functional compound attaches to a secondary compound, it is necessary for a bond somewhere in that functional compound to be broken so that a new bond can form to the secondary compound. Examples of such processes include the loss of a leaving group from the functional compound when it becomes a functional moiety bound to the secondary molecule, the loss of a proton when the functional compound reacts via a hydrogen-atom containing nucleophilic group such as an —OH or —SH group, or the conversion of a double bond in the functional compound to a single bond when the functional compound reacts with the secondary compound via an electrophilic or nucleophilic additional reaction. Those skilled in the art would thus understand that a functional moiety that is, for example, a "protein" means a moiety that is formed by incorporation of a protein compound into a secondary molecule, with concomitant loss of a internal bond compared to the corresponding protein compound (for example, loss of a proton from an —OH, —SH or —NH$_2$ moiety when such a moiety forms the bond to the secondary molecule).

A functional moiety is typically a moiety that has a discrete biological significance in its native form (i.e., when it is not part of a bioconjugate). Preferably any functional moiety used in the present invention has a relative molecular weight of at least 200, more preferably at least 500, most preferably at least 1000. Preferably a functional moiety as described herein is a biomolecule.

As used herein, the term "detectable moiety" means a moiety which is capable of generating detectable signals in a test sample. Clearly, the detectable moiety can be understood to be a moiety which is derived from a corresponding "detectable compound" and which retains its ability to generate a detectable signal when it is linked to another functional moiety via a cross-linker in a conjugate of the present invention. Detectable moieties are also commonly known in the art as "tags", "probes" and "labels". Examples of detectable moieties include chromogenic moieties, fluorescent moieties, radioactive moieties and electrochemically active moieties. In the present invention, preferred detectable moieties are chromogenic moieties and fluorescent moieties. Fluorescent moieties are most preferred.

A chromogenic moiety is a moiety which is coloured, which becomes coloured when it is incorporated into a conjugate, or which becomes coloured when it is incorporated into a conjugate and the conjugate subsequently interacts with a secondary target species (for example, where the conjugate comprises a protein which then interacts with another target molecule).

Typically, the term "chromogenic moiety" refers to a group of associated atoms which can exist in at least two states of energy, a ground state of relatively low energy and an excited state to which it may be raised by the absorption of light energy from a specified region of the radiation spectrum. Often, the group of associated atoms contains delocalised electrons. Chromogenic moieties suitable for use in the present invention include conjugated moieties containing Π systems and metal complexes. Examples include porphyrins, polyenes, polyynes and polyaryls. Preferred chromogenic moieties are

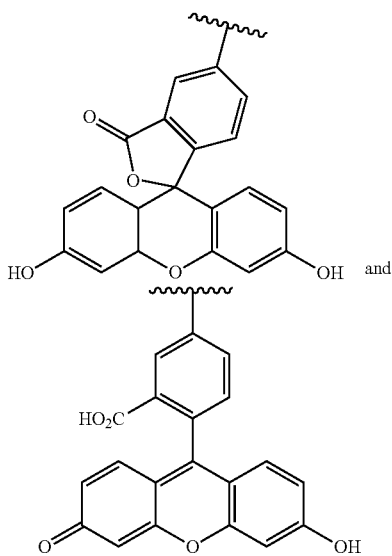

A fluorescent moiety is a moiety which comprises a fluorophore, which is a fluorescent chemical moiety. Examples of fluorescent compounds which are commonly incorporated as fluorescent moieties into secondary molecules such as the conjugates of the present invention include:
  the Alexa Fluor® dye family available from Invitrogen;
  cyanine and merocyanine;
  the BODIPY (boron-dipyrromethene) dye family, available from Invitrogen;
  the ATTO dye family manufactured by ATTO-TEC GmbH;
  fluorescein and its derivatives;
  rhodamine and its derivatives;
  naphthalene derivatives such as its dansyl and prodan derivatives;
  pyridyloxazole, nitrobenzoxadiazole and benzoxadiazole derivatives;
  coumarin and its derivatives;
  pyrene derivatives; and
  Oregon green, eosin, Texas red, Cascade blue and Nile red, available from Invitrogen.

Preferred fluorescent moieties for use in the present invention include fluorescein, rhodamine, coumarin, sulforhodamine 101 acid chloride (Texas Red) and dansyl. Fluorescein and dansyl are especially preferred.

A radioactive moiety is a moiety that comprises a radionuclide. Examples of radionuclides include iodine-131, iodine-125, bismuth-212, yttrium-90, yttrium-88, technetium-99m, copper-67, rhenium-188, rhenium-186, gallium-66, gallium-67, indium-111, indium-114m, indium-114, boron-10, tritium (hydrogen-3), carbon-14, sulfur-35, fluorine-18 and carbon-11. Fluorine-18 and carbon-11, for example, are frequently used in positron emission tomography.

In one embodiment, the radioactive moiety may consist of the radionuclide alone. In another embodiment, the radionuclide may be incorporated into a larger radioactive moiety, for example by direct covalent bonding to a linker group (such as a linker containing a thiol group) or by forming a co-ordination complex with a chelating agent. Suitable chelating agents known in the art include DTPA (diethylenetriamine-pentaacetic anhydride), NOTA (1,4,7-triazacyclononane-N,N',N''-triacetic acid), DOTA (1,4,7,10-tetraazacyclododecane-N,N',N'',N'''-tetraacetic acid), TETA (1,4,8,11-tetraazacyclotetra-decane-N,N',N'',N'''-tetraacetic acid), DTTA ($N^1$-(p-isothiocyanatobenzyl)-diethylene-triamine-$N^1$,$N^2$,$N^3$-tetraacetic acid) and DFA (N'-[5-[[5-[[5-acetylhydroxyamino)pentyl]amino]-1,4-dioxobutyl]hydroxyamino]pentyl]-N-(5-aminopentyl)-N-hydroxybutanediamide).

An electrochemically active moiety is a moiety that comprises a group that is capable of generating an electrochemical signal in an electrochemical method such as an amperometric or voltammetric method. Typically, an electrochemically active moiety is capable of existing in at least two distinct redox states.

A person of skill in the art would of course easily be able to select a detectable compound that would be suitable for use in accordance with the present invention from the vast array of detectable compounds that are routinely available. The methodology of the present invention can thus be used to produce a conjugate comprising a detectable moiety, which conjugate can then be used in any routine biochemical technique that involves detection of such species.

As used herein, the term "enzymatically active moiety" means an enzyme, a substrate for an enzyme or a cofactor for an enzyme. Preferably, the enzymatically active moiety is an enzyme.

As used herein, the term "affinity tag" means a chemical moiety which is capable of interacting with an "affinity partner", which is a second chemical moiety, when both the affinity tag and the affinity partner are present in a single sample. Typically, the affinity tag is capable of forming a specific binding interaction with the affinity partner. A specific binding interaction is a binding interaction which is stronger than any binding interaction that may occur between the affinity partner and any other chemical substance present in a sample. A specific binding interaction may occur, for example, between an enzyme and its substrate.

Affinity tags can be useful in applications such as detection or purification of biomolecules such as proteins. In such applications, a conjugate comprising the biomolecule and the affinity tag can be detected or purified by exploiting the specific binding interaction between the affinity tag and its affinity partner.

One affinity tag/affinity partner pair that is particularly widely used in biochemistry is the biotin/(strept)avidin pair.

Avidin and streptavidin are proteins which can be used as affinity partners for binding with high affinity and specificity to an affinity tag derived from biotin (5-[(3aS,4S,6aR)-2-oxohexahydro-1H-thieno[3,4-d]imidazol-4-yl]pentanoic acid). Other affinity tag/affinity partner pairs commonly used in the art include amylase/maltose binding protein, glutathione/glutathione-S-transferase and metal (for example, nickel or cobalt)/poly(His). As one of skill in the art would appreciate, either member of the pair could function as the "affinity tag", with the other member of the pair functioning as the "affinity partner". The terms "affinity tag" and "affinity partner" are thus interchangeable.

A person of skill in the art would be aware of the routine use of affinity tag/affinity partner interactions in biochemistry and in particular in the context of bioconjugate technology. A person of skill in the art would thus have no difficulty in selected an affinity tag for use in accordance with the present invention. The methodology of the present invention can therefore be used to produce conjugates adapted for use in routine biochemical techniques that make use of affinity tag/affinity partner interactions.

Preferred affinity tags according to the present invention are biotin, amylase, glutathione and poly(His). A particularly preferred affinity tag is biotin.

As used herein, the term, the term "hapten" means a moiety which comprises an epitope, which is not capable of stimulating an in vivo immune response in its native form, but which is capable of stimulating an in vivo immune response when linked to an immunogenic carrier molecule. Typically, a hapten is a non-proteinaceous moiety of relatively low molecular weight (for example, a molecular weight of less than 1000). An epitope is the part of a molecule or moiety which is recognized by the immune system and stimulates an immune response.

As used herein, the term "immunogenic carrier" means an antigen that is able to facilitate an immune response when administered in vivo and which is capable of being coupled to a hapten. Examples of immunogenic carriers include proteins, liposomes, synthetic or natural polymeric moieties (such as dextran, agarose, polylysine and polyglutamic acid moieties) and synthetically designed organic moieties. Commonly used protein immunogenic carriers have included keyhole limpet hemocyanin, bovine serum albumin, aminoethylated or cationised bovine serum albumin, thyroglobulin, ovalbumin and various toxoid proteins such as tetanus toxoid and diphtheria toxoid. Well known synthetically designed organic molecule carriers include the multiple antigentic peptide (MAP).

As a person of skill in the biochemical art would be aware, hapten-immunogenic carrier conjugates are widely used in, for example, immunology and proteomics. A person of skill in the art would therefore recognise that the methodology of the present invention could readily be applied to produce conjugates comprising a hapten and an immunogenic carrier, which conjugates could then be used in these well-established and routine techniques. Accordingly, in one preferred embodiment of the invention, one of the first functional moiety and the second functional moiety is a hapten and the other of the first functional moiety and the second functional moiety is an immunogenic carrier.

As used herein, the term "antibody or antibody fragment" means a protein that is capable of binding to a specific antigen via an epitope on the antigen, or a fragment of such a protein. Antibodies include monoclonal antibodies and polyclonal antibodies. Monoclonal antibodies are preferred.

As used herein, the term "antigen" means a substance that is capable of instigating an immune response when administered in vivo and which is capable of binding to an antibody produced during said immune response.

As used herein, the term "ligand" means a moiety that is able to interact with a biomolecule (for example, a protein) in such a way as to modify the functional properties of the biomolecule. Typically, the ligand is a moiety that binds to a site on a target protein. The interaction between the ligand and the biomolecule is typically non-covalent. For example, the interaction may be through ionic bonding, hydrogen bonding or van der Waals' interactions. However, it is also possible for some ligands to form covalent bonds to biomolecules. Typically, a ligand is capable of altering the chemical conformation of the biomolecule when it interacts with it.

Examples of ligands capable of interacting with a protein include substrates (which are acted upon by the enzyme upon binding, for example by taking part in a chemical reaction catalysed by the enzyme), inhibitors (which inhibit protein activity on binding), activators (which increase protein activity on binding) and neurotransmitters.

As used herein, the term "biologically active moiety" means a moiety that is capable of inducing a biochemical response when administered in vivo.

The biologically active moiety can be a drug. Drugs include cytotoxic agents such as doxorubicin, methotrexate and derivatives thereof, cytotoxin precursors which are capable of metabolising in vivo to produce a cytotoxic agent, anti-neoplastic agents, anti-hypertensives, cardioprotective agents, anti-arrhythmics, ACE inhibitors, anti-inflammatories, diuretics, muscle relaxants, local anaesthetics, hormones, cholesterol lowering drugs, anti-coagulants, antidepressants, tranquilizers, neuroleptics, analgesics such as a narcotic or anti-pyretic analgesics, anti-virals, anti-bacterials, anti-fungals, bacteriostats, CNS active agents, anticonvulsants, anxiolytics, antacids, narcotics, antibiotics, respiratory agents, anti-histamines, immunosuppressants, immunoactivating agents, nutritional additives, anti-tussives, diagnostic agents, emetics and anti-emetics, carbohydrates, glycosoaminoglycans, glycoproteins and polysaccharides, lipids, for example phosphatidyl-ethanolamine, phosphtidylserine and derivatives thereof, sphingosine, steroids, vitamins, antibiotics, including lantibiotics, bacteristatic and bactericidal agents, antifungal, anthelminthic and other agents effective against infective agents including unicellular pathogens, small effector molecules such as noradrenalin, alpha adrenergic receptor ligands, dopamine receptor ligands, histamine receptor ligands, GABA/benzodiazepine receptor ligands, serotonin receptor ligands, leukotrienes and triodothyronine, and derivatives thereof.

The biologically active moiety can also be a moiety derived from a compound which is capable of readily crossing biological membranes and which, when forming a conjugate molecule with a secondary functional moiety, is capable of enhancing the ability of the secondary functional moiety to cross the biological membrane. For example, the biologically active moiety may be a "protein transduction domain" (PTD) or a small molecule carrier ("SMC" or "molecular tug") such as those described in WO 2009/027679, the content of which is hereby incorporated by reference in its entirety. Accordingly, in one preferred embodiment of the invention, one of the first functional moiety and the second functional moiety is such a protein transduction domain or a small molecule carrier and the other of the first functional moiety and the second functional moiety is a drug.

In a preferred embodiment of the present invention, the biologically active moiety is a drug.

As used herein, the term "liposome" means a structure composed of phospholipid bilayers which have amphiphilic properties. Liposomes suitable for use in accordance with the present invention include unilamellar vesicles and multilamellar vesicles.

As used herein, the term "polymeric moiety" means a single polymeric chain (branched or unbranched), which is derived from a corresponding single polymeric molecule. Polymeric moieties may be natural polymers or synthetic polymers. Typically, though, the polymeric molecules are not polynucleotides.

As is well known in the biochemical field, creation of conjugates comprising a polymeric moiety is useful in many in vivo and in vitro applications. For example, various properties of a macromolecule such as a protein can be modified by attaching a polymeric moiety thereto, including solubility properties, surface characteristics and stability in solution or on freezing. Another common application involves conjugating a polymeric moiety to a biologically active compound such as a drug with the aim of enhancing biocompatibility, reducing or eliminating immune response on administration, and/or increasing in vivo stability.

A person of skill in the art would therefore recognise that the methodology of the present invention can be used to prepare a conjugate comprising a polymeric moiety, which conjugate can then be used in any known application for polymeric-moiety-containing conjugates. A person of skill in the art would easily be able to select suitable polymeric moieties for use in accordance with the present invention, on the basis of those polymeric moieties used routinely in the art.

The nature of the polymeric moiety will therefore depend upon the intended use of the conjugate molecule. Exemplary polymeric moieties for use in accordance with the present invention include polysaccharides, polyethers, polyamino acids (such as polylysine), polyvinyl alcohols, polyvinylpyrrolidinones, poly(meth)acrylic acid and derivatives thereof, polyurethanes and polyphosphazenes. Typically such polymers contain at least ten monomeric units. Thus, for example, a polysaccharide typically comprises at least ten monosaccharide units.

Two particularly preferred polymeric molecules are dextran and polyethylene glycol ("PEG"), as well as derivatives of these molecules (such as monomethoxypolyethylene glycol, "mPEG"). Preferably, the PEG or derivative thereof has a molecular weight of less than 20,000. Preferably, the dextran or derivative thereof has a molecular weight of 10,000 to 500,000. In one preferred embodiment, the compounds of the present invention comprise a biologically active moiety, for example a drug, and a PEG or derivative thereof.

As used herein, the term "amino acid" means a moiety containing both an amine functional group and a carboxyl functional group. However, preferably the amino acid is an α-amino acid. Preferably, the amino acid is a proteinogenic amino acid, i.e. an amino acid selected from alanine, arginine, asparagine, aspartic acid, cysteine, glutamic acid, glutamine, glycine, histidine, isoleucine, leucine, lysine, methionine, proline, phenylalanine, pyrrolysine, selenocysteine, serine, threonine, tryptophan, tyrosine and valine. However, the amino acid can also be a non-proteinogenic amino acid. Examples of non-proteinogenic amino acids include lanthionine, 2-aminoisobutyric acid, dehydroalanine, gamma-aminobutyric acid, ornithine, citrulline, canavanine and mimosine. A particularly preferred amino acid according to the present invention is cysteine.

As used herein, the terms "peptide" and "protein" mean a polymeric moiety made up of amino acid residues. As a person of skill in the art will be aware, the term "peptide" is typically used in the art to denote a polymer of relatively short length and the term "protein" is typically used in the art to denote a polymer of relatively long length. As used herein, the convention is that a peptide comprises up to 50 amino acid residues whereas a protein comprises more than 50 amino acids. However, it will be appreciated that this distinction is not critical since the functional moieties identified in the present application can typically represent either a peptide or a protein.

As used herein, the term "polypeptide" is used interchangeable with "protein".

As used herein, a peptide or a protein can comprise any natural or non-natural amino acids. For example, a peptide or a protein may contain only α-amino acid residues, for example corresponding to natural α-amino acids. Alternatively the peptide or protein may additionally comprise one or more chemical modifications. For example, the chemical modification may correspond to a post-translation modification, which is a modification that occurs to a protein in vivo following its translation, such as an acylation (for example, an acetylation), an alkylation (for example, a methylation), an amidation, a biotinylation, a formylation, glycosylation, a glycation, a hydroxylation, an iodination, an oxidation, a sulfation or a phosphorylation. A person of skill in the art would of course recognise that such post-translationally modified peptides or proteins still constitute a "peptide" or a "protein" within the meaning of the present invention. For example, it is well established in the art that a glycoprotein (a protein that carries one or more oligosaccharide side chains) is a type of protein.

As used herein, the term "cell" means a single cell of a living organism.

As used herein, the term "carbohydrate" includes monosaccharides and oligosaccharides. Typically an oligosaccharide contains from two to nine monosaccharide units. Thus, as used herein, a polysaccharide is classified as a "polymeric moiety" rather than as a carbohydrate. However, a person of skill in the art will appreciate that this distinction is not important, since the functional moieties used in accordance with the invention can typically constitute either of a "carbohydrate" and a "polysaccharide".

As used herein, the term "DNA" means a deoxyribonucleic acid made up of one or more nucleotides. The DNA may be single stranded or double stranded. Preferably, the DNA comprises more than one nucleotide.

As used herein, the term "RNA" means a ribonucleic acid comprising one or more nucleotides. Preferably, the RNA comprises more than one nucleotide.

As used herein, "conjugate" means a molecule which comprises a first functional moiety and a second functional moiety. The first functional moiety and the second functional moiety are covalently linked to one another via a cross-linker moiety, as described herein.

As used herein, the terms "group" and "moiety" are used interchangeably.

As used herein, a "reactive group" means a functional group on a first molecule that is capable of taking part in a chemical reaction with a functional group on a second molecule such that a covalent bond forms between the first molecule and the second molecule. Reactive groups include leaving groups, nucleophilic groups, and other reactive groups as described herein.

As used herein, the term "electrophilic leaving group" means a substituent attached to a saturated or unsaturated carbon atom which can be replaced by a nucleophile following a nucleophilic attack at that carbon atom. Those of skill in the art are routinely able to select electrophilic leaving groups that would be suitable for locating on a particular compound and for reacting with a particular nucleophile.

As used herein, the term "nucleophile" means a functional group or compound which is capable of forming a chemical bond by donating an electron pair.

As used herein, the term "linker group" means a group which is capable of linking one chemical moiety to another. The nature of the linker groups used in accordance with the present invention is not important. A person of skill in the art would recognise that linker groups are routinely used in the construction of conjugate molecules. Typically, a linker group for use in the present invention is an organic group. Typically, such a linker group has a molecular weight of 50 to 1000, preferably 100 to 500. Examples of linker groups appropriate for use in accordance with the present invention are common general knowledge in the art and described in standard reference text books such as "Bioconjugate Techniques" (Greg T. Hermanson, Academic Press Inc., 1996), the content of which is herein incorporated by reference in its entirety.

As used herein, the term "alkyl" includes both saturated straight chain and branched alkyl groups. Preferably, an alkyl group is a $C_{1-20}$ alkyl group, more preferably a $C_{1-15}$, more preferably still a $C_{1-12}$ alkyl group, more preferably still, a $C_{1-6}$ alkyl group, and most preferably a $C_{1-4}$ alkyl group. Particularly preferred alkyl groups include, for example, methyl, ethyl, propyl, isopropyl, butyl, isobutyl, tert-butyl, pentyl and hexyl. The term "alkylene" should be construed accordingly.

As used herein, the term "alkenyl" refers to a group containing one or more carbon-carbon double bonds, which may be branched or unbranched. Preferably the alkenyl group is a $C_{2-20}$ alkenyl group, more preferably a $C_{2-15}$ alkenyl group, more preferably still a $C_{2-12}$ alkenyl group, or preferably a $C_{2-6}$ alkenyl group, and most preferably a $C_{2-4}$ alkenyl group. The term "alkenylene" should be construed accordingly.

As used herein, the term "alkynyl" refers to a carbon chain containing one or more triple bonds, which may be branched or unbranched. Preferably the alkynyl group is a $C_{2-20}$ alkynyl group, more preferably a $C_{2-15}$ alkynyl group, more preferably still a $C_{2-12}$ alkynyl group, or preferably a $C_{2-6}$ alkynyl group and most preferably a $C_{2-4}$ alkynyl group. The term "alkynylene" should be construed accordingly.

Unless otherwise specified, an alkyl, alkenyl or alkynyl group is typically unsubstituted. However, where such a group is indicated to be unsubstituted or substituted, one or more hydrogen atoms are optionally replaced by halogen atoms or sulfonic acid groups. Preferably, a substituted alkyl, alkenyl or alkynyl group has from 1 to 10 substituents, more preferably 1 to 5 substituents, more preferably still 1, 2 or 3 substituents and most preferably 1 or 2 substituents, for example 1 substituent. Preferably a substituted alkyl, alkenyl or alkynyl group carries not more than 2 sulfonic acid substituents. Halogen atoms are preferred substituents. Preferably, though, an alkyl, alkenyl or alkynyl group is unsubstituted.

In the moiety that is an alkyl, alkenyl or alkynyl group or an alkylene, alkenylene or alkynylene group, in which (a) 0, 1 or 2 carbon atoms may be replaced by groups selected from $C_{6-10}$ arylene, 5- to 10-membered heteroarylene, $C_{3-7}$ carbocyclylene and 5- to 10-membered heterocyclylene groups, and (b) 0, 1 or 2 —$CH_2$— groups may be replaced by groups selected from —O—, —S—, —S—S—, —C(O)— and —N($C_{1-6}$ alkyl)- groups, a total of 0, 1 or 2 of said carbon atoms and —$CH_2$— groups are preferably replaced, more preferably a total of 0 or 1. Most preferably, none of the carbon atoms or —$CH_2$— groups is replaced.

Preferred groups for replacing a —$CH_2$— group are —O—, —S— and —C(O)— groups. Preferred groups for replacing a carbon atom are phenylene, 5- to 6-membered heteroarylene, $C_{5-6}$ carbocyclylene and 5- to 6-membered heterocyclylene groups. As used herein, the reference to "0, 1 or 2 carbon atoms" means any terminal or non-terminal carbon atom in the alkyl, alkenyl or alkynyl chain, including any hydrogen atoms attached to that carbon atom. As used herein, the reference to "0, 1 or 2 —$CH_2$— groups" refers to a group which does not correspond to a terminal carbon atom in the alkyl, alkenyl or alkynyl chain.

As used herein, a $C_{6-10}$ aryl group is a monocyclic or polycyclic 6- to 10-membered aromatic hydrocarbon ring system having from 6 to 10 carbon atoms. Phenyl is preferred. The term "arylene" should be construed accordingly.

As used herein, a 5- to 10-membered heteroaryl group is a monocyclic or polycyclic 5- to 10-membered aromatic ring system, such as a 5- or 6-membered ring, containing at least one heteroatom, for example 1, 2, 3 or 4 heteroatoms, selected from O, S and N. When the ring contains 4 heteroatoms these are preferably all nitrogen atoms. The term "heteroarylene" should be construed accordingly.

Examples of monocyclic heteroaryl groups include thienyl, furyl, pyrrolyl, imidazolyl, thiazolyl, isothiazolyl, pyrazolyl, oxazolyl, isoxazolyl, triazolyl, thiadiazolyl, oxadiazolyl, pyridinyl, pyridazinyl, pyrimidinyl, pyrazinyl, triazinyl and tetrazolyl groups.

Examples of polycyclic heteroaryl groups include benzothienyl, benzofuryl, benzimidazolyl, benzothiazolyl, benzisothiazolyl, benzoxazolyl, benzisoxazolyl, benztriazolyl, indolyl, isoindolyl and indazolyl groups. Preferred polycyclic groups include indolyl, isoindolyl, benzimidazolyl, indazolyl, benzofuryl, benzothienyl, benzoxazolyl, benzisoxazolyl, benzothiazolyl and benzisothiazolyl groups, more preferably benzimidazolyl, benzoxazolyl and benzothiazolyl, most preferably benzothiazolyl. However, monocyclic heteroaryl groups are preferred.

Preferably the heteroaryl group is a 5- to 6-membered heteroaryl group. Particularly preferred heteroaryl groups are thienyl, pyrrolyl, imidazolyl, thiazolyl, isothiazolyl, pyrazolyl, oxazolyl, isoxazolyl, triazolyl, pyridinyl, pyridazinyl, pyrimidinyl and pyrazinyl groups. More preferred groups are thienyl, pyridinyl, pyridazinyl, pyrimidinyl, pyrazinyl, pyrrolyl and triazinyl, most preferably pyridinyl.

As used herein, a 5- to 10-membered heterocyclyl group is a non-aromatic, saturated or unsaturated, monocyclic or polycyclic $C_{5-10}$ carbocyclic ring system in which one or more, for example 1, 2, 3 or 4, of the carbon atoms are replaced with a moiety selected from N, O, S, S(O) and $S(O)_2$. Preferably, the 5- to 10-membered heterocyclyl group is a 5- to 6-membered ring. The term "heterocyclyene" should be construed accordingly.

Examples of heterocyclyl groups include azetidinyl, oxetanyl, thietanyl, pyrrolidinyl, imidazolidinyl, oxazolidinyl, isoxazolidinyl, thiazolidinyl, isothiazolidinyl, tetrahydrofuranyl, tetrahydrothienyl, tetrahydropyranyl, tetrahydrothiopyranyl, dithiolanyl, dioxolanyl, pyrazolidinyl, piperidinyl, piperazinyl, hexahydropyrimidinyl, methylenedioxyphenyl, ethylenedioxyphenyl, thiomorpholinyl, S-oxothiomorpholinyl, S,S-dioxo-thiomorpholinyl, morpholinyl, 1,3-dioxolanyl, 1,4-dioxolanyl, trioxolanyl, trithianyl, imidazolinyl, pyranyl, pyrazolinyl, thioxolanyl, thioxothiazolidinyl, 1H-pyrazol-5-(4H)-onyl, 1,3,4-thiadiazol-2(3H)-thionyl, oxopyrrolidinyl, oxothiazolidinyl, oxopyrazolidinyl, succinimido and maleimido groups and moieties. Preferred heterocyclyl groups are pyrrolidinyl, imidazolidinyl, oxazolidinyl, isoxazolidinyl, thiazolidinyl, isothiazolidinyl, tetrahydrofuranyl, tetrahydrothienyl, tetrahydropyranyl, tetrahydrothiopyranyl, dithiolanyl, dioxolanyl, pyrazolidinyl, piperidinyl, piperazinyl, hexahydropyrimidinyl, thiomorpholinyl and morpholinyl groups and moieties. More preferred heterocyclyl groups are tetrahydropyranyl, tetrahydrothiopyranyl, thiomorpholinyl, tetrahydrofuranyl, tetrahydrothienyl, piperidinyl, morpholinyl and pyrrolidinyl groups.

For the avoidance of doubt, although the above definitions of heteroaryl and heterocyclyl groups refer to an "N" moiety which can be present in the ring, as will be evident to a skilled chemist the N atom will be protonated (or will carry a substituent as defined below) if it is attached to each of the adjacent ring atoms via a single bond. As used herein, a $C_{3-7}$ carbocyclyl group is a non-aromatic saturated or unsaturated hydrocarbon ring having from 3 to 7 carbon atoms. Preferably it is a saturated or mono-unsaturated hydrocarbon ring (i.e. a cycloalkyl moiety or a cycloalkenyl moiety) having from 3 to 7 carbon atoms, more preferably having from 5 to 6 carbon atoms. Examples include cyclopropyl, cyclobutyl, cyclopentyl and cyclohexyl and their mono-unsaturated variants. Particularly preferred carbocyclic groups are cyclopentyl and cyclohexyl. The term "carbocyclylene" should be construed accordingly.

Where specified, 0, 1 or 2 carbon atoms in a carbocyclyl or heterocyclyl group may be replaced by —C(O)— groups. As used herein, the "carbon atoms" being replaced are understood to include the hydrogen atoms to which they are attached. When 1 or 2 carbon atoms are replaced, preferably two such carbon atoms are replaced. Preferred such carbocyclyl groups include a benzoquinone group and preferred such heterocyclyl groups include succinimido and maleimido groups.

Unless otherwise specified, an aryl, heteroaryl, carbocyclyl or heterocyclyl group is typically unsubstituted. However, where such a group is indicated to be unsubstituted or substituted, one or more hydrogen atoms are optionally replaced by halogen atoms or $C_{1-6}$ alkyl, $C_{1-6}$ alkoxy, $C_{1-6}$ alkylthiol, —N($C_{1-6}$ alkyl)($C_{1-6}$ alkyl), nitro or sulfonic acid groups. Preferably, a substituted aryl, heteroaryl, carbocyclyl or heterocyclyl group has from 1 to 4 substituents, more preferably 1 to 2 substituents and most preferably 1 substituent. Preferably a substituted aryl, heteroaryl, carbocyclyl or heterocyclyl group carries not more than 2 nitro substituents and not more than 2 sulfonic acid substituents. Preferred substituents are halogen atoms and $C_{1-4}$ alkyl and $C_{1-4}$ alkoxy groups. Particularly preferred substituents are halogen atoms. Preferably, though, an aryl, heteroaryl, carbocyclyl or heterocyclyl group is unsubstituted.

As used herein, halogen atoms are typically F, Cl, Br or I atoms, preferably Br or Cl atoms, more preferably Br atoms.

As used herein, a $C_{1-6}$ alkoxy group is a $C_{1-6}$ alkyl (e.g. a $C_{1-4}$ alkyl) group which is attached to an oxygen atom.

As used herein, a $C_{1-6}$ alkylthiol group is a $C_{1-6}$ alkyl (e.g. a $C_{1-4}$ alkyl) group which is attached to a sulfur atom.

As used herein, a 5- to 10-membered heterocyclylthiol is a 5- to 10-membered (e.g., a 5- to 6-membered) heterocyclyl group which is attached to a sulfur atom.

As used herein, a $C_{6-10}$ arylthiol is a $C_{6-10}$ aryl (e.g., a phenyl) group which is attached to a sulfur atom.

As used herein, a $C_{3-7}$ carbocyclylthiol is a $C_{3-7}$ carbocyclyl (e.g., a $C_{5-6}$ carbocyclyl) group which is attached to a sulfur atom.

In the present invention the moiety of formula (I) constitutes a cross-linking reactive moiety which is capable of linking together a thiol-containing first functional moiety and a second functional moiety.

Preferably X and X' are the same or different and each represents oxygen, sulfur or a group of formula =NH. More preferably, X and X' are the same or different and each represents oxygen or sulfur. Preferably at least one of X and X' represents oxygen. Most preferably, X and X' are both oxygen.

Y is preferably a halogen atom or a triflate, tosylate, mesylate, N-hydroxysuccinimidyl, N-hydroxysulfosuccinimidyl, $C_{1-6}$ alkylthiol, 5- to 10-membered heterocyclylthiol, $C_{6-10}$ arylthiol, $C_{3-7}$ carbocyclylthiol, —OC(O)CH$_3$, —OC(O)CF$_3$, phenyloxy, —NR$_x$R$_y$R$_z^+$ or —PR$_x$R$_y$R$_z^+$ group. More preferably, Y is a halogen atom or a triflate, tosylate, mesylate, N-hydroxysuccinimidyl, N-hydroxysulfosuccinimidyl, $C_{1-6}$ alkylthiol, 5- to 10-membered heterocyclylthiol, $C_{6-10}$ arylthiol or $C_{3-7}$ carbocyclylthiol. More preferably still Y is a halogen atom or a $C_{1-6}$ alkylthiol, 5- to 10-membered heterocyclylthiol, $C_{6-10}$ arylthiol or $C_{3-7}$ carbocyclylthiol group. Most preferably Y is a halogen atom, particularly a bromine atom.

$R_x$, $R_y$ and $R_z$ are each preferably selected from hydrogen atoms and $C_{1-6}$ alkyl groups. More preferably $R_x$, $R_y$ and $R_z$ are each preferably selected from hydrogen atoms and methyl and ethyl groups. Preferably, in a particular —NR$_x$R$_y$R$_z^+$ or —PR$_x$R$_y$R$_z^+$ group, $R_x$, $R_y$ and $R_z$ are the same.

The compound of formula $R_1$—H comprises at least a first thiol group, SH. In the present invention, this first thiol group is capable of reacting with the moiety of formula (I) by nucleophilic attack at the 2-position. The outcome of reacting the compound of formula $R_1$—H with the moiety of formula (I) is a moiety in which the electrophilic leaving group of formula Y at the 2-position in the moiety of formula (I) is replaced by the group of formula $R_1$. More specifically, the group of formula $R_1$ becomes attached at the 2-position through a thiol bond of formula —S— which is derived from the first SH group on the corresponding compound of formula $R_1$—H. It will therefore be clear that the hydrogen atom in the first thiol group SH of $R_1$—H constitutes the hydrogen atom attached to the group of formula $R_1$. Thus, when $R_1$ becomes attached to the cross-linker the hydrogen atom in this first thiol group is lost in order to form the —S— bond between $R_1$ and the cross-linker.

$R_1$ can be a group of formula —S-L-F$_1$, in which case the sulfur atom of the first thiol group is attached to the linker group of formula L. In this embodiment, therefore, it will be clear that the linker can be used to provide a thiol group capable of reacting with the moiety of formula (I), which linker group is then attached to a first functional moiety that does not contain such a thiol group. However, preferably $R_1$ is a group of formula F$_1$, and more particularly a first functional moiety which, together with the H-atom to which it is attached in the compound of formula $R_1$—H, contains a first SH group.

In a preferred embodiment, at least one of the first functional moiety and the second functional moiety is an enzymatically active moiety, a hapten, an immunogenic carrier, an antibody or antibody fragment, an antigen, a ligand, a biologically active moiety, an amino acid, a peptide, a protein, a carbohydrate, a DNA or an RNA. Preferably the first functional moiety is an enzymatically active moiety, a hapten, an immunogenic carrier, an antibody or antibody fragment, an antigen, a ligand, a biologically active moiety, an amino acid, a peptide, a protein, a carbohydrate, a DNA or an RNA. Preferred combinations of first functional moiety/second functional moiety include those set out in Table 1 below.

TABLE 1

Preferred combinations of first functional moiety/second functional moiety

| First or second functional moiety | Second or first functional moiety |
| --- | --- |
| Antibody or antibody fragment, amino acid, peptide, protein, DNA or RNA | Detectable moiety |
| Hapten | Immunogenic carrier |
| Antibody or antibody fragment | Enzymatically active moiety (preferably an enzyme) |
| Antibody or antibody fragment | Biologically active moiety, for example a cytotoxic agent or cytoxin precursor |
| Detectable moiety, enzymatically active moiety, antibody or antibody fragment, antigen, hapten, biologically active moiety, amino acid, peptide, protein, DNA or RNA | Liposome |
| Enzymatically active moiety, antibody or antibody fragment, antigen, amino acid, peptide, protein, DNA or RNA | Affinity tag |
| Biologically active moiety | Polymeric moiety |
| Enzymatically active moiety | DNA or RNA |

In a particularly preferred embodiment, $R_1$ is a group of formula $F_1$ and $F_1$ is a peptide or protein comprising at least a first cysteine residue. For the avoidance of doubt, a cysteine residue in a peptide or protein is a residue of formula

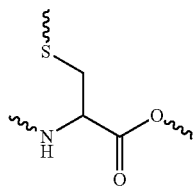

wherein in the compound of formula $R_1$—H the peptide or protein is attached to the hydrogen atom through the sulfur atom of the cysteine residue. In this embodiment, it will be understood that the "first cysteine residue" means a cysteine residue that is located at such a position on the peptide or protein such that it can react with the moiety of formula (I). More specifically, the group $R_1$ becomes attached to the moiety of formula (I) via nucleophilic attack of the thiol group of the first cysteine residue at the 2-position of the moiety of formula (I), such that the group Y is replaced by the thiol group in the first cysteine residue in the group $R_1$.

In a particularly preferred embodiment of the invention where $R_1$ is a group of formula $F_1$ and $F_1$ is a peptide or protein comprising at least a first cysteine residue, $R_1$ further comprises at least a second cysteine residue. For the avoidance of doubt, the second cysteine residue is located at such a position on the peptide or protein such that it can also react with the moiety of formula (I). Furthermore, in this embodiment the moiety of formula (I) is a compound of formula (Ia) wherein the group $R_2$ is an electrophilic leaving group of formula Y. The group $R_1$ then becomes further attached to the compound of formula (Ia) via nucleophilic attack of the thiol group of the second cysteine residue at the 3-position of the moiety of formula (Ia), such that the group $R_2$ is replaced by the thiol group in the second cysteine residue in the group $R_1$. This embodiment of the invention is particularly useful when the first functional moiety is a peptide or protein containing a disulfide bridge, since it allows the cross-linker reagent to be added across the disulfide bridge. Preferably, when a peptide or protein containing a disulfide bridge is to be reacted with the moiety of formula (I), the disulfide bridge is first reduced using techniques known in the art. For example, the reduction can be carried out by using standard phosphine reagents such as (tris(2-carboxyethyl)phosphine) or by carrying out a thiol-disulfide exchange reaction.

Reduction of a disulfide group can be carried out by reaction with a reducing agent such as a phosphine, a thiol or a hydride agent. Preferred reducing agents are tris(2-carboxyethyl)phosphine, glutathione, 2-mercaptoethanol and dithiothreitol. A preferred group of reagents is 1,2-ethanedithiol, 2-mercaptoethanol, dithiothreitol, glutathione and tris(2-carboxyethyl)phosphine.

It will be clear that the moiety of formula (I) represents the key reactive moiety which according to the present invention allows a thiol-containing functional moiety to be conjugated to a secondary functional moiety. Accordingly, a compound containing the moiety of formula (I) can be used as reagent for linking a first functional moiety to a second functional moiety. In the moiety of formula (I) (and the moiety of formula (II), as described in detail elsewhere), the symbol

〜〜 means a point of attachment to another group. It will be appreciated that the identity of the groups attached via these points of attachment is unimportant to the present invention. Those of skill in the art would readily understand that it would be possible to choose the groups attached via these points of attachment to suit a particular purpose, for example based on the specific identity of the functional moieties to be linked together. As would be well known to those of skill in the art, cross-linking reagents are routinely designed which carry functional groups adapted to react with functional moieties having particular reactive groups and which are spaced by linker groups (which typically do not play a significant role in the reactions). A person of skill in the art would immediately understand that the moiety of formula (I) could readily be incorporated into routine cross-linker reagents, for example, by replacing conventional moieties designed to react with thiol groups (for example, maleimide groups). Detailed information on the design of cross-linker reagents suitable for adaptation in this manner can be found, for example, in "Bioconjugate Techniques" (Greg T. Hermanson, Academic Press Inc., 1996), the content of which is herein incorporated by reference in its entirety.

The moiety of formula (I) is capable of linking together at least a first functional moiety and a second functional moiety. Where a cross-linker compound containing a moiety of formula (I) does not carry any reactive groups other than those on the moiety of formula (I), the first functional moiety can react at the 2-position by replacing the leaving group Y and the second functional moiety can then add by electrophilic addition across the carbon-carbon double bond between the 2- and 3-positions. Alternatively, the cross-linker reagent may comprise one or more additional reactive groups capable of reacting with further functional moieties.

In a further embodiment, the second functional moiety may be a moiety containing an alkene moiety and can be attached to the moiety of formula (I) by engaging in a photocatalytic [2+2] cycloaddition with the carbon-carbon double bond between the 2- and 3-positions of the moiety of formula (I). This procedure results in a cyclobutane ring moiety containing the 2- and 3-carbon atoms from the moiety of formula (I) and in which the carbon-carbon double bond has been saturated.

Preferably, the compound containing a moiety of formula (I) according to the present invention is a compound of formula (Ia)

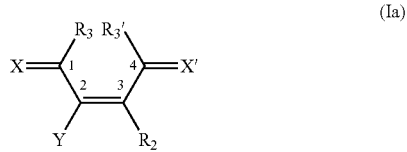

wherein:
X and X' are the same or different and each represents oxygen, sulfur or a group of formula =NQ, in which Q is hydrogen, hydroxyl, $C_{1-6}$ alkyl or phenyl;
either:
  $R_3$ and $R_3'$ are the same or different and each represents a hydrogen atom or a group of formula E, Nu, -L(Z)$_n$ or IG; or
  $R_3$ and $R_3'$ together form a group of formula —O— or —N($R_{33'}$), wherein $R_{33'}$ represents a hydrogen atom or a group of formula Y, Nu, -L(Z)$_n$ or IG; or
  $R_3$ and $R_3'$ together form a group of formula —N($R_{33'}$)—N($R_{33'}$)—, wherein each $R_{33'}$ is the same or different and represents a hydrogen atom or a group of formula Y, Nu, -L(Z)$_n$ or IG;
$R_2$ represents a hydrogen atom or a group of formula Y, Nu, -L(Z)$_n$ or IG;
each group of formula E and Y is the same or different and represents an electrophilic leaving group;
each group of formula Nu is the same or different and represents a nucleophile selected from —OH, —SH, —NH$_2$ and —NH(C$_{1-6}$ alkyl);
each group of formula L is the same or different and represents a linker group;
each group of formula Z is the same or different and represents a reactive group attached to a group of formula L which is capable of reacting with a compound containing a second functional moiety as defined in claim 1 such that said second functional moiety becomes linked to said group of formula L;
n is 1, 2 or 3; and
each group of formula IG is the same or different and represents a moiety which is a $C_{1-20}$ alkyl group, a $C_{2-20}$ alkenyl group or a $C_{2-20}$ alkynyl group, which is unsubstituted or substituted by one or more substituents selected from halogen atoms and sulfonic acid groups, and in which (a) 0, 1 or 2 carbon atoms are replaced by groups selected from $C_{6-10}$ arylene, 5- to 10-membered heteroarylene, $C_{3-7}$ carbocyclylene and 5- to 10-membered heterocyclylene groups, and (b) 0, 1 or 2 —CH$_2$— groups are replaced by groups selected from —O—, —S—, —S—S—, —C(O)— and —N(C$_{1-6}$ alkyl)- groups, wherein:
(i) said arylene, heteroarylene, carbocyclylene and heterocyclylene groups are unsubstituted or substituted by one or more substituents selected from halogen atoms and $C_{1-6}$ alkyl, $C_{1-6}$ alkoxy, $C_{1-6}$ alkylthiol, —N(C$_{1-6}$ alkyl)(C$_{1-6}$ alkyl), nitro and sulfonic acid groups; and
(ii) 0, 1 or 2 carbon atoms in said carbocyclylene and heterocyclylene groups are replaced by —C(O)— groups.

Preferably in the compound of formula (Ia) $R_3$ and $R_3'$ are the same or different and each represents a hydrogen atom or a group of formula E, Nu, -L(Z)$_n$ or IG; or $R_3$ and $R_3'$ together form a group of formula —N($R_{33'}$), wherein $R_{33'}$ represents a hydrogen atom or a group of formula Y, Nu, -L(Z)$_n$ or IG.

Preferred groups X, X' and Y in the formula (Ia) are as defined above.

When $R_3$ and $R_3'$ are the same or different and each represents a hydrogen atom or a group of formula E, Nu, -L(Z)$_n$ or IG, preferably $R_3$ and $R_3'$ are the same or different and each represents a group of formula E, Nu, -L(Z)$_n$ or IG. In this embodiment, preferably at least one of $R_3$ and $R_3'$ represents a group of formula E, Nu or -L(Z)$_n$.

Preferably $R_3$ and $R_3'$ together form a group of formula —N($R_{33'}$).

$R_{33'}$ preferably represents a hydrogen atom or a group of formula -L(Z)$_n$ or IG. Particularly preferred $R_{33'}$ groups are hydrogen atoms and groups of formula IG. Most preferably, $R_{33'}$ is a hydrogen atom or a $C_{1-6}$ alkyl group.

$R_2$ is preferably a hydrogen atom or a group of formula Y, -L(Z)$_n$ or IG. More preferably, $R_2$ is preferably a hydrogen atom or a group of formula Y or IG. Most preferably, $R_2$ is a hydrogen or halogen atom or a $C_{1-6}$ alkyl group.

E is preferably a halogen atom or a $C_{1-6}$ alkoxy, thiol, $C_{1-6}$ alkylthiol, —N(C$_{1-6}$ alkyl)(C$_{1-6}$ alkyl), triflate, tosylate, mesylate, N-hydroxysuccinimidyl, N-hydroxysulfosuccinimidyl, imidazolyl, phenyloxy or nitrophenyloxy group. More preferred groups of formula E are halogen atoms and triflate, tosylate and mesylate groups.

Nu is preferably a group of formula —OH or —SH. In another embodiment, Nu is preferably a group of formula —OH, —NH$_2$ or —SH, more preferably —NH$_2$ or —SH.

The linker moiety L links together two other moieties in the compounds of the present invention (i.e., it is at least a divalent moiety). However, in some embodiments certain linker moieties L may link together more than two other moieties (for example, where $R_2$, $R_3$, $R_3'$ or $R_{33'}$ represents -L(Z)$_n$ wherein n is 2 or 3), in which case it is to be understood that the third other moiety and any further other moiety each replace a hydrogen atom on the corresponding divalent linker moiety L.

L preferably represents a moiety which is a $C_{1-20}$ alkylene group, a $C_{2-20}$ alkenylene group or a $C_{2-20}$ alkynylene group, which is unsubstituted or substituted by one or more substituents selected from halogen atoms and sulfonic acid groups, and in which (a) 0, 1 or 2 carbon atoms are replaced by groups selected from $C_{6-10}$ arylene, 5- to 10-membered heteroarylene, $C_{3-7}$ carbocyclylene and 5- to 10-membered heterocyclylene groups, and (b) 0, 1 or 2 —CH$_2$— groups are replaced by groups selected from —O—, —S—, —S—S—, —C(O)— and —N(C$_{1-6}$ alkyl)- groups, wherein:
(i) said arylene, heteroarylene, carbocyclylene and heterocyclylene groups are unsubstituted or substituted by one or more substituents selected from halogen atoms and $C_{1-6}$ alkyl, $C_{1-6}$ alkoxy, $C_{1-6}$ alkylthiol, —N(C$_{1-6}$ alkyl)(C$_{1-6}$ alkyl), nitro and sulfonic acid groups; and
(ii) 0, 1 or 2 carbon atoms in said carbocyclylene and heterocyclylene groups are replaced by —C(O)— groups.

More preferably, L represents a moiety which is an unsubstituted $C_{1-6}$ alkylene group, $C_{2-6}$ alkenylene group or $C_{2-6}$ alkynylene group, in which (a) 0 or 1 carbon atom is replaced by a group selected from phenylene, 5- to 6-membered heteroarylene, $C_{5-6}$ carbocyclylene and 5- to 6-membered heterocyclylene groups, wherein said phenylene, heteroarylene, carbocyclylene and heterocyclylene groups are unsubstituted or substituted by one or two substituents selected from halogen atoms and $C_{1-4}$ alkyl and $C_{1-4}$ alkoxy groups, and (b) 0, 1 or 2 —CH$_2$— groups are replaced by groups selected from —O—, —S— and —C(O)— groups.

Most preferably, L is a moiety which is an unsubstituted $C_{1-4}$ alkylene group, in which 0 or 1 carbon atom is replaced by an unsubstituted phenylene group.

Z represents a reactive group attached to a group of formula L which is capable of reacting with a functional moiety such that the functional moiety becomes linked to the group of formula L. As those of skill in the art would understand, the nature of the reactive group itself is not important. A very wide range of reactive groups are now routinely used in the art to connect a functional moiety to a cross-linker reagent. Such reactive groups may be capable, for example, of attaching an amine compound, a thiol compound, a carboxyl compound, a hydroxyl compound, a carbonyl compound or a compound containing a reactive hydrogen, to a cross-linker. Those of skill in the art would of course immediately recognise that any such reactive group would be suitable for use in accordance with the present invention. Those of skill in the art would be able to select an appropriate reactive group from common general knowledge, with reference to standard text books such as "Bioconjugate Techniques" (Greg T. Hermanson, Academic Press Inc., 1996), the content of which is herein incorporated by reference in its entirety.

Z is preferably:
(a) a group of formula -LG, —C(O)-LG, —C(S)-LG or —C(NH)-LG wherein LG is an electrophilic leaving group;
(b) a nucleophile Nu' selected from —OH, —SH, —NH$_2$, —NH(C$_{1-6}$ alkyl) and —C(O)NHNH$_2$ groups;
(c) a cyclic moiety Cyc, which is capable of a ring-opening electrophilic reaction with a nucleophile;
(d) a group of formula —S(O$_2$)(Hal), wherein Hal is a halogen atom;
(e) a group of formula —N=C=O or —N=C=S;
(f) a group of formula —S—S(IG') wherein IG' represents a group of formula IG as defined herein;
(g) a group AH, which is a C$_{6-10}$ aryl group that is substituted by one or more halogen atoms;
(h) a photoreactive group capable of being activated by exposure to ultraviolet light;
(i) a group of formula —C(O)H or —C(O)(C$_{1-6}$ alkyl);
(j) a maleimido group;
(k) a group of formula —C(O)CHCH$_2$;
(l) a group of formula —C(O)C(N$_2$)H or -PhN$_2^+$, where Ph represents a phenyl group; or
(m) an epoxide group.

Most preferably, Z is selected from:
(a) groups of formula -LG, —C(O)-LG and —C(S)-LG, wherein LG is selected from halogen atoms and —O(C$_{1-6}$ alkyl), —SH, —S(C$_{1-6}$ alkyl), triflate, tosylate, mesylate, N-hydroxysuccinimidyl and N-hydroxysulfosuccinimidyl groups;
(b) groups of formula —OH, —SH and —NH$_2$;
(c) a group of formula

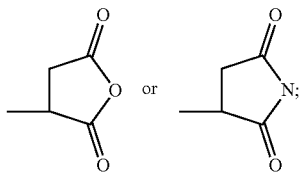

and
(d) a maleimido group.

LG is preferably selected from halogen atoms and —O(IG'), —SH, —S(IG'), —NH$_2$, NH(IG'), —N(IG')(IG"), —N$_3$, triflate, tosylate, mesylate, N-hydroxysuccinimidyl, N-hydroxysulfosuccinimidyl, imidazolyl and azide groups, wherein IG' and IG" are the same or different and each represents a group of formula IG.

Nu' is preferably selected from —OH, —SH and —NH$_2$ groups.

Cyc is preferably selected from the groups

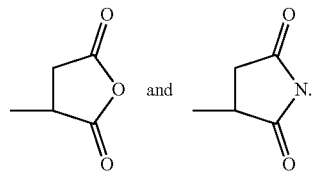

Hal is preferably a chlorine atom.

AH is preferably a phenyl group that is substituted by at least one fluorine atom.

The photoreactive group is preferably selected from:
(a) a C$_{6-10}$ aryl group which is substituted by at least one group of formula —N$_3$ and which is optionally further substituted by one or more halogen atoms;
(b) a benzophenone group;
(c) a group of formula —C(O)C(N$_2$)CF$_3$; and
(d) a group of formula -PhC(N$_2$)CF$_3$, wherein Ph represents a phenyl group.

n is preferably 1 or 2, and most preferably 1.

IG preferably represents a moiety which is an unsubstituted C$_{1-6}$ alkyl group, C$_{2-6}$ alkenyl group or C$_{2-6}$ alkynyl group, in which (a) 0 or 1 carbon atom is replaced by a group selected from phenylene, 5- to 6-membered heteroarylene, C$_{5-6}$ carbocyclylene and 5- to 6-membered heterocyclylene groups, wherein said phenylene, heteroarylene, carbocyclylene and heterocyclylene groups are unsubstituted or substituted by one or two substituents selected from halogen atoms and C$_{1-4}$ alkyl and C$_{1-4}$ alkoxy groups, and (b) 0, 1 or 2 —CH$_2$— groups are replaced by groups selected from —O—, —S— and —C(O)— groups.

More preferably, IG represents a moiety which is an unsubstituted C$_{1-6}$ alkyl group, in which (a) 0 or 1 carbon atom is replaced by a group selected from unsubstituted phenylene, 5- to 6-membered heteroarylene, C$_{5-6}$ carbocyclylene and 5- to 6-membered heterocyclylene groups.

Most preferably, IG represents an unsubstituted C$_{1-6}$ alkyl group.

Preferably the compound of formula (Ia) is a compound of formula (Ib):

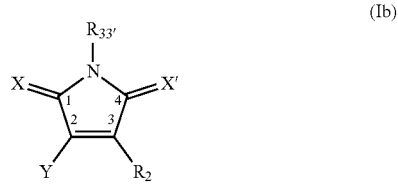

(Ib)

wherein X, X', Y, R$_2$ and R$_{33'}$ are all as herein defined.

In the compound of formula (Ib), preferably:
X and X' each represent an oxygen atom;
R$_{33'}$ represents a hydrogen atom or a C$_{1-6}$ alkyl group;
Y represents a halogen atom; and
R$_2$ represents a hydrogen or halogen atom or a C$_{1-6}$ alkyl group.

Embodiment (1) of the present invention relates to use of a compound containing the moiety of formula (I), as defined above, as a reagent for linking the compound of formula $R_1$—H which comprises a first functional moiety of formula $F_1$ to a second functional moiety of formula $F_2$. Typically, this use involves carrying out a process of the present invention, as defined in embodiment (2) or embodiment (3) described below.

Preferably in the use of embodiment (1) the compound containing a moiety of formula (I) is not dibromomaleic acid if the compound of formula $R_1$—H is 2-mercaptoethanol.

Embodiment (2) of the present invention relates to a process for producing a conjugate. In a step (i) of this process, a compound containing a moiety of formula (I) is reacted with a compound of formula $R_1$—H to produce a compound containing a moiety of formula (II):

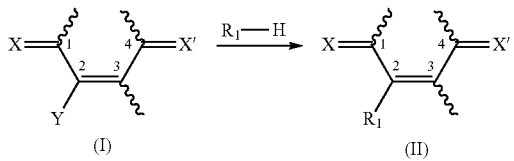

This step (i) involves attaching the group $R_1$ via nucleophilic attack of the first SH group in the compound of formula $R_1$—H at the 2-position of the moiety of formula (I), such that the group Y at the 2-position is replaced by the group $R_1$.

In a step (ii) of the process of embodiment (2), a moiety of formula $F_2$ is linked to the moiety of formula (II), thus producing the conjugate. Several procedures can be used to carry out step (ii), for example those set out under paragraphs (a), (b), (c) and (d) below:

(a) The process may comprise linking $F_2$ to the moiety of formula (II) via an electrophilic addition reaction of $F_2$ across the carbon-carbon double bond between the 2-position and the 3-position of the formula (II).
(b) Where the compound containing a moiety of formula (I) is a compound of formula (Ia), $R_3$ and $R_3$' together form a group of formula —N($R_{33'}$), and $R_{33'}$ represents a hydrogen atom or a group of formula Y, Nu or -L(Z)$_n$, the process may comprise linking $F_2$ to the moiety of formula (II) via a reaction between $F_2$ and (i) the nitrogen atom of the moiety of formula —N($R_{33'}$) or (ii) said group of formula Y, Nu or -L(Z)$_n$.
(c) Where the compound containing a moiety of formula (I) is a compound of formula (Ia), $R_3$ and $R_3$' do not together a group of formula —N($R_{33'}$), and at least one of $R_3$ and $R_3$' represents a group of formula E, Nu or -L(Z)$_n$, the process may comprise linking $F_2$ to the moiety of formula (II) via a reaction between $F_2$ and said group of formula E, Nu or -L(Z)$_n$.
(d) Where the compound containing a moiety of formula (I) is a compound of formula (Ia) and $R_2$ represents a group of formula Y, Nu or -L(Z)$_n$, the process may comprise linking $F_2$ to the moiety of formula (II) via a reaction between $F_2$ and said group of formula Y, Nu or -L(Z)$_n$.

In a further embodiment, the moiety of formula $F_2$ is linked to the moiety of formula (II) by a effecting a photocatalytic [2+2] cycloaddition reaction between an alkene group on the moiety of formula $F_2$ and the carbon-carbon double bond between the 2-position and the 3-position of the formula (II). This procedure results in a cyclobutane ring moiety containing the 2- and 3-carbon atoms from the moiety of formula (II) and in which the carbon-carbon double bond has been saturated.

In a still further embodiment, when $R_3$ and $R_3$' together form a group of formula —O— and the moiety of formula $F_2$ carries a nucleophilic group, such as a primary or secondary amine group, the moiety of formula $F_2$ can link to the moiety of formula (II) by engaging in a nucleophilic ring-opening and then nucleophilic ring closing reaction. For example, when X and/or X' are O and $R_3$ and $R_3$' together form a group of formula —O—, the moiety of formula (II) is a cyclic acid anhydride. Thus, it can be seen that a moiety of formula $F_2$ carrying, for example, an amine group can engage in nucleophilic ring-opening and then nucleophilic ring closing with the overall effect that the group —O— is replaced by the group —N(functional moiety)-.

An alternative process for producing a conjugate is provided by embodiment (3) of the present invention. In this process, a compound of formula $R_1$—H is reacted with a compound comprising (a) a moiety of formula (I) and (b) at least one moiety of formula $F_2$ linked thereto. The process involves attaching the group $R_1$ via nucleophilic attack of the first SH group in the compound of formula $R_1$—H at the 2-position of the moiety of formula (I), such that the group Y at the 2-position is replaced by the group $R_1$.

Preferably according to the above-described process of embodiment (3), the compound comprising (a) the moiety of formula (I) and (b) at least one moiety of formula $F_2$ linked thereto, is a compound of formula (IIa)

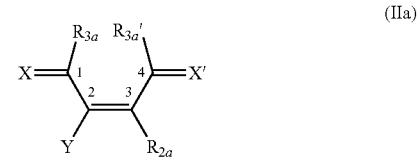

wherein:
either:
$R_{3a}$ represents a group of formula $R_3$ or a group of formula $F_2$ or -L($F_2$)$_m$(Z)$_{n-m}$ and $R_{3a}$' independently represents a group of formula $R_3$' or a group of formula $F_2$ or -L($F_2$)$_m$(Z)$_{n-m}$; or
$R_{3a}$ and $R_{3a}$' together form a group of formula —O— or —N($R_{33a'}$), wherein $R_{33a'}$ represents a group of formula $R_{33'}$ or a group of formula $F_2$ or -L($F_2$)$_m$(Z)$_{n-m}$; or
$R_{3a}$ and $R_{3a}$' together form a group of formula —N($R_{33a'}$)—N($R_{33a'}$)—, wherein each $R_{33a'}$ is the same or different and represents a group of formula $R_{33'}$ or a group of formula $F_2$ or -L($F_2$)$_m$(Z)$_{n-m}$;
$R_{2a}$ represents a group of formula $R_2$ or a group of formula $F_2$ or -L($F_2$)$_m$(Z)$_{n-m}$;
m is an integer having a value of from zero to n;
the compound of formula (IIa) comprises at least one group of formula $F_2$; and
$F_2$, X, X', $R_3$, $R_3$', $R_{33'}$, $R_2$, L, Z and n are all as defined herein.

Preferably according to the above-described process of embodiment (3), $R_{3a}$ represents a group of formula $R_3$ or a group of formula $F_2$ or -L($F_2$)$_m$(Z)$_{n-m}$ and $R_{3a}$' independently represents a group of formula $R_3$' or a group of formula $F_2$ or -L($F_2$)$_m$(Z)$_{n-m}$; or $R_{3a}$ and $R_{3a}$' together form a group of formula —N($R_{33a'}$), wherein $R_{33a'}$ represents a group of formula $R_{33'}$ or a group of formula $F_2$ or -L($F_2$)$_m$(Z)$_{n-m}$.

As will be clear to those of skill in the art, the compound of formula (IIa) is related to the compound of formula (II) as described above. However, the compound of formula (IIa) comprises at least one functional moiety $F_2$. Accordingly, the compound of formula (IIa) can readily be prepared by linking a functional moiety $F_2$ to its corresponding compound of formula (II) using methods routinely known in the art.

Preferably according to the above-described process of embodiment (3), the compound comprising (a) the moiety of formula (I) and (b) at least one moiety of formula $F_2$ linked thereto, is a compound of formula (IIa) in which:
either:
$R_{3a}$ represents a group of formula $R_3$ or a group of formula $F_2$ and $R_{3a}'$ independently represents a group of formula $R_3'$ or a group of formula $F_2$; or
$R_{3a}$ and $R_{3a}'$ together form a group of formula —$N(R_{33a'})$, wherein $R_{33a'}$ represents a group of formula $R_{33'}$ or a group of formula $F_2$; and
$R_{2a}$ represents a group of formula $R_2$ or a group of formula $F_2$.

Preferably the compound of formula (IIa) comprises at most three groups of formula $F_2$, more preferably one or two groups of formula $F_2$, and most preferably one group of formula $F_2$.

Clearly, after carrying the process of embodiment (2) or (3) of the present invention one or more further reactive groups may remain on the conjugate product (including a carbon-carbon double bond located at a position corresponding to the 2- and 3-positions of the cross-linker reagent as well as further nucleophilic groups, electrophilic groups, and reactive groups of formula Z). Accordingly, in further aspects the processes of embodiments (2) and (3) of the present invention further comprise linking one or more further functional moieties to said conjugate, wherein each further functional moiety is the same or different and is selected from a detectable moiety, an enzymatically active moiety, an affinity tag, a hapten, an immunogenic carrier, an antibody or antibody fragment, an antigen, a ligand, a biologically active moiety, a liposome, a polymeric moiety, an amino acid, a peptide, a protein, a cell, a carbohydrate, a DNA and an RNA.

The chemical reactions taking place in the processes of embodiments (2) and (3) can be carried out using routine techniques known in the art for attaching cross-linker reagents to functional moieties, such as those described in "Bioconjugate Techniques" (Greg T. Hermanson, Academic Press Inc., 1996), the content of which is herein incorporated by reference in its entirety. Further examples of suitable conditions for carrying out such reactions can be found in the Examples section of the present specification.

As would be understood by those of skill in the art, where a reagent (for example, a compound carrying a functional moiety or a cross-linker reagent) carries more than one reactive group, it may be desirable to effect chemical protection of reactive groups that are not intended to take part in the reaction. For example, it may be necessary to protect groups such as hydroxyl, amino and carboxy groups, where these are desired in the final product, to avoid their unwanted participation in the reactions (see, for example, Greene, T. W., "Protecting Groups in Organic Synthesis", John Wiley and Sons, 1999). Conventional protecting groups may be used in conjunction with standard practice. In some instances deprotection may be used in an intermediate or final step, and thus the processes of embodiments (2) and (3) according to the invention described herein are understood to extend to addition and removal of such protecting groups.

Preferably in embodiment (2) the compound containing a moiety of formula (I) is not dibromomaleic acid if the compound of formula $R_1$—H is 2-mercaptoethanol.

Preferably in embodiment (3) the compound comprising (a) a moiety of formula (I) and (b) at least one moiety of formula $F_2$ linked thereto is not N-phenyl 3,4-dibromomaleimide, wherein the N-phenyl groups is substituted or unsubstituted, if the compound of formula $R_1$—H is 2-mercaptoethanol.

It will be appreciated that in some embodiments the conjugate produced according to the process of embodiment (2) or (3) will contain a maleimide ring. Specifically, this occurs when in the moiety of formula (I) the carbon atoms at positions 1 and 4 are linked together via a group —$N(R_{33'})$—. When the conjugate comprises a maleimide ring the process of embodiment (2) or (3) may further comprise effecting ring opening of said maleimide ring. Ring opening of maleimide rings can be effected by hydrolysis reactions that are known in the art. Effecting ring opening of the maleimide may be advantageous in certain applications since it can render the functional moieties irreversibly bound to the conjugate.

In embodiment (4), the present invention relates to a process for cleaving the bond between a thiol-containing functional moiety and the cross-linker moiety (which may additionally be linked to one or more further functional moieties). More specifically, the cleavage is effected on a compound comprising a moiety of formula (II).

Examples of techniques in which the process of embodiment (4) is particularly usefully include protein purification, proteomic analysis and processes for probing the binding site of an enzyme. In a preferred embodiment of the process of embodiment (4) the first functional moiety of formula $F_1$ is a protein, especially a protein that is expensive or time-consuming to obtain, such as proteins that are difficult to express (e.g., a GPCR protein). In another preferred embodiment of the process of embodiment (4), the first functional moiety of formula $F_1$ is a biologically active moiety (e.g., a drug) since here the methodology can be exploited in, for example, drug delivery methods.

In a first preferred embodiment of the process of embodiment (4) the compound comprising a moiety of formula (II) is a compound of formula (III)

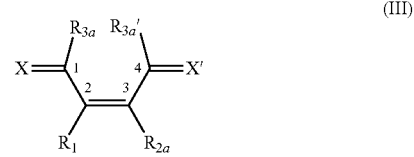

wherein:
either:
$R_{3a}$ represents a group of formula $R_3$ or a group of formula $F_2$ or -$L(F_2)_m(Z)_{n-m}$ and $R_{3a}'$ independently represents a group of formula $R_3'$ or a group of formula $F_2$ or -$L(F_2)_m(Z)_{n-m}$; or
$R_{3a}$ and $R_{3a}'$ together form a group of formula —O— or —$N(R_{33a'})$, wherein $R_{33a'}$ represents a group of formula $R_{33'}$ or a group of formula $F_2$ or -$L(F_2)_m(Z)_{n-m}$; or
$R_{3a}$ and $R_{3a}'$ together form a group of formula —$N(R_{33a'})$—$N(R_{33a'})$—, wherein each $R_{33a'}$ is the same or different and represents a group of formula $R_{33'}$ or a group of formula $F_2$ or -$L(F_2)_m(Z)_{n-m}$;

$R_{2a}$ represents a group of formula $R_2$ or a group of formula $F_2$ or $-L(F_2)_m(Z)_{n-m}$;

m is an integer having a value of from zero to n; and $R_1, F_2, X, X', R_3, R_3', R_{33'}, R_2, L, Z$ and n are all as defined herein.

More preferably in this embodiment, $R_{3a}$ represents a group of formula $R_3$ or a group of formula $F_2$ or $-L(F_2)_m(Z)_{n-m}$ and $R_{3a}'$ independently represents a group of formula $R_3'$ or a group of formula $F_2$ or $-L(F_2)_m(Z)_{n-m}$; or $R_{3a}$ and $R_{3a}'$ together form a group of formula $-N(R_{33a'})$, wherein $R_{33a'}$ represents a group of formula $R_{33'}$ or a group of formula $F_2$ or $-L(F_2)_m(Z)_{n-m}$.

In a second preferred embodiment of the process of embodiment (4) the compound comprising a moiety of formula (II) is a compound of formula (IIIa)

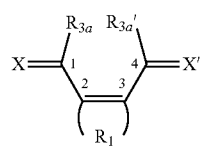

(IIIa)

wherein:
either:
  $R_{3a}$ represents a group of formula $R_3$ or a group of formula $F_2$ or $-L(F_2)_m(Z)_{n-m}$ and $R_{3a}'$ independently represents a group of formula $R_3'$ or a group of formula $F_2$ or $-L(F_2)_m(Z)_{n-m}$; or
  $R_{3a}$ and $R_{3a}'$ together form a group of formula $-O-$ or $-N(R_{33a'})$, wherein $R_{33a'}$ represents a group of formula $R_{33'}$ or a group of formula $F_2$ or $-L(F_2)_m(Z)_{n-m}$; or
  $R_{3a}$ and $R_{3a}'$ together form a group of formula $-N(R_{33a'})-N(R_{33a'})-$, wherein each $R_{33a'}$ is the same or different and represents a group of formula $R_{33'}$ or a group of formula $F_2$ or $-L(F_2)_m(Z)_{n-m}$;

m is an integer having a value of from zero to n;

$R_1$ is as hereinbefore defined, and wherein $R_1$ comprises at least a first thiol group and a second thiol group, said first thiol group being attached to the 2-position in the compound of formula (IIIa) and second thiol group being attached to the 3-position in the compound of formula (IIIa);

$F_2, X, X', R_3, R_3', R_{33'}, L, Z$ and n are all as herein defined; and step (ii) further involves cleaving the bond between the group $R_1$ and the carbon atom at the 3-position of the moiety of formula (IIIa).

In this second preferred embodiment, $R_{3a}$ preferably represents a group of formula $R_3$ or a group of formula $F_2$ or $-L(F_2)_m(Z)_{n-m}$ and $R_{3a}'$ independently represents a group of formula $R_3'$ or a group of formula $F_2$ or $-L(F_2)_m(Z)_{n-m}$; or $R_{3a}$ and $R_{3a}'$ together form a group of formula $-N(R_{33a'})$, wherein $R_{33a'}$ represents a group of formula $R_{33'}$ or a group of formula $F_2$ or $-L(F_2)_m(Z)_{n-m}$.

Accordingly, this second preferred embodiment provides a process for cleaving a cross-linker moiety from a functional moiety which contains at least two thiol groups. An example of such a functional moiety is a moiety which contains a disulfide group, such as a protein containing two cysteine residues which are linked to one another via a disulfide bridge.

Preferably, in the process of embodiment (4) the compound comprising a moiety of formula (II) also comprises at least one functional moiety of formula $F_2$.

In the process of embodiment (4), the step (ii) of cleaving the bond(s) to the group of formula $R_1$ can be carried out using routine methods for cleaving a thiol bond at an unsaturated carbon centre, for example using routine methods for cleaving a thiol attached to an electron deficient alkene.

Preferably, step (ii) of the process of embodiment (4) is effected by incubating the compound with a reagent that is capable of acting as a nucleophile in a Michael reaction. Examples of reagents that are well known to be capable of acting as a nucleophile in a Michael reaction include phosphine compounds, phosphite compounds, thiols, selenols, amines and soft carbon nucleophilic compounds. Phosphine compounds and phosphite compounds both contain a trivalent phosphorous atom. In a phosphine, the phosphorous atom is attached to hydrogen or carbon atoms, while in a phosphite the phosphorous atom is attached to oxygen atoms (it being understood that the carbon atoms and oxygen atoms are themselves further attached to other groups in the respective compounds). Thiols are organic compounds containing a thiol group $-SH$. Selenols are organic compounds containing an $-SeH$ group. Amines are compounds containing an amine functional group. Soft carbon nucleophiles are compounds which contain a soft nucleophilic carbon centre. Exemplary soft carbon nucleophiles are disclosed in U.S. Pat. No. 5,414,074, the content of which is herein incorporated by reference in its entirety. Those of skill in the art would of course be able to select appropriate reagents that are capable of acting as a nucleophile in a Michael reaction as a matter of routine, for example by routinely selecting a suitable reagent from amongst the exemplified list of classes of reagent herein described.

Presently preferred reagents are phosphine compounds and thiols. A particularly preferred phosphine is tris(2-carboxyethyl)phosphine, which is commonly known as "TCEP" and is commonly used in the art to reduce disulfide bonds in compounds, for example, in proteins. Tris(2-carboxyethyl)phosphine can also be supplied in the form of a salt, such as its hydrochloride salt. A particularly preferred thiol is glutathione. Further preferred thiols are 1,2-ethanedithiol, 2-mercaptoethanol and dithiothreitol (i.e., $HSCH_2CH(OH)CH(OH)CH_2SH$, commonly known as DTT). A preferred group of reagents is 1,2-ethanedithiol, 2-mercaptoethanol, dithiothreitol, glutathione and tris(2-carboxyethyl)phosphine.

For the avoidance of doubt, as used herein, the term "reagent that is capable of acting as a nucleophile in a Michael reaction" means a reagent that is capable of reacting with an α,β-unsaturated moiety in a compound, and in particular a moiety of formula (V)

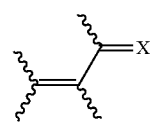

(V)

wherein X is as herein defined. Such reagents are sometimes known as "reagents that are capable of acting as a nucleophile in a conjugate addition reaction". Clearly, the reagents are not limited to reagents which react through a nucleophilic carbon centre (e.g., soft carbon nucleophiles), but also include reagents which react through a nucleophilic non-carbon centre, such as the exemplary reagents that are described herein.

The present invention also provides a process which comprises:
(i) carrying out a process for producing a conjugate as defined in embodiment (2) or (3); and
(ii) subsequently regenerating the compound of formula $R_1$—H from said conjugate.

Typically, in this process the step (ii) is effected by incubating the compound with a reagent that is capable of acting as a nucleophile in a Michael reaction, for example a reagent as defined in connection with embodiment (4).

The methodology of the present invention also gives rise to a series of new compounds, which constitute embodiments (5), (6), (7), (8) and (9) of the present invention.

Embodiment (5) of the present invention relates to a compound of formula (IIa). This compound comprises (a) the moiety of formula (I) and (b) at least one moiety of formula $F_2$ linked thereto. Accordingly, it will be clear that this compound can be used to functionalise a thiol-containing functional compound (herein referred to as the compound $R_1$—H) with a moiety of formula $F_2$, specifically by using it as a reagent in carrying out the process of embodiment (3).

Preferably in embodiment (5) the compound of formula (IIa) is not an N-phenyl 3,4-dibromomaleimide, wherein the N-phenyl groups is substituted or unsubstituted.

Preferably in the compound of formula (IIa) of embodiment (5) either $R_{3a}$ represents a group of formula $R_3$ or a group of formula $F_2$ or -L($F_2$)$_m$(Z)$_{n-m}$ and $R_{3a}'$ independently represents a group of formula $R_3'$ or a group of formula $F_2$ or -L($F_2$)$_m$(Z)$_{n-m}$ or $R_{3a}$ and $R_{3a}'$ together form a group of formula —N($R_{33a'}$), wherein $R_{33a'}$ represents a group of formula $R_{33'}$ or a group of formula $F_2$ or -L($F_2$)$_m$(Z)$_{n-m}$.

Embodiment (6) of the present invention is directed to a compound of formula (IIb), provided that that $R_3$ and $R_3'$ do not together form a group of formula —N($R_{33'}$). For the avoidance of doubt, therefore, in this compound, $R_3$ and $R_3'$ are the same or different and each represents a hydrogen atom or a group of formula E, Nu, -L(Z)$_n$ or IG or $R_3$ and $R_3'$ together form a group of formula —O— or —N($R_{33'}$)—N($R_{33'}$)—, wherein each $R_{33'}$ is the same or different and represents a hydrogen atom or a group of formula Y, Nu, -L(Z)$_n$ or IG. Preferably $R_3$ and $R_3'$ are the same or different and each represents a hydrogen atom or a group of formula E, Nu, -L(Z)$_n$ or IG.

The compound of embodiment (6) thus constitutes an intermediate obtained by carrying out step (i) of the process of embodiment (2) of the present invention, and specifically it is an intermediate which carries the first functional moiety attached to the reactive cross-linking reagent of the present invention. This intermediate can then readily be converted into a conjugate molecule further comprising the second functional moiety by carrying out step (ii) of the process of embodiment (2) of the present invention.

Embodiment (7) of the present invention relates to a compound of formula (III), which comprises at least one group of formula $F_2$ and in which $R_{2a}$ is not a hydrogen atom. Clearly, therefore, this compound constitutes a conjugate obtainable according to the use and processes of the present invention, which comprises both the first functional moiety and the second functional moiety cross-linked via the cross-linking moiety of the present invention. One experiment described in Hong et al. (J. Am. Chem. Soc., 2009, 131 (29), pp 9986-9994) uses a substituted 7-oxanorbornadiene moiety as a cross-linker and generates a conjugate containing a maleimide cross-linker. However, this methodology necessarily generates a hydrogen atom at the substituent position corresponding to the $R_{2a}$ substituent. In contrast, it will be immediately clear to those of skill in the art that the methodology of the present invention can readily be applied to obtain an $R_{2a}$ substituent other than hydrogen, simply by selecting a group other than a hydrogen atom to be attached to the moiety of formula (I) when carrying out a suitable process to synthesise the conjugate. The compound of formula (III) according to embodiment (7) can thus be used, for example, to effect further functionalisations (where $R_{2a}$ is an electrophilic leaving group, a nucleophilic group or a linker group carrying a reactive group). Alternatively, the second functional moiety $F_2$ may itself be located at this substituent position (either being directly attached to the 3-position or being attached thereto via a linker group). Still further, the group of formula $R_{2a}$ may constitute an inert group of formula IG, for example a bulky, chemically unreactive substituent which discourages further reactions from occurring to the conjugate molecule.

Preferably in embodiment (7) the compound of formula (III) is not a compound of formula (N):

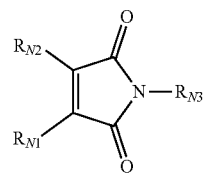

(N)

wherein
$R_{N1}$ and $R_{N2}$ are independently selected from hydrogen, amino, hydroxy, cyano, nitro, carboxylate, carboxamide, optionally substituted alkyl, optionally substituted alkenyl, optionally substituted alkynyl, optionally substituted carbocyclic aryl, optionally substituted heteroaryl, optionally substituted alkoxy, optionally substituted mercaptoalkyl, optionally substituted mono- or di-alkyl amino, optionally substituted cycloalkyl, optionally substituted heteroalicyclic, or optionally substituted aminoalkyl;
$R_{N3}$ is optionally substituted alkyl, optionally substituted alkenyl, optionally substituted alkynyl, optionally substituted carbocyclic aryl, optionally substituted heteroaryl, optionally substituted cycloalkyl, or optionally substituted heteroalicyclic group; and pharmaceutically acceptable salts thereof.

Embodiment (8) of the present invention is directed to a compound of formula (IIIa). In particular, this compound comprises a first functional moiety having at least a first and a second thiol group which are attached to the cross-linker reagent. The compound optionally further comprises at least one additional functional moiety. Preferably, the compound of formula (IIIa) comprises at least one functional moiety of formula $F_2$. Preferably, the group of formula $R_1$ is a peptide or protein comprising at least two cysteine residues, for example two cysteine residues which in the unbound peptide or protein typically form an internal disulfide bridge in the peptide or protein.

Embodiment (9) of the present invention relates to a compound of formula (IVa) or (IVb). It will be appreciated that these compounds constitute a conjugate molecule since they comprise both a first functional moiety and a second functional moiety and furthermore that they comprise a single, rather than a double, carbon-carbon bond between the 2-position and the 3-position. However, unlike conjugates prepared using conventional maleimide reagents, the compounds of formula (IVa) and (IVb) carry a total of at least two functional moieties at the 2- and 3-positions.

The compounds of formula (IVa) and (IVb) can be prepared using straightforward methods. In one such method, the conjugate molecule is prepared by carrying out a process of embodiment (2) of the present invention, in which the step (ii) involves an electrophilic addition reaction of $F_2$ across the carbon-carbon double bond between the 2-position and the 3-position of the formula (II). In another method, a conjugate is firstly prepared which still contains the carbon-carbon double bond between the 2-position and the 3-position and then an electrophilic addition reaction is carried out to saturate the double bond. This electrophilic addition reaction may involve the addition of a further functional moiety (for example, a thiol-containing further functional moiety). Alternatively, it may involve any other reagent routinely used to carry out electrophilic addition reactions at unsaturated carbon-carbon centres. For example, the reagent may be a hydrogen halide, a dihalogen, sulfuric acid, water, an alcohol, $H_2S$, a mercaptan or a carboxylic acid.

Embodiment (10) of the present invention relates to a process for producing a compound of formula (IVa) or (IVb). It will be appreciated that the position at which the group $R_4$ from the compound of formula $R_4$—H adds to the compound of formula (III) will depend on the precise structure of the compound of formula (III), the nature of the reagent $R_4$—H and the reaction conditions under which the reaction is carried out. Usually, the group of formula $R_4$ will add to the carbon atom which is capable of forming the most stable cationic intermediate upon addition of a proton to the compound of formula (III) (i.e., in accordance with Markovnikov's rule). A person skilled in the art would appreciate that if a specific location is desired for addition of the group of formula $R_4$, routine selection of the reaction conditions and the identity of the other groups on the compound of formula (III) may be capable of achieving such regioselectivity.

As will be clear to those of skill in the art, the methodology of the present invention is broadly applicable to known processes and methods which involve conjugation of functional moieties. Typically, conventional processes and methods of this type can straightforwardly be modified by replacing a conventionally known thiol-reactive group on a cross-linking molecule which links together two functional molecules (such as a maleimide group) by the moiety of formula (I) of the present invention.

Examples of routine processes include processes for detecting a substance, particularly a substance of biological interest such as an antigen or a DNA, processes for purifying a thiol compound containing a functional moiety and assay processes for identifying whether a substance interacts with such a compound. Accordingly, the present invention also provides the following embodiments (11), (12) and (13), which are directed to detection, purification and assay processes carried out in accordance with the methodology of the present invention.

Embodiment (11) relates to a process for detecting whether a substance is present in a sample. Typically, the substance is a substance of biological interest, for example an antigen, an antibody, a DNA or an RNA. A compound of the present invention is incubated with the sample. This compound is a conjugate which comprises at least two functional moieties: firstly, a functional moiety that is capable of generating a detectable signal and secondly a functional moiety that is capable of interacting with the substance under test. The functional moiety that is capable of generating a detectable signal is most preferably an enzyme, but can also be, for example, a detectable moiety or an affinity tag. Clearly, the nature of the functional moiety that is capable of interacting with the substance under test depends on the nature of the substance itself. For example, where the substance is an antigen, this functional moiety is typically an antibody. Where the substance is a DNA or an RNA, this functional moiety is typically a complementary strand of DNA or RNA, where "complementary" means that the functional moiety is capable of interacting with the substance (i.e., hybridising to it).

Preferably, the step of incubating is followed by a step of removing any amount of conjugate that has not interacted with (i.e., bound to) the substance under test, for example a step of washing. This can be achieved, for example, by employing an assay in which the substance is attached to a solid substrate (for example, via an interaction between the substance and a further functional moiety which is (a) capable of interacting with the substance and (b) attached to the substrate). In that case, non-interacting conjugate can readily be removed by washing while retaining conjugate that is bound to the substance under test.

The process of embodiment (11) also comprises a step of monitoring for a signal under conditions allowing for generation of a detectable signal from said functional moiety that is capable of generating a detectable signal. For example, where this functional moiety is an enzyme, this step comprises adding a substrate for the enzyme which generates a detectable signal when it is turned over by the enzyme (such as generating a coloured or fluorescent product). Preferred enzymes include horseradish peroxidase, alkaline phosphatase, β-galactrosidase and glucose oxidase.

Preferably the process of embodiment (11) constitutes an ELISA ("enzyme-linked immunosorbent assay") process, a LAB ("labelled avidin-biotin") assay process or a BRAB ("bridged avidin-biotin") assay process or an ABC ("avidin-biotin complex") assay process. All of these assay processes are routine immunoassay processes and would be familiar to those of skill in the art. Most preferably, the process of embodiment (11) constitutes an ELISA process.

Embodiment (12) relates to a process for purifying a compound of formula $R_1$—H from a sample. The process comprises incubating the sample with a compound comprising (a) a moiety of formula (I) and (b) at least one affinity tag linked thereto, to effect a process according to embodiment (3) and thereby obtain a conjugate comprising the group $R_1$ and an affinity tag. The conjugate is then incubated with a compound comprising at least one affinity tag partner under conditions allowing for purification of said conjugate from said sample. A particularly suitable affinity tag is biotin and a particularly suitable affinity tag partner is avidin or streptavidin.

Embodiment (12) is directed to a process for identifying whether a substance interacts with a functional moiety of formula $R_1$. The process involves the following steps:

producing a conjugate comprising (a) said functional moiety of formula $R_1$ and (b) a detectable moiety which is capable of producing a signal which can be modified by said substance, by carrying out a process of embodiment (2) or (3);

incubating the conjugate with the substance;

obtaining a signal from the detectable moiety; and comparing the signal with a control signal obtainable when the conjugate has not been contacted with the substance, thus determining whether the substance interacts with the conjugate.

Förster resonance energy transfer, or "FRET", assays are an exemplary embodiment of the process of embodiment (12). In a FRET assay, the detectable moiety attached to the functional moiety of formula $R_1$ is a donor chromophore and the substance is labelled with an acceptor chromophore. Donor chromophore/acceptor chromophore pairs are well known in the art. One example is the cyan fluorescent protein (CFP)/yellow fluorescent protein (YFP) pair. FRET assays can be used, for example, to study protein-protein interactions, protein-DNA interactions and protein conformational changes.

Conjugates of the present invention, specifically those of embodiments (7), (8) and (9) are also suitable for use in methods of medical treatment or diagnosis. The present invention therefore provides, in an embodiment (14), use of such a compound in a method of treatment of the human or animal body by surgery or therapy or a diagnostic method practised on the human or animal body. Embodiment (14) also relates to a method of treatment of the human or animal body or a diagnostic method practised on the human or animal body which comprises administering to the human or animal body such a compound.

As those skilled in the art would immediately recognise, conjugates suitable for use in the embodiment (14) are typically those which comprise at least one biologically active moiety. In one preferred embodiment, the first functional moiety is a biologically active moiety and the second functional moiety is a polymeric moiety (for example, a moiety capable of enhancing bioavailability and/or stability in vivo, such as a polyethylene glycol moiety) or an antibody (for example, in order to form an immunotoxin conjugate for use in targeting specific antigens, such as in treatment of cancers). In another preferred embodiment, the conjugate comprises a radioactive moiety and a biologically active moiety, for use in a PET (positron emission tomography) diagnostic method.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will be determined by clinical trial, but an exemplary dosage would be 0.1-1000 mg per day.

The medical compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricant, for example magnesium stearate, talc, polyethylene glycol or silica; disintegrants, for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the medical compounds may be made up into a cream, lotion or ointment. Cream or ointment formulations which may be used for the drug are conventional formulations well known in the art, for example as described in standard textbooks of pharmaceutics such as the British Pharmacopoeia.

For topical application by inhalation, the medical compounds may be formulated for aerosol delivery for example, by pressure-driven jet atomizers or ultrasonic atomizers, or preferably by propellant-driven metered aerosols or propellant-free administration of micronized powders, for example, inhalation capsules or other "dry powder" delivery systems. Excipients, such as, for example, propellants (e.g. Frigen in the case of metered aerosols), surface-active substances, emulsifiers, stabilizers, preservatives, flavourings, and fillers (e.g. lactose in the case of powder inhalers) may be present in such inhaled formulations. For the purposes of inhalation, a large number of apparata are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described in European Patent Application EP 0 505 321).

For topical application to the eye, the medical compounds may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

The medical compounds of the invention may be used in conjunction with a number of known pharmaceutically active substances.

The present invention further provides a compound containing a moiety of formula (VI) and a functional moiety linked thereto

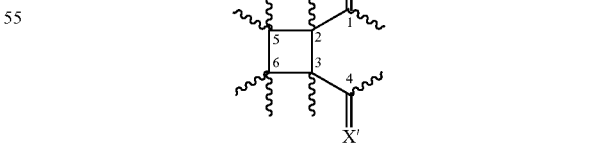

(VI)

wherein:
X and X' are the same or different and each represents oxygen, sulfur or a group of formula =NQ, in which Q is hydrogen, hydroxyl, $C_{1-6}$ alkyl or phenyl; and
said functional moiety is selected from a detectable moiety, an enzymatically active moiety, an affinity tag, a hapten, an immunogenic carrier, an antibody or antibody fragment, an antigen, a ligand, a biologically active moiety, a liposome, a polymeric moiety, an amino acid, a peptide, a protein, a cell, a carbohydrate, a DNA and an RNA.

Typically said functional moiety is linked to the 5-position or 6-position of the moiety of formula (VI). Thus, the compound can be produced by reacting a functional moiety containing an alkene moiety with the carbon-carbon double bond between the 2- and 3-positions of a compound containing a moiety of formula (I) or (II), or a compound of formula (Ia), (Ib), (IIa), (IIb), (III) or (IIIa), in a photocatalytic [2+2]cycloaddition reaction.

Preferably the moiety of formula (VI) comprises at least one, for example one, further functional moiety which is itself independently selected from a detectable moiety, an enzymatically active moiety, an affinity tag, a hapten, an immunogenic carrier, an antibody or antibody fragment, an antigen, a ligand, a biologically active moiety, a liposome, a polymeric moiety, an amino acid, a peptide, a protein, a cell, a carbohydrate, a DNA and an RNA. In this embodiment, preferably one such further functional moiety carries a thiol moiety and is linked to the 2-position of the moiety of formula (VI) via the sulfur atom of said thiol moiety. Thus, this compound can be produced from a compound containing a moiety of formula (I) by:

reacting the compound containing a moiety of formula (I) with said further functional moiety carrying a thiol moiety, thus creating an intermediate product which is a compound containing a moiety of formula (II); and reacting this intermediate compound with a functional moiety containing an alkene moiety to effect a photocatalytic [2+2] cycloaddition reaction between said alkene moiety and the carbon-carbon double bond between the 2- and 3-positions of the intermediate product.

Preferably, the compound containing a moiety of formula (VI) and a functional moiety linked thereto is a compound of formula (VIa)

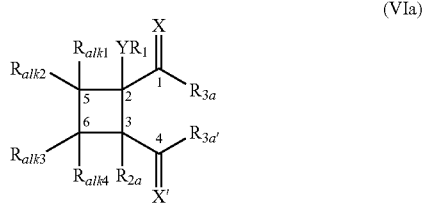

(VIa)

wherein:
X and X' are the same or different and each represents oxygen, sulfur or a group of formula =NQ, in which Q is hydrogen, hydroxyl, $C_{1-6}$ alkyl or phenyl;
$YR_1$ is a group of formula Y or $R_1$;
Y is an electrophilic leaving group;
$R_1$ is a group of formula $-F_1$ or $-S-L-F_1$, wherein $R_1$ carries a thiol moiety and is linked to the 2-position of the moiety of formula (VIa) via the sulfur atom of said thiol moiety;
$R_{2a}$, $R_{3a}$ and $R_{3a}'$ are each as defined in relation to the compound of formula (IIa);
Each of $R_{alk1}$, $R_{alk2}$, $R_{alk3}$ and $R_{alk4}$ is the same or different and is a group of formula $R_{2a}$, with the proviso that at least one of $R_{alk1}$, $R_{alk2}$, $R_{alk3}$ and $R_{alk4}$ contains a group of formula $F_2$; and $F_1$ and any group of formula $F_2$ are the same or different and are each selected from a detectable moiety, an enzymatically active moiety, an affinity tag, a hapten, an immunogenic carrier, an antibody or antibody fragment, an antigen, a ligand, a biologically active moiety, a liposome, a polymeric moiety, an amino acid, a peptide, a protein, a cell, a carbohydrate, a DNA and an RNA.

Preferably $YR_1$ is a group of formula $R_1$, with $R_1$ preferably being a group of formula $-F_1$. Preferably the compound of formula (VIa) comprises one group of formula $F_2$.

EXAMPLES

The following Examples illustrate the scientific principles underlying the present invention. Many of the Examples are Reference Examples since they do not involve linkage of two functional moieties. However, linkage of a functional moiety to linking groups relevant to the invention, cleavage of the functional moieties therefrom, and linkage of a functional moiety, via linking groups relevant to the invention, to numerous other secondary moieties (including other functional moieties) has been exhaustively demonstrated. A large degree of structural variation is shown to be readily tolerated, evidencing the broad applicability of the present invention.

A) Preliminary Examples $^1$H and $^{13}$C NMR spectra were recorded at room temperature on a Bruker Avance 500 instrument operating at a frequency of 500 MHz for $^1$H and 125 MHz for $^{13}$C. $^1$H NMR spectra were referenced to the $CDCl_3$ (7.26 ppm) signal. $^{13}$C NMR spectra were referenced to the $CDCl_3$ (77.67 ppm) signal.

Infra-red spectra were run on a PerkinElmer Spectrum 100 FT-IR spectrometer operating in ATR mode with frequencies given in reciprocal centimetres ($cm^{-1}$). Mass spectra and high resolution mass data were recorded on a VG70-SE mass spectrometer (EI mode and CI mode).

Melting points (m.p.) were taken on a Gallenkamp heating block and are uncorrected. Optical rotation measurements were carried out using a PerkinElmer 343 polarimeter with a cell length of 10 cm.

Abbreviations

Boc Tert-butyloxycarbonyl group.
Cys Cysteine
Mal Maleimide
DMF Dimethylformamide
TCEP (tris(2-carboxyethyl)phosphine)
LC-ESI-MS Liquid chromatography electron spray ionisation mass spectroscopy
Pn GrB2-SH2 domain L111C (used as a model protein)
Gc Glucose Reference Example 1: Preparation of Bromomaleimide (Compound 1)

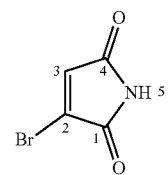

To maleimide (2.00 g, 0.02 mol) in chloroform (15 mL) was added bromine (1.16 mL, 0.02 mol) in chloroform (15 mL) dropwise. The reaction mixture was refluxed for 2 hours and left to cool to room temperature over 1 hour. Solid yellow precipitate was filtered off and washed with cold chloroform (2×50 mL) to afford white crystals of crude 2,3-dibromosuccinimide (4.09 g, 0.016 mol). The crude succinimide was dissolved in tetrahydrofuran (50 mL) and triethylamine (2.4 mL, 0.017 mol) in tetrahydrofuran (10 mL) was added over 5 minutes at 0° C. The reaction mixture was allowed to warm to room temperature and stirred for 48 hours. The solid was filtered off and washed with tetrahydrofuran (50 mL) to afford a pale yellow powder (2.14 g, 0.012 mol) in 59% yield.

$^1$H NMR (500 MHz, CDCl$_3$): δ=7.67 (br s, 1H, NH), 6.89 (s, 1H, C=CH); $^{13}$C NMR (125 MHz, CDCl$_3$): δ=173.8 (C=O), 170.5 (C=O), 136.9 (—(Br)C=C—), 135.4 (—C=CH—); IR (solid, cm$^{-1}$): 3235 (s), 1709 (s); MS (CI+) m/z, (%): 178 ($^{81}$M+, 32), 176 ($^{79}$M+, 32), 125 (25), 86 (100); Mass calculated for C$_4$H$_3$O$_2$N$^{79}$Br: 175.93472. Found: 175.93493; m.p. 148-151° C.

Reference Example 2: Preparation of N-methylbromomaleimide (Compound 2)

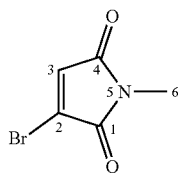

To N-methyl maleimide (0.5 g, 4.5 mmol) in methanol (22.5 mL) was added bromine (0.52 mL, 10 mmol) dropwise. The reaction mixture was stirred at room temperature for 24 hours. Solvent was removed in vacuo and the reaction mass was dissolved in tetrahydrofuran (20 mL) and triethylamine (0.8 mL, 5.85 mmol) added, then stirred for 24 hours at room temperature. The material was purified by flash chromatography on silica gel (petroleum ether:ethyl acetate, 7:3) to afford a pale white powder (0.761 g, 4.0 mmol) in 89% yield.

$^1$H NMR (500 MHz, CDCl$_3$): δ=6.90 (s, 1H, C=CH), 3.09 (s, 3H, N—CH$_3$); $^{13}$C NMR (125 MHz, CDCl$_3$): δ=168.6 (C=O), 165.4 (C=O), 131.9 (—C=CH—), 131.4 ((Br)C=C—), 24.7 (—N—CH$_3$); IR (solid, cm$^{-1}$): 3106 (s), 1708 (s); MS (CI) m/z, (%): 192 ($^{81}$M+, 99), 190 ($^{79}$M+, 100); Mass calculated for C$_5$H$_5$O$_2$N$^{79}$Br: 189.95037. Found: 189.95052; m.p: 77-79° C.

Reference Example 3: Preparation of N-Boc-Cys(Mal)-OMe (Compound 4)

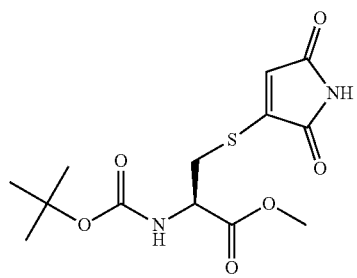 [SMILES: COC(=O)[C@H](CSC1=CC(=O)NC1=O)NC(=O)OC(C)(C)C]

To a stirring solution of N-Boc-Cys-OMe (compound 3) (36 mg, 0.153 mmol) and sodium acetate (13 mg, 0.153 mmol) in methanol (3 mL) was added bromomaleimide (30 mg, 0.169 mmol) in methanol (3 mL). After 1 minute solvent was removed in vacuo. The material was purified by flash chromatography on silica gel (petroleum ether:ethyl acetate, gradient elution from 9:1 to 7:3) to afford a pale yellow powder (51 mg, 0.153 mmol) in 100% yield.

$^1$H NMR (500 MHz, CDCl$_3$): δ=7.63 (s, 1H, NH), 6.27 (s, 1H, C=CH), 5.40 (d, 1H, J=6.8, NH), 4.67 (ddd, 1H, J=6.8, 5.4 and 5.1, —HN—CH—C(O)—), 3.80 (s, 3H, O—CH$_3$), 3.48 (dd, 1H, J=13.8 and 5.1, —S—CHH—), 3.62 (dd, 1H, J=14.1 and 5.4, —S—CHH—) 1.45 (s, 9H, 3×CH$_3$); $^{13}$C NMR (125 MHz, CDCl$_3$): δ=170.2 (C=O), 168.9 (C=O), 167.6 (C=O), 155.2 (C=O), 155.9 (—C=CH—), 119.7 (—C=CH—), 81.1 ((CH$_3$)CO—), 53.3 (O—CH$_3$), 52.7 (CH), 34.0 (CH$_2$), 28.3 (3×CH$_3$); IR (solid, cm$^{-1}$) 3236 (w), 1715 (s); MS (CI+) m/z, (%): 331 (M+H, 5), 275 (20), 231 (100); Mass calculated for [C$_{13}$H$_{18}$O$_6$N$_2$S]+H: 331.09638. Found: 331.09684; $^{20}$α$_D$: −41.9° (c=1.0, Methanol); m.p. 145-147° C.

Reference Example 4: Preparation of N-Boc-Cys(N-Me-Mal)-OMe (Compound 5)

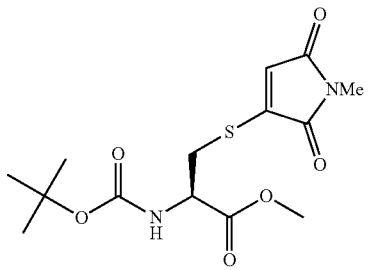 [SMILES: COC(=O)[C@H](CSC1=CC(=O)N(C)C1=O)NC(=O)OC(C)(C)C]

To a stirring solution of N-Boc-Cys-OMe (32 mg, 0.136 mmol) in methanol (4 mL) was added sodium acetate (82 mg, 0.408 mmol). To this was added N-methyl bromomaleimide (25.8 mg, 0.136 mmol) in methanol (4 mL) over 10 minutes. The reaction turned light yellow. The solvent was removed in vacuo and the residue was purified by flash chromatography on silica gel (petroleum ether:ethyl acetate, gradient elution from 9:1 to 7:3) to afford a pale white powder (39.3 mg, 0.114 mmol) in 84% yield.

$^1$H NMR (500 MHz, CDCl$_3$): δ=6.26 (s, 1H, C=CH), 5.36 (d, 1H, J=6.3, NH), 4.66 (m, 1H, —HN—CH—), 3.79 (s, 3H, O—CH$_3$), 3.46 (dd, 1H, J=5.2 and 5.0, —S—CHH—), 3.35 (dd, 1H, J=13.7 and 5.1, —S—CHH—), 3.00 (s, 3H, —N—CH$_3$), 1.44 (s, 9H, 3×CH$_3$); $^{13}$C NMR (125 MHz, CDCl$_3$): δ=170.2 (C=O), 169.5 (C=O), 167.9 (C=O), 155.0 (C=O), 149.9 (—C=CH—), 118.7 (—C=CH—), 80.9 ((CH$_3$)$_3$CO—), 53.1 (O—CH$_3$), 52.7 (CH), 33.8 (CH$_2$), 28.3 (3×CH$_3$), 24.1 (—N—CH$_3$); IR (solid, cm$^{-1}$) 3367.8, 2977.1, 1694.7; MS (ES+) m/z, (%): 367(46), 311 (M, 100); Mass calculated for C$_{14}$H$_{20}$N$_2$O$_6$NaS: 367.0940. Found: 367.0931; $^{20}$α$_D$: −18.55° (c=1.0, Methanol); m.p. 101-103° C.

Reference Example 5: Preparation of N-Boc-Cys(Succ)-OMe (Compound 6)

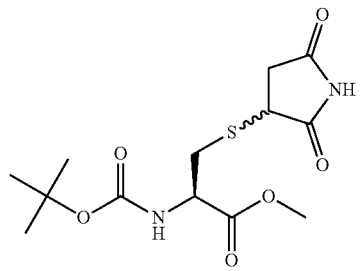 [SMILES: COC(=O)[C@H](CSC1CC(=O)NC1=O)NC(=O)OC(C)(C)C]

To a stirring solution of N-Boc-Cys-OMe (36 mg, 0.153 mmol) in methanol (3 mL) was added maleimide (17 mg, 0.169 mmol) in methanol (3 mL). After 1 minute solvent was removed in vacuo. The material was purified by flash chromatography on silica gel (dichloromethane:methanol, gradient elution from 99:1 to 7:3) to afford a colourless oil (51 mg, 0.153 mmol) in 100% yield that was a 1:1 mixture of diastereomers.

$^1$H NMR (500 MHz, CDCl$_3$): δ=9.00 (s, 1H, NH), 8.95 (s, 1H, NH), 5.59 (1H, d, J=7.6, NH), 5.41 (d, 1H, J=7.6, NH), 4.65-4.56 (m, 2H, 2×—HN—HC—C(O)—) C=CHH), 3.93 (dd, 1H, J=9.3 and 3.9, CH), 3.86 (dd, 1H, J=9.2 and 4.2, CH), 3.76 (s, 3H, OCH$_3$), 3.76 (s, 3H, OCH$_3$), 3.51 (dd, 1H, J=13.8 and 4.6, —CHH—), 3.36 (dd, 1H, J=14.1 and 6.0, —CHH—), 3.19-3.11 (m, 3H, 3×—CHH—), 2.96 (dd, 1H, J=13.1 and 7.1, —CHH—), 2.54-2.02 (m, 2H, —CHH—) 1.43 (s, 18H, 9×CH$_3$); $^{13}$C NMR (125 MHz, CDCl$_3$): δ=177.2 (C=O), 177.1 (C=O), 175.1 (C=O), 175.0 (C=O), 172.0 (C=O), 171.5 (C=O), 155.5 (C=O), 155.3 (C=O), 80.6 (2×—OCCH$_3$), 53.6 (CH), 52.91 (OCH$_3$), 52.85 (OCH$_3$), 50.8 (CH), 40.6 (CH), 40.0 (CH), 37.3 (CH$_2$), 37.0 (CH$_2$), 34.6 (CH$_2$), 34.1 (CH$_2$), 28.3 (6×CH$_3$); IR (oil, cm$^{-1}$) 3233 (w), 2980 (w), 1783 (w), 1709 (s); MS (CI+) m/z, (%): 333 (M+H, 15), 277 (50), 233 (100); Mass calculated for C$_{13}$H$_{20}$O$_6$N$_2$S: 332.10420. Found: 332.10475;

Reference Example 6: Demonstration that Maleimide does not Displace Thiol from N-Boc-Cys(Mal)-OMe and that Bromomaleimide does not Displace Thiol from N-Boc-Cys(Succ)-OMe To a stirring solution of N-Boc-Cys-OMe (36 mg, 0.153 mmol) and sodium acetate (13 mg, 0.153 mmol) in methanol (3 m L) was added bromomaleimide (30 mg, 0.169 mmol) in methanol (3 mL). After 10 minutes maleimide (17 mg, 0.169 mmol) was added. Solvent was removed in vacuo and $^1$H NMR analysis showed only compound 4 and unreacted maleimide.

To a stirring solution of N-Boc-Cys-OMe (36 mg, 0.153 mmol) and sodium acetate (13 mg, 0.153 mmol) in methanol (3 m L) was added maleimide (17 mg, 0.169 mmol) in methanol (3 mL). After 10 minutes bromomaleimide (30 mg, 0.169 mmol) was added. Solvent was removed in vacuo and $^1$H NMR analysis showed only compound 6 and unreacted bromomaleimide.

Reference Example 7: Competition Reaction Between Bromomaleimide and Maleimide for N-Boc-Cys-OMe To a stirring solution of N-Boc-Cys-OMe (36 mg, 0.153 mmol) and sodium acetate (13 mg, 0.153 mmol) in methanol (3 m L) was added a mixture of bromomaleimide (30 mg, 0.169 mmol) and maleimide (17 mg, 0.169 mg) in methanol (3 mL). After 1 minute solvent was removed in vacuo. The material was purified by flash chromatography on silica gel (petroleum ether:ethyl acetate, gradient elution from 9:1 to 7:3) to afford a pale yellow powder 4 (36 mg, 0.108 mmol) in 70% yield and a colourless oil 6 (15 mg, 0.045 mmol) in 30% yield.

Reference Example 6 demonstrated that, once attached to a succinimide or maleimide moiety, the cysteine moiety is not capable of detaching in the presence of these reagents. Reference Example 7 therefore demonstrates that the cysteine reagent reacts more rapidly with bromomaleimide than with maleimide (i.e., the reaction kinetics are more favourable for formation of compound 4).

Reference Example 8: Demonstration of Selectivity of the Bromomaleimide Reagent for N-Boc-Cys-OMe Compared to Propylamine To a stirring solution of N-Boc-Cys-OMe (36 mg, 0.153 mmol) and propylamine (10 µL, 0.153 mmol) in methanol (3 m L) was added bromomaleimide (30 mg, 0.169 mmol) in methanol (3 mL). After 1 minute solvent was removed in vacuo. The material was purified by flash chromatography on silica gel (petroleum ether:ethyl acetate, gradient elution from 9:1 to 7:3) to afford a pale yellow powder (51 mg, 0.153 mmol) in 100%. Data matched those obtained above for N-Boc-Cys(Mal)-OMe 4.

Example 1: Cleavage of N-Boc-Cys(Mal)-OMe to Regenerate N-Boc-Cys-OMe

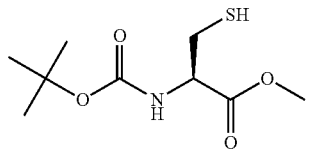

To a stirring solution of 4 (50 mg, 0.151 mmol) in dimethylformamide (2 mL) was added 20 mL of an aqueous buffer (150 mM NaCl, 100 mM NaH$_2$PO$_4$, pH 8.0). Tris(2-carboxyethyl)phosphine (430 mg 1.51 mmol) in 20 mL of an aqueous buffer (150 mM NaCl, 100 mM NaH$_2$PO$_4$, pH 8.0) was added to the solution. After 5 minutes the aqueous solution was extracted with ethyl acetate (3×25 mL), washed with saturated lithium chloride solution (5×25 mL), water (25 mL) and brine (25 mL) and dried over MgSO$_4$. Solvent was removed in vacuo to afford a colourless oil (34.5 mg, 0.148 mmol) in 98% yield. $^1$H and $^{13}$C NMR of this oil showed it to be the commercially available N-Boc-cysteine methyl ester 3.

Example 2: Reaction of 2,3-Dibromomaleimide with Somatostatin

Somatostatin is peptide hormone which is known to exist in a form in which two cysteine residues within the molecule are attached via a disulfide bridge.

1 mg of lyophilised somatostatin (Sigma-Aldrich) was resolubilised in 2 ml of 50 mM NaHPO$_4^-$, pH 6.2, 40% MeCN, 2.5% DMF. 500 µl were transferred to a Eppendorf reaction tube and diluted in the same buffer to a final concentration of 0.25 mg/ml (152.6 µM). 2.0 equivalents of TCEP (100× stock solution in 50 mM NaHPO$_4^-$, pH 6.2, 40% MeCN) were added and the reaction incubated for 1 hour at ambient temperature. After reduction of the disulfide bond 1.4 equivalents of 2,3-dibromomaleimide (Sigma-Aldrich, 100× stock solution in 50 mM NaHPO$_4^-$, pH 6.2, 40% MeCN, 2.5% DMF) were added, the solution gently mixed and incubated for a further 12 h at 4° C.

Maleimide-bridged somatostatin was detected by LC-ESI-MS (ES$^+$/ES$^-$). Controls included untreated peptide and somatostatin treated with 2,3-dibromomaleimide or TCEP only. Complete reduction was detected by the reaction of TCEP-treated peptide with maleimide (Sigma-Aldrich, 100× stock solution in 50 mM NaHPO$_4^-$, pH 6.2, 40% MeCN, 2.5% DMF).

Experimental Data

Untreated somatostatin: [ES+] 1638.04 (m/z 1), 819.82 (m/z 2), 546.95 (m/z 3). Maleimide-bridged somatostatin: [ES+] 1734.14 Da (m/z 1), 867.40 Da (m/z 2), 578.73 (m/z 3).

Reference Example 9: Expression of GrB2-SH2 Domain L111C

The protein GrB2-SH2 domain L111C was used as a model protein. This model protein contains a single cysteine residue.

LC-MS was performed on a Waters Acquity uPLC connected to Waters Acquity Single Quad Detector (SQD). Column: Acquity uPLC BEH C18 1.7 μm 2.1×50 mm. Wavelength: 254 nm. Mobile Phase: 95:5 Water (0.1% Formic Acid): MeCN (0.1% Formic Acid) Gradient over 4 min (to 5:95 Water (0.1% Formic Acid): MeCN (0.1% Formic Acid). Flow Rate: 0.6 mL/min. MS Mode:ES+. Scan Range: m/z=85-2000. Scan time: 0.25 sec. Data obtained in continuum mode. The electrospray source of the MS was operated with a capillary voltage of 3.5 kV and a cone voltage of 50 V.

Nitrogen was used as the nebulizer and desolvation gas at a total flow of 600 L/h. Total mass spectra were reconstructed from the ion series using the MaxEnt 1 algorithm preinstalled on MassLynx software.

The model protein was over-expressed in *E. coli*, and the hexa-His-tagged protein purified using both Ni-affinity chromatography and size-exclusion chromatography via standard techniques. Analysis using LC-MS showed a single protein species of mass 14169 which corresponds to the desired protein.

To a solution of model protein (100 μL, [Protein] 2.0 mg/mL, 100 mM sodium phosphate, 150 mM NaCl, pH 8.0) at 0° C. was added Ellman's reagent (5 μL, 282 mM solution in H$_2$O) at 0° C. The mixture was vortexed for 1 s and maintained at 0° C. for 10 mins, after which the mixture was analysed by LC-MS. Analysis showed that a single reaction had occurred yielding a single product with a mass of 14366 showing that C111 was available for functionalisation.

Reference Example 10: Reaction of GrB2-SH2 Domain L111C with Bromomaleimide

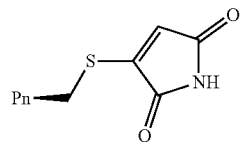

To a solution of model protein (100 μL, [Protein] 2.0 mg/mL, 100 mM sodium phosphate, 150 mM NaCl, pH 8.0) at 0° C. was added bromomaleimide (5 μL, 2.82 mM solution in DMF). The mixture was vortexed for 1 s then maintained at 0° C. for 1 h. Analysis using LC-MS showed a single protein species of mass 14265 which corresponds to the desired protein.

The mixture was treated with Ellman's reagent (5 μL, 282 mM solution in H$_2$O) at 0° C. The mixture was vortexed for 1 s and maintained at 0° C. for 10 mins after which the mixture was analysed by LC-MS. Analysis showed that no reaction with Ellman's reagent was evident, highlighting that bromomaleimide functionalisation had occurred at C111.

Reference Example 11: Reaction of GrB2-SH2 Domain L111C with N-methylbromomaleimide

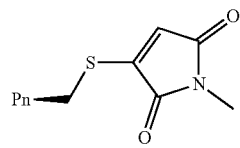

To a solution of model protein (100 μL, [Protein] 2.0 mg/mL, 100 mM sodium phosphate, 150 mM NaCl, pH 8.0) at 0° C. was added N-methylbromomaleimide (5 μL, 2.82 mM solution in DMF). The mixture was vortexed for 1 s then maintained at 0° C. for 1 h. Analysis using LC-MS showed a single protein species of mass 14278 which corresponds to the desired protein.

The mixture was treated with Ellman's reagent (5 μL, 282 mM solution in H$_2$O) at 0° C. The mixture was vortexed for 1 s and maintained at 00° C. for 10 mins after which the mixture was analysed by LC-MS. Analysis showed that no reaction with Ellman's reagent was evident, highlighting that N-methylbromomaleimide functionalisation had occurred at C111.

Example 3: Phosphine-Mediated Reductive Cleavage of GrB2-SH2 Domain L111C/Bromomaleimide Adduct

To a solution of model protein (100 μL, [Protein] 2.0 mg/mL, 100 mM sodium phosphate, 150 mM NaCl, pH 8.0) at 0° C. was added bromomaleimide (5 μL, 2.82 mM solution in DMF). The mixture was vortexed for 1 s then maintained at 0° C. for 1 h. Analysis using LC-MS showed a single protein species of mass 14265 which corresponds to protein/bromomaleimide adduct.

The mixture was treated with TCEP.HCl (5 μL, 282 mM solution in H$_2$O) at 0° C. The mixture was vortexed for 1 s and maintained at 0° C. for 3 h after which the mixture was analysed by LC-MS. Analysis showed that the protein/bromomaleimide adduct had been cleanly cleaved yielding GrB2-SH2 domain L111C (mass=14168) in 85% yield. The remaining material was unreacted protein/bromomaleimide adduct.

Example 4: Phosphine-Mediated Reductive Cleavage of GrB2-SH2 Domain L111C/N-methylbromomaleimide Adduct

To a solution of model protein (100 μL, [Protein] 2.0 mg/mL, 100 mM sodium phosphate, 150 mM NaCl, pH 8.0) at 0° C. was added N-methylbromomaleimide (5 μL, 2.82 mM solution in DMF). The mixture was vortexed for 1 s then maintained at 0° C. for 1 h. Analysis using LC-MS showed a single protein species of mass 14278 which corresponds to protein/N-methylbromomaleimide adduct.

The mixture was treated with TCEP.HCl (5 μL, 282 mM solution in H$_2$O) at 0° C. The mixture was vortexed for 1 s and maintained at 0° C. for 3 h after which the mixture was analysed by LC-MS. Analysis showed that the protein/N-methylbromomaleimide adduct had been cleanly cleaved yielding GrB2-SH2 domain L111C (mass=14168) in 85% yield. The remaining material was unreacted protein/N-methylbromomaleimide adduct.

Example 5: Synthesis of GrB2-SH2 Domain L111C/bromomaleimide/2-Mercaptoethanol Adduct

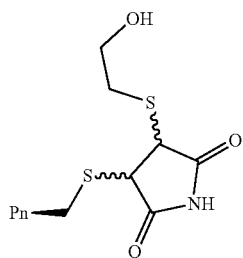

To a solution of model protein (100 μL, [Protein] 2.0 mg/mL, 100 mM sodium phosphate, 150 mM NaCl, pH 8.0) at 0° C. was added bromomaleimide (5 μL, 2.82 mM solution in DMF). The mixture was vortexed for 1 s then maintained at 0° C. for 1 h. Analysis using LC-MS showed a single protein species of mass 14265 which corresponds to protein/bromomaleimide adduct.

The mixture was treated with 2-mercaptoethanol (5 μL, 2.82 mM solution in H$_2$O) at 0° C. The mixture was vortexed for 1 s and maintained at 0° C. for 3 h after which the mixture was analysed by LC-MS. Analysis showed that the protein/bromomaleimide/2-mercaptoethanol adduct had been formed (mass=14339) in 55% yield. The remaining material was GrB2-SH2 domain L111C.

Example 6: Synthesis of GrB2-SH2 Domain L111C/N-Methylbromomaleimide/2-Mercaptoethanol Adduct

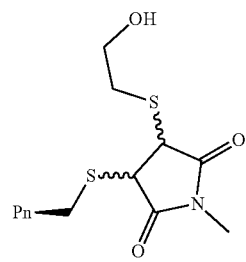

To a solution of model protein (100 μL, [Protein] 2.0 mg/mL, 100 mM sodium phosphate, 150 mM NaCl, pH 8.0) at 0° C. was added N-methylbromomaleimide (5 μL, 2.82 mM solution in DMF). The mixture was vortexed for 1 s then maintained at 0° C. for 1 h. Analysis using LC-MS showed a single protein species of mass 14278 which corresponds to protein/N-methylbromomaleimide adduct.

The mixture was treated with 2-mercaptoethanol (5 μL, 2.82 mM solution in H$_2$O) at 0° C. The mixture was vortexed for 1 s and maintained at 0° C. for 3 h after which the mixture was analysed by LC-MS. Analysis showed that the protein/N-methylbromomaleimide/2-mercaptoethanol adduct had been formed (mass=14356) in 61% yield. The remaining material was GrB2-SH2 domain L111C.

Reference Example 12: Synthesis of GrB2-SH2 Domain L111C/Dibromomaleimide Adduct

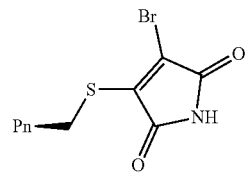

To a solution of model protein (100 μL, [Protein] 2.0 mg/mL, 100 mM sodium phosphate, 150 mM NaCl, pH 8.0) at 0° C. was added dibromomaleimide (5 μL, 2.82 mM solution in DMF). The mixture was vortexed for 1 s then maintained at 0° C. for 4 h. Analysis using LC-MS showed a single protein species of mass 14346 which corresponds to protein/dibromomaleimide adduct.

Example 7: Synthesis of GrB2-SH2 Domain L111C/Dibromomaleimide/Glutathione Adduct

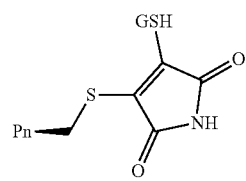

To a solution of model protein (100 μL, [Protein] 2.0 mg/mL, 100 mM sodium phosphate, 150 mM NaCl, pH 8.0) at 0° C. was added dibromomaleimide (5 μL, 2.82 mM solution in DMF). The mixture was vortexed for 1 s then maintained at 0° C. for 4 h. Analysis using LC-MS showed a single protein species of mass 14346 which corresponds to protein/dibromomaleimide adduct.

The mixture was treated with glutathione (5 μL, 2.82 mM solution in H$_2$O) at 0° C. The mixture was vortexed for 1 s and maintained at 0° C. for 2 h after which the mixture was analysed by LC-MS. Analysis showed that the protein/dibromomaleimide/glutathione adduct was the only protein species present (mass=14572).

Example 8: Glutathione-Mediated Cleavage of GrB2-SH2 Domain L111C/Dibromomaleimide/Glutathione Adduct at Physiological Relevant Glutathione Concentration (5 mM)

To a solution of model protein (100 μL, [Protein] 2.0 mg/mL, 100 mM sodium phosphate, 150 mM NaCl, pH 8.0) at 0° C. was added dibromomaleimide (5 μL, 2.82 mM solution in DMF). The mixture was vortexed for 1 s then maintained at 0° C. for 4 h. Analysis using LC-MS showed a single protein species of mass 14346 which corresponds to protein/dibromomaleimide adduct.

The mixture was treated with glutathione (5 μL, 2.82 mM solution in H$_2$O) at 0° C. The mixture was vortexed for 1 s and maintained at 0° C. for 2 h after which the mixture was analysed by LC-MS. Analysis showed that the protein/dibromomaleimide/glutathione adduct was the only protein species present (mass=14572).

The mixture was treated with glutathione (5 μL, 100 mM solution in H$_2$O) at 0° C. The mixture was vortexed for 1 s and maintained at 0° C. for 4 h after which the mixture was analysed by LC-MS. Analysis showed that GrB2-SH2 domain L111C was the only protein species present (mass=14173).

B) Further Examples

General Procedures $^1$H and $^{13}$C NMR spectra were recorded at room temperature on a Bruker Avance 500 instrument operating at a frequency of 500 MHz for $^1$H and 125 MHz for $^{13}$C. $^1$H NMR spectra were referenced to the CDCl$_3$ (7.26 ppm) signal. $^{13}$C NMR spectra were referenced to the CDCl$_3$ (77.67 ppm) signal. Infra-red spectra were run on a Perkin Elmer Spectrum 100 FT-IR spectrometer operating in ATR mode with frequencies given in reciprocal centimeters (cm$^{-1}$). Mass spectra and high resolution mass data for small molecules were recorded on a VG70-SE mass spectrometer (EI mode and CI mode). Melting points were taken on a Gallenkamp heating block and are uncorrected. 3,4-Dibromomaleimide, lyophilized somatostatin, PEG5000, TCEP and benzeneselenol were purchased from Sigma-Aldrich and used without further purification.

Protein and Peptide Mass Spectrometry

LC-MS was performed on protein samples using a Waters Acquity uPLC connected to Waters Acquity Single Quad Detector (SQD). Column: Acquity uPLC BEH C18 1.7 μm 2.1×50 mm. Wavelength: 254 nm. Mobile Phase: 95:5 Water (0.1% Formic Acid): MeCN (0.1% Formic Acid) Gradient over 4 min (to 5:95 Water (0.1% Formic Acid): MeCN (0.1% Formic Acid). Flow Rate: 0.6 mL/min. MS Mode: ES+. Scan Range: m/z=85-2000. Scan time: 0.25 sec. Data obtained in continuum mode. The electrospray source of the MS was operated with a capillary voltage of 3.5 kV and a cone voltage of 50 V. Nitrogen was used as the nebulizer and desolvation gas at a total flow of 600 L/h. Total mass spectra were reconstructed from the ion series using the MaxEnt 1 algorithm pre-installed on MassLynx software. MALDI-TOF analysis was performed on a MALDI micro MX (Micromass). Data was obtained in reflectron positive ion mode with a source voltage of 12 kV and a reflectron voltage of 5 kV at a laser wavelength of 337 nm. Samples were prepared as outlined below and those containing peptide were dialysed for 24 h in deionised H$_2$O. The peptide and its derivates (0.1-0.3 mg/ml) were spotted onto a MALDI plate in 2 μl sinapinic acid (10 mg/ml) after pre-spotting of trifluoroacetic acid (10 mg/ml). ACTH (10 ng/ml) was used for mass calibration.

Reference Example 13: Preparation of Bromomaleimide

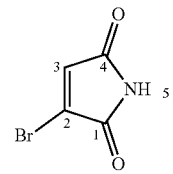

To maleimide (2.00 g, 0.02 mol) in chloroform (15 mL) was added bromine (1.16 mL, 0.02 mol) dropwise in chloroform (15 mL). The reaction mixture was refluxed for 2 hours and left to cool to room temperature over 1 hour. Solid yellow precipitate was filtered off and washed with cold chloroform (2×50 mL) to afford off white crystals of crude 2,3-dibromosuccinimide (4.09 g, 0.016 mol). The crude succinimide was dissolved in tetrahydrofuran (50 mL) and triethylamine (2.4 mL, 0.017 mol) in tetrahydrofuran (10 mL) was added over 5 minutes at 0° C. The reaction mixture was allowed to warm to room temperature and stirred for 48 hours. The solid was filtered off and washed with tetrahydrofuran (50 mL). Purification by flash chromatography (5% ethyl acetate in petroleum ether) afforded the desired compound as a pale yellow powder (2.14 g, 0.012 mol) in 59% yield. $\delta_H$ (500 MHz, CDCl$_3$) 7.67 (br s, 1H, NH), 6.89 (s, 1H, H-3); $\delta_C$ (125 MHz, CDCl$_3$) 173.8 (C=O), 170.5 (C=O), 136.9 (C$_2$), 135.4 (C$_3$); IR (solid, cm$^{-1}$) 3235 (s), 1709 (s); MS (CI+) m/z, (relative intensity): 178 ([$^{81}$M+H], 32), 176 ([$^{79}$M+H], 32), 125 (25), 86 (100); Mass calcd for [C$_4$H$_2$O$_2$N$^{79}$Br]+H: 175.9347 Found 175.9349 (CI+); m.p. 148-151° C.; UV (Acetonitrile) $\varepsilon_{242}$=13800 and $\varepsilon_{276}$=1700 cm$^{-1}$M$^{-1}$d$^3$.

Reference Example 14: Preparation of N-Methylbromomaleimide

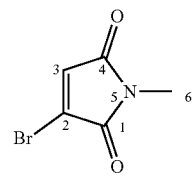

To N-methylmaleimide (0.5 g, 4.5 mmol) in methanol (10 mL) was added bromine (232 µL, 4.5 mmol) dropwise in methanol (5 mL). The reaction mixture was stirred at room temperature for 12 hours. The solvent was removed in vacuo and dissolved in tetrahydrofuran (20 mL). Triethylamine (815 µL, 5.9 mmol) in tetrahydrofuran (5 mL) was added over 5 minutes, whereupon a precipitate formed. The reaction mixture was stirred for 24 hours. The solid was filtered off and washed with tetrahydrofuran (50 mL). Purification by flash chromatography (10% ethyl acetate in petroleum ether) afforded the desired compound as a pale yellow powder (563 mg, 2.96 mmol) in 66% yield. $\delta_H$ (500 MHz, CDCl$_3$) 6.90 (s, 1H, H-3), 3.09 (s, 3H, H$_3$-6); $\delta_C$ (125 MHz, CDCl$_3$) 168.6 (C=O), 165.4 (C=O), 131.9 (C$_3$), 131.4 (C$_2$), 24.7 (C$_6$); IR (solid, cm$^{-1}$) 3106 (s), 1708 (s); MS (CI+) m/z, (relative intensity): 192 ([$^{81}$M+H], 99), 190 ([$^{79}$M+H], 100); Exact mass calcd for [C$_5$H$_4$O$_2$N$^{79}$Br]+H requires 189.9504. Found 189.9505 (CI+); m.p: 77-79° C.; UV (Acetonitrile) $\epsilon_{209}$=17100, $\epsilon_{238}$=13200, 8299=290 cm$^{-1}$M$^{-1}$ d$^3$.

Reference Example 15: Preparation of N-Phenylbromomaleimide

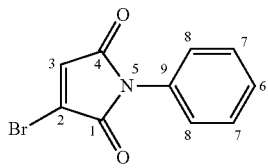 [SMILES: O=C1C=C(Br)C(=O)N1c1ccccc1]

To N-phenylmaleimide (2 g, 11.50 mmol) in chloroform (15 mL) was added bromine (0.65 mL, 12.70 mmol) dropwise in chloroform (5 mL). The reaction mixture was refluxed for 1 hour, and then allowed to cool to room temperature. The precipitate was filtered off and washed with chloroform (50 mL). This solid (2.70 g, 8.10 mmol) was dissolved in tetrahydrofuran (50 mL) and to this was added dropwise dropwise a solution of triethylamine (1.2 mL, 8.9 mmol) in tetrahydrofuran (10 mL) at 0° C. and the mixture was stirred for 2 hours. The mixture was allowed to warm to room temperature and solvent removed in vacuo. The residue was dissolved in ethyl acetate and washed with H$_2$O (50 mL) brine (50 mL) and dried (Na$_2$SO$_4$). Solvent was removed in vacuo to afford the desired compound as a pale yellow solid (1.80 g, 7.14 mmol) in 62% yield. Data matched literature: Sahoo et al., Synthesis, 2003, 346

Reference Example 16: Preparation of N-Phenyldibromomaleimide

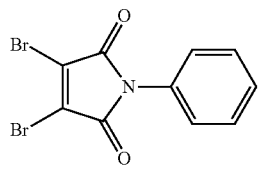 [SMILES: O=C1C(Br)=C(Br)C(=O)N1c1ccccc1]

Aniline (72 µL, 0.788 mmol) was added to a solution of dibromomaleic anhydride (200 mg, 0.788 mmol) in AcOH (10 mL). The mixture was stirred for 3 h at RT and at 130° C. for 90 mins. After cooling, the mixture was concentrated to dryness and traces of AcOH removed by azeotrope with toluene. The tan residue was purified using silica flash chromatography (5% EtOAc/95% petroleum ether) to yield the desired compound as a pale yellow solid (166 mg, 60%). $\delta_H$ (600 MHz, CDCl$_3$) 7.48 (m, 2H, ArH), 7.41 (tt, 1H, J=7.4 and 1.1 Hz, ArH), 7.33 (m, 2H, ArH); $\delta_C$ (150 MHz, CDCl$_3$) 163.0, 131.0, 130.0, 129.5, 128.8, 126.2.

Reference Example 17: Preparation of 3,4-Diiodo-pyrrole-2,5-dione

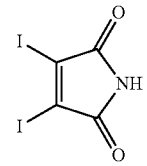

To dibromomaleimide (500.0 mg, 2.0 mmol) in acetic acid (50 ml) was added sodium iodide (886.5 mg, 5.9 mmol). The reaction mixture was heated to 120° C. and refluxed for 2 h. The reaction was allowed to cool down to RT, H$_2$O (50 ml) was added and kept at 4° C. for 15 h. The yellow precipitate was filtered off and air dried to afford the desired compound as an orange crystalline powder (415 mg, 60%). $^1$H NMR (500 MHz, MeOD): no signals; $^{13}$C NMR (125 MHz, MeOD): $\delta$=169.3 (C), 119.5 (C); IR (solid, cm$^{-1}$): 3244 (s), 2944 (m), 2833 (m); MS (EI) m/z, (%): 349 (M, 83), 179 (100); Mass calc. for C$_4$H$_{12}$O$_2$N: 348.80912. Found: 348.81026. m.p. 238-241° C. (Literature: 254-255° C.).

Reference Example 18: Preparation of 3,4-Bis-(2-hydroxy-ethylsulfanyl)-pyrrole-2,5-dione

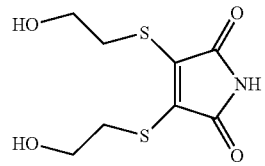 [SMILES: O=C1NC(=O)C(SCCO)=C1SCCO]

To 2-mercaptoethanol (683.8 µl, 9.8 mmol) in buffer (100 ml, 150 mM NaCl, 100 mM sodium phosphate, pH 8.0, 5.0% DMF) was added di-bromomaleimide (1 g, 3.9 mmol) in DMF (2.5 ml, final concentration DMF 7.5%). The reaction was stirred for 30 min at RT and lithium chloride (20 g) was added. The aqueous reaction mixture was extracted with ethyl acetate (7×150 ml). The organic layers were combined, the solvent removed in vacuo and the residual material was purified by flash chromatography on silica gel (petroleum ether:ethyl acetate, gradient elution from 1:1 to 1:9). Fractions containing the product were collected and the solvent were removed in vacuo. The still impure product was purified by flash chromatography on silica gel (methanol:dichloromethane, gradient elution from 0.5-10.0% methanol) to afford the desired compound as a yellow solid (518 mg, 53%). $\lambda_{max}$ (50 mM sodium phosphate, pH 6.2, 40% MeCN, 2.5% DMF)/318 nm ($\epsilon$/dm$^3$ mol$^{-1}$ cm$^{-1}$1855); $^1$H NMR (500 MHz, MeOD): $\delta$=3.74 (t, 4H, J=6.4, 2×HO—CH$_2$), 3.41 (t, 4H, J=6.3, 2×S—CH$_2$) $^{13}$C NMR (125 MHz, MeOD): $\delta$=168.5 (C), 137.2 (C), 62.3 (CH$_2$), 34.4 (CH$_2$); IR (solid, cm$^{-1}$): 3344 (s), 2500 (m), 2078 (w); MS (EI) m/z, (%): 250 (M, 43), 232 (100), 161 (37); Mass calc. for $C_5H_{11}O_4NS_2$: 250.02077. Found: 250.02126; m.p. 46-50° C.

Reference Example 19: Preparation of 3,4-Bis-phenylsulfanyl-pyrrole-2,5-dione

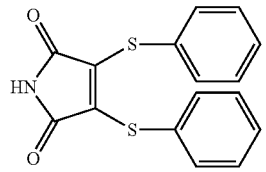

To dibromomaleimide (80.0 mg, 0.3 mmol) and sodium hydrogencarbonate (130.2 mg, 1.6 mmol) in methanol (6 ml) was slowly added benzenethiol (66.6 µl, 0.7 mmol) in methanol (1 ml). The reaction was stirred for 15 min at RT. The solvent was removed in vacuo and the residual material was purified by flash chromatography on silica gel (petroleum ether:ethyl acetate, gradient elution from 9:1 to 7:3) to afford the desired product as bright yellow crystals (73 mg, 75%). $\lambda_{max}$ (50 mM sodium phosphate, pH 6.2, 40% MeCN, 2.5% DMF)/412 nm ($\epsilon/dm^3$ $mol^{-1}$ $cm^{-1}$ 2245); $^1H$ NMR (500 MHz, MeOD): δ=7.27-7.22 (m, 6H, Ar—H), 7.16-7.14 (m, 4H, Ar—H); $^{13}C$ NMR (125 MHz, MeOD): δ=169.3 (C), 137.6 (C), 135.4 (C), 132.4 (CH), 130.1 (CH), 129.1 (CH); IR (solid, $cm^{-1}$): 3285 (m), 3059 (w), 2924 (w), 1774 (m), 1715 (s); MS (CI) m/z, (%): 314 (M+H, 100), 206 (13), 111 (12); Mass calc. for $C_{16}H_{11}O_2NS_2[+H]$: 314.0231. Found: 314.0309; m.p. 102-104° C. (Literature: 123-126° C.).

Reference Example 20: Preparation of 3,4-Bis-(pyridine-2-ylsulfanyl)-pyrrole-2,5-dione

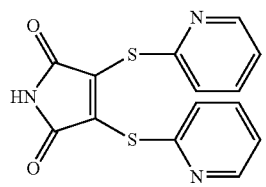 [SMILES: O=C1NC(=O)C(Sc2ccccn2)=C1Sc1ccccn1]

To dibromomaleimide (300.0 mg, 1.2 mmol) and sodium acetate (480.0 mg, 5.9 mmol) in methanol (15 ml) was slowly added 1H-pyridine-2-thione (275.8 mg, 2.5 mmol) in methanol (4 ml). The reaction was stirred for 15 min at RT. The solvent was removed in vacuo and the residual material was purified by flash chromatography on silica gel (methanol:dichloromethane, gradient elution from 0.5-3.0%) to afford the desired product as a dark yellow powder (190 mg, 51%). $\lambda_{max}$ (50 mM sodium phosphate, pH 6.2, 40% MeCN, 2.5% DMF)/395 nm ($\epsilon/dm^3$ $mol^{-1}$ $cm^{-1}$ 3508); $^1H$ NMR (500 MHz, MeOD): δ=8.37 (d, 2H, J=3.8, 2×N—CH), 7.70 (t, 2H, J=6.9, 2×C—CH—CH), 7.38 (d, 2H, J=7.9, 2×C—CH), 7.26 (t, 2H, J=6.5, 2×N—CH—CH); $^{13}C$ NMR (125 MHz, MeOD): δ=168.5 (C), 154.7 (C), 150.9 (CH), 140.0 (C), 139.0 (CH), 126.8 (CH), 123.7 (CH); IR (solid, $cm^{-1}$): 2926 (m), 2734 (w), 1771 (w), 1726 (s), 1619 (m); MS (CI) m/z, (%): 316 (M+H, 5), 152 (10), 126 (34), 112 (100); Mass calc. for $C_{14}H_9O_2N_3S_2[+H]$: 316.0214. Found: 316.0223. m.p. 70-72° C.

Reference Example 21: Preparation of N-PEG300 dibromomaleimide

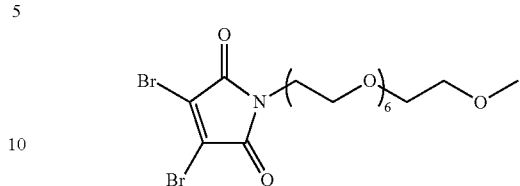

The reaction was carried out under strictly dry conditions. To triphenylphosphine (193.9 mg, 0.7 mmol) in THF (5 mL) was added drop-wise diisopropyl azodicarboxylate (145.6 µl, 0.7 mmol) at −78° C. The reaction was stirred for 5 min and PEG300 (200.0 mg, 0.6 mmol) in THF (4 mL) was added drop-wise. The reaction was stirred for 5 min and neopentyl alcohol (45.8 mg, 0.5 mmol) in THF (1 ml) was added. The reaction was stirred for 5 min and 3,4-dibromomaleimide (189.4 mg, 0.7 mmol) in THF (2 ml) was added. The reaction was stirred for 10 min, the cold bath removed and stirred for 20 h at ambient temperature. The solvent was removed in vacuo and the residual material was purified by flash chromatography on silica gel (methanol:dichloromethane, gradient elution from 0.5-5.0% methanol). Fractions containing the product were collected and the solvent was removed in vacuo. The still impure product was purified by flash chromatography on silica gel (petroleum ether:ethyl acetate, gradient elution from 7:3 to 2:8) to afford the desired compound as a yellow oil (137 mg, 40%) with 97.5% purity. $^1H$ NMR (500 MHz, $CDCl_3$): δ=3.76 (t, 2H, J=5.6, N—$CH_2$), 3.64-3.52 (m, 24H, 12×$CH_2$—O), 3.49 (t, 2H, J=4.4, N—$CH_2$—$CH_2$), 3.32 (s, 3H, O—$CH_3$); $^{13}C$ NMR (125 MHz, $CDCl_3$): δ=163.8 (2×C), 129.5 (2×C), 72.0 ($CH_2$), 70.7-70.5 (9×$CH_2$), 70.1 (2×$CH_2$), 67.5 ($CH_2$), 59.1 ($CH_3$), 39.0 ($CH_2$); IR (solid, $cm^{-1}$): 3496 (w), 2869 (m), 1786 (m), 1720 (s), 1594 (m); MS (CI) m/z, (%): 580 ($^{81}$ M+H, 12), 578 ($^{81, 79}$ M+H, 23), 576 ($^{79}$M+H, 12), 279 (100), 84 (61); Mass calc. for $C_{19}H_{31}^{79}Br_2O_9N[+H]$: 576.0444. Found: 576.0437.

Reference Example 22: Preparation of N-PEG5000 dibromomaleimide

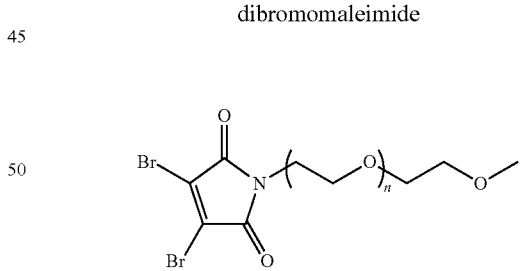

The reaction was carried out under strictly dry conditions. To triphenylphosphine (154.6 mg, 0.6 mmol) in a mixture of THF (8 mL) and DCM (3 mL) was added drop-wise diisopropyl azodicarboxylate (116.0 µl, 0.6 mmol) at −78° C. The reaction was stirred for 5 min and PEG5000 (2950.0 mg, 0.6 mmol) in dichloromethane (7 mL) was added drop-wise. The reaction was stirred for 5 min and neopentyl alcohol (26.5 mg, 0.3 mmol) in a mixture of THF (1 ml) and DCM (1 ml) was added. The reaction was stirred for 5 min and 3,4-dibromomaleimide (150.0 mg, 0.6 mmol) in THF (2 ml) was added. The reaction was stirred for 5 min, the cold bath removed and stirred for 20 h at ambient temperature. The solvent was removed in vacuo and the residual material was purified by flash chromatography on silica gel (methanol:dichloromethane, gradient elution from 0.5-5.0% methanol). Fractions containing the product were collected and the solvent was removed in vacuo. The still impure product was purified by very slow flash chromatography on silica gel (methanol:dichloromethane, gradient elution from 0.5-6.0% methanol) to afford desired compound as a pale green crystalline powder (417 mg, 13%). $^1$H NMR (500 MHz, CDCl$_3$): δ=3.58 (s, 4×n H, CH$_2$); $^{13}$C NMR (125 MHz, CDCl$_3$): δ=163.8 (C), 129.5 (C), 70.6 (CH$_2$); IR (solid, cm$^{-1}$): 3517 (w), 2872 (s), 1977 (w), 1727 (m), 1641 (w); m.p. 51-55° C.

Reference Example 23: Preparation of N-PEG5000 dithiophenolmaleimide

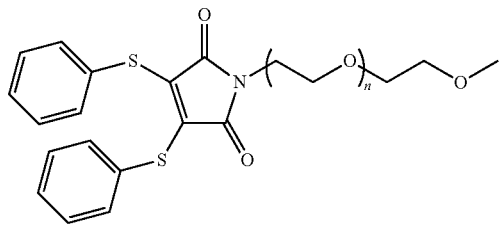

The reaction was carried out under strictly dry conditions. To triphenylphosphine (167.7 mg, 0.6 mmol) in a mixture of THF (8 ml) and DCM (3 ml) was added drop-wise diisopropyl azodicarboxylate (125.9 μl, 0.6 mmol) at −78° C. The reaction was stirred for 5 min and PEG5000 (1600.0 mg, 0.3 mmol) in DCM (7 ml) was added drop-wise. The reaction was stirred for 5 min and neopentyl alcohol (56.3 mg, 0.6 mmol) in a mixture of THF (1 ml) and DCM (1 ml) was added. The reaction was stirred for 5 min and 3,4-dithiophenolmaleimide (200.0 mg, 0.6 mmol) in THF (3 ml) was added. The reaction was stirred for 5 min, the cold bath removed and stirred for 20 h at ambient temperature. The solvent was removed in vacuo and the residual material was purified by flash chromatography on silica gel (methanol:dichloromethane, gradient elution from 0.5-10.0% methanol). Fractions containing the product were collected and the solvent was removed in vacuo. The still impure product was purified by flash chromatography on TLC grade silica gel (methanol:dichloromethane, gradient elution from 0.0-10.0% methanol) to afford the desired compound as a bright yellow crystalline powder (1.24 g, 73%). $^1$H NMR (500 MHz, CDCl$_3$): δ=7.26 (dd, H, J=7.7, J=4.5, CH), 7.23 (dd, 2H, J=8.4, J=6.6, CH), 7.19 (dd, 2H, J=8.4, J=6.8, CH), 3.63 (s, 4×n H, CH$_2$); $^{13}$C NMR (125 MHz, CDCl$_3$): δ=166.7 (C), 135.7 (C), 131.9 (CH), 129.1 (C), 129.0 (CH), 128.4 (CH), 70.6 (CH$_2$); IR (solid, cm$^{-1}$): 3498 (w), 2881 (s), 1959 (w), 1711 (m); m.p. 57-59° C.

Reference Example 24: Preparation of 2,3-dibromo-maleic anhydride

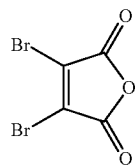

Under an inert atmosphere, a solution of maleic anhydride (1.50 g, 15.3 mmol, 1 eq), aluminium trichloride (300 mg, 0.21 mmol, cat.) and bromine (4.95 g, 30.6 mmol, 2 eq) was heated at 160° C. in a sealed ampule (note—blast shield) for 16 h. Upon cooling to 21° C. the reaction mixture was stirred for a further 24 h and carefully opened to air. EtOAc was added and the solid filtered off and repeatedly washed with further EtOAc. The filtrate was finally concentrated in vacuo to give the title compound was a yellow solid which was used without further purification (3.05 g, 11.9 mmol, 78% yield). m.p 107-110° C.; $^{13}$C NMR (150 MHz, CD$_3$OD) δ 163.33 (s), 125.28 (s); IR (MeOH) 1769, 1706, 1590 cm$^{-1}$; HRMS (CI) calcd for C$_4$O$_3$Br$_2$ [M]$^+$ 253.82087, 253.82082 observed.

Reference Example 25: Preparation of tert-Butyl N-(2-(2-(2-aminoethoxy)ethoxy)ethyl)carbamate

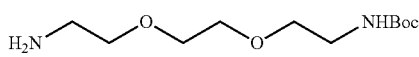

A solution of di-tert-butyl-dicarbonate (1.10 g, 5.00 mmol, 1 eq) in CH$_2$Cl$_2$ (5 mL) was added dropwise to a solution of 2-[2-(2-aminoethoxy)ethoxy]ethanamine (7.32 mL, 50.0 mmol, 10 eq) in CH$_2$Cl$_2$ (15 mL). The resulting reaction mixture was stirred at 21° C. for 24 h. The CH$_2$Cl$_2$ was then removed in vacuo to leave a colourless residue. Addition of EtOAc (125 mL) caused formation of a white precipitate, which was washed with a saturated solution of Na$_2$CO$_3$ (3×50 mL), dried over MgSO$_4$, and concentrated in vacuo. Further purification by column chromatography (8:2 CH$_2$Cl$_2$/MeOH) furnished the desired monoprotected amine as a colourless oil (0.69 g, 2.80 mmol, 56% yield). $^1$H NMR (500 MHz, CDCl$_3$) δ 5.27 (bs, 1H, NH), 3.54-3.52 (m, 4H, OCH$_2$), 3.47-3.42 (m, 4H, OCH$_2$), 3.23-3.22 (m, 2H, NCH$_2$), 2.80 (t, J=5.0, 2H, NCH$_2$), 2.05 (bs, 2H, NH), 1.35 (s, 9H, CH$_3$); $^{13}$C NMR (125 MHz, CDCl$_3$) δ 156.08 (s), 79.09 (s), 73.19 (t), 70.21 (t), 70.16 (t), 41.59 (t), 40.32 (t), 28.40 (q), *1t missing; IR (neat) 3344, 2869, 1692 cm$^{-1}$; HRMS (CI) calcd for C$_{11}$H$_{25}$N$_2$O$_4$ [M+H]$^+$ 249.18143, observed 249.18251.

Reference Example 26: Preparation of tert-Butyl-N-(2-(2-(2-(5-(2-oxo-1,3,3a,4,6,6a-hexahydrothieno(3,4-d)imidazol-6-yl)pentanoylamino)ethoxy)ethoxy) ethyl)carbamate

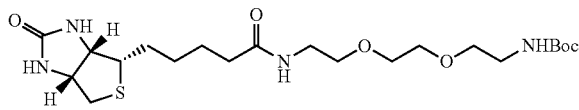 [SMILES: CC(C)(C)OC(=O)NCCOCCOCCNC(=O)CCCC[C@@H]1SC[C@@H]2NC(=O)N[C@@H]21]

A solution of biotin (0.59 g, 2.42 mmol, 1.5 eq), HBTU (0.79 g, 2.10 mmol, 1.3 eq) and DIEA (0.45 mL, 2.60 mmol, 1.6 eq) in DMF (15 mL) was stirred for 20 min at 21° C. before being added dropwise to a solution of tert-butyl-N-(2-(2-(2-aminoethoxy)ethoxy)ethyl)carbamate (400 mg, 1.61 mmol, 1 eq) in DMF (10 mL). The reaction mixture was stirred for 2 h at 21° C., after which the DMF was removed in vacuo to give a yellow residue. The crude product was purified by column chromatography (gradient 2-10% MeOH/CH$_2$Cl$_2$) to yield the desired compound as a white solid (0.61 g, 1.29 mmol, 80% yield). m.p. 106-108° C.; $[\alpha]_D^{20.0}$+23.0 (c 0.6, $CH_2Cl_2$); $^1H$ NMR (500 MHz, $CDCl_3$) δ 4.55 (dd, J=5.0, 7.5 Hz, 1H, NHC(O)NHCH), 4.36 (dd, J=5.0, 7.5 Hz, 1H, NHC(O)NHCH), 3.62 (bs, 6H, $OCH_2$), 3.59-3.55 (m, 2H, $OCH_2$), 3.46 (m, 2H, $NCH_2$), 3.31 (m, 2H, $NCH_2$), 3.17 (dt, 3.0, 5.0 Hz, 1H, SCH), 2.92 (dd, J=5.0, 13.0 Hz, 1H, SCHH), 2.79 (d, J=13.0 Hz, 1H, SCHH), 2.27 (t, J=7.0 Hz, 2H, NHC(O)$CH_2CH_2CH_2$), 1.71 (m, 4H, NHC(O)$CH_2CH_2CH_2CH_2$), 1.47 (br, 11H, $C(CH_3)_3$ & NHC(O)$CH_2CH_2CH_2CH_2$); $^{13}C$ NMR (125 MHz, $CDCl_3$) δ 173.69 (s), 163.92 (s), 155.99 (s), 79.14 (s), 70.03 (t), 69.69 (br t), 61.58 (d), 60.06 (d), 55.19 (d), 40.16 (t), 39.96 (t), 38.91 (t), 35.44 (t), 28.09 (q), 27.80 (t), 27.67 (t), 25.23 (t), *2t absent; IR (neat) 3307, 2933, 1691 $cm^{-1}$; HRMS (ES) calcd for $C_{21}H_{38}N_4O_6NaS$ $[M+Na]^+$ 497.2410, observed 497.2423.

Reference Example 27: Preparation of 2-(2-(2-(5-(2-oxo-1,3,3a,4,6,6a-hexahydrothieno(3,4-d)imidazol-6-yl)pentanoylamino)ethoxy)ethoxy)ethylammonium; 2,2,2-trifluoroacetate

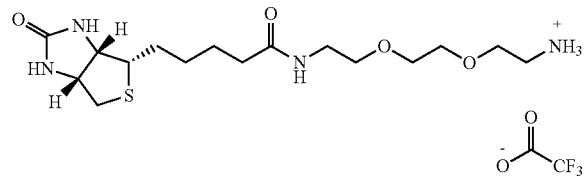 [SMILES: NCCOCCOCCNC(=O)CCCC[C@@H]1SC[C@@H]2NC(=O)N[C@@H]21 ; O=C(O)C(F)(F)F]

A solution of tert-butyl N-(2-(2-(2-(5-(2-oxo-1,3,3a,4,6,6a-hexahydrothieno(3,4-d)imidazol-6-yl)pentanoylamino)ethoxy)ethoxy)ethyl)carbamate (0.61 g, 1.29 mmol) in $CH_2Cl_2$ (5 mL) and TFA (5 mL) was stirred at 21° C. for 24 h. Toluene was then added (×2) and the solvent removed in vacuo to yield the desired compound as an oil (0.63 g, 1.29 mmol, 100% yield). $[\alpha]_D^{20.0}$+41.0 (c 0.49, MeOH); $^1H$ NMR (400 MHz, $CD_3OD$) δ 4.53 (dd, J=5.0, 7.5 Hz, 1H, NHC(O)NHCH), 4.33 (dd, J=5.0, 7.5 Hz, 1H, NHC(O)NHCH), 3.71 (t, J=5.0 Hz, 2H, $OCH_2CH_2NH_3$), 3.65 (br, 4H, $OCH_2$), 3.57 (t, J=5.0 Hz, 2H, $OCH_2$), 3.38 (t, J=5.0 Hz, 2H, $OCH_2$), 3.22 (dt, J=5.0, 8.5 Hz, 1H, SCH), 3.13 (t, J=5.0 Hz, 2H, C(O)$NHCH_2CH_2O$), 2.94 (dd, J=5.0, 13.0 Hz, 1H, SCHH), 2.74 (d, J=13.0 Hz, 1H, SCHH), 2.24 (t, J=7.5 Hz, 2H, NHC(O)$CH_2CH_2CH_2$), 1.76-1.43 (m, 6H, NHC(O)$CH_2CH_2CH_2CH_2$); $^{13}C$ NMR (100 MHz, $CD_3OD$) δ 174.98 (s), 164.76 (s), 69.92 (t), 69.83 (t), 69.22 (t), 66.46 (t), 62.08 (d), 60.36 (d), 55.59 (d), 39.65 (t), 39.24 (t), 38.77 (t), 35.29 (t), 28.29 (t), 28.06 (t), 25.44 (t); IR (MeOH) 3300, 2941, 1686 $cm^{-1}$; HRMS (ES) calcd for $C_{16}H_{31}N_4O_4S$ $[M+H]^+$ 375.2066, observed 375.2060.

Reference Example 28: Preparation of N-(2-(2-(2-(3-bromo-2,5-dioxo-pyrrol-1-yl)ethoxy)ethoxy)ethyl)-5-(2-oxo-1,3,3a,4,6,6a-hexahydrothieno(3,4-d)imidazol-6-yl)pentanamide

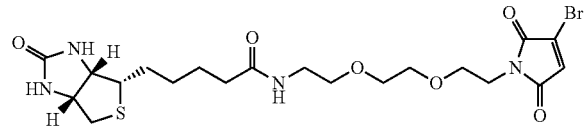 [SMILES: O=C(CCCC[C@@H]1SC[C@@H]2NC(=O)N[C@@H]21)NCCOCCOCCN1C(=O)C=C(Br)C1=O]

Monobromomaleic anhydride (45.0 mg, 0.25 mmol, 1 eq) was added in one portion to a solution of 2-(2-(2-(5-(2-oxo-1,3,3a,4,6,6a-hexahydrothieno(3,4-d)imidazol-6-yl)pentanoylamino)ethoxy)ethoxy)ethylammonium 2,2,2-trifluoroacetate (124 mg, 0.25 mmol, 1 eq) in AcOH (10 mL) and the reaction mixture heated to 170° C. for 3 h. Upon cooling to 21° C. toluene was added and the AcOH azeotropically removed in vacuo (×2) to give crude product. Column chromatography (gradient 2-10% MeOH/$CH_2Cl_2$) yielded the desired compound as a white solid (70.0 mg, 0.13 mmol, 52% yield). m.p. 95-98° C.; $[\alpha]_D^{20.0}$+65.1 (c 0.15, MeOH); $^1H$ NMR (600 MHz, $CD_3OD$) δ 7.17 (s, 1H, CHCBr), 4.51 (dd, J=5.0, 8.0 Hz, 1H, NHC(O)NHCH), 4.33 (dd, J=5.0, 8.0 Hz, 1H, NHC(O)NHCH), 3.77 (t, J=5.5 Hz, 2H, $OCH_2$), 3.68 (t, J=5.5 Hz, 2H, $OCH_2$), 3.63 (m, 2H, $OCH_2$), 3.58 (m, 2H, $OCH_2$), 3.53 (t, J=5.5 Hz, 2H, $NCH_2$), 3.37 (t, J=5.5 Hz, 2H, $NCH_2$), 3.24 (td, J=5.0, 8.0 Hz, 1H, SCH), 2.95 (dd, J=5.0, 12.5 Hz, 1H, SCHH), 2.73 (d, J=12.5 Hz, 1H, SCHH), 2.26 (t, J=7.0 Hz, 2H, NHC(O)$CH_2CH_2CH_2$), 1.69 (m, 4H, $CH_2CH_2CH_2$), 1.47 (quintet, J=7.0 Hz, 2H, $CH_2CH_2CH_2$); $^{13}C$ NMR (150 MHz, $CD_3OD$) δ 176.12 (s), 170.13 (s), 166.97 (s), 166.08 (s), 133.63 (s), 132.05 (d), 71.22 (t), 71.11 (t), 70.61 (t), 68.69 (t), 63.35 (d), 61.61 (d), 57.03 (d), 41.09 (t), 40.31 (t), 39.09 (t), 36.75 (t), 29.78 (t), 29.50 (t), 26.87 (t); IR (MeOH) 3355, 2970, 1737 $cm^{-1}$; HRMS (ES) calcd for $C_{20}H_{29}N_4O_6NaSBr$ $[M+Na]^+$ 555.0889, observed 555.0905.

Reference Example 29: Preparation of N-(2-(2-(2-(3,4-dibromo-2,5-dioxo-pyrrol-1-yl)ethoxy)ethoxy)ethyl)-5-(2-oxo-1,3,3a,4,6,6a-hexahydrothieno(3,4-d)imidazol-6-yl)pentanamide Dibromomaleic anhydride (108 mg, 0.42 mmol, 1 eq) was added in one portion to a solution of 2-(2-(2-(5-(2-oxo-1,3,3a,4,6,6a-hexahydrothieno(3,4-d)imidazol-6-yl)pentanoylamino)ethoxy)ethoxy)ethylammonium 2,2,2-trifluoroacetate (205 mg, 0.42 mmol, 1 eq) in AcOH (10 mL) and the reaction mixture heated to 170° C. for 2 h. Upon cooling to 21° C. toluene was added and the AcOH azeotropically removed in vacuo (×2) to give crude product. Column chromatography (gradient 2-7% MeOH/$CH_2Cl_2$) yielded the desired compound as a white solid (123 mg, 0.20 mmol, 48% yield). m.p. 100-102° C.; $[\alpha]_D^{20.0}$+71.0 (c 0.15, MeOH); $^1H$ NMR (600 MHz, $CD_3OD$) δ 4.53 (dd, J=5.0, 8.0 Hz, 1H, NHC(O)NHCH), 4.34 (dd, J=5.0, 8.0 Hz, 1H, NHC(O)NHCH), 3.82 (t, J=5.5 Hz, 2H, $OCH_2$), 3.70 (t, J=5.5 Hz, 2H, $OCH_2$), 3.63 (m, 2H, $OCH_2$), 3.59 (m, 2H, $OCH_2$), 3.53 (t, J=5.5 Hz, 2H, $NCH_2$), 3.37 (t, J=5.5 Hz, 2H, $NCH_2$), 3.24 (dt, J=5.0, 8.0 Hz, 1H, SCH), 2.96 (dd, J=5.0, 13.0 Hz, 1H, SCHH), 2.73 (d, J=13.0 Hz, 1H, SCHH), 2.26 (t, J=7.5 Hz, 2H, NHC(O)$CH_2CH_2CH_2$), 1.74 (m, 4H, $CH_2CH_2CH_2$), 1.49 (quintet, J=7.5 Hz, 2H, $CH_2CH_2CH_2$); $^{13}C$ NMR (150 MHz, $CD_3OD$) δ 174.83 (s), 164.71 (s), 164.06 (s), 129.00 (s), 69.80 (t), 69.72 (t), 69.24 (t), 67.19 (t), 61.97 (d), 60.22 (d), 55.64 (d), 39.67 (t), 39.03 (t), 38.56 (t), 35.42 (t), 28.39 (t), 28.11 (t), 25.47 (t); IR (MeOH) 2970, 1724, 1365, 1217 $cm^{-1}$; HRMS (ES) calcd for $C_{20}H_{28}N_4O_6NaSBr_2$ $[M+Na]^+$ 631.9916, observed 631.9937.

Reference Example 30: Preparation of N-Fluorescein bromomaleimide

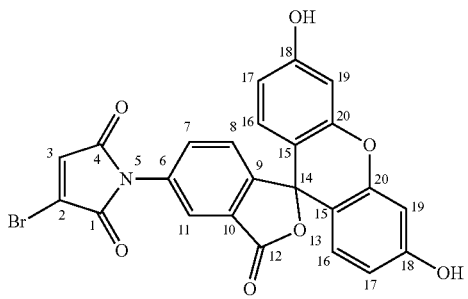 [SMILES: O=C1OC2(c3ccc(O)cc3Oc3cc(O)ccc32)c2ccc(N3C(=O)C=C(Br)C3=O)cc21]

Dibromomaleic anhydride (346 mg, 1.95 mmol) was added in one portion to a solution of fluoresceinamine isomer 1 (678 mg, 1.95 mmol) in acetic acid (65 mL) and the reaction mixture was stirred for 12 hours at room temperature in a sealed tube. The reaction mixture was then heated to 150° C. for 3 h. Upon cooling to room temperature the solid was filtered and dried (toluene azeotrope) to afford the desired compound as an orange solid (722 mg, 1.43 mmol, 73% yield). $^1$H NMR (600 MHz, DMSO) δ 7.99 (d, 1H, J=1.7, 1H, H-11), 7.77 (dd, 1H, J=1.9 and 8.2, 1H, H-7), 7.73 (s, 1H, H-3), 7.43 (d, J=8.2, 1H, H-8), 6.69 (m, 6H, 2×H-16, 2×H-17, 2×H-18); $^{13}$C NMR (175 MHz, DMSO) δ 167.93 (C=O), 167.63 (C=O), 164.48 (C=O), 159.62 (2×C18), 151.79 (2×C20), 151.52 (C6), 133.68 (C7), 133.02 (Ar), 132.90 (C3), 131.23 (C), 129.15 (2×Ar-H), 126.73 (C), 124.82 (C11), 122.29 (C8), 112.77 (2×Ar-H), 109.08 (2×Ar), 102.30 (2×Ar-H), 83.36 (C14); IR (solid, cm$^{-1}$) 3064 (w), 1726 (s); MS (ES+) m/z, (relative intensity): 508 ([$^{81}$M], 95), 506 ([$^{79}$M], 100); Exact mass calcd for [$C_{24}H_{13}O_7N^{79}Br$] requires 505.9875 Found 505.9833 (ES+).

Reference Example 31: Preparation of N-Fluorescein dibromomaleimide

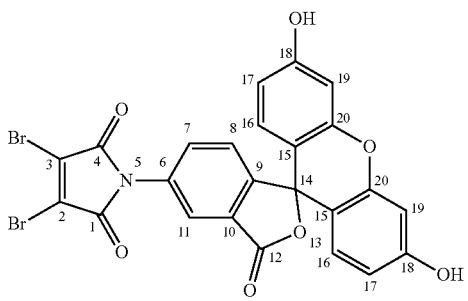 [SMILES: O=C1OC2(c3ccc(O)cc3Oc3cc(O)ccc32)c2ccc(N3C(=O)C(Br)=C(Br)C3=O)cc21]

Dibromomaleic anhydride (77.0 mg, 0.30 mmol) was added in one portion to a solution of fluoresceinamine isomer 1 (105 mg, 0.30 mmol) in acetic acid (10 mL) and the reaction mixture was stirred for 6 h at room temperature. The solid was then filtered off, washed with ethyl acetate, and redissolved in acetic acid (10 mL). The reaction mixture was then heated to reflux for 3 h. Upon cooling to room temperature toluene (10 ml) was added and the solvent removed in vacuo, affording the desired compound as an orange solid (148 mg, 0.25 mmol, 84% yield). 8 $^1$H NMR (400 MHz, CD$_3$OD) δ 8.07 (d, 1H, J=1.5, H-11), 7.81 (dd, 1H, J=1.5 and 8.0, H-7), 7.34 (d, 1H, J=8.5, H-8), 6.71-6.58 (m, 6H, 6×Ar-H); $^{13}$C NMR (100 MHz, CD$_3$OD) δ 170.23 (C=O), 164.34 (2×C=O), 161.63 (2×C), 154.18 (2×C), 152.93 (C), 134.59 (C), 134.19 (Ar—H), 131.01 (C), 130.35 (Ar—H), 129.25 (2×C), 126.25 (2×Ar-H), 123.63 (Ar—H), 113.84 (2×Ar-H), 111.02 (2×C), 103.55 (2×Ar-H); IR (solid, cm$^{-1}$) 3064 (w), 1732 (s); MS (ES+) m/z, (relative intensity): 586 ([$^{81+81}$M], 30), 584 ([$^{79+81}$M], 100), 582 ([$^{79+79}$M], 100); Exact mass calcd for [$C_{24}H_{10}O_7N^{79}Br_2$] requires 581.8824 Found 581.8824 (ES+).

Reference Example 32: Preparation of Tert-butyl 2-aminoethylcarbamate

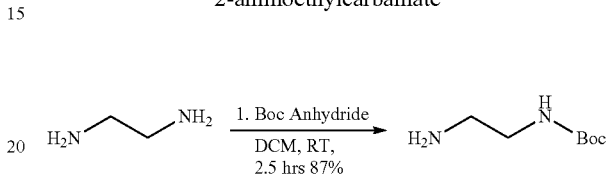

Di-tertbutyldicarbonate (3.26 g, 15 mmol, 1 eq) in DCM (30 mL) was added, dropwise, to a solution of ethylenediamine (10 ml, 150 mmol, 10 eq) in DCM (30 mL) under an argon atmosphere over two hours using an autoinjecter. Based on TLC analysis (eluent: 90% EtOAc: 10% MeOH R$_{f(8)}$=0.23) the reaction reached completion 30 minutes after the end of the addition. The DCM was removed under reduced pressure using a Büchi. The resultant residue was taken up in EtOAc (40 mL) and washed with saturated Na$_2$CO$_3$ (3×20 mL), dried over MgSO4, and concentrated in vacuo to obtain the desired product (2.08 g; 12.98 mmol, 87%) as a white foam. mp (104-106° C.), δ$_H$ $^1$H NMR (300 MHz CDCl$_3$): 4.95 (broad singlet, 1H, NH), 3.12 (q, J=6.4 Hz, 2H, CH$_2$), 2.78 (t, J=5.9 Hz, 2H, CH$_2$), 1.42 (s, 9H, 3CH$_3$). 13C NMR (CDCl3): 28.06, 41.51, 43.02, 78.82, 155.9 IR: 3354.9 cm$^{-1}$, [M+H]$^+$: 161.00

Reference Example 33: Preparation of tert-butyl 2-(5-(dimethylamino)naphthalene-1-sulfonamido) ethylcarbamate

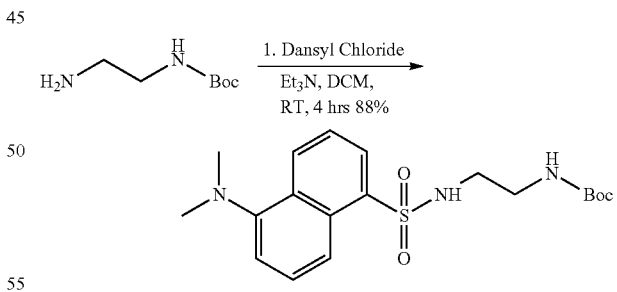

A round bottom flask was flame dried and equipped with a stirrer bar and a solution of amine (0.57 g, 3.6 mmol, 1 eq) in dry DCM (150 mL) under an argon atmosphere. Dansyl chloride (1.05 g, 3.92 mmol, 1.1 eq) in dry DCM (150 mL) and triethylamine (1.3 ml, 9.29 mmol, 2.5 eq) were added through a septum in one portion. Reaction was monitored by TLC (eluent: 35% EtOAc: 65% Petroleum ether R$_{f(9)}$=0.27, fluorescent green under long UV), the reaction was complete after 4 hours. Following purification by column chromatography (eluent: 35% EtOAc: 65% Petroleum ether), the desired compound was formed (1.24 g, 3.15 mmol, 88%) as a sticky, clear green oil. $\delta_H$ ¹H NMR (CDCl3): 8.55 (d, J=8.55 Hz, 1H, CH), 8.46 (d, J=8.51 Hz, 1H, CH), 8.33 (d, J=8.67 Hz, 1H, CH), 7.57 (m, 2H, 2×CH), 7.26 (d, J=7.08 Hz, 1H, CH), 3.07 (quartet, J=6.58 Hz, 2H, CH₂), 2.89 (m, 2H, CH₂), 2.85 (s, 6H, 2×CH₃), 1.35 (s, 9H, 3×CH₃). 13C NMR (CDCl₃): 158.01, 153.05, 136.5, 131.49, 131.09, 130.02, 129.54, 124.48, 120.59, 116.41, 80.41, 45.9, 43.81, 41.5, 28.5. MS: [M+H]⁺: 393.16.

Reference Example 34: Preparation of 5-(3-aminopropylsulfonyl)-N,N-dimethylnaphthalen-1-amine 2,2,2-trifluoroacetate

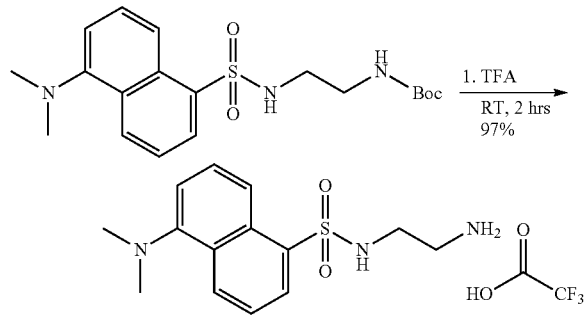

To a flask containing BOC-carbamate (1.24 g, 3.15 mmol), TFA (40 ml) was added in one portion. The resulting grey solution was stirred for 2 hours at room temperature (ca. 25° C.). Upon completion the solution was concentrated in vacuo and azeotroped with tolune (5×10 ml). The resultant crude product was then purified by column chromatography (eluent:EtOAc 1:2 Petroleum ether $R_{f(10)}$=0.20). After concentrating the relevant fractions in vacuo, to the yellow oil that resulted, DCM (100 ml) was added and the solution placed in an ice bath for 2 hours, this solution was fluorescent under long-wave UV. The desired compound (1.25 g, 3.10 mmol, 97%) crashed out of solution as a white solid and it was filtered off and washed with diethyl ether under gravity. Mp (114-116° C.); $\delta_H$ ¹H NMR (500 MHz MeOD): 8.64 (d, J=8.3 Hz, 1H, CH), 8.35 (d, J=8.45 Hz, 1H, CH), 8.32 (d, J=8.65 Hz, 1H, CH), 7.67 (m, 2H, 2×CH), 7.34 (d, J=7.3 Hz, 1H, CH), 3.03 (quartet, 4H, 2×CH₂), 2.84 (s, 6H, 2×CH₃). $\delta_C$ ¹³C NMR (500 MHz MeOD): 153.41, 135.78, 131.69, 131.32, 130.81, 130.56, 129.48, 124.29, 120.07, 116.635, 66.91, 45.79, 41.27, 40.78, 15.45. ¹⁹F NMR (300 MHz CDCl₃); −76.89; IR: 3092 cm⁻¹, 2901.5 cm⁻¹, MS: [M+H]⁺: 294

Reference Example 35: Preparation of (E)-2-bromo-4-(2-(5-(dimethylamino)naphthalene-1-sulfonamido)ethylamino)-4-oxobut-2-enoic acid

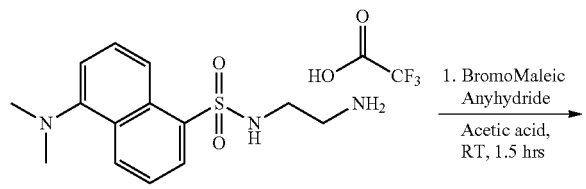

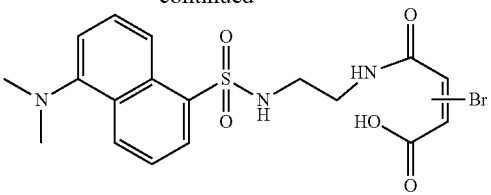

An oven-dried 500 ml round bottomed flask was equipped with a stirring bar. Amine salt (1.09 g,) was dissolved in 25 ml acetic acid and added to the flask. To the resulting light yellow solution, Bromomaleic anhydride was added and reaction was monitored by TLC (eluent; 10% methanol: 90% EtOAc, $R_{f(11)}$=0.7). After 1.5 hours of stirring at room temperature (25° C.) the acetic acid was removed in vacuo. The desired compound was used without further purification. 1H NMR (500 Mz CDCl3 (Crude)): $\delta_H$ 8.6 (d, J=8.56 Hz, 1H, CH), 8.35 (d, 1H, J=8.27 Hz, CH), 8.22 (d, 1H, J=8.57 Hz, CH), 7.64 (m, 2H, 2×CH), 7.30 (d, J=7.60 Hz, 1H, CH), 5.48 (s, 1H, CH)/5.03 (s, 1H, CH), 3.00 (m, 4H, 2×CH₂), 2.88 (s, 9H, 2×CH₃)

Reference Example 36: Preparation of N-(2-(3-bromo-2,5-dioxo-2,5-dihydro-1H-pyrrol-1-yl)ethyl)-5-(dimethylamino)naphthalene-1-sulfonamide

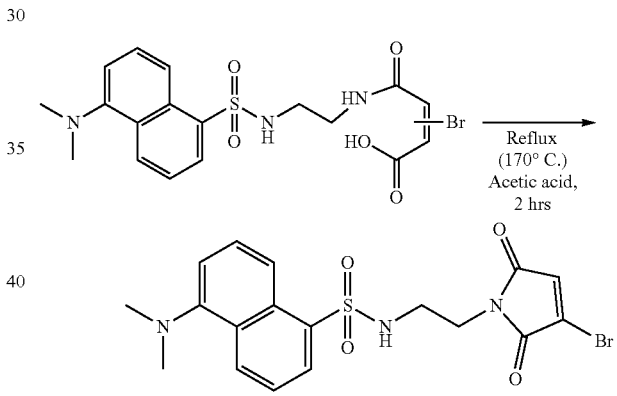

The acid was dissolved in acetic acid (25 mL) and loaded into an oven dried 500 ml round bottom flask. A condenser was fitted and the reaction was placed under reflux (170° C.) for 2 hours. The acetic acid was then removed from the crude mixture in vacuo and the resultant oil was aziotroped with toluene (5×10 ml). The resultant oil was purified by column chromatography (eluent: 30% ethylacetate: 70% petroleum ether, $R_f$(12)=0.2 in the aforementioned eluent system). Once the very slow column was completed, the more mobile fraction was collected and the solvent removed. The resultant brown oil was left to stand in neat ethyl acetate (50 ml) for 1 hour in an ice bath. The desired product (0.961 g, 80%) crashed out of solution as a brown solid (powder like texture), this was filtered under gravity and washed with diethyl ether (20 ml). mp (166-170° C.); ¹H NMR (600 MHz DMSO): $\delta_H$ 8.53 (d, J=8.46 Hz, 1H, CH), 8.21 (d, 1H, J=8.40 Hz, CH), 8.17 (d, 1H, J=8.58 Hz, CH), 7.56 (m, 2H, 2×CH), 7.18 (d, J=7.50 Hz, 1H, CH), 6.46 (s, 1H, maleimide olefin C—H), 5.11 (t, J=6.24, 1H, NH), 3.56 (m, 2H, CH₂), 3.2 (m, 2H, CH₂), 3.91 (s, 6H, 2×CH₃). $\delta_C$ ¹³C NMR (600 MHz DMSO): 168.62, 165.33, 151.38, 151.38, 135.62, 132.33, 130.13, 129.60, 129.09, 128.85, 128.30, 127.96, 123.61, 118.99, 115.22, 45.11, 40.05, 39.37, 38.47.

Reference Example 37: Preparation of 4-Bromo-1,2-diethyl-1,2-dihydro-pyridazine-3,6-dione (BrD-DPD)

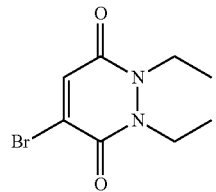

A mixture of monobromomaleic anhydride (177 mg, 1.0 mmol) and N,N-diethylhydrazine (88 mg, 1.0 mmol) in glacial AcOH (3 mL) was heated at 130° C. for 16 h. The solvent was removed in vacuo and the crude residue purified by column chromatography (neat $CH_2Cl_2$-5% MeOH/$CH_2Cl_2$) to give 4-bromo-1,2-diethyl-1,2-dihydro-pyridazine-3,6-dione as a yellow solid (159 mg, 0.64 mmol, 64%): $^1$H NMR (600 MHz, CDCl$_3$) δ 7.31 (s, 1H), 4.14 (q, J=7.0 Hz, 2H), 4.07 (q, J=7.0 Hz, 2H), 1.26 (t, J=7.0 Hz, 3H), 1.22 (t, J=7.0 Hz, 3H); $^{13}$C NMR (150 MHz, CDCl$_3$) δ 156.2 (s), 154.3 (s), 136.0 (d), 133.7 (s), 41.9 (t), 40.7 (t), 13.3 (q), 13.3 (q); IR (solid) 3058, 2979, 2938, 1631, 1595 cm$^{-1}$; LRMS (CI) 249 (100, [M$^{81}$Br+H]$^+$), 247 (100, [M$^{79}$Br+H]$^+$); HRMS (CI) calcd for $C_8H_{12}BrN_2O_2$[M+H]$^+$ 249.0082, observed 249.0086.

Reference Example 38: Preparation of 4,5-Dibromo-1,2-diethyl-1,2-dihydro-pyridazine-3,6-dione (DiBrDDPD)

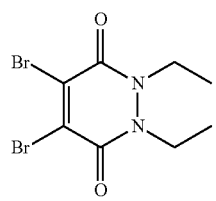

A mixture of dibromomaleic anhydride (256 mg, 1.0 mmol) and N,N-diethylhydrazine (88 mg, 1.0 mmol) in glacial AcOH (3 mL) was heated at 130° C. for 16 h. The solvent was removed in vacuo and the crude residue purified by column chromatography (neat $CH_2Cl_2$-5% MeOH/$CH_2Cl_2$) to give 4,5-dibromo-1,2-diethyl-1,2-dihydro-pyridazine-3,6-dione as a yellow solid (202 mg, 0.62 mmol, 62%): $^1$H NMR (600 MHz, CDCl$_3$) δ 4.17 (q, J=7.0 Hz, 4H), 1.28 (t, J=7.0 Hz, 6H); $^{13}$C NMR (150 MHz, CDCl$_3$) δ 153.3 (s), 136.1 (s), 42.4 (t), 13.2 (q); IR (solid) 2979, 2937, 1630, 1574 cm$^{-1}$; LRMS (EI) 328 (50, [M$^{81}$Br$^{81}$Br]$^{+\cdot}$), 326 (100, [M$^{81}$Br$^{79}$Br]$^{+\cdot}$), 324 (50, [M$^{79}$Br$^{79}$Br]$^{+\cdot}$); HRMS (EI) calcd for $C_5H_{10}Br_2N_2O_2$ [M$^{79}$Br$^{79}$Br]$^{+\cdot}$ 323.9104, observed 323.9097.

Reference Example 39: Preparation of N-Boc-Cys(Mal)-OMe

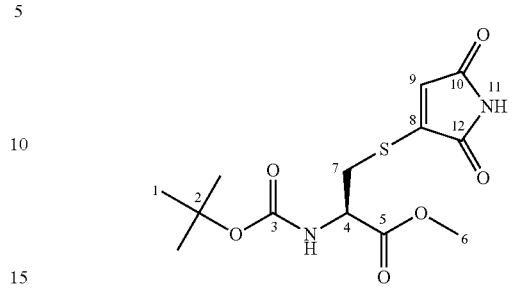

To a stirring solution of N-Boc-Cys-OMe (36 mg, 0.15 mmol) and sodium acetate (13 mg, 0.15 mmol) in methanol (3 mL) was added bromomaleimide (30 mg, 0.17 mmol) in methanol (3 mL). After 1 minute solvent was removed in vacuo. Purification by flash chromatography (gradient elution in 50% ethyl acetate in petroleum ether to ethyl acetate) afforded a pale yellow powder N-Boc-Cys(Mal)-OMe (51 mg, 0.15 mmol) in 100%. $δ_H$ (500 MHz, CDCl$_3$) 7.63 (s, 1H, mal-NH), 6.27 (s, 1H, 9-H), 5.40 (d, 1H, J=6.8, NH), 4.67 (ddd, 1H, J=5.1, 5.4 and 6.8, H-4), 3.80 (s, 3H, H$_3$-6), 3.48 (dd, 1H, J=5.1 and 13.8, HH-7), 3.62 (dd, 1H, J=5.4 and 14.1, HH-7) 1.45 (s, 9H, 3×H$_3$-1); $δ_C$ (125 MHz, CDCl$_3$) 170.2 (C=O), 168.9 (C=O), 167.6 (C=O), 155.2 (C=O), 155.9 (C8), 119.7 (C9), 81.1 (C2), 53.3 (C6), 52.7 (C4), 34.0 (C7), 28.3 (3×C1); IR (solid, cm$^{-1}$) 3236 (w), 1715 (s); MS (CI+) m/z, (relative intensity): 331 ([M+H], 5), 275 (20), 231 (100); Mass calcd for [$C_{13}H_{18}O_6N_2S$]+H requires 331.0964. Found 331.0968 (CI+); $^{20}α_D$: −41.9° (c=1.0, Methanol); m.p. 145-147° C.; UV (Acetonitrile) $ε_{245}$=14200 and $ε_{339}$=8600 cm$^{-1}$M$^{-1}$d$^3$.

Reference Example 40: Preparation of N-Boc-Cys(N′-Me-Mal)-OMe

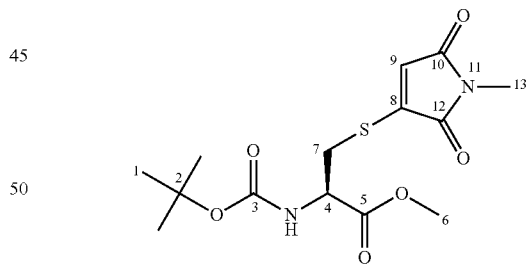

To a stirring solution of N-Boc-Cys-OMe (32 mg, 0.136 mmol) in methanol (4 mL) was added sodium acetate (82 mg, 0.408 mmol). To this was added N-methyl bromomaleimide (25.8 mg, 0.136 mmol) in methanol (4 mL) over 10 minutes. The solvent was removed in vacuo purification by flash chromatography (gradient elution in 10% ethyl acetate in petroleum ether to 30% ethyl acetate in petroleum ether) to afford the desired compound as a pale white powder (39.3 mg, 0.114 mmol) in 84% yield. $δ_H$ (500 MHz, CDCl3) 6.26 (s, 1H, H-9), 5.36 (d, 1H, J=6.3, 'Boc' NH), 4.66 (m, 1H, H-4), 3.79 (s, 3H, H$_3$-6), 3.46 (dd, 1H, J=5.0 and 5.2, HH-7), 3.35 (dd, 1H, J=5.1 and 13.7, HH-7), 3.00 (s, 3H, H$_3$-13), 1.44 (s, 9H, 3×H$_3$-1); $δ_C$ (125 MHz, CDCl3) 170.2 (C=O), 169.5 (C=O), 167.9 (C=O), 155.0 (C=O), 149.9 (C8), 118.7 (C9), 80.9 (C2), 53.1 (C6), 52.7 (C4), 33.8 (C7), 28.3 (3×C1), 24.1 (C13); IR (solid, cm$^{-1}$) 3368 (m), 2977 (m), 1695 (s); MS (ES+) m/z, (relative intensity): 311 (M+, 100); Mass calcd for $C_{14}H_{20}N_2O_6NaS$ requires 367.0940. Found: 367.0931; $^{20}α_D$: −18.55° (c=1.0, Methanol); m.p. 101-103° C.

Example 9: Preparation of 2,3-Di(N-Boc-Cys-OMe)succinimide (Mix of diastereomers)

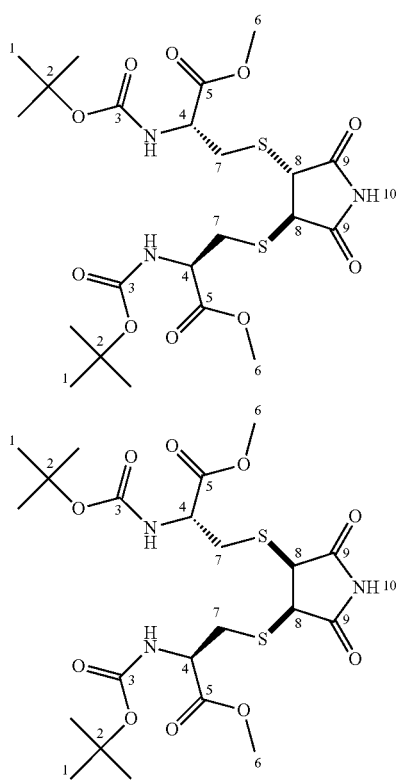

To a stirred solution of bromomaleimide (50 mg, 0.28 mmol) in aqueous buffer (100 mM sodium phosphate, 150 mM NaCl, pH 8.0):DMF, 95:5 (9.25 mL) was added N-Boc-Cys-OMe (660 mg, 2.81 mmol) in DMF (0.25 mL). After 5 minutes the aqueous reaction mixture was extracted with ethyl acetate (3×25 mL) and the combined organic layers washed with saturated lithium chloride solution (aq) (5×25 mL), water (25 mL) and brine (25 mL), dried (MgSO$_4$), filtered and the solvent removed in vacuo. Purification by column chromatography (10-40% ethyl acetate in petroleum ether) afforded 2,3-Di(N-Boc-Cys-OMe)succinimide (mix of diastereomers) as a yellow waxy oil (150 mg, 0.27 mmol, 94% yield), an inseparable 1:1 mix of two symmetrical diastereomers; $δ_H$ (400 MHz, CDCl$_3$) 8.62 (s, 1H, maleimide NH from one symmetrical diastereomer), 8.66 (s, 1H, maleimide NH from one symmetrical diastereomer), 5.62 (d, 2H, J=8.4, 2×'Boc' NH from one symmetrical diastereomer), 5.51 (d, 2H, J=8.0, 2×'Boc' NH from one symmetrical diastereomer), 4.72-4.58 (m, 4×H-4 from both diastereomers), 3.80 (s, 6H, 2×H$_3$-6 from one symmetrical diastereomer), 3.79 (s, 6H, 2×H$_3$-6 from one symmetrical diastereomer), 3.68 (s, 2H, 2×H-8 from one symmetrical diastereomer), 3.64 (s, 2H, 2×H-8 from one symmetrical diastereomer), 3.46 (dd, 2H, J=4.8 and 12.0 Hz, 2×HH-7* from one symmetrical diastereomer), 3.37 (dd, 2H, J=6.0 and 14.4, 2×HH-7† from one symmetrical diastereomer), 3.21 (dd, 2H, J=4.8 and 14.0 Hz, 2×HH-7† from one symmetrical diastereomer), 3.11 (dd, 2H, J=6.4 and 14.0 Hz, 2×HH-7 from one symmetrical diastereomer), 1.463 (s, 18H, 6×H$_3$-1 from one symmetrical diastereomer), 14.460 (s, 18H, 6×H$_3$-1 from one symmetrical diastereomer);

*—signals shown as part of the same AB system by HMQC data
†—signals shown as part of the same AB system by HMQC data $δ_C$ (125 MHz, CDCl$_3$) 174.32 (2×C=O), 171.25 (2×C=O), 155.33 (2×C=O), 80.61 (2×C2), 80.58 (2×C2), 53.51 (2×C4), 53.18 (2×C4), 52.91 (2×C6), 52.90 (2×C6), 48.45 (2×C8), 47.89 (2×C8), 34.66 (2×C7), 34.59 (2×C7), 28.37 (6×C1), 28.36 (6×C1) Several carbon signals are missing due to overlap of the diastereomers; IR (thin film, neat) 3348, 2978, 1719 cm$^{-1}$; MS (EI) m/z (relative intensity): 566 ([M+H], 20), 564 ([M−H], 100); Exact mass calcd for $[C_{22}H_{35}N_3O_{10}S_2]$—H requires 564.1669 Found 564.1686.

Reference Example 41: Preparation of N-Ac-Cys(Mal)-Benzylamine

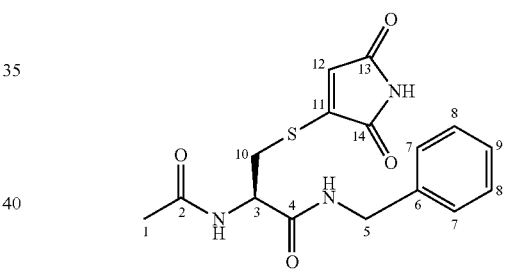

To N-Ac-Cys-Benzylamine (1.00 g, 4.00 mmol) above) in methanol (42 mL), was added bromomaleimide (777 mg, 4.37 mmol) in methanol (42 mL) dropwise over 5 minutes. After 10 minutes, solvent removed in vacuo and residue subjected to flash chromatography using 10% ethyl acetate in petroleum ether afford the desired compound as an off-white solid (429 mg, 1.2 mmol) in 100% yield, based on 69% recovery of the bromomaleimide. $δ_H$ (500 MHz, MeOD) 7.32-7.20 (m, 5H, 5×Ar-H), 6.45 (s, 1H, H-12), 4.71 (t, 1H, J=7.3, H-3), 4.38 (d, 2H, J=2.7, H$_2$-5), 3.40 (dd, 1H, J=7.0 and 13.6, HH-10), 3.25 (dd, 1H, J=7.2 and 13.6, HH-10), 1.99 (s, 3H, H$_3$-1); $δ_C$ (125 MHz, MeOD) 173.51 (C=O), 172.22 (C=O), 171.44 (C=O), 170.51 (C=O), 151.58 (C11), 139.48 (C6), 129.54 (2×Ar-H), 128.51 (2×Ar-H), 128.26 (C9), 121.01 (C12) 53.04 (C3), 44.25 (C5), 33.72 (C10), 22.42 (C1); IR (film, cm$^{-1}$) 3187 (w), 1717 (s), 1646 (s); MS (ES+) m/z (relative intensity): 370 ([M+Na], 20), 337 (50), 325 (90), 309 (100); Exact Mass Calcd for $[C_{16}H_{17}N_3O_4SN]$+Na requires m/z 370.0873 Found 370.0852 (ES+); UV (Acetonitrile) $ε_{213}$=19400, $ε_{247}$=4800 and $ε_{337}$=2700 cm$^{-1}$M$^{-1}$d$^3$; White solid decomposes at 180° C.

Reference Example 42: Preparation of N-Methyl hexylsulfanylmaleimide

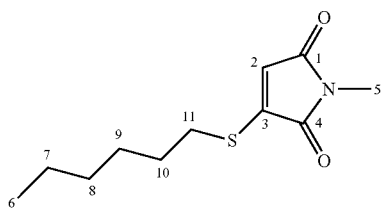

To N-methyl bromomaleimide (100 mg, 0.53 mmol) and sodium acetate trihydrate (70 mg, 0.53 mmol) in methanol (15 mL) was added hexanethiol (74 µL, 0.58 mmol) in methanol (100 mL) dropwise over 1 hour with vigorous stirring. After 5 minutes solvent was removed in vacuo. Purification by column chromatography (gradient elution in 10% ethyl acetate in petroleum ether to 30% ethyl acetate in petroleum ether) afforded the desired compound as a bright yellow solid (99 mg, 0.44 mmol) in 83% yield. $\delta_H$ (600 MHz, CDCl$_3$) 6.03 (s, 1H, H-2), 3.01 (s, 3H, H$_3$-5), 2.89 (t, 2H, J=7.6, 2H, H$_2$-11), 1.76-1.71 (m, 2H, H$_2$-10), 1.46-1.41 (m, 2H, H$_2$-9), 1.33-1.27 (m, 4H, H$_2$-7 and CH$_2$-8), 0.89 (t, 3H, J=6.5, H$_3$-6); $\delta_C$ (125 MHz, CDCl$_3$) 171.47 (C=O), 169.94 (C=O), 151.84 (C3), 117.27 (C2), 31.92 (C11), 31.31 (CH$_2$), 28.64 (CH$_2$), 27.75 (CH$_2$), 24.10 (C5), 24.10 (C7), 14.09 (C6); IR (oil, cm$^{-1}$) 2727 (w), 1708 (s); MS (FAB+) m/z (relative intensity): 250 ([M+Na], 40), 228 (35), 199 (30), 176 (100); Exact Mass Calcd for [C$_{11}$H$_{17}$NO$_2$S]+Na requires m/z 250.0878 Found 250.0880 (FAB+)

Reference Example 43: Preparation of 2,3 Dihexylsulfanylsuccinimide and Hexylsulfanylmaleimide

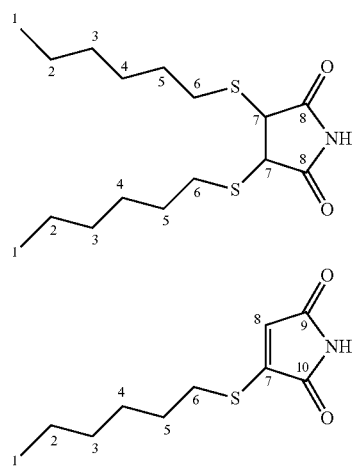

Method A

To bromomaleimide (300 mg, 1.69 mmol) and sodium acetate (138 mg, 1.69 mmol) in methanol (60 mL) was added hexanethiol (356 µL, 2.50 mmol). After 5 minutes solvent removed in vacuo and purification by flash chromatography (10% ethyl acetate in petroleum ether) afforded 2,3 dihexanethiosuccinimide as a bright yellow paste (13 mg, 0.04 mmol) in 2% and hexylsulfanylmaleimide as a cream powder (alkene 310 mg, 1.46 mmol) in 86% yield.

2,3 Dihexylsulfanylsuccinimide $\delta_H$ (500 MHz, CDCl$_3$) 8.21 (s, 1H, NH), 3.49 (s, 2H, 2×H-7), 2.89-2.83 (m, 2H, 2×HH-6), 2.79-2.83 (m, 2H, 2×HH-6), 1.71-1.57 (m, 4H, 2×CH$_2$), 1.44-1.37 (m, 4H, 2×CH$_2$), 1.34-1.26 (m, 8H, 4×CH$_2$), 0.89 (t, 6H, J=6.8, 2×H$_3$-1); $\delta_C$ (125 MHz, CDCl$_3$) 174.60 (2×C=O), 48.23 (2×C$_7$), 32.34 (2×CH$_2$), 31.26 (2×CH$_2$), 28.99 (2×CH$_2$) 28.46 (2×CH$_2$), 22.56 (2×CH$_2$), 14.27 (2×C1); IR (solid, cm$^{-1}$) 3198 (m), 2928 (m), 1703 (s); No mass ion found.

Hexylsulfanylmaleimide $\delta_H$ (500 MHz, CDCl$_3$) 7.35 (s, 1H, NH), 6.04 (s, 1H, H-8), 2.91 (t, 2H, H$_2$-6), 1.78-1.72 (m, 2H, H$_2$-5), 1.48-1.42 (m, 2H, CH$_2$), 1.33-1.30 (m, 4H, 2×CH$_2$), 0.90 (t, 3H, J=6.9, H$_3$-1); $\delta_C$ (125 MHz, CDCl$_3$) 169.06 (C=O), 167.69 (C=O), 152.74 (C7), 118.24 (C8), 32.06 (C6), 31.26 (CH$_2$), 28.58 (CH$_2$), 27.70 (CH$_2$), 22.52 (CH$_2$), 14.03 (C1); IR (solid, cm$^{-1}$) 3200 (m), 2918 (m), 1703 (s); MS (ES−) m/z (relative intensity): 212 ([M−H], 100); Exact Mass Calcd for [C$_{10}$H$_{15}$NO$_2$S]—H requires m/z 212.0745. Found 212.0753 (ES−); m.p. 99-101° C.; UV (Acetonitrile) $\epsilon_{247}$=12000 and $\epsilon_{347}$=9500 cm$^{-1}$M$^{-1}$ d$^3$.

Method B

To bromomaleimide (300 mg, 1.69 mmol) and sodium acetate (138 mg, 1.69 mmol) in methanol (100 mL) was added hexanethiol (237 µL, 1.69 mmol). After 5 minutes solvent removed in vacuo and purification by flash chromatography (10% ethyl acetate in petroleum ether) afforded hexylsulfanylmaleimide as a cream powder (362 mg, 1.69 mmol) in 100% yield.

Reference Example 44: Preparation of N-Methylenecyclohexane hexylsulfanylmaleimide

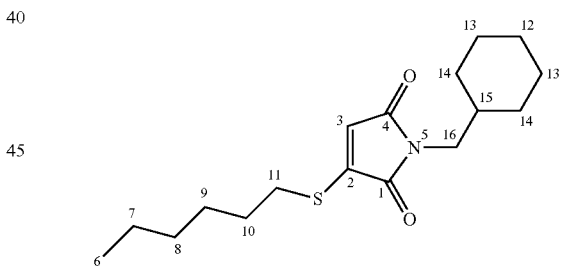

To N-methylenecyclohexane bromomaleimide (50 mg, 0.19 mmol) in methanol (50 mL), was added hexanethiol (52 µL, 0.37 mmol) and sodium acetate (50 mg, 0.37 mmol) in methanol (50 mL) dropwise over 5 minutes. After 10 minutes, solvent removed in vacuo and residue subjected to flash chromatography (petroleum ether) to afford the desired compound as an off-white solid (29 mg, 0.09 mmol) in 84% yield. $\delta_H$ (600 MHz, CDCl$_3$) 6.01 (s, 1H, H-3), 6.27 (s, 1H, 9-H), 3.42 (d, 1H, J=6.8, NH), 4.67 (ddd, 1H, J=5.1, 5.4 and 6.8, H-4), 3.80 (s, 3H, H$_3$-6), 3.48 (dd, 1H, J=5.1 and 13.8, HH-7), 3.62 (dd, 1H, J=5.4 and 14.1, HH-7) 1.45 (s, 9H, 3×H$_3$-1); $\delta_C$ (125 MHz, CDCl$_3$) 170.23 (C=O), 16844 (C=O), 151.49 (C2), 117.08 (C3), 44.36 (C16), 37.00 (C15), 31.91 (2×CH$_2$), 31.32 (2×CH$_2$), 30.73 (CH$_2$), 28.66 (CH$_2$), 27.78 (CH$_2$), 26.33 (CH$_2$), 25.73 (2×CH$_2$), 22.58 (CH$_2$), 14.10 (C6); IR (solid, cm$^{-1}$) 2927 (m), 1700 (s); MS (ES+) m/z, (relative intensity): 310 ([M+H], 100), 180 (40); Mass calcd for [C$_{17}$H$_{27}$O$_2$NS]+H requires 310.1841 Found 310.1828 (ES+).

Reference Example 45: Preparation of 3-Mercaptopropylthiomaleimide and 1,5-Dithio-8-aza-bicyclo[5,3,0]decan-7,9-dione

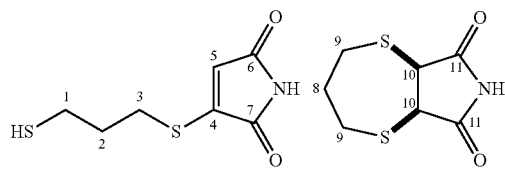

To bromomaleimide (30 mg, 0.17 mmol) and sodium acetate (14 mg, 0.17 mmol) in methanol (6 mL) was added 1,3-propanedithiol (17 μl, 0.17 mmol). After five minutes solvent was removed in vacuo and purification by flash chromatography (10% ethyl acetate in petroleum ether) afforded 3-mercaptopropylthiomaleimide and 1,5-dithio, 8-aza-bicyclo[5,3,0]decan-7,9-dione as a pale yellow powder that was a mix of two inseparable isomers 3-mercaptopropylthiomaleimide (7 mg, 0.03 mmol) in 21% yield, 1,5-dithio, 8-aza-bicyclo[5,3,0]decan-7,9-dione (12 mg, 0.06 mmol) in 34% yield. $\delta_H$ (500 MHz, MeOD) 6.28 (s, 1H, H-5), 4.41 (s, 3.2H, 2×H-10), 3.15 (t, 2H, J=7.3, H$_2$-3), 2.82-2.77 (m, 3.2H, CH$_2$), 2.35 (t, 3.2H, J=13.1, CH$_2$), 2.30-2.25 (m, 2H, CH$_2$), 2.20-2.13 (m, 2H, CH$_2$), 1.91-1.83 (m, 3.2H, CH$_2$); $\delta_C$ (125 MHz, MeOD) 177.79 (2×C$_{11}$), 172.33 (C=O), 170.56 (C=O), 152.37 (C$_4$), 120.30 (C$_5$), 54.52 (2×C$_{10}$), 34.94 (2×C$_9$), 32.16 (CH$_2$), 31.10 (CH$_2$) 30.96 (CH$_2$), 27.49 (CH$_2$); IR (solid, cm$^{-1}$) 3246 (m), 1703 (s); MS (ES−) m/z (relative intensity): 202 ([M−H], 100); Exact Mass Calcd for [C$_7$H$_9$NO$_2$S$_2$]—H requires m/z 201.9996 Found 201.9996 (ES−).

Reference Example 46: Preparation of N-Phenyl hexylsulfanylmaleimide

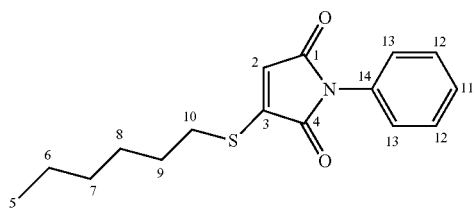 [SMILES: CCCCCCSC1=CC(=O)N(c2ccccc2)C1=O]

To hexanethiol (111 μL, 0.79 mmol) and sodium acetate trihydrate (108 mg, 0.79 mmol) in methanol (60 mL) was added in N-phenyl monobromomaleimide (200 mg, 0.79 mmol) in methanol (60 mL) dropwise over 1 hour with vigorous stirring. After 5 minutes solvent was removed in vacuo. Purification by column chromatography (gradient elution in 10% ethyl acetate in petroleum ether to 30% ethyl acetate in petroleum ether) afforded the desired compound as a pale yellow solid (109 mg, 0.38 mmol) in 48% yield. $\delta_H$ (600 MHz, CDCl$_3$) 7.45 (dd, 2H, J=7.1 and 8.0, 2×H-12), 7.36 (d, 2H, J=6.0, H-11), 7.35 (d, 2H, J=8.1, 2×H-13), 6.19 (s, 1H, H-2), 2.96 (t, 2H, J=7.9, H$_2$-10), 1.81-1.76 (m, 2H, H$_2$-9), 1.50-1.45 (m, 2H, H$_2$-8), 1.34-1.32 (m, 4H, H$_2$-6 and H$_2$-7), 0.91 (t, 3H, J=6.9, H$_3$-5); $\delta_C$ (125 MHz, CDCl$_3$) 168.59 (C=O), 166.96 (C=O), 152.20 (C3), 131.53 (C14), 129.21 (2×Ar-H), 127.93 (C11), 126.09 (2×Ar-H), 117.24 (C2), 32.03 (C10), 31.33 (CH$_2$), 28.68 (CH$_2$), 27.78 (CH$_2$), 22.59 (CH$_2$), 14.11 (C5); IR (oil, cm$^{-1}$) 2931 (w), 1703 (s); MS (CI+) m/z (relative intensity): 290 ([M+H], 100); Exact Mass Calcd for [C$_{16}$H$_{20}$NO$_2$S]+H requires m/z 290.1215 Found 290.1224 (CI+);

Reference Example 47: Preparation of Phenylthiomaleimide

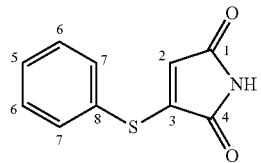 [SMILES: O=C1C=C(Sc2ccccc2)C(=O)N1]

To thiophenol (57 μL, 0.56 mmol) and sodium acetate trihydrate (136 mg, 0.56 mmol) in methanol (30 mL) was added in monobromomaleimide (100 mg, 0.56 mmol) in methanol (30 mL) dropwise over 1 hour with vigorous stirring. After 5 minutes solvent was removed in vacuo. Purification by column chromatography (gradient elution in 10% ethyl acetate in petroleum ether to 30% ethyl acetate in petroleum ether) afforded the desired compound as a pale yellow solid (22 mg, 0.11 mmol) in 19% yield. $\delta_H$ (600 MHz, CDCl$_3$) 7.56 (dd, 2H, J=1.6 and 7.8, 2×H-7), 7.50-7.48 (m, 3H, 3×Ar), 5.63 (s, 1H, H-2); $\delta_C$ (125 MHz, CDCl$_3$) 169.42 (C=O), 167.98 (C=O), 153.60 (C3), 134.45 (2×Ar-H), 130.68 (C5), 130.42 (2×Ar-H), 127.27 (C8), 119.91 (C2); IR (oil, cm$^{-1}$) 3265 (m), 1770 (m), 1701 (s); MS (CI+) m/z (relative intensity): 206 ([M+H], 100), 111 (40); Exact Mass Calcd for [C$_{10}$H$_7$NO$_2$S]+H requires m/z 206.0276 Found 206.0273 (CI+);

Reference Example 48: Preparation of 1,4-Dithia-7-aza-spiro[4.4]nonane-6,8-dione

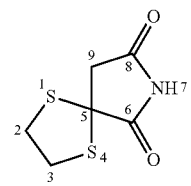

To bromomaleimide (30 mg, 0.17 mmol) and sodium acetate (14 mg, 0.17 mmol) in methanol (6 mL) was added 1,2-ethanedithiol (17 μl, 0.17 mmol). After five minutes solvent removed in vacuo and purification by flash chromatography (10% ethyl acetate in petroleum ether) afforded the desired compound as a pale yellow powder (13 mg, 0.07 mmol) in 41% yield. $\delta_H$ (500 MHz, CDCl$_3$) 8.39 (s, 1H, NH), 3.75-3.69 (m, 2H, HH-2 and HH-3), 3.60-3.53 (m, 2H, HH-2 and HH-3), 3.30 (s, 2H, H$_2$-9); $\delta_C$ (125 MHz, CDCl$_3$) 177.93 (C=O), 172.76 (C=O), 61.23 (C$_5$), 43.12 (C$_9$), 41.05 (C$_2$ and C$_3$); IR (solid, cm$^{-1}$) 3290 (m), 1703 (m), 1629 (s); MS (ES−) m/z (relative intensity): 188 ([M−H], 100); Exact Mass Calcd for [C$_6$H$_7$NO$_2$S$_2$]—H requires m/z 187.9840 Found 187.9839 (ES−); m.p. 112-115° C.

Example 10: Preparation of (S)-methyl 2-(tert-butoxycarbonylamino)-3-(1-(2-(5-(dimethylamino)naphthalene-1-sulfonamido)ethyl)-2,5-dioxo-2,5-dihydro-1H-pyrrol-3-ylthio)propanoate

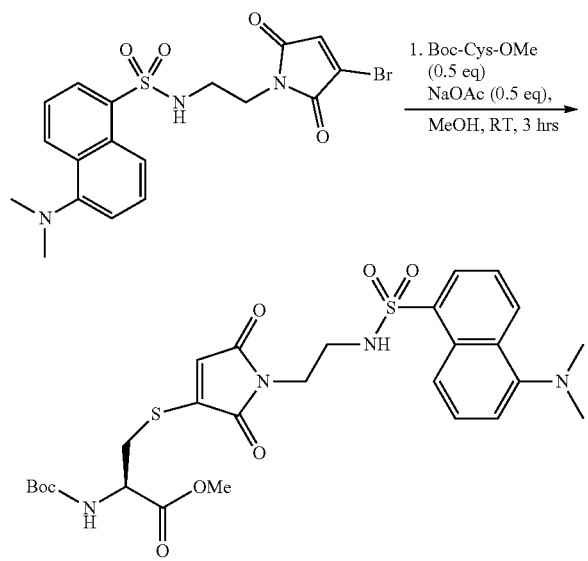

Dansyl-bromomaleimide (100 mg) was dissolved in methanol (200 ml) by briefly heating the stirring solution using a heat gun. To the resulting pale yellow solution, N-Boc-Cys-OMe (22 μl, 0.1 mmol, 0.5 eq) and sodium acetate (14.5 mg, 0.1 mmol, 0.5 eq)) were added over 3 hours. The reaction was monitored by TLC (eluent: 40% EtOAc: 60% Petroleum ether) Once the addition was complete the methanol was removed in vacuo to yield a yellow oil. Purification by column chromatography yielded the desired product (48.29 mg, 0.08 mmol, 79.7%). $^1$H NMR (600 MHz CDCl3): $\delta_H$ 8.54 (d, J=8.56 Hz, 1H, CH), 8.21 (d, 1H, J=8.27 Hz, CH), 8.13 (d, 1H, J=8.57 Hz, CH), 7.55 (m, 2H, 2×CH), 7.25 (d, J=7.60 Hz, 1H, CH), 5.92 (s, 1H, CH), 4.44 (m, 1H, HN—CH—CO), 3.77 (s, 3H, OMe), 3.48 (m, 2H, CH$_2$), 3.44 (m, 2H, CH$_2$), 3.38 (s, 6H, 2×CH$_3$), 3.13 (t, J=5.79, 2H, S—CH$_2$) 2.88 (s, 9H, 3×CH$_3$). $^{13}$C NMR (600 MHz CDCl3): 173.08, 170.52, 169.69, 168.96 (4×C=O), 157.73 (—C=CH), 153.16, 150.71, 136.48, 131.39, 131.25, 131.18, 130.74, 130.65, 129.31, 124.35, 120.61, 119.22, 81.12, 53.58, 52.95, 45.89, 41.53, 33.98, 28.66. IR: 3324.7 cm$^{-1}$, 1775 cm$^{-1}$. [M+H]$^+$: 605.1756, calculated; 605.1740.

Example 11: Preparation of (2R,2'R)-dimethyl 3,3'-(1-(2-(5-(dimethylamino)naphthalene-1-sulfonamido)ethyl)-2,5-dioxopyrrolidine-3,4-diyl)bis(sulfanediyl)bis(2-($^t$butoxycarbonylamino)propanoate)

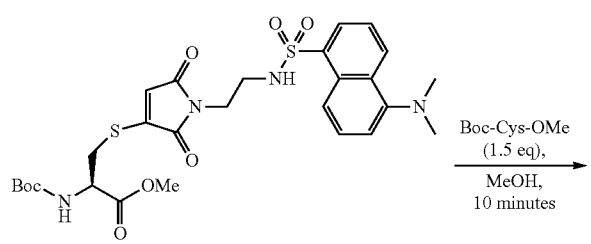

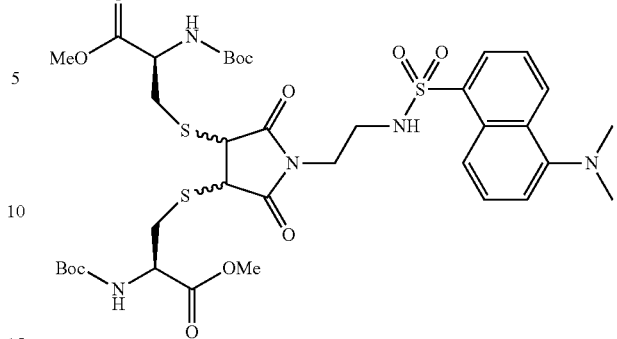

Dansyl/maleimide/cysteine adduct (15 mg, 0.0247 mmol, 1 eq) was dissolved in methanol (100 ml). To the resulting clear solution, N-Boc-Cys-OMe (3.1 μl, 0.0247 mmol, 1 eq) was added over 1 hour. The reaction was monitored by TLC (eluent: 40% EtOAc: 60% Petroleum ether) Once the addition was complete the methanol was removed in vacuo to yield the desired product (12.51 mg, 0.08 mmol, 60%). $^1$H NMR (600 MHz CDCl3): $\delta_H$ 8.44 (d, J=8.56 Hz, 1H, CH), 8.13 (m, 2H, 2×CH), 7.49 (m, 2H, 2×CH), 7.17 (m, 2H, 2×CH), 4.49 (bs, 1H, HN—CH—CO), 3.77 (s, 3H, OMe), 3.48 (m, 2H, CH$_2$), 3.44 (m, 2H, CH$_2$), 3.38 (s, 6H, 2×CH$_3$), 3.13 (t, J=5.79, 2H, S—CH$_2$) 2.88 (s, 9H, 3×CH$_3$).

Example 12: Preparation of Di-dansyl-cystamine-maleimide

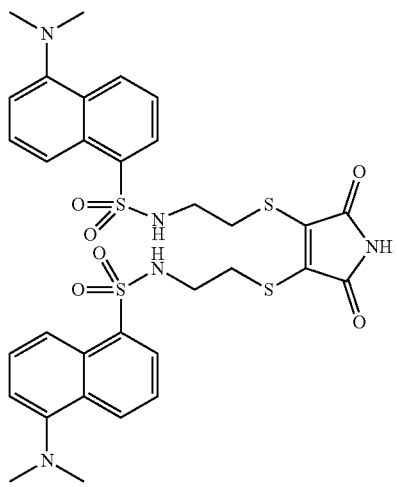 [SMILES: CN(C)c1cccc2c(S(=O)(=O)NCCSC3=C(SCCNS(=O)(=O)c4cccc5c(N(C)C)cccc45)C(=O)NC3=O)cccc12]

A round bottomed flask was charged with di-dansyl cystamine (100 mg, 0.16 mmol), TCEP (46 mg, 1 eq) and MeOH (10 ml). The reaction mixture was stirred at ambient temperature under argon for 3 hrs. Dibromomaleimide (36 mg, 0.9 eq), in MeOH (5 ml) was then added to the reaction mixture. After 30 mins NaOAc (56 mg, 4 eq), was added to the reaction mixture and the solvent evaporated in vacuo. The residue was worked up with DCM and brine. The organic layers were combined, dried (MgSO$_4$), filtered and concentrated in vacuo. Purification by flash chromatography (silica gel, 0-20% EtOAc-DCM) afforded the desired compound as a yellow gum (40 mg, 40%). $^1$HNMR (CDCl$_3$, 600 MHz), δ8.5 (2H, d J 8.5 Hz aromatic H's), δ8.2 (4H, m aromatic H's), δ7.53 (1H, s CONH), δ7.46 (4H, m, aromatic H's), δ7.1 (2H, d, J 7.4 Hz aromatic H's), δ5.65 (2H, t, J 6.27

SO₂NH), δ3.3 (4H, t, J 6.0 SCH₂), δ3.17 (4H, q, J 6.0 NHCH₂), δ2.8 (12H, s NCH₃); ¹³CNMR (CDCl₃, 150 MHz), δ165.9, 152.0, 136.5, 134.7, 130.7, 129.94, 129.85, 129.62, 129.57, 128.63, 123.3, 118.8, 115.4, 45.5, 43.6, 31.8; IR (cm⁻¹) 3288 (br) 1720 (s) MS (Na+) m/z relative intensity: 736 (M, 100); Exact mass calculated for [C₃₂H₃₅N₅O₆NaS₄] requires m/z 736.1368, Found 736.1390 (Na+).

Reference Example 49: Preparation of Bromo-dansyl-cystamine-maleimide

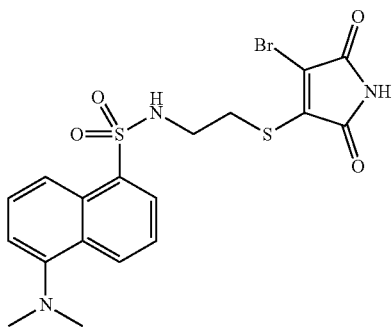 [SMILES: CN(C)c1cccc2c(S(=O)(=O)NCCSC3=C(Br)C(=O)NC3=O)cccc12]

A round bottomed flask was charged with di-dansyl cystamine (48 mg, 0.08 mmol), TCEP (23 mg, 1 eq), and MeOH (10 ml). The reaction mixture was stirred at ambient temperature under argon for 3 hrs. Dibromomaleimide (41 mg, 2 eq) in MeOH (10 ml), was added to the reaction mixture. After 16 hrs, the reaction mixture was concentrated in vacuo. The residue was worked up with DCM and brine. The organic layers were combined, dried (MgSO₄) and purified by flash chromatography (silica gel, 0-15% EtOAC-DCM) to yield the desired compound (17 mg, 22%). ¹HNMR (CDCl₃, 600 MHz), δ8.5 (1H, d J 8.5 Hz aromatic H's), δ8.2 (2H, m aromatic H's), δ7.6 (1H, s CONH), δ7.53 (2H, m, aromatic H's), δ7.15 (1H, d, J 7.4 Hz aromatic H's), δ5.30 (1H, t, J 5.6 SO₂NH), δ3.38 (2H, t, J 6.3 SCH₂), δ3.26 (2H, q, J 6.3 NHCH₂), δ2.88 (6H, s NCH₃); ¹³CNMR (CDCl₃, 150 MHz), δ165.5, 162.9, 152.2, 142.5, 134.5, 130.95, 129.94, 129.92, 129.5, 128.7, 123.3, 119.0, 118.5, 115.4, 45.5, 43.7, 30.5; IR (cm⁻¹) 3295 (br) 1726 (s) MS (ES+) m/z relative intensity: 485 (M, 100); Exact mass calculated for [C₁₈H₁₉N₃O₄S₂Br] requires m/z 484.0000, Found 783.9982.

Reference Example 50: Preparation of Dansyl-cystamine-maleimide

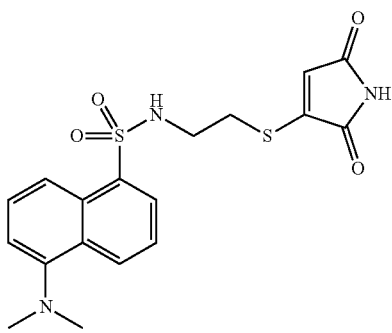 [SMILES: CN(C)c1cccc2c(S(=O)(=O)NCCSC3=CC(=O)NC3=O)cccc12]

A round bottomed flask was charged with di-dansyl cystamine (100 mg, 0.16 mmol), TCEP (46 mg, 1 eq), and MeOH (10 ml). The reaction mixture was stirred at ambient temperature under argon for 3 hrs. Bromomaleimide (56 mg, 2 eq) in MeOH (5 ml), was added to the reaction mixture. After 16 hrs, the reaction mixture was concentrated in vacuo. The residue was worked up with DCM and brine. The organic layers were combined, dried (MgSO₄) and purified by flash chromatography (silica gel, 0-30% EtOAC-CHCl₃) to yield the desired compound (73 mg, 55%). ¹HNMR (CDCl₃, 600 MHz), δ8.5 (1H, dJ 8.5 Hz aromatic H's), δ8.2 (2H, m aromatic H's), δ8.1 (1H, s CONH), δ7.5 (2H, m, aromatic H's), δ7.15 (1H, d, J 7.5 Hz aromatic H's), δ6.0 (1H, s, CO₂CH) δ5.89 (1H, t, J 6.4 SO₂NH), δ3.20 (2H, q, J 6.7 NHCH₂), δ3.99 (2H, t, J 6.9 SCH₂), δ2.86 (6H, s NCH₃); ¹³CNMR (CDCl₃, 150 MHz), δ169.6, 168.0, 152.0, 150.7, 134.4, 131.0, 129.9, 129.7, 129.5, 128.8, 123.4, 119.3, 118.7, 115.6, 45.5, 41.0, 31.8; IR (cm⁻¹) 3277 (br) 1720 (s) MS (ES-) m/z relative intensity: 404 (M, 100); Exact mass calculated for [C₁₈H₁₈N₃O₄S₂] requires m/z 404.0739, Found 404.0733.

Example 13: Preparation of N-propionic-acid-methyl-ester-di-dansyl-cystamine-maleimide

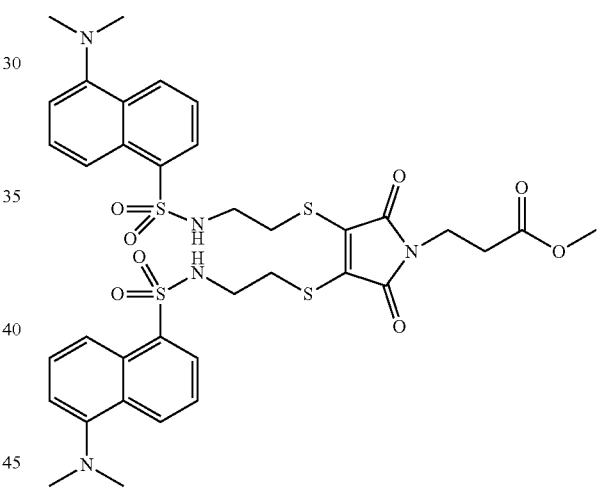

A round bottomed flask was charged with di-dansyl cystamine (132 mg, 0.214 mmol), TCEP (61 mg, 1 eq) and MeOH (10 ml). The reaction mixture was stirred at ambient temperature under argon for 3 hrs. The dibromomaleimide (70 mg, 1 eq), in MeOH (5 ml) was then added to the reaction mixture. After 30 mins NaOAc (88 mg, 5 eq), was added to the reaction mixture and the solvent evaporated in vacuo. The residue was worked up with DCM and brine. The organic layers were combined, dried (MgSO₄), filtered and concentrated in vacuo. Purification by flash chromatography (silica gel, 0-20% EtOAc-DCM) afforded the desired compound as a yellow gum (32 mg, 20%). ¹HNMR (CDCl₃, 300 MHz), δ8.5 (2H, d J 8.5 Hz aromatic H's), δ8.2 (4H, m aromatic H's), δ7.53 (1H, s CONH), δ7.45 (4H, m, aromatic H's), δ7.1 (2H, d, J 7.5 Hz aromatic H's), δ5.7 (2H, t, J 6.1 SO₂NH), δ3.75 (2H, t, J 7.0 CONCH₂), δ3.6 (3H, s, OCH₃), δ3.2 (4H, m, SCH₂), δ3.18 (4H, m, NHCH₂), δ2.9 (12H, s, NCH₃), δ2.6 (2H, t, J 7.1 NHCH₂); ¹³CNMR (CDCl₃, 75 MHz), δ171.3, 165.9, 135.8, 134.8, 130.5, 129.8, 129.5, 129.4, 128.4, 123.3, 119.0, 115.3, 51.9, 45.5, 43.5, 34.3, 32.6

31.9; IR (cm$^{-1}$) 3295 (br) 2948 (br) 1702 (s) MS (ES−) m/z relative intensity: 798 (M, 100); Exact mass calculated for [$C_{36}H_{40}N_5O_8S_4$] requires m/z 798.1760, Found 798.1715.

Reference Example 51: Preparation of N-propionic-acid-methyl-ester-bromo-dansyl-cystamine-maleimide

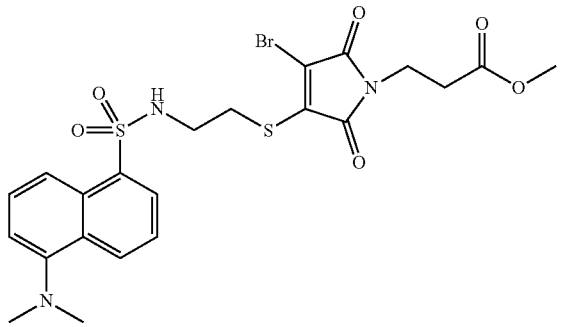 [SMILES: COC(=O)CCN1C(=O)C(Br)=C(SCCNS(=O)(=O)c2cccc3c(N(C)C)cccc23)C1=O]

A round bottomed flask was charged with di-dansyl cystamine (66 mg, 0.107 mmol), TCEP (31 mg, 1 eq) and MeOH (10 ml). The reaction mixture was stirred at ambient temperature under argon for 3 hrs. The dibromomaleimide (70 mg, 0.5 eq), in MeOH (5 ml) was then added to the reaction mixture. After 16 hrs NaOAc (88 mg, 5 eq), was added to the reaction mixture and the solvent evaporated in vacuo. The residue was worked up with DCM and brine. The organic layers were combined, dried (MgSO$_4$), filtered and concentrated in vacuo. Purification by flash chromatography (silica gel, 0-2% MeOH—CHCl$_3$) afforded the desired compound as a yellow gum (20 mg, 16%). $^1$HNMR (CDCl$_3$, 300 MHz), δ8.5 (1H, m, aromatic H), δ8.2 (2H, m aromatic H's), δ7.5 (2H, m, aromatic H's), δ7.2 (1H, d, J 7.5 Hz aromatic H), δ5.2 (1H, t, J 6.1 SO$_2$NH), δ3.8 (2H, t, J 7.0 CONCH$_2$), δ3.7 (3H, s, OCH$_3$), δ3.4 (2H, m, SCH$_2$), δ3.3 (2H, m, NHCH$_2$), δ2.9 (6H, s, NCH$_3$), δ2.6 (2H, t, J 7.1 NHCH$_2$); $^{13}$CNMR (CDCl$_3$, 75 MHz), δ170.95, 165.5, 163.3, 141.6, 134.5, 130.8, 129.8, 129.5, 128.5, 123.2, 118.6, 115.3, 52.0, 45.4, 43.6, 34.8, 32.5 30.6; IR (cm$^{-1}$) 3296 (br) 2948 (br) 1713 (s)

Example 14: Preparation of N-diethylene-glycol-monomethyl-ether-di-dansyl-cystamine-maleimide

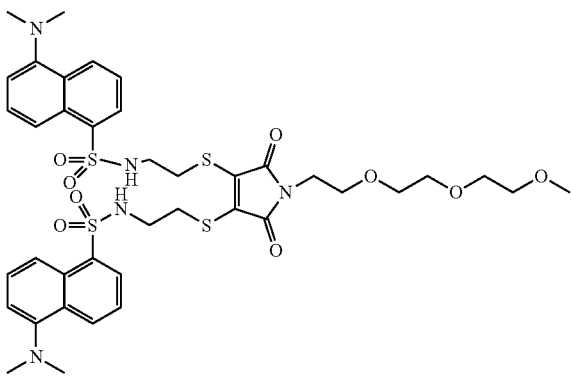 [SMILES: COCCOCCOCCN1C(=O)C(SCCNS(=O)(=O)c2cccc3c(N(C)C)cccc23)=C(SCCNS(=O)(=O)c2cccc3c(N(C)C)cccc23)C1=O]

A round bottomed flask was charged with di-dansyl cystamine (155 mg, 0.25 mmol), TCEP (72 mg, 1 eq) and MeOH (10 ml). The reaction mixture was stirred at ambient temperature under argon for 3 hrs. PEG-dibromomaleimide (100 mg, 1 eq), in MeOH (5 ml) was then added to the reaction mixture. After 16 hrs NaOAc (102 mg, 5 eq), was added to the reaction mixture and the solvent evaporated in vacuo. The residue was worked up with DCM and brine. The organic layers were combined, dried (MgSO$_4$), filtered and concentrated in vacuo. Purification by flash chromatography (silica gel, 0-10% THF-DCM) afforded the desired compound as a yellow gum (13 mg, 6%). $^1$HNMR (MeOH, 300 MHz), δ8.5 (2H, m, aromatic H's), δ8.3 (2H, m aromatic H's), δ8.13 (2H, m, aromatic H's), δ7.5 (4H, m, aromatic H's), δ7.2 (2H, m, aromatic H's), δ3.5 (12H, m, CONCH$_2$, OCH$_2$), δ3.3 (3H, s, OCH$_3$), δ3.1 (8H, m, SCH$_2$, NHCH$_2$), δ2.8 (12H, s, NCH$_3$); $^{13}$CNMR (CDCl$_3$, 150 MHz), δ167.4, 153.2, 136.9, 136.2, 131.3, 131.2, 130.9, 130.2, 129.6, 124.3, 120.5, 116.4, 72.9, 71.4, 71.3, 71.1, 68.7, 59.1, 45.8, 44.5, 38.98, 36.97; IR (cm$^{-1}$) 3323 (br) 2946 (br) 2946 (s) 1017 (s) MS (Na+) m/z relative intensity: 882 (M, 100); Exact mass calculated for [$C_{39}H_{49}N_5O_9NaS_4$] requires m/z 882.2311, Found 882.2294 (Na+).

Reference Example 52: Preparation of Glu-Cys(Mal)-Gly

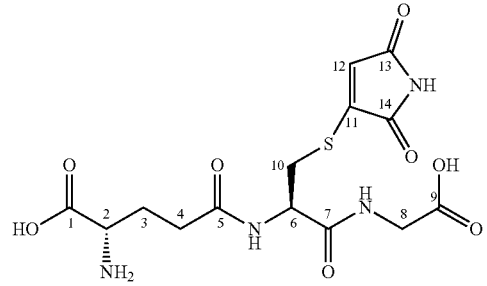 [SMILES: N[C@@H](CCC(=O)N[C@@H](CSC1=CC(=O)NC1=O)C(=O)NCC(=O)O)C(=O)O]

To glutathione (47 mg, 0.15 mmol) in methanol (3 mL) was added bromomaleimide (30 mg, 0.15 mmol) in methanol (3 mL). After five minutes solvent removed in vacuo to afford the desired compound as a thick colourless oil (62 mg, 0.15 mmol) in 100% yield. $δ_H$ (500 MHz, MeOD) 6.47 (s, 1H, H-12), 4.79 (dd, 1H, J=5.7 and 8.2, H-6), 4.06 (t, 1H, J=6.5, H-2), 3.95 (s, 2H, H$_2$-8), 3.49 (dd, 1H, J=5.8 and 13.9, HH-10), 3.29 (dd, 1H, J=8.3 and 13.6, HH-10), 2.61 (t, 2H, J=7.1, H$_2$-4), 2.29-2.15 (m, 2H, H$_2$-3); $δ_C$ (125 MHz, MeOD) 174.68 (C=O), 172.81 (C=O), 172.39 (C=O), 171.89 (C=O), 171.62 (C=O), 170.59 (C=O), 151.75 (C11), 120.91 (C12), 53.79 (C6), 52.76 (C2), 42.01 (C8), 33.92 (C10) 32.42 (C4), 27.03 (C3); IR (oil, cm$^{-1}$) 3259 (m), 2928 (m), 1717 (s); MS (ES−) m/z (relative intensity): 401 ([M−H], 100), 272 (30); Exact Mass Calcd for [$C_{14}H_{18}N_4O_8S$]—H requires m/z 401.0767 Found 401.0773 (ES−); UV (Acetonitrile) $ε_{204}$=8100, $ε_{25}3$=5600 and $ε_{342}$=1900 cm$^{-1}$M$^{-1}$d$^3$.

Reference Example 53: Preparation of Preparation of Boc-Cys(MeMal)-Phe-$^i$Pr

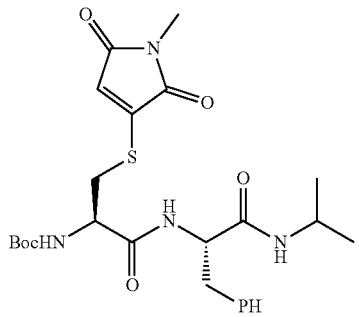

O-(Benzotriazol-1-yl)-N,N,N',N'-tetramethyluronium hexafluorophosphate (344 mg, 0.82 mmol) was added to a stirred solution of (2R)-2-[(tert-butoxycarbonyl)amino]-3-[(1-methyl-2,5-dioxo-2,5-dihydro-1H-pyrrol-3-yl)sulfanyl] propanoic acid (313 mg, 0.95 mmol) and 1-hydroxybenzotriazole hydrate (139 mg) in DMF (2 mL) and the reaction was stirred at 21° C. for 3 mins. A solution of (2S)-1-oxo-3-phenyl-1-(propan-2-ylamino)propan-2-ammonium trifluoroacetate (262 mg, 0.82 mmol) in DMF (1.5 mL) was added to the reaction mixture followed by N,N-diisopropylethylamine (294 µL, 1.64 mmol) and the reaction stirred at 21° C. for 4 h. The solvent was removed in vacuo and the residue dissolved in EtOAc (60 mL) and washed with 1 M HCl (×3), H$_2$O (×1), sat NaHCO$_3$ (×3), 10% LiCl (×1) and sat. NaCl (×1), dried (MgSO$_4$), filtered and the solvent removed in vacuo. Purification by precipitation (CHCl$_3$/petroleum ether 40-60) gave the desired compound as a pale brown solid (359 mg, 0.69 mmol, 84% yield): $^1$H NMR (600 MHz, CD$_3$CN, 25° C.) δ 7.32-7.28 (m, 2H), 7.25-7.21 (m, 3H), 7.11 (d, J=7.7 Hz, 1H), 6.46 (d, J=6.3 Hz, 1H), 6.42 (s, 1H), 4.46 (td, J=7.6, 6.5 Hz, 1H), 4.31 (td, J=7.3, 6.4 Hz), 3.88 (septets of doublet, J=6.6, 6.3 Hz, 1H), 3.30 (dd, J=13.7, 5.8 Hz, 1H), 3.16 (dd, J=13.7, 7.4 Hz, 1H), 2.95 (dd, J=13.8, 7.5 Hz, 1H), 2.93 (s, 3H), 1.43 (s, 9H), 1.07 (d, J=6.6 Hz, 3H), 1.02 (d, J=6.6 Hz, 3H); $^{13}$C NMR (151 MHz, CD$_3$CN, 25° C.) δ 169.39, 168.84, 168.77, 167.85, 155.17, 149.33, 136.77, 129.10, 127.98, 126.30, 118.57, 79.49, 54.10, 52.62, 40.91, 37.44, 32.43, 27.15, 22.95, 21.24, 21.17; IR (thin film) 3301, 2973, 1770, 1701, 1674, 1641, 1525 cm$^{-1}$; LRMS (EI) 518 (24%, [M]$^+$·), 432 (23), 219 (33), 149 (21) 110 (27), 86 (37), 84 (100); HRMS (EI) calcd for C$_{25}$H$_{34}$N$_4$O$_6$S [M]$^+$· 518.2194, observed 518.2199.

Reference Example 54: Deprotection of Boc-Cys(MeMal)-Phe-$^i$Pr

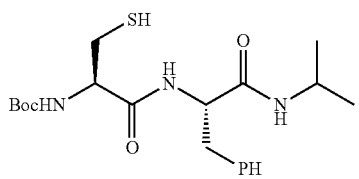

Tris(2-carboxyethyl)phosphine hydrochloride (138 mg, 0.48 mmol) in 150 mM phosphate buffer (pH 8, 25 mL) was added to a stirred solution of Boc-Cys(MeMal)-Phe-$^i$Pr (50 mg, 97 µmol) in MeCN (25 mL) and the reaction stirred at 21° C. for 10 min. Synthesis of Boc-Cys-Phe-$^i$Pr was confirmed by LCMS (ES$^-$) 408.7 (100%).

Reference Example 55: Cloning and Expression of Grb2-SH2 L111C Mutant

Sequence of Grb2-SH2 L111C (residues 53-163):
(SEQ ID NO: 1)
M G I E M K P H P W F F G K I P R A K A E E M L S
K Q R H D G A F L I R E S E S A P G D F S L S V K
F G N D V Q H F K V C R D G A G K Y F L W V V K F
N S L N E L V D Y H R S T S V S R N Q Q I F L R D
I E Q V P Q Q P T Y V Q A G S R S H H H H H H
Stop.
Calculated mass = 14171

The DNA construct for the Grb2 SH2 domain contained the primary amino acid sequence 53-163 and was cloned on plasmid QE-60 (Qiagen). The Grb2 SH2 L111C mutant was constructed by site-directed mutagenesis (Stratagene Kit) using oligonucleotides coding for the mutated residue. Both constructs were expressed in *Escherichia coli* (M15 [pREP4], Qiagen) using a T5 promoter and a C-terminal 6-His Tag was incorporated for the purification. Cultures (1 L) were grown at 37° C. in T.B. from a single colony, and expression was induced with 1.0 mM IPTG when an O.D.$_{600}$ of 0.9 was reached. Cultures were allowed to express protein for roughly 3 h before the cells were pelletised. Pellets were lysed in 0.1M sodium phosphate, 300 mM NaCl, 50 mM imidazole, pH 7.2 containing a protease inhibitor cocktail (Roche). The lysate was centrifuged, and the supernatant was applied to a Ni-NTA column (Qiagen). Grb2-SH2 L111C was eluted from the Ni-NTA column with 0.1M sodium phosphate, 300 mM NaCl, 200 mM imidazole at pH 7.2. The collected Grb2 SH2 L111C was ~95% pure as visualized by Coomassie-stained SDS-PAGE. Dimerization of Grb2 SH2 domain through domain-swapping has been previously observed. Dimeric and monomeric Grb2-SH2 were separated on a Sephacryl S-100 column (320 mL) that had been pre-equilibrated with 0.1 M sodium phosphate and 150 mM NaCl at pH 8.0. Two peaks eluted, corresponding to the molecular weights of monomer (~14 kDa) and dimer (~28 kDa) Grb2-SH2. Almost, 60% of the Grb2-SH2 L111C domain eluted from the column as monomer. Separated monomer and dimer were found to be surprisingly kinetically stable, as very little interconversion was seen over a course of months at 4° C. The monomer was concentrated using Amicon® Ultra-4 centrifugal filter units (Millipore) and the final concentration of the protein was determined by absorbance at 280 nm using the extinction coefficient obtained by McNemar and coworkers (15,600M$^{-1}$). The protein was frozen at 2 mg/mL concentration in 100 mL aliquots which were thawed as required for experiments. The mass of the monomeric protein (mass 14170) was obtained using ESI-MS.

To a solution of model protein (100 μL, [Protein] 2.0 mg/mL, 100 mM sodium phosphate, 150 mM NaCl, pH 8.0) at 0° C. was added Ellman's reagent (5 μL, 282 mM solution in H$_2$O) at 0° C. The mixture was vortexed for 1 s and maintained at 0° C. for 10 mins after which the mixture was analysed by LC-MS. Analysis showed that a single reaction had occurred yielding a single product with a mass of 14370 showing that C111 was available for functionalisation.

Reference Example 56: Preparation of GrB2-SH2 Domain L111C/Bromomaleimide Adduct

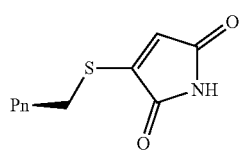

To a solution of model protein (100 μL, [Protein] 2.0 mg/mL, 100 mM sodium phosphate, 150 mM NaCl, pH 8.0) at 0° C. was added bromomaleimide (5 μL, 2.82 mM solution in DMF). The mixture was vortexed for 1 s then maintained at 0° C. for 1 h. Analysis using LC-MS showed that the desired product had been formed in quantitative conversion (mass 14266).

The mixture was treated with Ellman's reagent (5 μL, 282 mM solution in H$_2$O) at 0° C. The mixture was vortexed for 1 s and maintained at 0° C. for 10 mins after which the mixture was analysed by LC-MS. Analysis showed that no reaction with Ellman's reagent was evident highlighting that bromomaleimide functionalisation had occurred at C111.

Reference Example 57: Preparation of GrB2-SH2 Domain L111C/N-Methylbromomaleimide Adduct

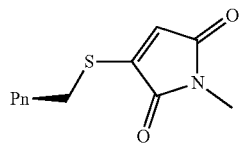

To a solution of model protein (100 μL, [Protein] 2.0 mg/mL, 100 mM sodium phosphate, 150 mM NaCl, pH 8.0) at 0° C. was added N-methylbromomaleimide (5 μL, 2.82 mM solution in DMF). The mixture was vortexed for 1 s then maintained at 0° C. for 1 h. Analysis using LC-MS showed that the desired product had been formed in quantitative conversion (mass 14280).

The mixture was treated with Ellman's reagent (5 μL, 282 mM solution in H$_2$O) at 0° C. The mixture was vortexed for 1 s and maintained at 0° C. for 10 mins after which the mixture was analysed by LC-MS. Analysis showed that no reaction with Ellman's reagent was evident highlighting that N-methylbromomaleimide functionalisation had occurred at C111.

Reference Example 58: Phosphine-Mediated Reductive Cleavage of GrB2-SH2 Domain L111C/Bromomaleimide Adduct

To a solution of model protein (100 μL, [Protein] 2.0 mg/mL, 100 mM sodium phosphate, 150 mM NaCl, pH 8.0) at 0° C. was added bromomaleimide (5 μL, 2.82 mM solution in DMF). The mixture was vortexed for 1 s then maintained at 0° C. for 1 h. Analysis using LC-MS showed a single protein species of mass 14265 which corresponded to protein/bromomaleimide adduct.

The mixture was treated with TCEP.HCl (5 μL, 282 mM solution in H$_2$O) at 0° C. The mixture was vortexed for 1 s and maintained at 0° C. for 3 h after which the mixture was analysed by LC-MS. Analysis showed that the protein/bromomaleimide adduct had been cleanly cleaved yielding the desired product (mass=14169) in 80% conversion Reference Example 59: β-Mercaptoethanol-Mediated Reductive Cleavage of GrB2-SH2 Domain L111C/Bromomaleimide Adduct

To a solution of model protein (100 μL, [Protein] 2.0 mg/mL, 100 mM sodium phosphate, 150 mM NaCl, pH 8.0) at 0° C. was added bromomaleimide (5 μL, 2.82 mM solution in DMF). The mixture was vortexed for 1 s then maintained at 0° C. for 1 h. Analysis using LC-MS showed a single protein species of mass 14265 which corresponded to protein/bromomaleimide adduct.

The mixture was treated with β-mercaptoethanol (5 μL, 282 mM solution in H$_2$O), vortexed for 1 s and maintained at 37° C. for 4 h. Analysis showed that the protein/bromomaleimide adduct had been cleanly cleaved yielding the desired product (mass=14173) in quantitative conversion.

Reference Example 60: Glutathione-Mediated Cleavage of GrB2-SH2 Domain L111C/Bromomaleimide Adduct

To a solution of model protein (100 μL, [Protein] 2.0 mg/mL, 100 mM sodium phosphate, 150 mM NaCl, pH 8.0) at 0° C. was added bromomaleimide (5 μL, 2.82 mM solution in DMF). The mixture was vortexed for 1 s then maintained at 0° C. for 1 h. Analysis using LC-MS showed a single protein species of mass 14265 which corresponded to protein/bromomaleimide adduct.

The mixture was treated with glutathione (5 μL, 282 mM solution in H$_2$O), vortexed for 1 s and maintained at 37° C. for 4 h. Analysis showed that the protein/bromomaleimide adduct had been cleanly cleaved yielding the desired product (mass=14173) in quantitative conversion.

Reference Example 61: Phosphine-Mediated Reductive Cleavage of GrB2-SH2 Domain L111C/N-Methylbromomaleimide Adduct

To a solution of model protein (100 µL, [Protein] 2.0 mg/mL, 100 mM sodium phosphate, 150 mM NaCl, pH 8.0) at 0° C. was added N-methylbromomaleimide (5 µL, 2.82 mM solution in DMF). The mixture was vortexed for 1 s then maintained at 0° C. for 1 h. Analysis using LC-MS showed a single protein species of mass 14278 which corresponded to protein/N-methylbromomaleimide adduct.

The mixture was treated with TCEP.HCl (5 µL, 282 mM solution in H$_2$O) at 0° C. The mixture was vortexed for 1 s and maintained at 0° C. for 3 h after which the mixture was analysed by LC-MS. Analysis showed that the protein/N-methylbromomaleimide adduct had been cleanly cleaved yielding the desired product (mass=14168) in 85% conversion.

Reference Example 62: β-Mercaptoethanol-Mediated Reductive Cleavage of GrB2-SH2 Domain L111C/N-Methylbromomaleimide Adduct

To a solution of model protein (100 µL, [Protein] 2.0 mg/mL, 100 mM sodium phosphate, 150 mM NaCl, pH 8.0) at 0° C. was added N-methylbromomaleimide (5 µL, 2.82 mM solution in DMF). The mixture was vortexed for 1 s then maintained at 0° C. for 1 h. Analysis using LC-MS showed a single protein species of mass 14280 which corresponded to protein/N-methylbromomaleimide adduct.

The mixture was treated with β-mercaptoethanol (5 µL, 282 mM solution in H$_2$O), vortexed for 1 s and maintained at 37° C. for 4 h. Analysis showed that the protein/N-methylbromomaleimide adduct had been cleanly cleaved yielding the desired product (mass=14173) in quantitative conversion.

Reference Example 63: Glutathione-Mediated Cleavage of GrB2-SH2 Domain L111C/N-Methylbromomaleimide Adduct

To a solution of model protein (100 µL, [Protein] 2.0 mg/mL, 100 mM sodium phosphate, 150 mM NaCl, pH 8.0) at 0° C. was added N-methylbromomaleimide (5 µL, 2.82 mM solution in DMF). The mixture was vortexed for 1 s then maintained at 0° C. for 1 h. Analysis using LC-MS showed a single protein species of mass 14280 which corresponded to protein/N-methylbromomaleimide adduct.

The mixture was treated with glutathione (5 µL, 282 mM solution in H$_2$O), vortexed for 1 s and maintained at 37° C. for 4 h. Analysis showed that the protein/N-methylbromomaleimide adduct had been cleanly cleaved yielding the desired product (mass=14173) in quantitative conversion.

Reference Example 64: Ethanedithiol-Mediated Cleavage of GrB2-SH2 Domain L111C/bromomaleimide Adduct

To a solution of model protein (100 µL, [Protein] 2.0 mg/mL, 100 mM sodium phosphate, 150 mM NaCl, pH 8.0) at 0° C. was added bromomaleimide (5 µL, 2.82 mM solution in DMF). The mixture was vortexed for 1 s then maintained at 0° C. for 1 h. Analysis using LC-MS showed a single protein species of mass 14265 which corresponded to protein/bromomaleimide adduct.

The mixture was treated with ethanedithiol (5 µL, 282 mM solution in H$_2$O), vortexed for 1 s and maintained at 37° C. for 4 h. Analysis showed that the protein/bromomaleimide adduct had been cleanly cleaved yielding the desired product (mass=14173) in quantitative conversion.

Reference Example 65: Preparation of GrB2-SH2 Domain L111C/Bromomaleimide/2-Mercaptoethanol Adduct

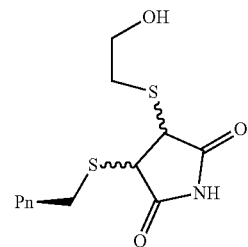

To a solution of model protein (100 µL, [Protein] 2.0 mg/mL, 100 mM sodium phosphate, 150 mM NaCl, pH 8.0) at 0° C. was added bromomaleimide (5 µL, 2.82 mM solution in DMF). The mixture was vortexed for 1 s then maintained at 0° C. for 1 h. Analysis using LC-MS showed a single protein species of mass 14265 which corresponded to protein/bromomaleimide adduct.

The mixture was treated with 2-mercaptoethanol (5 µL, 2.82 mM solution in H$_2$O) at 0° C. The mixture was vortexed for 1 s and maintained at 0° C. for 3 h after which the mixture was analysed by LC-MS. Analysis showed that the protein/bromomaleimide/2-mercaptoethanol adduct had been formed (mass=14345) in 54% yield. The remaining material was GrB2-SH2 domain L111C.

Reference Example 66: Preparation of GrB2-SH2 Domain L111C/N-Methylbromomaleimide/2-Mercaptoethanol Adduct

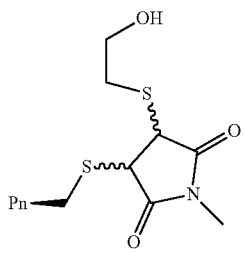

To a solution of model protein (100 μL, [Protein] 2.0 mg/mL, 100 mM sodium phosphate, 150 mM NaCl, pH 8.0) at 0° C. was added N-methylbromomaleimide (5 μL, 2.82 mM solution in DMF). The mixture was vortexed for 1 s then maintained at 0° C. for 1 h. Analysis using LC-MS showed a single protein species of mass 14278 which corresponded to protein/N-methylbromomaleimide adduct.

The mixture was treated with 2-mercaptoethanol (5 μL, 2.82 mM solution in H₂O) at 0° C. The mixture was vortexed for 1 s and maintained at 0° C. for 3 h after which the mixture was analysed by LC-MS. Analysis showed that the desired product (mass=14359) had been formed in 90% yield. The remaining material was GrB2-SH2 domain L111C.

Example 15: Preparation of GrB2-SH2 Domain L111C/Bromomaleimide/Glutathione Adduct

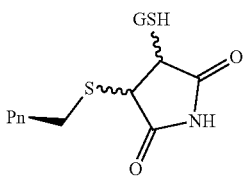

To a solution of model protein (100 μL, [Protein] 2.0 mg/mL, 100 mM sodium phosphate, 150 mM NaCl, pH 8.0) at 0° C. was added bromomaleimide (5 μL, 2.82 mM solution in DMF). The mixture was vortexed for 1 s then maintained at 0° C. for 1 h. Analysis using LC-MS showed a single protein species of mass 14265 which corresponds to protein/bromomaleimide adduct.

The mixture was treated with glutathione (5 μL, 2.82 mM solution in H₂O) at 0° C. The mixture was vortexed for 1 s and maintained at 0° C. for 3 h after which the mixture was analysed by LC-MS. Analysis showed that the protein/bromomaleimide/glutathione adduct had been formed (mass=14574) in 44% conversion. The remaining material was GrB2-SH2 domain L111C.

Example 16: Preparation of GrB2-SH2 Domain L111C/N-Methylbromomaleimide/Glutathione Adduct

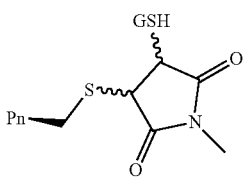

To a solution of model protein (100 μL, [Protein] 2.0 mg/mL, 100 mM sodium phosphate, 150 mM NaCl, pH 8.0) at 0° C. was added N-methylbromomaleimide (5 μL, 2.82 mM solution in DMF). The mixture was vortexed for 1 s then maintained at 0° C. for 1 h. Analysis using LC-MS showed a single protein species of mass 14278 which corresponded to protein/N-methylbromomaleimide adduct.

The mixture was treated with 2-mercaptoethanol (5 μL, 2.82 mM solution in H₂O) at 0° C. The mixture was vortexed for 1 s and maintained at 0° C. for 3 h after which the mixture was analysed by LC-MS. Analysis showed that the protein/N-methylbromomaleimide/glutathione adduct had been formed (mass=14588) in 95% conversion. The remaining material was GrB2-SH2 domain L111C.

Reference Example 67: Preparation of GrB2-SH2 Domain L111C/Dibromomaleimide Adduct

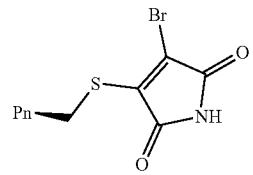

To a solution of model protein (100 μL, [Protein] 2.0 mg/mL, 100 mM sodium phosphate, 150 mM NaCl, pH 8.0) at 0° C. was added dibromomaleimide (5 μL, 2.82 mM solution in DMF). The mixture was vortexed for 1 s then maintained at 0° C. for 4 h. Analysis using LC-MS showed that the desired product had been formed in quantitative yield (mass 14345).

Reference Example 68: 2-Mercaptoethanol-Mediated Reductive Cleavage of the GrB2-SH2 Domain L111C/Dibromomaleimide Adduct

To a solution of model protein (100 μL, [Protein] 2.0 mg/mL, 100 mM sodium phosphate, 150 mM NaCl, pH 8.0) at 0° C. was added dibromomaleimide (5 μL, 2.82 mM solution in DMF). The mixture was vortexed for 1 s then maintained at 0° C. for 4 h. Analysis using LC-MS showed a single protein species of mass 14346 which corresponded to protein/dibromomaleimide adduct.

The mixture was treated with 2-mercaptoethanol (5 μL, 282 mM solution in H₂O) at 0° C. The mixture was vortexed for 1 s and maintained at 0° C. for 4 h after which the mixture was analysed by LC-MS. Analysis showed that the protein/bromomaleimide adduct had been cleanly cleaved yielding the desired product (mass=14171) in quantitative yield.

Reference Example 69: Glutathione-Mediated Reductive Cleavage of the GrB2-SH2 Domain L111C/Dibromomaleimide Adduct

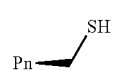

To a solution of model protein (100 μL, [Protein] 2.0 mg/mL, 100 mM sodium phosphate, 150 mM NaCl, pH 8.0) at 0° C. was added dibromomaleimide (5 μL, 2.82 mM solution in DMF). The mixture was vortexed for 1 s then maintained at 0° C. for 4 h. Analysis using LC-MS showed a single protein species of mass 14346 which corresponded to protein/dibromomaleimide adduct.

The mixture was treated with glutathione (5 μL, 282 mM solution in H$_2$O) at 0° C. The mixture was vortexed for 1 s and maintained at 0° C. for 4 h after which the mixture was analysed by LC-MS. Analysis showed that the protein/bromomaleimide adduct had been cleanly cleaved yielding the desired product (mass=14170) in quantitative yield.

Example 17: Preparation of GrB2-SH2 Domain L111C/Dibromomaleimide/Glutathione Adduct

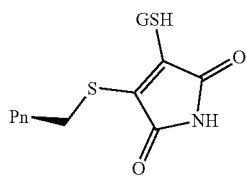

To a solution of model protein (100 μL, [Protein] 2.0 mg/mL, 100 mM sodium phosphate, 150 mM NaCl, pH 8.0) at 0° C. was added dibromomaleimide (5 μL, 2.82 mM solution in DMF). The mixture was vortexed for 1 s then maintained at 0° C. for 4 h. Analysis using LC-MS showed a single protein species of mass 14346 which corresponded to protein/dibromomaleimide adduct.

The mixture was treated with glutathione (5 μL, 2.82 mM solution in H$_2$O) at 0° C. The mixture was vortexed for 1 s and maintained at 0° C. for 2 h after which the mixture was analysed by LC-MS. Analysis showed that the desired product had been formed (mass=14573) in quantitative conversion.

Example 18: Preparation of GrB2-SH2 Domain L111C/Dibromomaleimide/β-1-Thioglucose Adduct

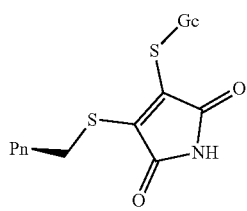

To a solution of model protein (100 μL, [Protein] 2.0 mg/mL, 100 mM sodium phosphate, 150 mM NaCl, pH 8.0) at 0° C. was added dibromomaleimide (5 μL, 2.82 mM solution in DMF). The mixture was vortexed for 1 s then maintained at 0° C. for 4 h. Analysis using LC-MS showed a single protein species of mass 14346 which corresponded to protein/dibromomaleimide adduct.

The mixture was treated with β-1-thioglucose, sodium salt (5 μL, 2.82 mM solution in H$_2$O) at 0° C. The mixture was vortexed for 1 s and maintained at 0° C. for 2 h after which the mixture was analysed by LC-MS. Analysis showed that the desired product (mass=14461) was formed in near quantitative yield.

Example 19: Glutathione-Mediated Cleavage of GrB2-SH2 Domain L111C/Dibromomaleimide/Glutathione Adduct

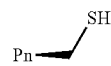

To a solution of model protein (100 μL, [Protein] 2.0 mg/mL, 100 mM sodium phosphate, 150 mM NaCl, pH 8.0) at 0° C. was added dibromomaleimide (5 μL, 2.82 mM solution in DMF). The mixture was vortexed for 1 s then maintained at 0° C. for 4 h. Analysis using LC-MS showed a single protein species of mass 14346 which corresponded to protein/dibromomaleimide adduct.

The mixture was treated with glutathione (5 μL, 2.82 mM solution in H$_2$O) at 0° C. The mixture was vortexed for 1 s and maintained at 0° C. for 2 h after which the mixture was analysed by LC-MS. Analysis showed that the protein/dibromomaleimide/glutathione adduct was the only protein species present (mass=14573).

The mixture was treated with glutathione (5 μL, 282 mM solution in H$_2$O) at 0° C. The mixture was vortexed for 1 s and maintained at 0° C. for 4 h after which the mixture was analysed by LC-MS. Analysis showed that the desired product (mass=14173) was formed in quantitative yield.

Example 20: Glutathione-Mediated Cleavage of GrB2-SH2 Domain L111C/Dibromomaleimide/Glutathione Adduct at Physiologically Relevant Glutathione Concentration (5 mM)

To a solution of model protein (100 μL, [Protein] 2.0 mg/mL, 100 mM sodium phosphate, 150 mM NaCl, pH 8.0) at 0° C. was added dibromomaleimide (5 μL, 2.82 mM solution in DMF). The mixture was vortexed for 1 s then maintained at 0° C. for 4 h. Analysis using LC-MS showed a single protein species of mass 14346 which corresponded to protein/dibromomaleimide adduct.

The mixture was treated with glutathione (5 μL, 2.82 mM solution in H$_2$O) at 0° C. The mixture was vortexed for 1 s and maintained at 0° C. for 2 h after which the mixture was analysed by LC-MS. Analysis showed that the protein/dibromomaleimide/glutathione adduct was the only protein species present (mass=14573).

The mixture was treated with glutathione (5 μL, 100 mM solution in H$_2$O) at 0° C. The mixture was vortexed for 1 s and maintained at 0° C. for 4 h after which the mixture was analysed by LC-MS. Analysis showed that the desired product (mass=14173) was formed in quantitative yield.

Example 21: Glutathione-Mediated Cleavage of GrB2-SH2 Domain L111C/Dibromomaleimide/Glutathione Adduct at Physiologically Relevant Glutathione Concentration (1 mM)

To a solution of model protein (100 µL, [Protein] 2.0 mg/mL, 100 mM sodium phosphate, 150 mM NaCl, pH 8.0) at 0° C. was added dibromomaleimide (5 µL, 2.82 mM solution in DMF). The mixture was vortexed for 1 s then maintained at 0° C. for 4 h. Analysis using LC-MS showed a single protein species of mass 14346 which corresponded to protein/dibromomaleimide adduct.

The mixture was treated with glutathione (5 µL, 2.82 mM solution in H$_2$O) at 0° C. The mixture was vortexed for 1 s and maintained at 0° C. for 2 h after which the mixture was analysed by LC-MS. Analysis showed that the protein/dibromomaleimide/glutathione adduct was the only protein species present (mass=14573).

The solution of protein/dibromomaleimide/glutathione adduct was subjected to a buffer swap (Micro Bio-Spin 6 Chromatography Column, Bio-Rad) yielding the adduct (95 µL, [adduct] 0.2 mg/mL, 20 mM HEPES, 100 mM KCl, 1 mM MgCl2, 1 mM EDTA, pH 7.4). To this was added glutathione (5 µL, 20 mM solution in 20 mM HEPES, 100 mM KCl, 1 mM MgCl2, 1 mM EDTA, pH 7.4). The mixture was vortexed for 1 s then maintained at 37° C. for 4 h. Analysis showed that Grb2-SH2 (L111C) was formed (mass) 14170) in quantitative conversion.

Example 22: β-Mercaptoethanol-Mediated Cleavage of GrB2-SH2 Domain L111C/Dibromomaleimide/Glutathione Adduct

To a solution of model protein (100 µL, [Protein] 2.0 mg/mL, 100 mM sodium phosphate, 150 mM NaCl, pH 8.0) at 0° C. was added dibromomaleimide (5 µL, 2.82 mM solution in DMF). The mixture was vortexed for 1 s then maintained at 0° C. for 4 h. Analysis using LC-MS showed a single protein species of mass 14346 which corresponded to protein/dibromomaleimide adduct.

The mixture was treated with glutathione (5 µL, 2.82 mM solution in H$_2$O) at 0° C. The mixture was vortexed for 1 s and maintained at 0° C. for 2 h after which the mixture was analysed by LC-MS. Analysis showed that the protein/dibromomaleimide/glutathione adduct was the only protein species present (mass=14573).

The mixture was treated with β-mercaptoethanol (5 µL, 282 mM solution in H$_2$O) at 0° C. The mixture was vortexed for 1 s and maintained at 0° C. for 4 h after which the mixture was analysed by LC-MS. Analysis showed that the desired product (mass=14172) was formed in quantitative conversion.

Example 23: Glutathione-Mediated Cleavage of GrB2-SH2 Domain L111C/Dibromomaleimide/β-1-thioglucose Adduct

To a solution of model protein (100 µL, [Protein] 2.0 mg/mL, 100 mM sodium phosphate, 150 mM NaCl, pH 8.0) at 0° C. was added dibromomaleimide (5 µL, 2.82 mM solution in DMF). The mixture was vortexed for 1 s then maintained at 0° C. for 4 h. Analysis using LC-MS showed a single protein species of mass 14346 which corresponded to protein/dibromomaleimide adduct.

The mixture was treated with β-1-thioglucose (5 µL, 2.82 mM solution in H$_2$O) at 0° C. The mixture was vortexed for 1 s and maintained at 0° C. for 2 h after which the mixture was analysed by LC-MS. Analysis showed that the protein/dibromomaleimide/β-1-thioglucose adduct was the only protein species present (mass=14461).

The mixture was treated with glutathione (5 µL, 282 mM solution in H$_2$O) at 0° C. The mixture was vortexed for 1 s and maintained at 0° C. for 4 h after which the mixture was analysed by LC-MS. Analysis showed that desired product was formed (mass=14173) in quantitative conversion.

Example 24: β-Mercaptoethanol-Mediated Cleavage of GrB2-SH2 Domain L111C/Dibromomaleimide/β-1-thioglucose Adduct

To a solution of model protein (100 µL, [Protein] 2.0 mg/mL, 100 mM sodium phosphate, 150 mM NaCl, pH 8.0) at 0° C. was added dibromomaleimide (5 µL, 2.82 mM solution in DMF). The mixture was vortexed for 1 s then maintained at 0° C. for 4 h. Analysis using LC-MS showed a single protein species of mass 14346 which corresponded to protein/dibromomaleimide adduct.

The mixture was treated with β-1-thioglucose (5 µL, 2.82 mM solution in H$_2$O) at 0° C. The mixture was vortexed for 1 s and maintained at 0° C. for 2 h after which the mixture was analysed by LC-MS. Analysis showed that the protein/dibromomaleimide/β-1-thioglucose adduct was the only protein species present (mass=14461).

The mixture was treated with β-mercaptoethanol (5 µL, 282 mM solution in H$_2$O) at 0° C. The mixture was vortexed for 1 s and maintained at 0° C. for 4 h after which the mixture was analysed by LC-MS. Analysis showed that desired product was formed (mass=14172) in quantitative conversion.

Reference Example 70: Preparation of GrB2-SH2 Domain L111C/N-Phenylbromomaleimide Adduct

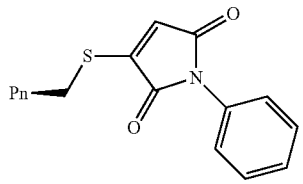

To a solution of model protein (100 µL, [Protein] 2.0 mg/mL, 100 mM sodium phosphate, 150 mM NaCl, pH 8.0) at 0° C. was added N-phenylbromomaleimide (5 µL, 2.82 mM solution in DMF). The mixture was vortexed for 1 s then maintained at 0° C. for 1 h. Analysis using LC-MS showed that the desired product had been formed in quantitative yield (mass 14351).

Reference Example 71: Preparation of GrB2-SH2 Domain L111C/N-Phenyldibromomaleimide Adduct

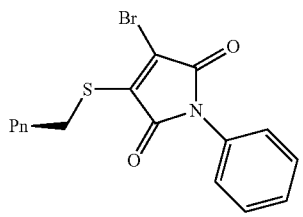

To a solution of model protein (100 µL, [Protein] 2.0 mg/mL, 20 mM MES, 150 mM NaCl, pH 6) at 0° C. was added N-phenylbromomaleimide (5 µL, 2.82 mM solution in DMF). The mixture was vortexed for 1 s then maintained at 0° C. for 1 h. Analysis using LC-MS showed that the desired product had been formed in quantitative yield (mass 14431).

Reference Example 72: β-Mercaptoethanol-Mediated Cleavage of GrB2-SH2 Domain L111C/N-Phenyldibromomaleimide Adduct

To a solution of model protein (100 µL, [Protein] 2.0 mg/mL, 20 mM MES, 150 mM NaCl, pH 6) at 0° C. was added N-phenylbromomaleimide (5 µL, 2.82 mM solution in DMF). The mixture was vortexed for 1 s then maintained at 0° C. for 1 h. Analysis using LC-MS showed that protein/N-phenyldibromomaleimide adduct had been formed in quantitative yield (mass 14431).

The mixture was treated with β-mercaptoethanol (5 µL, 282 mM solution in $H_2O$) at 0° C. The mixture was vortexed for 1 s and maintained at 0° C. for 4 h after which the mixture was analysed by LC-MS. Analysis showed that desired product was formed (mass=14179) in quantitative conversion.

Example 25: Preparation of GrB2-SH2 Domain L111C/N-Phenyldibromomaleimide/β-1-thioglucose Adduct

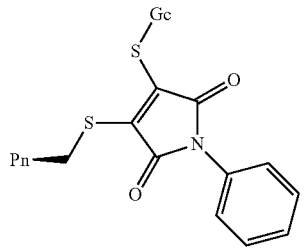

To a solution of model protein (100 µL, [Protein] 2.0 mg/mL, 20 mM MES, 150 mM NaCl, pH 6) at 0° C. was added N-phenylbromomaleimide (5 µL, 2.82 mM solution in DMF). The mixture was vortexed for 1 s then maintained at 0° C. for 1 h. Analysis using LC-MS showed that the protein/N-phenyldibromomaleimide adduct had been formed in quantitative yield (mass 14431).

The mixture was treated with β-1-thioglucose (5 µL, 2.82 mM solution in $H_2O$) at 0° C. The mixture was vortexed for 1 s and maintained at 0° C. for 2 h after which the mixture was analysed by LC-MS. Analysis showed that the protein/N-phenyldibromomaleimide/β-1-thioglucose adduct was the only protein species present (mass=14547).

Example 26: β-Mercaptoethanol-Mediated Cleavage of GrB2-SH2 Domain L111C/N-Phenyldibromomaleimide/β-1-thio glucose Adduct

To a solution of model protein (100 µL, [Protein] 2.0 mg/mL, 20 mM MES, 150 mM NaCl, pH 6) at 0° C. was added N-phenylbromomaleimide (5 µL, 2.82 mM solution in DMF). The mixture was vortexed for 1 s then maintained at 0° C. for 1 h. Analysis using LC-MS showed that the protein/N-phenyldibromomaleimide adduct had been formed in quantitative yield (mass 14431).

The mixture was treated with β-1-thioglucose (5 µL, 2.82 mM solution in $H_2O$) at 0° C. The mixture was vortexed for 1 s and maintained at 0° C. for 2 h after which the mixture was analysed by LC-MS. Analysis showed that the protein/N-phenyldibromomaleimide/β-1-thioglucose adduct was the only protein species present (mass=14547).

The mixture was treated with β-mercaptoethanol (5 µL, 282 mM solution in $H_2O$) at 0° C. The mixture was vortexed for 1 s and maintained at 0° C. for 4 h after which the mixture was analysed by LC-MS. Analysis showed that desired product was formed (mass=14178) in quantitative conversion.

Example 27: Preparation of GrB2-SH2 Domain L111C/Biotin-PEG-bromomaleimide Adduct

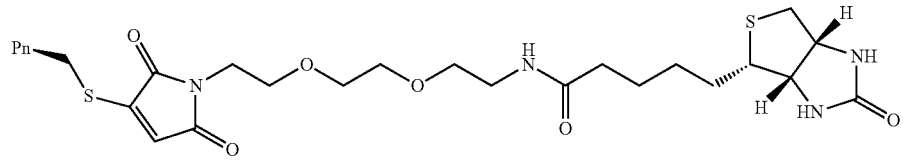

To a solution of model protein (100 μL, [Protein] 2.0 mg/mL, 100 mM sodium phosphate, 150 mM NaCl, pH 8.0) at 0° C. was added biotin-PEG-bromomaleimide (5 μL, 2.82 mM solution in DMF). The mixture was vortexed for 1 s then maintained at 0° C. for 1 h. Analysis using LC-MS showed that the desired product had been formed in quantitative yield (mass 14634).

Example 28: β-Mercaptoethanol-Mediated Cleavage of GrB2-SH2 Domain L111C/Biotin-PEG-bromomaleimide Adduct

To a solution of model protein (100 μL, [Protein] 2.0 mg/mL, 100 mM sodium phosphate, 150 mM NaCl, pH 8.0) at 0° C. was added biotin-PEG-bromomaleimide (5 μL, 2.82 mM solution in DMF). The mixture was vortexed for 1 s then maintained at 0° C. for 1 h. Analysis using LC-MS showed that the protein/biotin-PEG-bromomaleimide adduct had been formed in quantitative yield (mass 14634).

The mixture was treated with β-mercaptoethanol (5 μL, 282 mM solution in H$_2$O) at 37° C. The mixture was vortexed for 1 s and maintained at 37° C. for 4 h after which the mixture was analysed by LC-MS. Analysis showed that desired product was formed (mass=14180) in quantitative conversion.

Example 29: Preparation of GrB2-SH2 Domain L111C/Biotin-PEG-dibromomaleimide Adduct

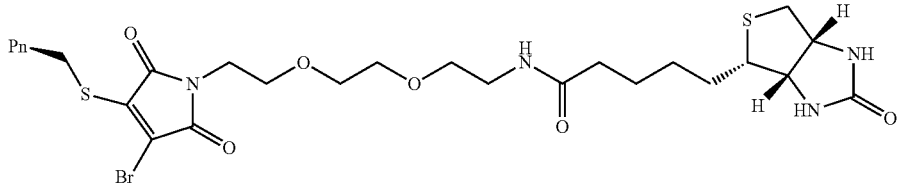

To a solution of model protein (100 μL, [Protein] 2.0 mg/mL, 100 mM sodium phosphate, 150 mM NaCl, pH 8.0) at 0° C. was added biotin-PEG-dibromomaleimide (5 μL, 2.82 mM solution in DMF). The mixture was vortexed for 1 s then maintained at 0° C. for 2 h. Analysis using LC-MS showed that the desired product had been formed in >80% yield (mass 14701).

Example 30: β-Mercaptoethanol-Mediated Cleavage of GrB2-SH2 Domain L111C/Biotin-PEG-dibromomaleimide Adduct

To a solution of model protein (100 μL, [Protein] 2.0 mg/mL, 100 mM sodium phosphate, 150 mM NaCl, pH 8.0) at 0° C. was added biotin-PEG-dibromomaleimide (5 μL, 2.82 mM solution in DMF). The mixture was vortexed for 1 s then maintained at 0° C. for 1 h. Analysis using LC-MS showed that the protein/biotin-PEG-dibromomaleimide adduct had been formed in >80% conversion (mass 14701). The mixture was treated with β-mercaptoethanol (5 μL, 282 mM solution in H$_2$O) at 0° C. The mixture was vortexed for 1 s and maintained at 0° C. for 4 h after which the mixture was analysed by LC-MS. Analysis showed that desired product was formed (mass=14171) in >80% conversion.

Example 31: Pull-Down and Release of GrB2-SH2 Domain L111C/Biotin-PEG-bromomaleimide Adduct onto Neutravidin Coated Agarose Beads

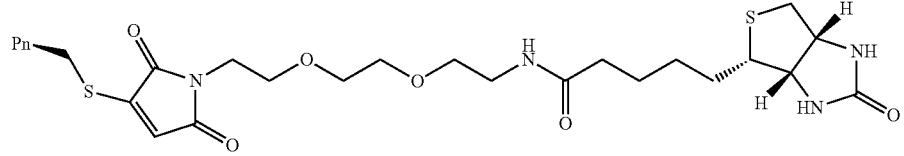

To a solution of model protein (200 μL, [Protein] 1.0 mg/mL, 100 mM sodium phosphate, 150 mM NaCl, pH 8.0) at 0° C. was added biotin-PEG-bromomaleimide (5 μL, 2.82 mM solution in DMF). The mixture was vortexed for 1 s then maintained at 0° C. for 1 h. Analysis using LC-MS showed that the desired product had been formed in quantitative yield (mass 14634).

Protein/biotin-PEG-bromomaleimide adduct (200 μL) and unmodified model protein (200 μL) were washed independently with PBS buffer (3×500 μL) in a concentrator (Vivaspin, cut off 10 k) yielding protein solutions (300 μL) (In). For each of the protein solutions obtained, neutravidin-coated agarose beads (750 μL of 50% aqueous slurry) were washed with PBS (2×500 μL). Protein solution (300 μL) was then added to the beads and the mixture incubated at 4° C. for 30 mins. The mixture was centrifuged and the flow through (FT) collected. The beads were washed with PBS (2×500 μL) and both wash fractions collected (W1 and W2). Protein was released from the beads by incubation in PBS (300 μL) containing β-mercaptoethanol (25 mM) for 2 h at 37° C. The sample was centrifuged and the eluant (El) containing cleaved GrB2-SH2 domain L111C collected. The results are shown in FIG. 1.

The amount of protein recovered was determined as 44% by comparison with a protein series dilution via densitometry. However, correcting for irreversibly physisorbed protein (determined using the unmodified protein control) the corrected recovery was 71%.

Example 32: Preparation of GrB2-SH2 Domain L111C/N-Fluorescein bromomaleimide Adduct

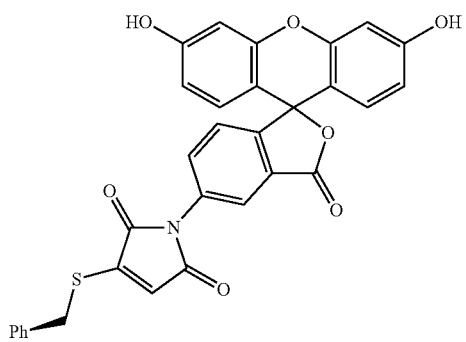

To a solution of model protein (100 μL, [Protein] 2.0 mg/mL, 100 mM sodium phosphate, 150 mM NaCl, pH 7.0) at 0° C. was added N-fluorescein bromomaleimide (5 μL, 2.82 mM solution in DMF). The mixture was vortexed for 1 s then maintained at 0° C. for 1 h. Analysis using LC-MS showed that the desired product had been formed in 90% conversion (mass 14597).

Example 33: β-Mercaptoethanol-Mediated Cleavage of GrB2-SH2 Domain L111C/N-Fluorescein bromomaleimide Adduct

To a solution of model protein (100 μL, [Protein] 2.0 mg/mL, 100 mM sodium phosphate, 150 mM NaCl, pH 7.0) at 0° C. was added N-fluorescein bromomaleimide (5 μL, 2.82 mM solution in DMF). The mixture was vortexed for 1 s then maintained at 0° C. for 1 h. Analysis using LC-MS showed that the protein/fluorescein bromomaleimide adduct had been formed in 90% conversion (mass 14597).

The mixture was treated with β-mercaptoethanol (5 μL, 282 mM solution in H$_2$O) at 37° C. The mixture was vortexed for 1 s and maintained at 37° C. for 4 h after which the mixture was analysed by LC-MS. Analysis showed that desired product was formed (mass=14171) in 87% conversion.

Example 34: Preparation of GrB2-SH2 Domain L111C/N-Fluorescein dibromomaleimide Adduct

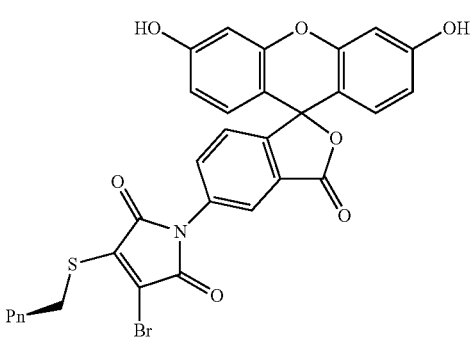

To a solution of model protein (100 μL, [Protein] 2.0 mg/mL, 100 mM sodium phosphate, 150 mM NaCl, pH 8.0) at 0° C. was added N-fluorescein dibromomaleimide (5 μL, 2.82 mM solution in DMF). The mixture was vortexed for 1 s then maintained at 0° C. for 1 h. Analysis using LC-MS showed that the desired product had been formed in 61% conversion (mass 14675).

Example 35: β-Mercaptoethanol-Mediated Cleavage of GrB2-SH2 Domain L111C/N-Fluorescein dibromomaleimide Adduct

To a solution of model protein (100 μL, [Protein] 2.0 mg/mL, 100 mM sodium phosphate, 150 mM NaCl, pH 7.0) at 0° C. was added N-fluorescein dibromomaleimide (5 μL, 2.82 mM solution in DMF). The mixture was vortexed for 1 s then maintained at 0° C. for 1 h. Analysis using LC-MS showed that the protein/fluorescein dibromomaleimide adduct had been formed in 61% conversion (mass 14597).

The mixture was treated with β-mercaptoethanol (5 μL, 282 mM solution in H$_2$O) at 37° C. The mixture was vortexed for 1 s and maintained at 37° C. for 4 h after which the mixture was analysed by LC-MS. Analysis showed that desired product was formed (mass=14171) in 85% conversion.

Reference Example 73: Preparation of GrB2-SH2 Domain L111C/BrDDPD Adduct

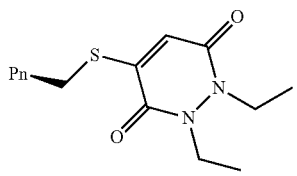

To a solution of model protein (100 μL, [Protein] 2.0 mg/mL, 100 mM sodium phosphate, 150 mM NaCl, pH 8.0) at 0° C. was added BrDDPD (5 μL, 282 mM solution in DMF). The mixture was vortexed for 1 s then maintained at 37° C. for 1 h. Analysis using LC-MS showed that the desired product had been formed in quantitative yield (mass 14348).

Reference Example 74: β-Mercaptoethanol-Mediated Cleavage of GrB2-SH2 Domain L111C/BrDDPD Adduct

To a solution of model protein (100 μL, [Protein] 2.0 mg/mL, 100 mM sodium phosphate, 150 mM NaCl, pH 8.0) at 0° C. was added BrDDPD (5 μL, 282 mM solution in DMF). The mixture was vortexed for 1 s then maintained at 37° C. for 1 h. Analysis using LC-MS showed that the protein/BrDDPD adduct had been formed in quantitative yield (mass 14348).

The mixture was dialysed for 40 h at 4° C. (100 mM sodium phosphate, 150 mM NaCl, pH 8.0) and treated with β-mercaptoethanol (5 μL, 2.82 M solution in H$_2$O) at 37° C. The mixture was vortexed for 1 s and maintained at 37° C. for 2 h after which the mixture was analysed by LC-MS. Analysis showed that desired product was formed (mass=14180) in quantitative conversion.

Reference Example 75: Preparation of GrB2-SH2 Domain L111C/DiBrDDPD Adduct

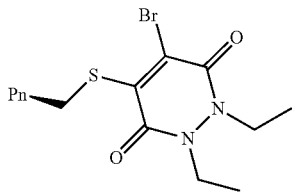

To a solution of model protein (100 μL, [Protein] 2.0 mg/mL, 100 mM sodium phosphate, 150 mM NaCl, pH 8.0) at 0° C. was added DiBrDDPD (5 μL, 282 mM solution in DMF). The mixture was vortexed for 1 s then maintained at 37° C. for 1 h. Analysis using LC-MS showed that the desired product had been formed in quantitative yield (mass 14427).

Reference Example 76: β-Mercaptoethanol-Mediated Cleavage of GrB2-SH2 Domain L111C/DiBrDDPD Adduct

To a solution of model protein (100 μL, [Protein] 2.0 mg/mL, 100 mM sodium phosphate, 150 mM NaCl, pH 8.0) at 0° C. was added DiBrDDPD (5 μL, 282 mM solution in DMF). The mixture was vortexed for 1 s then maintained at 37° C. for 1 h. Analysis using LC-MS showed that the protein/DiBrDDPD adduct had been formed in quantitative yield (mass 14427).

The mixture was dialysed for 40 h at 4° C. (100 mM sodium phosphate, 150 mM NaCl, pH 8.0) then treated with β-mercaptoethanol (5 μL, 2.82 M solution in H$_2$O) at 37° C. The mixture was vortexed for 1 s and maintained at 37° C. for 2 h after which the mixture was analysed by LC-MS. Analysis showed that desired product was formed (mass=14180) in quantitative conversion.

Example 36: Preparation of GrB2-SH2 Domain L111C/DiBrDDPD/β-1-thioglucose Adduct

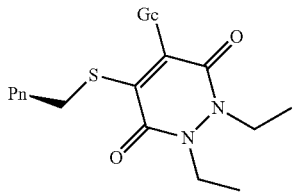

To a solution of model protein (100 μL, [Protein] 2.0 mg/mL, 100 mM sodium phosphate, 150 mM NaCl, pH 8.0) at 0° C. was added DiBrDDPD (5 μL, 282 mM solution in DMF). The mixture was vortexed for 1 s then maintained at 37° C. for 1 h. Analysis using LC-MS showed that the protein/DiBrDDPD adduct had been formed in quantitative yield (mass 14427).

The mixture was dialysed for 40 h at 4° C. (100 mM sodium phosphate, 150 mM NaCl, pH 8.0) then treated with β-1-thioglucose (5 µL, 28.2 mM solution in H$_2$O) at 0° C. The mixture was vortexed for 1 s and maintained at RT for 1 h after which the mixture was analysed by LC-MS. Analysis showed that the protein/DiBrDDPD/β-1-thioglucose adduct was the only protein species present (mass=14543).

Example 37: β-Mercaptoethanol-Mediated Cleavage of GrB2-SH2 Domain L111C/DiBrDDPD/β-1-thioglucose Adduct

To a solution of model protein (100 µL, [Protein] 2.0 mg/mL, 100 mM sodium phosphate, 150 mM NaCl, pH 8.0) at 0° C. was added DiBrDDPD (5 µL, 282 mM solution in DMF). The mixture was vortexed for 1 s then maintained at 37° C. for 1 h. Analysis using LC-MS showed that the protein/DiBrDDPD adduct had been formed in quantitative yield (mass 14427).

The mixture was dialysed for 40 h at 4° C. (100 mM sodium phosphate, 150 mM NaCl, pH 8.0) then treated with β-1-thioglucose (5 µL, 28.2 mM solution in H$_2$O) at 0° C. The mixture was vortexed for 1 s and maintained at RT for 1 h after which the mixture was analysed by LC-MS. Analysis showed that the protein/DiBrDDPD/β-1-thioglucose adduct was the only protein species present (mass=14543).

The mixture was treated with β-mercaptoethanol (5 µL, 2.82 M solution in H$_2$O) at RT. The mixture was vortexed for 1 s and maintained at RT for 30 mins after which the mixture was analysed by LC-MS. Analysis showed that desired product was formed (mass=14180) in quantitative conversion.

Example 38: Preparation of GrB2-SH2 Domain L111C/BrDDPD/β-1-thioglucose Adduct

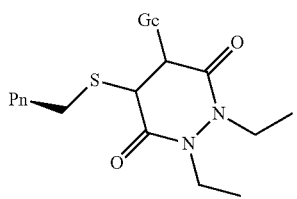

To a solution of model protein (100 µL, [Protein] 2.0 mg/mL, 100 mM sodium phosphate, 150 mM NaCl, pH 8.0) at 0° C. was added BrDDPD (5 µL, 282 mM solution in DMF). The mixture was vortexed for 1 s then maintained at 37° C. for 1 h. Analysis using LC-MS showed that the protein/BrDDPD adduct had been formed in quantitative yield (mass 14348).

The mixture was dialysed for 40 h at 4° C. (100 mM sodium phosphate, 150 mM NaCl, pH 8.0) then treated with β-1-thioglucose (5 µL, 28.2 mM solution in H$_2$O) at 0° C. The mixture was vortexed for 1 s and maintained at 37° C. for 1 h after which the mixture was analysed by LC-MS. Analysis showed that the protein/BrDDPD/β-1-thioglucose adduct was formed in 17% conversion (mass=14543).

Reference Example 77: Preparation of GrB2-SH2 Domain L111C/Z-2,3-Dibromo-but-2-enedioic Acid Dimethyl Ester Adduct

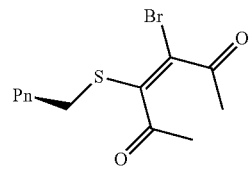

To a solution of model protein (100 µL, [Protein] 2.0 mg/mL, 100 mM sodium phosphate, 150 mM NaCl, pH 8.0) at 0° C. was added Z-2,3-dibromo-but-2-enedioic acid dimethyl ester (5 µL, 282 mM solution in DMF). The mixture was vortexed for 1 s then maintained at 37° C. for 1 h. Analysis using LC-MS showed that the desired product had been formed (mass 14440).

Reference Example 78: β-Mercaptoethanol-Mediated Cleavage of GrB2-SH2 Domain L111C/Z-2,3-Dibromo-but-2-enedioic Acid Dimethyl Ester Adduct

To a solution of model protein (100 µL, [Protein] 2.0 mg/mL, 100 mM sodium phosphate, 150 mM NaCl, pH 8.0) at 0° C. was added Z-2,3-dibromo-but-2-enedioic acid dimethyl ester (5 µL, 282 mM solution in DMF). The mixture was vortexed for 1 s then maintained at 37° C. for 1 h. Analysis using LC-MS showed that the desired product had been formed in quantitative yield (mass 14370).

The mixture was treated with β-mercaptoethanol (5 µL, 2.82 M solution in H$_2$O) at 37° C. The mixture was vortexed for 1 s and maintained at 37° C. for 2 h after which the mixture was analysed by LC-MS. Analysis showed that desired product was formed (mass=14180) in quantitative conversion.

Example 39: Modification and Regeneration of Somatostatin

Preparation of Reduced Somatostatin

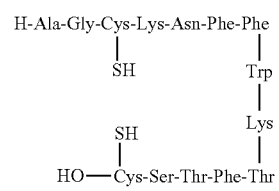

Lyophilised somatostatin (mass=1638) was solubilised in buffer (50 mM sodium phosphate, pH 6.2, 40% MeCN, 2.5% DMF) to yield a concentration of 152.6 μM (0.25 mg/ml) and reduced with 1.1 equiv of TCEP for 1 h at ambient temperature. Completeness of the reduction was confirmed by addition of 4 equiv of dibromomaleimide to an aliquot of the sample and analysis by LC-MS.

Bridging of Somatostatin with Halomaleimides and Derivatives

Figure 2:
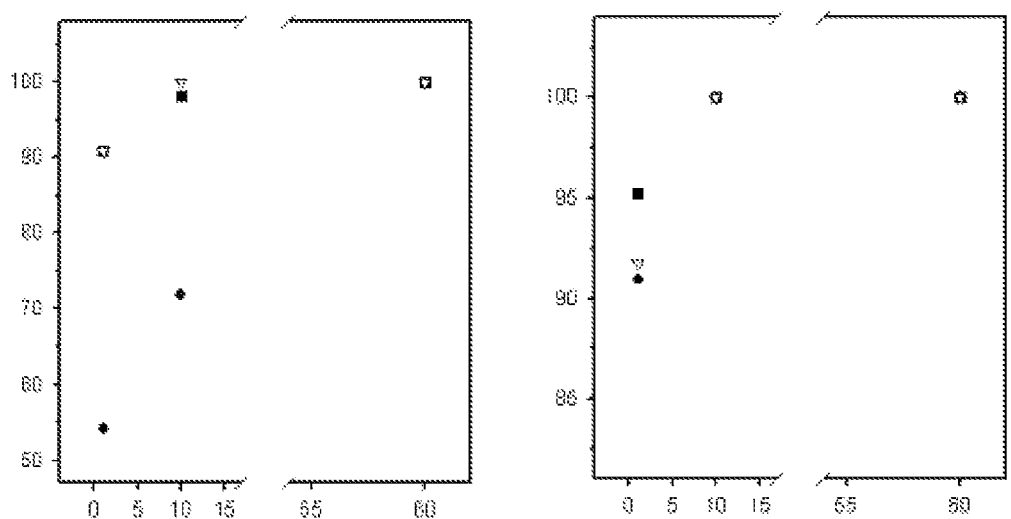
FIG. 2 shows the generation of somatostatin-maleimide adducts from halomaleimides according to the protocol described in Example 39 as measured by LC-MS (y-axis=signal %; x-axis=time/min). Top left: Generation of somatostatin adduct from dichloromaleimide (circle), dibromomaleimide (square) and diiodomaleimide (triangle). Top right: Generation of somatostatin adduct from monobromomaleimide (circle), N-methylmonobromomaleimide (square) and N-methyldibromomaleimide (triangle). Bottom left: Generation of somatostatin adduct from N-fluorescein-dibromomaleimide (circle), N-biotin-dibromomaleimide (square), N-PEG 5000-dibromomaleimide (triangle), N-PEG-5000-dithiophenolmaleimide (diamond) and N-PEG 300-dibromomaleimide (oval).
Figure 2:
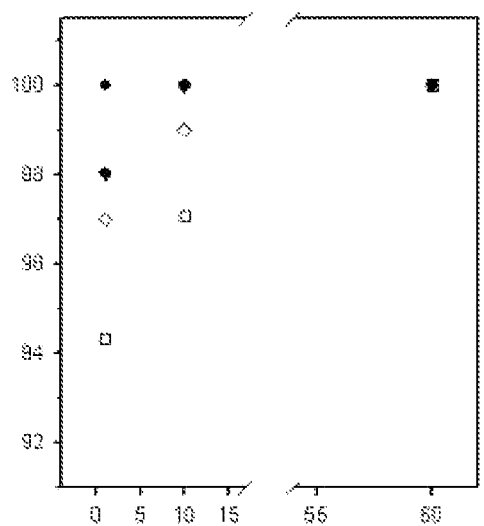

Reduced somatostatin was generated as described. 1.1 equiv of the halomaleimides or dibromomaleimide derivates (100× stocks in 50 mM sodium phosphate, pH 6.2, 40% MeCN, 2.5-15.0% DMF) were added at ambient temperature and the generation of product monitored over 1 h by LC-MS. The results are shown in FIG. 2.

Bridging of Somatostatin with Dithiomaleimides

Figure 3:
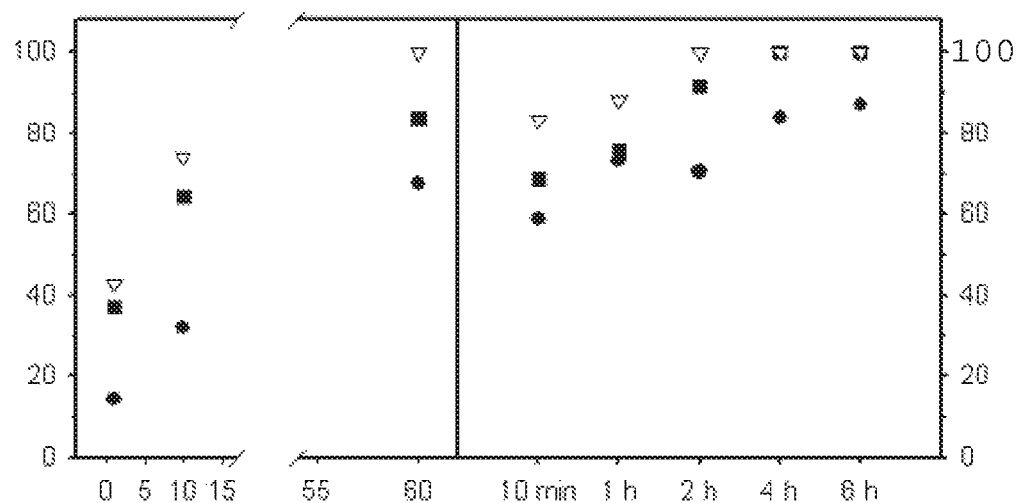
FIG. 3 shows the generation of somatostatin-maleimide adducts from dithiomaleimides according to the protocol described in Example 39 as measured by LC-MS (y-axis=signal %; x-axis=time/min). Top left: Generation of somatostatin adduct from di-2-mercaptoethanolmaleimide at 1 eq. (circle), 5 eq. (square) and 10 eq. (triangle). Top right: Generation of somatostatin adduct from dicysteine-maleimide at 1 eq. (circle), 5 eq. (square) and 10 eq. (triangle). Bottom left: Generation of somatostatin adduct from dithiophenolmaleimide at 1 eq. (circle), 5 eq. (square) and 10 eq. (triangle). Bottom right: Generation of somatostatin adduct from di-2-mercaptopyridinemaleimide at 1 eq. (circle), 5 eq. (square) and 10 eq. (triangle).
Figure 3:
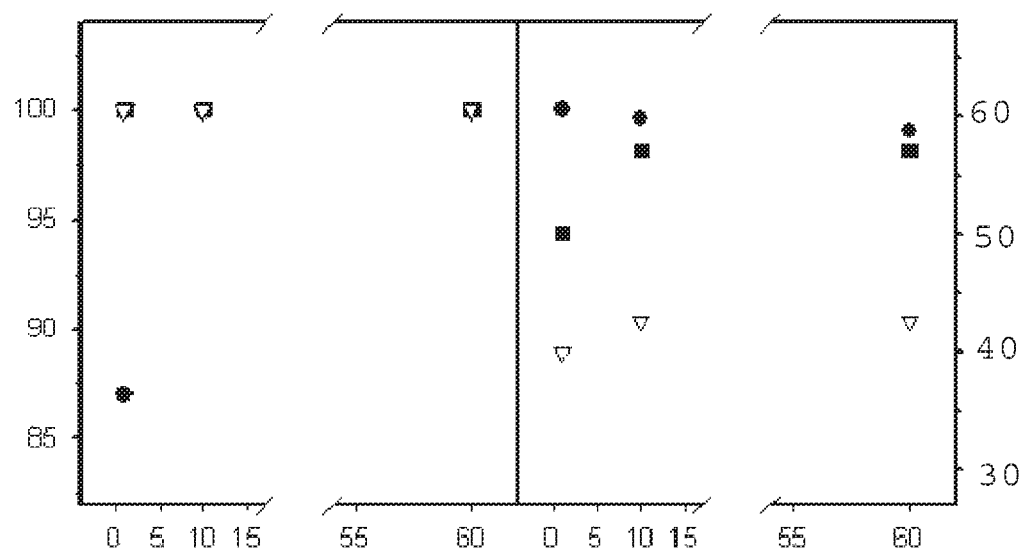

Reduced somatostatin was generated as described. Various amounts of dithiomaleimide (100× stocks in 50 mM sodium phosphate, pH 6.2, 40% MeCN, 2.5-7.5% DMF) were added at ambient temperature and the generation of product monitored over 1 h by LC-MS. The results are shown in FIG. 3.

Modification of Somatostatin with Bromomaleimide

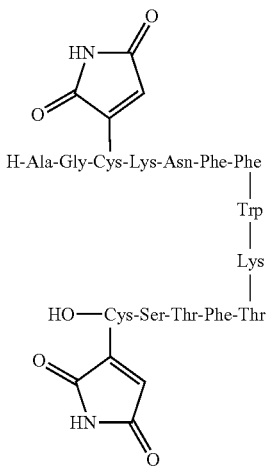

Reduced somatostatin was generated as described. 2.1 equiv of bromomaleimide (100× stock in 50 mM sodium phosphate, pH 6.2, 40% MeCN, 7.5% DMF) were added at ambient temperature and complete conversion to the di-addition product observed by LC-MS within 1 h.

Modification of Somatostatin with Dibromomaleic Anhydride

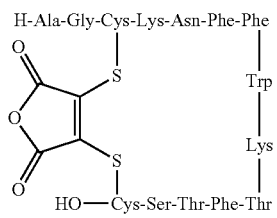

Reduced somatostatin was generated as described. 5 equiv of dibromomaleic anhydride (in DMF) were added and the generation of products monitored by LC-MS. 17.3% bridged somatostatin were generated within 90 min.

Cleavage of Bridged Somatostatin with Various Reducing Agents

Figure 4:
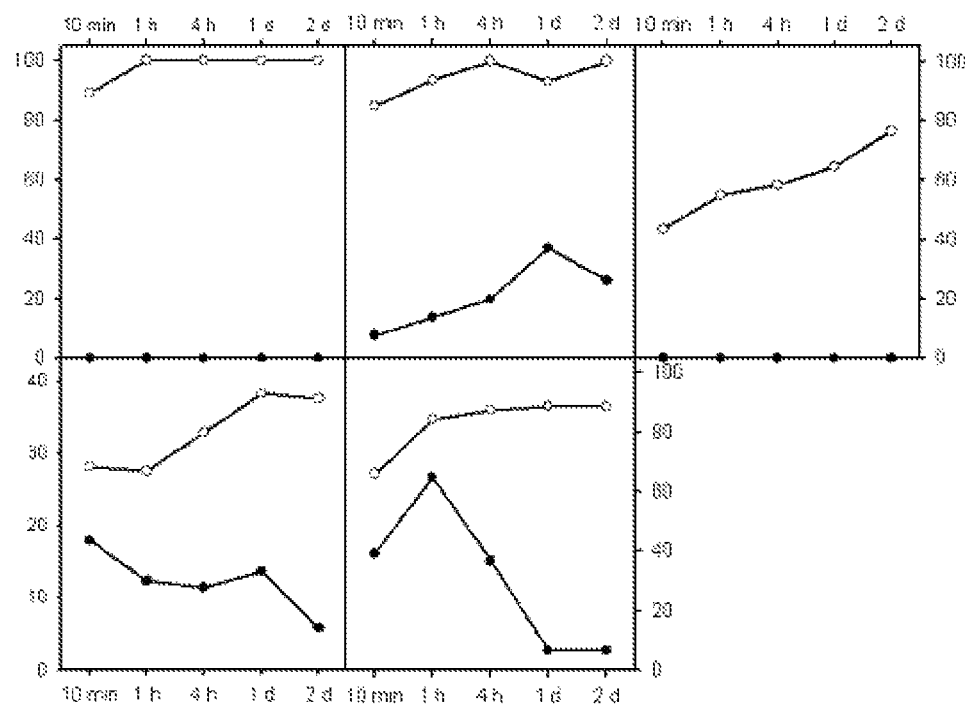
FIG. 4 shows cleavage of maleimide bridged somatostatin with various reducing agents according to the protocol described in Example 39 as measured by LC-MS (y-axis=signal %; x-axis=time in minutes (min), hours (h) and days (d)). Top left: Total modified somatostatin-maleimide with DTT (hollow circle) and total amount of side products (filled circle). Top middle: Total modified somatostatin-maleimide with 2-mercaptoethanol (hollow circle) and total amount of side products (filled circle). Top right: Total modified somatostatin-maleimide with GSH (hollow circle) and total amount of side products (filled circle). Bottom left: Total modified somatostatin-maleimide with TCEP (hollow circle) and total amount of side products (filled circle). Bottom right: Total modified somatostatin-maleimide with 1,2-ethanedithiol (hollow circle) and total amount of side products (filled circle).

Maleimide bridged somatostatin was prepared as described. 100 equiv of various reducing agents (1000× stock in 50 mM sodium phosphate, pH 6.2, 40% MeCN, 2.5% DMF) were added and the generation of unmodified peptide and side products (mixed disulfides of the reducing agents with the free peptide-cysteines) monitored at 4° C. over 2 d by LC-MS. Mixed disulfides of somatostatin with GSH could only be detected by MALDI-TOF MS. The results are shown in FIG. 4.

Figure 5:
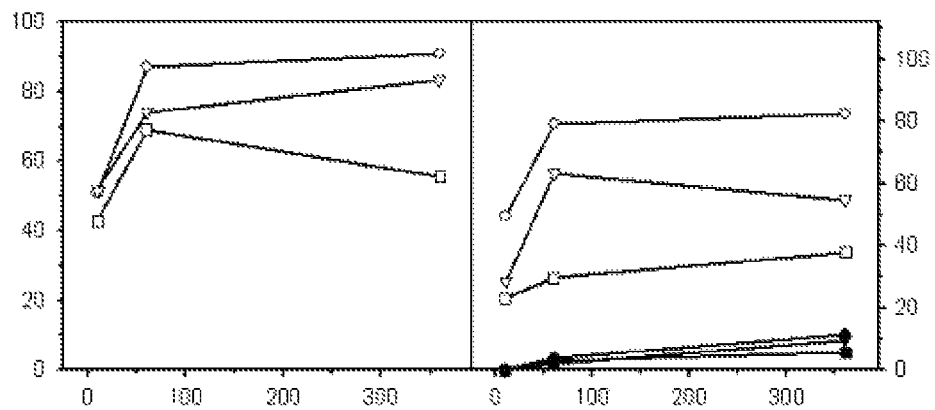
FIG. 5 shows cleavage of maleimide bridged somatostatin with various amounts of DTT and 2-mercaptoethanol according to the protocol described in Example 39 as measured by LC-MS (y-axis=signal %; x-axis=time/min). Left: Regeneration of somatostatin by DTT at 50 eq. (hollow circle), 20 eq. (hollow triangle) and 10 eq. (hollow square). Right: Regeneration of somatostatin by 2-mercaptoethanol at 50 eq. (hollow circle), 20 eq. (hollow triangle) and 10 eq. (hollow square) and total amount of side products at 50 eq. (filled circle), 20 eq. (filled triangle) and 10 eq. (filled square).

Cleavage of Bridged Somatostatin with Various Amounts of DTT and 2-mercaptoethanol Maleimide bridged somatostatin was prepared as described. Various amounts of DTT or 2-mercaptoethanol (1000× stock in 50 mM sodium phosphate, pH 6.2, 40% MeCN, 2.5% DMF) were added and the generation of unmodified peptide and side products (mixed disulfides of the reducing agents with the free peptide-cysteines) monitored at 4° C. over 6 h by LC-MS. The results are shown in FIG. 5.

Catalysed Cleavage of Bridged Somatostatin

Figure 6:
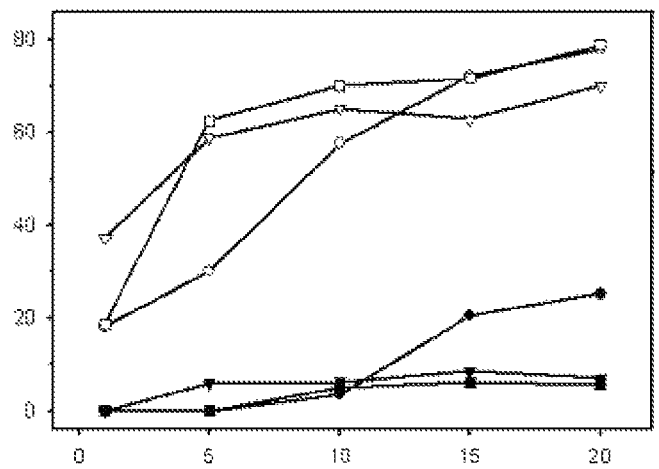
FIG. 6 shows catalysed cleavage of bridged somatostatin according to the protocol described in Example 39 as measured by LC-MS (y-axis=signal %; x-axis=time/min). Shown on the Figure are regeneration of somatostatin by 2-mercaptoethanol (hollow circle), 2-mercaptoethanol with NaI (hollow square) and 2-mercaptoethanol with benzeneselenol (hollow triangle), as well as total side products when using 2-mercaptoethanol (filled circle), 2-mercaptoethanol with NaI (filled square) and 2-mercaptoethanol with benzeneselenol (filled triangle).

Maleimide bridged somatostatin was prepared as described. 20 equiv of 2-mercaptoethanol (1000× stock in 50 mM sodium phosphate, pH 6.2, 40% MeCN, 2.5% DMF) were added followed by either buffer or 5 equiv of sodium iodide or benzeneselenol (100× stock in 50 mM sodium phosphate, pH 6.2, 40% MeCN, 7.5% DMF) and the generation of unmodified peptide and side products (mixed disulfides of 2-mercaptoethanol or benzeneselenol with the free peptide-cysteines) monitored at ambient temperature over 20 min by LC-MS. The results are shown in FIG. 6.

Cleavage of N-Functionalised Maleimide Bridged Somatostatin

Figure 7:
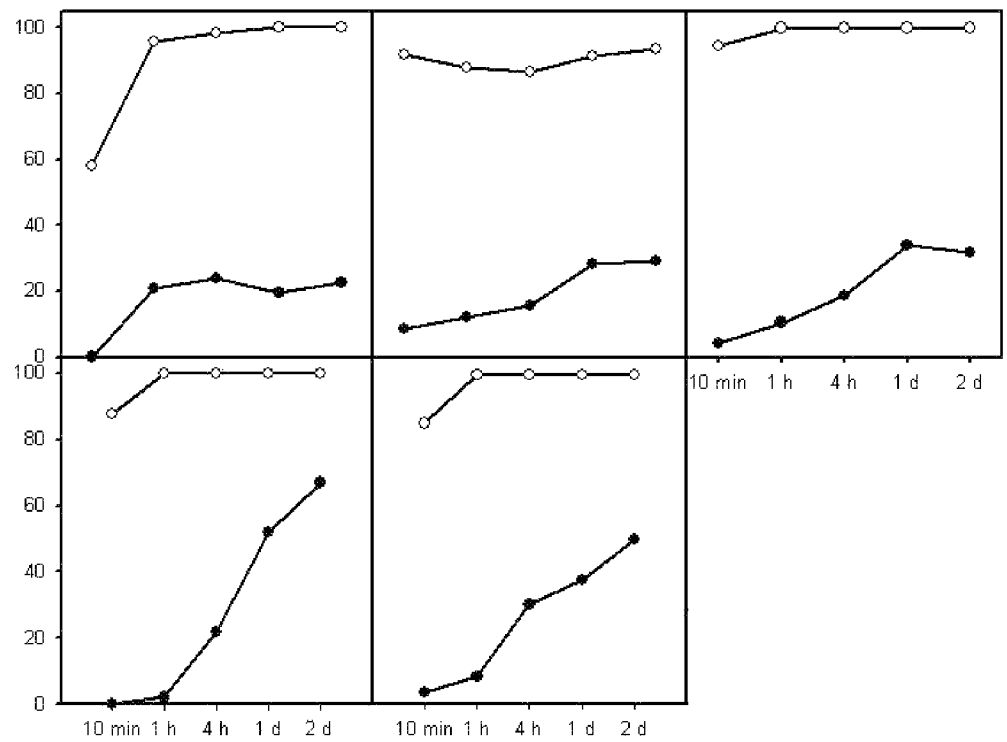
FIG. 7 shows cleavage of N-functionalised maleimide bridged somatostatin by 2-mercaptoethanol according to the protocol described in Example 39 as measured by LC-MS (y-axis=signal %; x-axis=time in minutes (min), hours (h) and days (d)). Top left: cleavage of N-methylmaleimide somatostatin adduct to give somatostatin (hollow circle) and total side products (filled circle). Top middle: cleavage of N-biotin maleimide somatostatin adduct to give somatostatin (hollow circle) and total side products (filled circle). Top right: cleavage of N-fluorescein maleimide somatostatin adduct to give somatostatin (hollow circle) and total side products (filled circle). Bottom left: cleavage of N-PEG 5000 maleimide somatostatin adduct to give somatostatin (hollow circle) and total side products (filled circle). Bottom middle: cleavage of N-PEG 300 maleimide somatostatin adduct to give somatostatin (hollow circle) and total side products (filled circle).

Somatostatin was reduced and bridged with N-functionalised maleimide derivates as described. 100 equiv of 2-mercaptoethanol (1000× stock in 50 mM sodium phosphate, pH 6.2, 40% MeCN, 2.5% DMF) were added and the generation of unmodified peptide and side products (mixed disulfides of 2-mercaptoethanol with the free peptide-cysteines) monitored at 4° C. over 2 d by LC-MS. The results are shown in FIG. 7.

Cleavage of Di-Addition Product of Monobromomaleimide to Somatostatin

Figure 8:
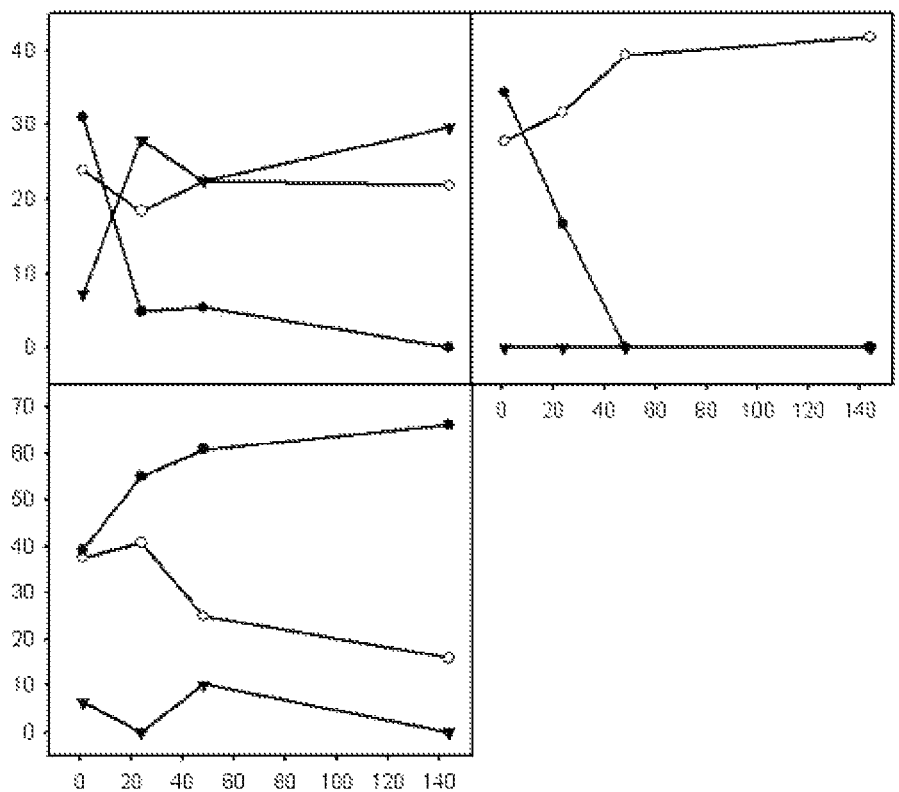
FIG. 8 shows cleavage of the diaddition product of monobromomaleimide with somatostatin according to the protocol described in Example 39 as measured by LC-MS (y-axis=signal %; x-axis=time/hours). Top left: Somatostatin-maleimide (hollow circle), somatostatin-bis-maleimide (filled circle) and total side products (triangle) using 2-mercaptoethanol. Top right: Somatostatin-maleimide (hollow circle), somatostatin-bis-maleimide (filled circle) and total side products (triangle) using DTT. Bottom left: Somatostatin-maleimide (hollow circle), somatostatin-bis-maleimide (filled circle) and total side products (triangle) using TCEP.

Reduced somatostatin was reacted with 2.1 equiv of monobromomaleimide to generate the di-addition product. Next 100 equiv of 2-mercaptoethanol (1000× stock in 50 mM sodium phosphate, pH 6.2, 40% MeCN, 2.5% DMF) were added and the generation of mono-addition product, unmodified peptide and side products (mixed disulfides of 2-mercaptoethanol with the free peptide-cysteines) monitored at ambient temperature over 2.5 h by LC-MS. The results are shown in FIG. 8.

Comparable In Situ Bridging of Somatostatin

Figure 9:
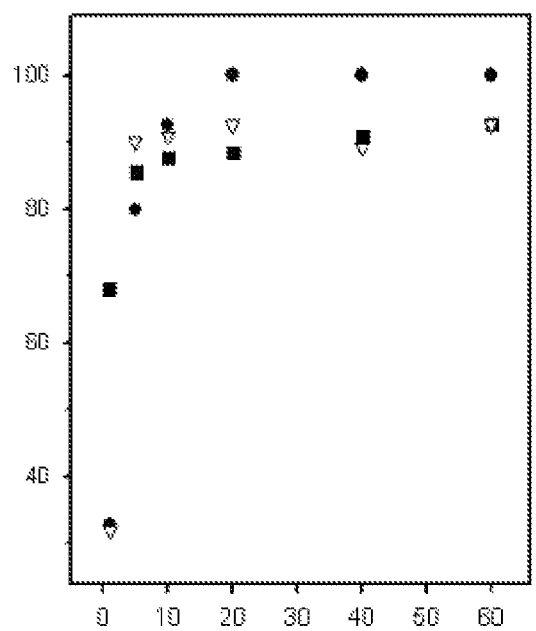
FIG. 9 shows comparable in situ bridging of somatostatin with various amounts of dithiomaleimides according to the protocol described in Example 39 as measured by LC-MS (y-axis=signal %; x-axis=time/min). The Figure shows generation of bridged somatostatin using TCEP initiator and thiophenol in a ratio of 3:5 (circle), selenol initiator with thiophenol in a ratio of 5:10 (square) and selenol initiator with 2-mercaptoethanol in a ratio of 10:20 (triangle).

To somatostatin were added various amounts of dithiomaleimides (100× stock in 50 mM sodium phosphate, pH 6.2, 40% MeCN, 2.5-7.5% DMF) and the reaction was incubated at ambient temperature for 10 min. Next various amounts of TCEP or benzeneselenol (100× stocks, freshly prepared in 50 mM sodium phosphate, pH 6.2, 40% MeCN, 2.5-7.5% DMF) were added and the generation of bridged somatostatin was monitored over 1 h at ambient temperature by LC-MS. The results are shown in FIG. 9.

In Situ PEGylation of Somatostatin

Figure 10:
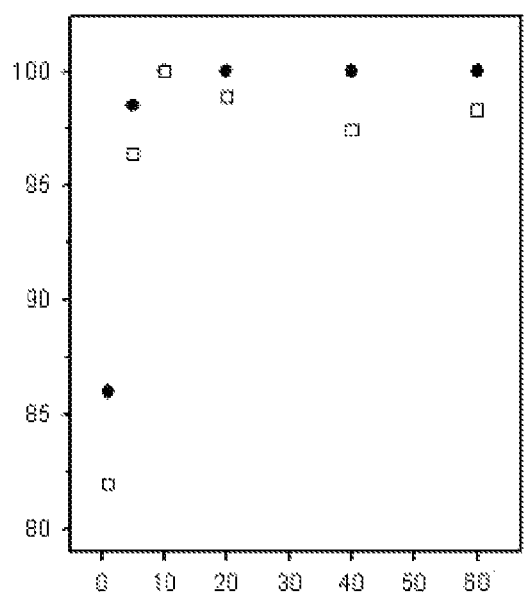
FIG. 10 shows in situ PEGylation of somatostatin according to the protocol described in Example 39 as measured by LC-MS (y-axis=signal %; x-axis=time/min). The Figure shows generation of PEGylated somatostatin using 5 eq. N-PEG5000-dithiophenolmaleimide and 3 eq. TCEP (circle) and using 10 eq. N-PEG5000-dithiophenolmaleimide and 5 eq. benzeneselenol (square).

To somatostatin were added either 5 equiv of N-PEG5000-dithiophenolmaleimide or 10 equiv of N-PEG5000-dithiophenolmaleimide (100× stocks in 50 mM sodium phosphate, pH 6.2, 40% MeCN, 2.5% DMF) and the reaction was incubated at ambient temperature for 10 min. Next 3 equiv of TCEP respectively 5 equiv of benzeneselenol (100× stocks, freshly prepared in 50 mM sodium phosphate, pH 6.2, 40% MeCN, 2.5-7.5% DMF) were added and the generation of PEGylated somatostatin was monitored over 2 h at ambient temperature by LC-MS. The results are shown in FIG. 10.

Modification of Somatostatin with DiBrDDPD

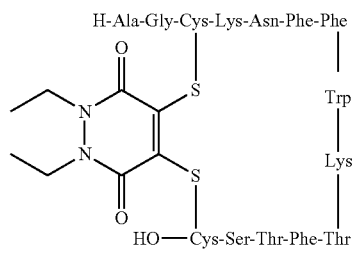

Lyophilized somatostatin (mass=1638) was solubilized in buffer (50 mM sodium phosphate, pH 6.2, 40% MeCN, 2.5% DMF) to yield a concentration of 152.6 µM (0.25 mg/mL) and reduced with 1.1 equiv of TCEP for 1 h at 21° C. Completeness of the reduction was confirmed by LCMS (mass=1640). DiBrDDPD (100 mol eq) was added and the reaction maintained at 21° C. for 10 mins. Somatostatin/DiBrDDPD adduct was observed to form quantitative conversion (mass=1803).

Demonstration the Retained Biological Activity of Bridged Somatostatins Using Patch-Clamping To examine whether the bridging modification had a deleterious effect on the activity of the resultant somatostatin analogues we tested the dibromomaleimide bridged analogue, the PEGylated-dibromomaleimide bridged analogue, and the fluorescein dibromomaleimide-bridged analogue via a patch clamp assay. HEK 293 cells expressing HKIR3.1/3.2 channel and human somatostatin receptor 2 were treated with these compounds, and whole cell patch-clamp current recordings taken. All three analogues induced a robust activation of GIRK currents in an amplitude comparable to somatostatin itself. As a control when cells were treated with Pertussis toxin, or by the GIRK inhibitor Tertiapin Q, currents were largely inhibited. This data confirms that the bridged somatostatin analogues retain the biological activity of somatostatin for agonism of the somatostatin receptor 2.

Cell Culture

Cell-culture methods and the generation of stable cell lines were carried out as described in *J Biol Chem* 275, 921-9 (2000). HEK293 cells (human embryonic kidney cell line) stably expressing Kir3.1 and Kir3.2A channels were maintained in minimum essential medium supplemented with 10% foetal calf serum and 727 µg of G418 (Invitrogen), at 37° C. in humidified atmosphere (95% $O_2$, 5% $CO_2$). Cells were transiently transfected with SSTR2 DNA (Missouri S&T cDNA Resource Center) along with pEGFP-N1 (Clontech) for visualization of transfected cells using epifluorescence. Transfections were performed with 5 µl of Fugene HD (Roche) and 800 ng SSTR2-DNA and 40 ng EGFP-DNA per 97 µl of cell culture medium (containing no serum or antibiotics).

Preparation of Somatostatin and Analogues for Patch-Clamp Experiments

Bridged somatostatins were prepared as described above. Somatostatin and its analogues were dialysed for 24 h at 4° C. in buffer (50 mM sodium phosphate, pH 6.2) to remove the organic solvents. After dialysis the concentration was determined and the peptides stored at 4° C. A final concentration of 20 µM somatostatin and analogues were used (dilution was done in the extracellular patch-clamp buffer).

Electrophysiology

Whole cell patch-clamp current recordings were performed with an Axopatch 200B amplifier (Axon Instruments) using fire-polished pipettes with a resistance of 3-4 MS pulled from filamented borosilicated glass capillaries (Harvard Apparatus, 1.5 mm OD×1.17 mm ID). Data was acquired and analysed via a Digidata 1322A interface (Axon Instruments) and pCLAMP software (version 8.1, Axon Instruments). A fast perfusion system was used to apply somatostatin and analogues (Rapid Solution Changer, RSC-160, Bio-Logic France). Cells were clamped at −60 mV. The extracellular solution was (mM): NaCl 80, KCl 60, $CaCl_2$ 2, $MgCl_2$ 1, HEPES 10, $NaH_2PO_4$ 0.33, glucose 10, pH 7.4; while the intracellular solution was (mM): K gluconate 110, KCl 20, NaCl 10, $MgCl_2$ 1, MgATP 2, EGTA 2 GTP 0.3, pH 7.4. After agonist application, current activated with a delay "lag" followed by a rapid rise to peak amplitude "time to peak". After removal of the agonist, the current decays back to baseline. For each cell it was assessed if flow artifacts resulting from the pressure of drug application were present. This was done by applying bath solution from one of the sewer pipes at the beginning of the recordings. Tertiapin, an inhibitor of GIRK current (Alomone), was used at a final concentration of 100 nM. Cells were incubated overnight with pertussis toxin (Sigma, 100 ng/ml), an inhibitor of Gi/o proteins. Drugs were prepared as concentrated stocks solutions and kept at −20° C.

Figure 11:
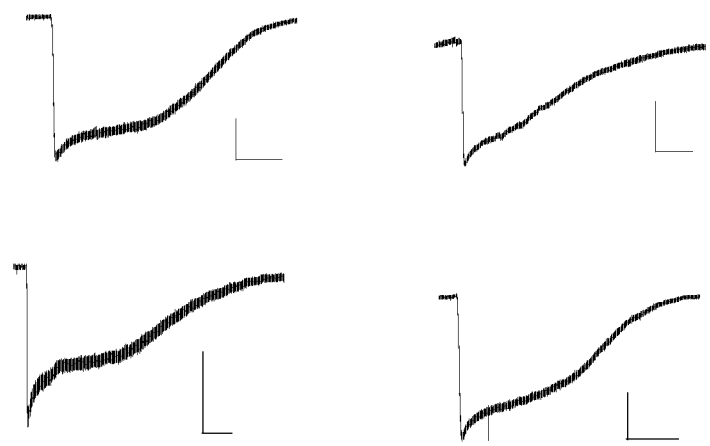
FIG. 11 shows whole cell patch-clamp current recordings obtained in the patch clamp assay described in Example 39. The Figure shows representative traces recorded from the GIRK 1/2A cell line expressing SSTR2. The cells were clamped at −60 mV and 20 μM of somatostatin or its derivatives were applied for 20 s. Top left: somatostatin (in the axes shown the vertical line represents 1000 pA and the horizontal line represents 20 ms). Top right: dibromomaleimide-bridged somatostatin (in the axes shown the vertical line represents 1000 pA and the horizontal line represents 20 ms). Bottom left: fluorescein dibromomaleimide-bridged somatostatin (in the axes shown the vertical line represents 1000 pA and the horizontal line represents 20 ms). Bottom right: PEGylated dibromomaleimide-bridged somatostatin (in the axes shown the vertical line represents 1000 pA and the horizontal line represents 20 ms).
Figure 12:
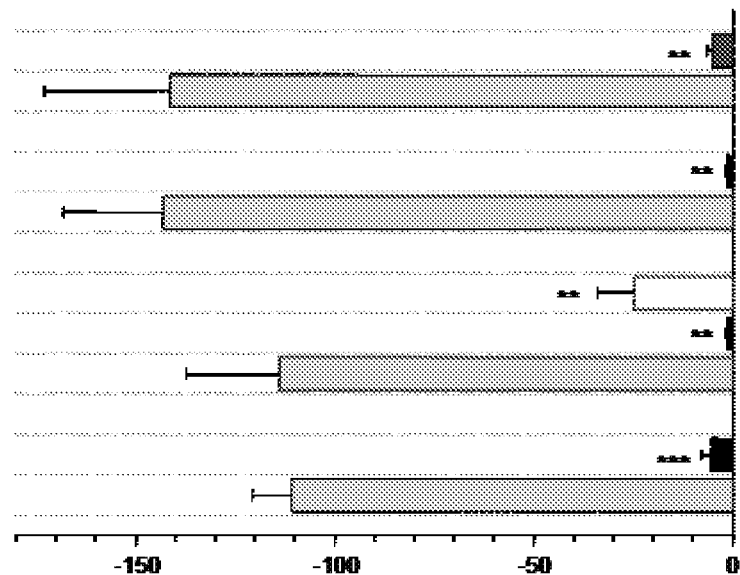
FIG. 12 shows the amplitudes of the currents activated by somatostatin and its analogues in the patch clamp assay described in Example 39. The x-axis represents current amplitude in pA/pF. Top two bars are from fluorescein dibromomaleimide-bridged somatostatin (black bar is after pre-treatment of cell with Pertussis toxin for 24 hr; grey bar is with no pre-treatment), next two bars are from PEGylated dibromomaleimide-bridged somatostatin (black bar is after pre-treatment of cell with Pertussis toxin for 24 hr; grey bar is with no pre-treatment), next three bars are from dibromomaleimide-bridged somatostatin (white bar is after pre-incubation with the GIRK inhibitor TertiapinQ, 100 nM for 5 minutes; black bar is after pre-treatment of cell with Pertussis toxin for 24 hr; grey bar is with no pre-treatment) and bottom two bars are from somatostatin (black bar is after pre-treatment of cell with Pertussis toxin for 24 hr; grey bar is with no pre-treatment).

The results are shown in FIGS. 11 and 12.

Reference Example 79: Preparation of Propylaminomaleimide

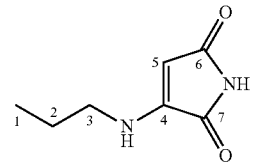

To propylamine (75 µL, 1.09 mmol) and sodium acetate (92 mg, 1.12 mmol) in methanol (15 mL) was added bromomaleimide (200 mg, 1.12 mmol) dropwise in methanol (15 mL). After 10 minutes, solvent was removed in vacuo and purification by flash chromatography (10% ethyl acetate in petroleum ether) afforded the desired compound as a bright yellow waxy solid (82 mg, 0.53 mmol) in 49% yield. $\delta_H$ (500 MHz, $CDCl_3$) 7.36 (s, 1H, NH), 5.45 (s, 1H, NH), 4.80 (d, 1H, J=1.3, H-5), 3.14 (dt, 2H, J=6.2 and 7.2, $H_2$-3), 1.71-1.63 (m, 2H, $H_2$-2), 0.99 (t, 3H, J=7.4, $H_3$-1); $\delta_C$ (125 MHz, $CDCl_3$) 172.31 (C=O), 167.73 (C=O), 149.83 (C4), 85.29 (C5), 46.16 (C3), 21.91 (C2), 11.42 (C1); IR (solid, $cm^{-1}$) 3190 (m), 2962 (m), 1693 (m), 1627 (s); MS (EI) m/z (relative intensity): 154 (M+, 60), 125 (98), 84 (100); Exact Mass Calcd for $[C_7H_{10}N_2O_2]+$ requires m/z 154.0737 Found 154.0734 (EI); UV (Acetonitrile) $\varepsilon_{240}$=7400 and 8348=5700 $cm^{-1}M^{-1}d^3$.

Reference Example 80: Preparation of But-3-enylaminomaleimide

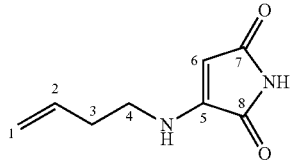

To 3-butenylamine hydrochloride (200 mg, 1.12 mmol) and sodium acetate (184 mg, 2.24 mmol) in methanol (15 mL) was added bromomaleimide (200 mg, 1.12 mmol) dropwise in methanol (15 mL). After 10 minutes, solvent was removed in vacuo and purification by flash chromatography (10% ethyl acetate in petroleum ether) afforded the desired compound as a bright yellow waxy solid (142 mg, 0.85 mmol) in 76% yield. $\delta_H$ (500 MHz, CDCl$_3$) 7.10 (s, 1H, NH), 5.77 (tdd, 1H, J=6.9, 10.7 and 17.4, H-2), 5.38 (s, 1H, NH), 5.18-5.15 (m, 2H, H$_2$-1), 4.83 (d, 1H, J=1.3, H-6), 3.24 (t, 2H, J=6.7, H$_2$-4), 2.40 (dtd, 2H, J=1.2, 6.8 and 6.9, H$_2$-3); $\delta_C$ (125 MHz, CDCl$_3$) 171.94 (C=O), 167.45 (C=O), 149.53 (C5), 133.89 (C2), 118.51 (C1), 85.80 (C6), 43.30 (C4), 32.68 (C3); IR (solid, cm$^{-1}$) 3290 (m), 1703 (m), 1629 (s); MS (ES−) m/z (relative intensity): 165 ([M−H], 100); Exact Mass Calcd for [C$_8$H$_{10}$N$_2$O$_2$]−H requires m/z 165.0659 Found 165.0664 (ES−); m.p. 68-76° C.; UV (Acetonitrile) $\varepsilon_{241}$=8300 and $\varepsilon_{348}$=6100 cm$^{-1}$M$^{-1}$d$^3$.

Reference Example 81: Preparation of N-Methyl propylaminomaleimide

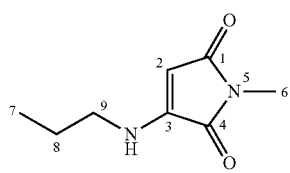

To propylamine (52 µL, 0.78 mmol) and sodium acetate (64 mg, 0.78 mmol) in methanol (30 mL) was added N-methylmonobromomaleimide (150 mg, 0.78 mmol) dropwise in methanol (30 mL). After 10 minutes, solvent was removed in vacuo and purification by flash chromatography (10% ethyl acetate in petroleum ether) afforded the desired compound as a bright yellow waxy solid (41 mg, 0.24 mmol) in 31% yield. $\delta_H$ (500 MHz, CDCl$_3$) 5.43 (s, 1H, NH), 4.80 (s, 1H, H-2), 3.16-3.13 (m, 2H, H$_2$-9), 2.98 (s, 3H, H$_3$-6), 1.71-1.64 (m, 2H, H$_2$-8), 0.99 (t, J=7.5, H$_3$-7); $\delta_C$ (125 MHz, CDCl$_3$) 172.71 (C=O), 167.66 (C=O), 149.51 (C3), 83.84 (C2), 46.01 (C9), 23.44 (C6), 21.87 (C8), 11.38 (C7); IR (film, cm$^{-1}$) 3317 (m), 2944 (w), 1698 (s), 1651 (s); MS (EI) m/z (relative intensity): 168 (M+, 70), 139 (100), 111 (40); Exact Mass Calcd for [C$_8$H$_{12}$N$_2$O$_2$]+ requires m/z 168.0893 Found 168.0887 (EI); UV (Acetonitrile) $\varepsilon_{210}$=15900, $\varepsilon_{240}$=2800, $\varepsilon_{283}$=500 and 8368=500 cm$^{-1}$M$^{-1}$d$^3$.

Reference Example 82: Preparation of 2,9-azatricyclo[5,3,0,0$^{10-4}$]decan-1,3-dione

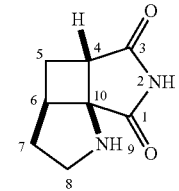

But-3-enylaminomaleimide (42 mg, 0.25 mmol) was dissolved in acetonitrile (25 mL), to provide a 0.01M solution. The resulting solution was degassed for 30 minutes and irradiated in pyrex glassware for 4 minutes with stirring. Solvent was removed in vacuo and purification by flash chromatography (gradient elution in ethyl acetate to 5% methanol in ethyl acetate) afforded the desired compound as an off-white solid (39 mg, 0.23 mmol) in 93% yield. $\delta_H$ (500 MHz, CDCl$_3$) 3.50 (ddd, 1H, J=2.6, 4.8 and 11.8, HH-8), 3.18-3.12 (m, 2H, HH-8 and H-6), 2.98 (dd, 1H, J=3.9 and 10.7, H-4), 2.21 (ddd, 1H, J=4.0, 8.6 and 13.2, HH-5), 2.01 (ddd, 1H, 5.8, 10.5 and 13.4, HH-5), 1.79 (m, 2H, H$_2$-7); $\delta_C$ (125 MHz, CDCl$_3$) 179.04 (C=O), 178.95 (C=O), 70.85 (C10), 48.43 (C8), 44.25 (C4), 43.82 (C6), 32.93 (C7) 24.96 (C5); IR (solid, cm$^{-1}$) 3198 (m), 2944 (m), 1701 (s); MS (EI) m/z (relative intensity): 166 (M+, 45), 125 (100); Exact Mass Calcd for [C$_8$H$_{10}$N$_2$O$_2$]+ requires m/z 166.07387 Found 166.07386 (EI); m.p. 110-113° C.

Reference Example 83: Preparation of (4SR, 6RS, 7SR) 2-Aza-4-hexylsulfanyl-6-carbonitrile-bicyclo[3.2.0]heptan-1,3-dione and (4RS, 5RS, 7RS) 2-Aza-4-hexylsulfanyl-5-carbonitrile-bicyclo[3.2.0]heptan-1,3-dione

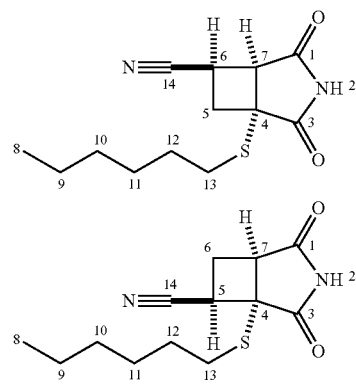

Hexylsulfanylmaleimide (25 mg, 0.12 mmol) was dissolved in acetonitrile (22.5 mL) and acrylonitrile (2.5 mL) to provide a 0.005M solution. The resulting solution was degassed for 30 minutes and irradiated in pyrex glassware for 5 minutes with stirring. Solvent was removed in vacuo and purification by flash chromatography (gradient elution 10% ethyl acetate in petroleum ether to 50% ethyl acetate in petroleum ether) afforded (4SR, 6RS, 7SR) 2-aza-4-hexylsulfanyl-6-carbonitrile-bicyclo[3.2.0]heptan-1,3-dione as a thick colourless oil (9 mg, 0.034 mmol) in 29% yield and (4RS, 7RS, 5RS) 2-aza-4-hexylsulfanyl-5-carbonitrile-bicyclo[3.2.0]heptan-1,3-dione as a thick colourless oil (12 mg, 0.045 mmol) in 39% yield.

(4SR, 6RS, 7SR) 2-Aza-4-hexylsulfanyl-6-carbonitrile-bicyclo[3.2.0]heptan-1,3-dione $\delta_H$ (500 MHz, CDCl$_3$) 3.53 (dt, 1H, J=1.4 and 8.1, H-6), 3.16-3.10 (m, 2H, HH-5 and H-7), 2.89-2.80 (m, 2H, H$_2$-13), 2.56-2.50 (m, 1H, HH-5), 1.67-1.55 (m, 4H, H$_2$-12 and H$_2$-11), 1.42-1.37 (m, 2H, H$_2$-10), 1.33-1.27 (m, 2H, H$_2$-9), 0.89 (t, 3H, J=6.9, H$_3$-8); $\delta_C$ (125 MHz, CDCl$_3$) 174.49 (C=O), 172.91 (C=O), 116.82 (C4), 52.38 (C14), 44.16 (C6), 31.33 (C13), 30.87 (C7), 30.29 (CH$_2$), 29.26 (CH$_2$), 28.64 (CH$_2$), 25.92 (CH$_2$), 22.82 (C5), 14.11 (C8); IR (oil, cm$^{-1}$) 3223 (w), 2926 (w), 1778 (w), 1714 (s); MS (CI+) m/z (relative intensity): 267 ([M+H], 40), 213 (70), 180 (100); Exact Mass Calcd for [C$_{13}$H$_{18}$N$_2$O$_2$S]+H requires m/z 267.1167 Found 267.1175 (CI+).

(4RS, 7RS, 5RS) 2-Aza-4-hexylsulfanyl-5-carbonitrile-bicyclo[3.2.0]heptan-1,3-dione $\delta_H$ (500 MHz, CDCl$_3$) 3.66 (dd, 1H, J=6.0 and 9.5, H-5), 3.23 (dd, 1H, J=5.2 and 10.9, H-7), 3.01-2.82 (m, 3H, HH-6 and H$_2$-13), 2.67 (ddd, 1H, J=5.3, 9.6 and 14.7, HH-6), 1.65-1.60 (m, 2H, H$_2$-12), 1.42-1.36 (m, 2H, H$_2$-11), 1.32-1.27 (m, 4H, H$_2$-9 and H$_2$-10), 0.88 (t, 3H, J=6.8, H$_3$-8); $\delta_C$ (125 MHz, CDCl$_3$) 175.08 (C=O), 174.82 (C=O), 117.13 (C4), 51.24 (C14), 44.26 (C5), 31.36 (C13), 30.96 (C7), 29.82 (CH$_2$), 29.19 (CH$_2$), 28.62 (CH$_2$), 25.72 (C6), 22.58 (CH$_2$), 14.26 (C8); IR (oil, cm$^{-1}$) 3247 (w), 2927 (w), 1717 (s); MS (CI) m/z (relative intensity): 267 ([M+H], 75), 214 (100), 180 (70); Exact Mass Calcd for [C$_{13}$H$_{18}$N$_2$O$_2$S]+H requires m/z 267.1167. Found 267.1158 (CI).

Reference Example 84: Preparation of (5RS, 9SR) 2-Aza-4-hexylsulfanyl-2-aza-tricylo[3.5.0.0$^{5,9}$]di-1,3-one

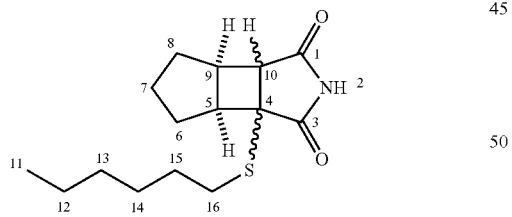

Hexylsulfanylmaleimide (25 mg, 0.12 mmol) was dissolved in acetonitrile (22.5 mL) and cyclopentene (3 mL, 36 mmol) to provide a 0.005M solution. The resulting solution was degassed for 30 minutes and irradiated in pyrex glassware for 5 minutes with stirring. Solvent was removed in vacuo and purification by flash chromatography (gradient elution 10% ethyl acetate in petroleum ether to 50% ethyl acetate in petroleum ether) afforded the desired compound as a thick colourless oil (12 mg, 0.045 mmol) in 77% yield, a 1:1 mix of two inseparable diastereomers. COSY analysis shows that certain signal arise from the same compound, denoted by subscripts 'a' and 'b', but the specific identity of each diastereomer is unknown.

Overlap of signals prevents NOe analysis. $\delta_H$ (500 MHz, CDCl$_3$) 3.15-3.07 (m, 2H, H-5$_a$ and H-10$_a$), 3.00 (t, 1H, J=6.8, H-5$_b$), 2.94 (td, 1H, J=3.9 and 6.6, H-9$_b$), 2.87-2.82 (m, 2H, H-9$_a$ and HH-16$_a$), 2.64-2.59 (m, 1H, HH-16$_b$), 2.52-2.47 (m, 3H, H-10$_b$, HH-16$_a$ and HH-16$_b$), 2.07 (dd, 2H, J=6.3 and 6.9, HH-15$_a$ and HH-15$_b$), 1.96-1.89 (m, 2H, HH-15$_a$ and HH-15$_b$) 1.88-1.82 (m, 4H, H$_2$-7$_a$ and H$_2$-7$_b$) 1.64-1.50 (m, 8H, H$_2$-8$_a$, H$_2$-6$_b$, H$_2$-8$_a$ and H$_2$-8$_b$), 1.38-1.25 (m, 12H, H$_2$-12$_a$, H$_2$-12$_b$, H$_2$-13$_a$, H$_2$-13$_b$, H$_2$-14$_a$ and H$_2$-14$_b$), 0.89-0.86 (m, 6H, H$_3$-11 and H$_3$-11$_b$); $\delta_C$ (125 MHz, CDCl$_3$) 179.09 (C=O), 177.12 (C=O), 176.93 (C=O), 171.83 (C=O), 51.31 (C4), 51.33 (C4), 50.68 (C10), 45.32 (C10), 43.26 (C9), 41.70 (C5), 32.38 (CH$_2$), 30.98 (CH$_2$), 30.95 (CH$_2$), 30.78 (CH$_2$), 28.92 (CH$_2$), 28.50 (CH$_2$), 28.30 (CH$_2$), 28.22 (CH$_2$), 28.10 (CH$_2$), 28.13 (CH$_2$), 25.09 (CH$_2$), 22.14 (CH$_2$), 22.11 (CH$_2$), 13.66 (2×C$_{11}$) Several carbon signals are missing due to overlap of the diastereomers; IR (oil, cm$^{-1}$) 3120 (w), 2927 (m), 1711 (s), 1627 (s); MS (ES−) m/z (relative intensity): 280 ([M−H], 50), 212 (100); Exact Mass Calcd for [C$_{15}$H$_{23}$NO$_2$S]—H requires m/z 280.1371 Found 280.1382 (ES−).

Reference Example 85: Preparation of 4-Hexylsulfanyl-1-phenyl-1,7-dihydro-2H-azepine-3,6-dione and (4RS, 5SR, 7RS) 2-Aza-4-hexylsulfanyl-5-phenyl-bicyclo[3.2.0]heptan-1,3-dione

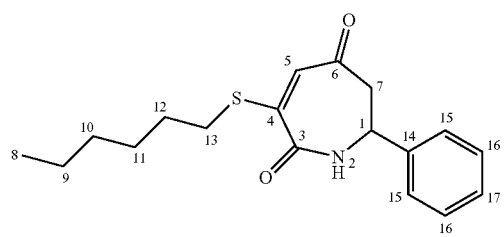 [SMILES: CCCCCCSC1=CC(=O)CC(c2ccccc2)NC1=O]

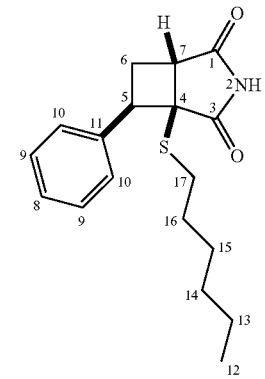 [SMILES: CCCCCCS[C@]12C(=O)NC(=O)[C@H]1C[C@@H]2c1ccccc1]

Hexylsulfanylmaleimide (25 mg, 0.12 mmol) was dissolved in acetonitrile (25 mL) to provide a 0.005M solution. The resulting solution was degassed for 30 minutes, styrene (133 μL, 1.2 mmol) added and the solution irradiated in pyrex glassware for 5 minutes with stirring. Solvent was removed in vacuo and purification by flash chromatography (gradient elution in petroleum ether to 30% ethyl acetate in petroleum ether) afforded 4-hexylsulfanyl-1-phenyl-1,7-dihydro-2H-azepine-3,6-dione as a thick colourless oil (11 mg, 0.034 mmol) in 30% yield and (4RS, 5SR, 7RS) 2-aza-4-hexylsulfanyl-5-phenyl-bicyclo[3.2.0]heptan-1,3-dione as a thick colourless oil (26 mg, 0.082 mmol) in 70% yield

4-Hexylsulfanyl-1-phenyl-1,7-dihydro-2H-azepine-3,6-dione $\delta_H$ (600 MHz, CDCl$_3$) 7.34-7.24 (m, 5H, 5×Ar-H), 6.15 (d, 1H, J=1.5, H-5), 4.11 (t, 1H, J=7.7, H-1), 3.01 (ddd, 1H, J=1.5, 7.8 and 15.8, HH-7), 2.96 (dd, 1H, J=7.8 and 15.6, HH-7), 2.36-2.26 (m, 2H, H$_2$-13), 1.50-1.41 (m, 2H, H$_2$-12), 1.35-1.33 (m, 6H, H$_2$-9, H$_2$-10 and H$_2$-11), 0.85 (t, 3H, J=7.0, H$_3$-8); $\delta_C$ (150 MHz, CDCl$_3$) 170.96 (C=O), 169.95 (C=O), 147.26 (C4), 141.10 (C14), 129.41 (C5), 128.89 (2×Ar-H), 127.86 (C17), 127.71 (2×Ar-H), 47.24 (C1), 32.47 (C13), 31.43 (CH$_2$), 29.19 (CH$_2$), 28.61 (CH$_2$), 22.60 (CH$_2$), 14.10 (C8); IR (oil, cm$^{-1}$) 3288 (w), 2928 (w), 1775 (w), 1717 (s); MS (FAB+) m/z (relative intensity): 340 ([M+Na], 20), 329 (35), 207 (20), 176 (100); Exact Mass Calcd for [C$_{16}$H$_{23}$NO$_2$S]+Na requires m/z 340.1347 Found 340.1351 (FAB+).

(4RS, 5SR, 7RS) 2-Aza-4-hexylsulfanyl-5-phenyl-bicyclo[3.2.0]heptan-1,3-dione $\delta_H$ (600 MHz, CDCl$_3$) 8.77 (s, 1H, NH), 7.39-7.31 (m, 5H, 5×Ar-H), 4.05 (t, 1H, J=8.8, H-5), 3.17 (dd, 1H, J=3.4 and 10.9, H-7), 3.04 (dd, 1H, J=8.4, 11.1 and 12.7, HH-6), 2.63 (ddd, 1H, J=3.6, 9.0 and 12.8, HH-6), 2.43 (ddd, 1H, J=6.7, 7.9 and 11.3, HH-17), 2.13 (ddd, 1H, J=6.6, 8.0 and 11.3, HH-17), 1.30-1.08 (m, 8H, H$_2$-13, H$_2$-14 and H$_2$-15 and H$_2$-16), 0.83 (t, 3H, J=7.3, H$_3$-12); $\delta_C$ (150 MHz, CDCl$_3$) 178.76 (C=O), 177.62 (C=O), 136.51 (C11), 128.77 (2×Ar-H), 128.70 (2×Ar-H), 128.03 (C8), 57.17 (C4), 45.70 (C5), 43.87 (C7), 31.26 (C17), 28.70 (CH$_2$), 28.65 (CH$_2$), 28.52 (CH$_2$), 26.22 (C6), 22.46 (CH$_2$), 14.10 (C12); IR (oil, cm$^{-1}$) 3218 (w), 2926 (w) 1771 (m), 1703 (s); MS (FAB+) m/z (relative intensity): 340 ([M+Na], 20), 199 (25), 176 (100); Exact Mass Calcd for [C$_{16}$H$_{23}$NO$_2$S]+Na requires m/z 340.1347. Found 340.1357 (FAB+).

Reference Example 86: Preparation of (4RS, 7SR, 5RS) 2-Aza-4-hexylsulfanyl-5-carboxylic acid methyl ester-bicyclo [3.2.0]heptan-1,3-dione

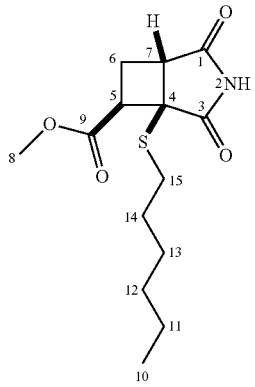 [SMILES: CCCCCCS[C@]12C(=O)NC(=O)[C@H]1C[C@@H]2C(=O)OC]

Hexylsulfanylmaleimide (25 mg, 0.12 mmol) was dissolved in acetonitrile (21.9 mL) and methyl acrylate (3.1 mL, 36 mmol) to provide a 0.005M solution. The resulting solution was degassed for 30 minutes and irradiated in pyrex glassware for 5 minutes with stirring. Solvent was removed in vacuo and purification by flash chromatography (gradient elution in 10% ethyl acetate in petroleum ether to 50% ethyl acetate in petroleum ether) afforded the desired compound as a thick colourless oil (17 mg, 0.056 mmol) in 48% yield.

$\delta_H$ (600 MHz, CDCl$_3$) 8.50 (s, 1H, NH), 3.81 (s, 3H, H$_3$-8), 3.57 (dd, 1H, J=5.8 and 8.5, H-5), 3.18 (dd, 1H, J=5.0 and 10.7, H-7), 3.11 (ddd, 1H, J=5.5, 11.0 and 12.9, HH-6), 2.73 (dt, 1H, J=7.5 and 11.5, HH-15), 2.64 (dt, 1H, J=7.5 and 11.5, HH-15), 2.29 (ddd, 1H, J=5.2, 8.5 and 13.2, HH-6), 1.52-1.47 (m, 2H, H$_2$-14), 1.35-1.30 (m, 2H, H$_2$-13), 1.29-1.21 (m, 4H, H$_2$-11 and H$_2$-12), 0.87 (t, 3H, J=6.7, H$_3$-10); $\delta_C$ (150 MHz, CDCl$_3$) 176.65 (C=O), 171.13 (C=O), 170.48 (C=O), 52.59 (C8), 52.39 (C4), 44.56 (C7), 44.06 (C5), 31.41 (C15), 29.73 (CH$_2$), 29.16 (CH$_2$), 28.68 (CH$_2$), 23.57 (C12), 22.57 (C11), 14.11 (C10); IR (oil, cm$^{-1}$) 3244 (w), 2928 (w) 1778 (w), 1714 (s); MS (FAB+) m/z (relative intensity): 322 ([M+Na], 100), 300 (30), 214 (25); Exact Mass Calcd for [C$_{14}$H$_{21}$NO$_4$SN]+Na requires m/z 322.1089 Found 322.1082 (FAB+).

Reference Example 87: Preparation of (4RS, 5SR, 7RS) 2-Aza-4-hexylsulfanyl-5-carboxylic acid phenyl ester-bicyclo [3.2.0]heptan-1,3-dione

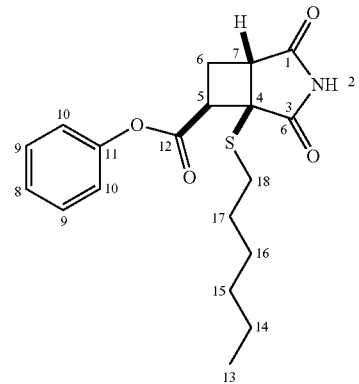 [SMILES: CCCCCCS[C@]12C(=O)NC(=O)[C@H]1C[C@@H]2C(=O)Oc1ccccc1]

Hexylsulfanylmaleimide (25 mg, 0.12 mmol) was dissolved in acetonitrile (25 mL) to provide a 0.005M solution. The resulting solution was degassed for 30 minutes, phenyl acrylate (160 µL, 1.20 mmol) added and irradiated in pyrex glassware for 5 minutes with stirring. Solvent was removed in vacuo and purification by flash chromatography (gradient elution in petroleum ether to 30% ethyl acetate in petroleum ether) afforded the desired compound as a thick colourless oil (21 mg, 0.058 mmol) in 48% yield and hexylsulfanylmaleimide dimer (12 mg, 0.028 mmol) in 47% yield. $\delta_H$ (600 MHz, CDCl$_3$) 8.41 (s, 1H, NH), 7.41-7.39 (m, 2H, 2×Ar-H), 7.27-7.25 (m, 1H, H-8), 7.20 (d, 1H, J=7.8, 2×Ar-H), 3.80 (dd, 1H, J=5.1 and 8.5, H-5), 3.29 (dd, 1H, J=5.1 and 10.7, H-7), 3.20 (ddd, 1H, J=5.5, 10.9 and 13.0, HH-6), 2.62 (dt, 1H, J=7.5 and 11.5, HH-18), 2.73 (dt, 1H, J=7.5 and 11.5, HH-18), 2.40 (ddd, 1H, J=5.6, 8.8 and 13.5, HH-6), 1.54-1.48 (m, 2H, H$_2$-17), 1.33-1.16 (m, 6H, H$_2$-14, H$_2$-15 and H$_2$-16), 0.84 (t, 3H, J=6.9, H$_3$-13); $\delta_C$ (150 MHz, CDCl$_3$) 176.35 (C=O), 176.19 (C=O), 168.85 (C=O), 150.66 (C11), 129.64 (2×Ar-H), 126.34 (C8), 121.54 (2×Ar-H), 52.59 (C4), 44.78 (C7), 44.17 (C5), 31.36 (CH$_2$), 29.94 (C18), 29.09 (CH$_2$), 28.68 (CH$_2$), 23.83 (C6), 22.56 (CH$_2$), 14.08 (C13); IR (oil, cm$^{-1}$) 3213 (w), 2927 (w) 1757 (m), 1715 (s); MS (CI+) m/z (relative intensity): 362 ([M+H], 35), 268 (100), 149 (25); Exact Mass Calcd for [C$_{19}$H$_{23}$NO$_4$S]+H requires m/z 362.1426 Found 362.1431 (CI+).

Reference Example 88: Preparation of (4RS, 5SR, 7RS) 2-Aza-4-hexylsulfanyl-5-(p-amino)phenyl-bicyclo[3.2.0]heptan-1,3-dione

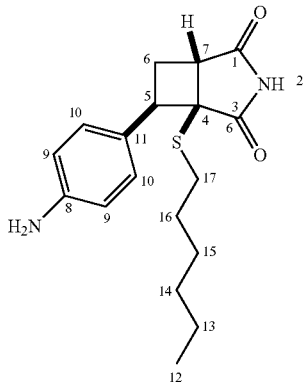 [SMILES: CCCCCCS[C@]12C(=O)NC(=O)[C@H]1C[C@@H]2c1ccc(N)cc1]

Hexylsulfanylmaleimide (25 mg, 0.12 mmol) was dissolved in acetonitrile (25 mL) to provide a 0.005M solution. The resulting solution was degassed for 30 minutes, 4-vinyl aniline (136 µL, 1.2 mmol) added and irradiated in pyrex glassware for 5 minutes with stirring. Solvent was removed in vacuo and purification by flash chromatography (gradient elution in petroleum ether to 30% ethyl acetate in petroleum ether) afforded the desired compound as a thick colourless oil (7 mg, 0.021 mmol) in 17% yield. $\delta_H$ (600 MHz, CDCl$_3$) 8.17 (s, 1H, NH), 7.10 (d, 2H, J=8.5, 2×Ar-H), 6.67 (d, 2H, J=8.5, 2×Ar-H), 3.94 (t, 1H, J=9.0, H-5), 3.13 (dd, 1H, J=3.7 and 11.1, H-7), 2.98 (ddd, 1H, J=8.8, 11.2 and 12.9, HH-6), 2.58 (ddd, 1H, J=3.5, 9.1 and 12.8, HH-6), 2.42 (dt, 1H, J=7.5 and 11.5, HH-17), 2.17 (dt, 1H, J=7.5 and 11.5, HH-17), 1.34-1.29 (m, 2H, H$_2$-16), 1.25-1.11 (m, 6H, H$_2$-13, H$_2$-14 and H$_2$-15), 0.80 (t, 3H, J=7.4, H$_3$-12); $\delta_C$ (150 MHz, CDCl$_3$) 178.64 (C=O), 177.48 (C=O), 146.28 (C8), 129.81 (2×Ar-H), 126.20 (C11), 114.81 (2×Ar-H), 57.97 (C4), 45.48 (C5), 43.79 (C7), 31.35 (CH$_2$), 29.07 (CH$_2$), 28.65 (C17), 26.41 (C6), 22.54 (CH$_2$), 14.12 (C12); IR (oil, cm$^{-1}$) 3214 (w), 2928 (w) 1769 (m), 1715 (s); MS (CI+) m/z (relative intensity): 333 ([M+H], 55), 119 (100); Exact Mass Calcd for [C-$_{18}$H$_{24}$N$_2$O$_2$S]+H requires m/z 333.1637 Found 333.1642 (CI+).

Reference Example 89: Preparation of 4-Hexylsulfanyl-1-(m-nitro)phenyl-1,7-dihydro-2H-azepine-3,6-dione, (4RS, 5SR, 7RS) 2-Aza-4-hexylsulfanyl-5-(m-nitro)phenyl-bicyclo[3.2.0]heptan-1,3-dione and (4RS, 5RS, 7RS) 2-Aza-4-hexylsulfanyl-5-(m-nitro)phenyl-bicyclo[3.2.0]heptan-1,3-dione

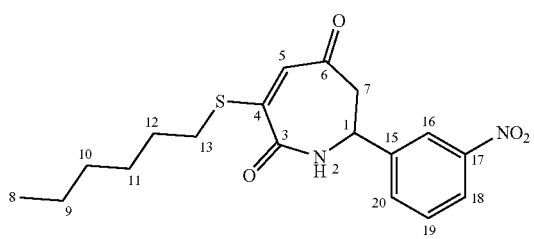

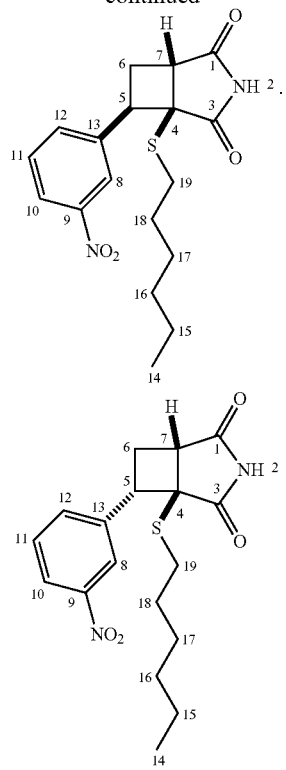

Hexylsulfanylmaleimide (25 mg, 0.12 mmol) was dissolved in acetonitrile (25 mL) to provide a 0.005M solution. The resulting solution was degassed for 30 minutes, 3-nitrostyrene (136 µL, 1.2 mmol) added and irradiated in pyrex glassware for 5 minutes with stirring. Solvent was removed in vacuo and purification by flash chromatography (gradient elution in petroleum ether to 30% ethyl acetate in petroleum ether) afforded 4-hexylsulfanyl-1-(m-nitro)phenyl-1,7-dihydro-2H-azepine-3,6-dione as a thick colourless oil (23 mg, 0.063 mmol) in 55% yield, (4RS, 5SR, 7RS) 2-aza-4-hexylsulfanyl-5-(m-nitro)phenyl-bicyclo[3.2.0]heptan-1,3-dione as a thick colourless oil (0.5 mg, 0.001 mmol) in 1% yield (alongside 4-hexylsulfanyl-1-(m-nitro)phenyl-1,7-dihydro-2H-azepine-3,6-dione), and (4RS, 5RS, 7RS) 2-aza-4-hexylsulfanyl-5-(m-nitro)phenyl-bicyclo[3.2.0]heptan-1,3-dione as a thick colourless oil (12 mg, 0.33 mmol) in 21% yield (alongside dimer).

2-Aza-4-hexylsulfanyl-1-(m-nitro)phenyl-1,7-dihydro-2H-azepine-3,6-dione $\delta_H$ (600 MHz, CDCl$_3$) 8.22 (s, 1H, H-16), 8.14 (d, 1H, J=8.5, Ar—H), 7.68 (t, 1H, J=7.6, Ar—H), 7.53 (t, 1H, J=7.8, H-19), 7.20 (s, 1H, NH), 6.29 (s, 1H, H-5), 4.25 (t, 1H, J=7.9, H-1), 3.03 (dd, 1H, J=8.4 and 15.4, HH-7), 2.98 (dd, 1H, J=7.4 and 15.2, HH-7), 2.37-2.26 (m, 2H, H$_2$-13), 1.30-1.24 (m, 2H, H$_2$-12), 1.21-1.08 (m, 6H, 3×CH$_2$), 0.81 (t, 3H, J=7.1, H$_3$-8); $\delta_C$ (150 MHz, CDCl$_3$) 170.70 (C=O), 169.54 (C=O), 148.60 (C16), 146.35 (C4), 143.94 (C14), 133.83 (Ar—H), 129.96 (Ar—H), 129.86 (C5), 122.96 (Ar—H), 122.59 (Ar—H), 46.78 (C1), 32.52 (C7), 31.56 (CH$_2$), 31.37 (C13), 29.03 (CH$_2$), 28.52 (CH$_2$), 22.57 (CH$_2$), 14.11 (C8); IR (oil, cm$^{-1}$) 3282 (w), 2928 (m) 1775 (w), 1717 (s); Mass ion not found.

(4RS, 5SR, 7RS) 2-Aza-4-hexylsulfanyl-5-(m-nitro) phenyl-bicyclo[3.2.0]heptan-1,3-dione Signals are Bold $\delta_H$ (600 MHz, CDCl$_3$) 8.59 (s, 0.2H, NH), 8.22-8.16 (m, 0.4H, 2×Ar-H), 8.15 (d, 1H, J=8.4, H-10), 8.07 (s, 1H, H-8), 7.84 (s, 1H, NH), 7.66 (d, 0.2H, J=7.5, Ar—H), 7.62 (d, 1H, J=7.6, H-12), 7.56 (t, 0.2H, J=8.0, H-11), 7.53 (t, 1H, J=8.0, H-11), 4.14 (t, 0.2H, J=8.6, H-5), 4.10 (t, 1H, J=9.4, H-5), 3.30 (dd, 1H, J=6.1 and 10.4, H-7), 3.23 (dd, 0.2H, J=3.0 and 11.6, H-7), 3.17 (dt, 1H, J=10.3 and 13.3, HH-6), 3.05 (ddd, 0.2H, J=8.5, 11.1 and 13.1, HH-6), 2.73 (ddd, 0.2H, J=3.6, 9.0 and 12.9, HH-6), 2.68-2.56 (m, 3H, HH-6 and H$_2$-9), 2.45 (ddd, 0.2H, J=6.7, 8.1 and 11.4, HH-19), 2.13 (ddd, 0.2H, J=6.8, 8.0 and 11.3, HH-19), 1.40-1.35 (m, 2.4H, H$_2$-18 and H$_2$-18), 1.31-1.23 (m, 6H, H$_2$-15, H$_2$-16 and H$_2$-17), 1.21-1.08 (m, 1.2H, H$_2$-15, H$_2$-16 and H$_2$-17), 0.87 (t, 3H, J=6.9, H$_3$-14), 0.81 (t, 0.6H, J=7.1, H$_3$-14); $\delta_C$ (150 MHz, CDCl$_3$) 176.25 (C=O), 174.16 (C=O), 148.44 (C9), 139.02 (C13), 133.88 (Ar—H), 129.69 (Ar—H), 123.07 (Ar—H), 121.92 (Ar—H), 57.34 (C4), 46.76 (C5), 44.18 (C7), 31.36 (CH$_2$), 30.21 (CH$_2$), 29.33 (C19), 28.68 (CH$_2$), 26.07 (C6), 22.57 (CH$_2$) 14.11 (C14); IR (oil, cm$^{-1}$) 2934 (w), 1719 (s); MS (CI+) m/z (relative intensity): 363 ([M+H], 65), 214 (90), 180 (100); Exact Mass Calcd for [C$_{18}$H$_{22}$N$_2$O$_4$S]+H requires m/z 363.1379 Found 363.1397 (CI+).

(4RS, 5RS, 7RS) 2-Aza-4-hexylsulfanyl-5-(m-nitro) phenyl-bicyclo[3.2.0]heptan-1,3-dione $\delta_H$ (600 MHz, CDCl$_3$) 8.59 (s, 1H, NH), 8.22-8.16 (m, 2H, 2×Ar-H), 7.66 (d, 1H, J=7.5, Ar—H), 7.56 (t, 1H, J=8.0, H-11), 4.14 (t, 1H, J=8.6, H-5), 3.23 (dd, 1H, J=3.0 and 11.6, H-7), 3.05 (ddd, 1H, J=8.5, 11.1 and 13.1, HH-6), 2.73 (ddd, 1H, J=3.6, 9.0 and 12.9, HH-6), 2.45 (ddd, 1H, J=6.7, 8.1 and 11.4, HH-19), 2.13 (ddd, 1H, J=6.8, 8.0 and 11.3, HH-19), 1.30-1.24 (m, 2H, H$_2$-18), 1.21-1.08 (m, 6H, H$_2$-15, H$_2$-16 and H$_2$-17), 0.81 (t, 3H, J=7.1, H$_3$-14); $\delta_C$ (150 MHz, CDCl$_3$) 177.94 (C=O), 176.84 (C=O), 148.14 (C9), 138.76 (C13), 135.29 (Ar—H), 129.24 (Ar—H), 123.39 (Ar—H), 123.16 (Ar—H), 56.71 (C4), 45.09 (C5), 43.69 (C7), 31.26 (CH$_2$), 28.88 (CH$_2$), 28.84 (C19), 28.51 (C6), 26.33 (CH$_2$), 22.57 (CH$_2$), 14.06 (C14); IR (oil, cm$^{-1}$) 3214 (w), 2928 (w) 1773 (m), 1709 (s); MS (CI+) m/z (relative intensity): 363 ([M+H], 10), 214 (15), 84 (100); Exact Mass Calcd for [C$_{18}$H$_{22}$N$_2$O$_4$S]+H requires m/z 363.1379 Found 363.1394 (CI+).

Reference Example 90: Preparation of (4RS, 5SR, 7RS) 2-Aza-4-(N-Boc-L-Cys-OMe)-5-phenyl-bicyclo[3.2.0]heptan-1,3-dione

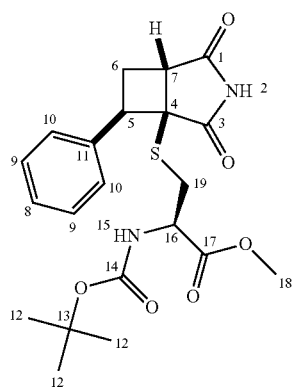

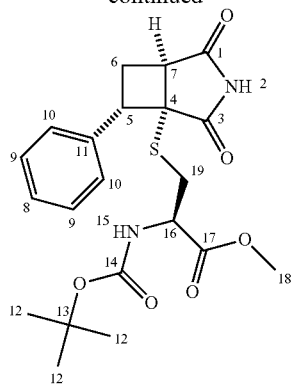

N-Boc-Cys(Mal)-OMe (50 mg, 0.15 mmol) was dissolved in acetonitrile (30 mL) to provide a 0.005M solution. The resulting solution was degassed for 30 minutes, styrene (136 µL, 1.2 mmol) added and irradiated in pyrex glassware for 5 minutes with stirring. Solvent was removed in vacuo and purification by flash chromatography (gradient elution in petroleum ether to 30% ethyl acetate in petroleum ether) afforded the desired compound as a thick colourless oil (16 mg, 0.037 mmol) in 24% yield as a mixture of two major diastereomers (small signals suggest two other diastereomers, possibly regioisomers regarding the addition of the styrene). Reanalysis of the crude suggests that the reaction was successful in at least 80%. $\delta_H$ (600 MHz, CDCl$_3$) 8.08 (s, 2H, 2×H-2), 7.40-7.31 (m, 10H, 10×Ar-H), 5.0 (d, 1H, J=8.2, H-15), 4.9 (d, 1H, J=7.5, H-15), 4.26-4.23 (m, 1H, H-16), 4.18-4.12 (m, 1H, H-16), 4.06 (t, 2H, J=8.5, 2×H-5), 3.669 (s, 3H, H$_3$-18), 3.674 (s, 3H, H$_3$-18), 3.19 (ddd, 1H, J=2.4 and 11.0, H-7), 3.11 (dd, 1H, J=3.2 and 11.0, H-7) 3.04-2.93 (m, 3H, 2×HH-6 and HH-19), 2.91 (dd, 1H, J=6.6 and 12.8, HH-19), 2.64-2.60 (m, 2H, 2×HH-6), 2.51 (dd, 1H, J=4.6 and 12.8, HH-19), 2.43 (dd, 1H, J=7.3 and 13.0, HH-19), 1.45 (s, 9H, 3×H$_3$-12), 1.43 (s, 9H, 3×H$_3$-12); $\delta_C$ (150 MHz, CDCl$_3$) 178.41 (C=O), 177.25 (C=O), 177.20 (C=O), 171.40 (C=O), 171.10 (C=O), 170.98 (C=O), 155.28 (C=O), 155.18 (C=O), 136.28 (C11), 136.25 (C11), 128.94 (2×Ar-H), 128.93 (2×Ar-H), 128.49 (2×Ar—H), 128.46 (2×Ar-H), 128.38 (C8), 128.33 (C8), 80.44 (2×C$_{13}$), 56.71 (C4), 56.48 (C4), 53.03 (C16), 52.87 (C16), 52.78 (C18), 52.75 (C18), 45.92 (C5), 45.82 (C5), 43.76 (C7), 43.61 (C7), 31.28 (C6), 31.09 (C6), 28.38 (6×C$_{12}$), 26.33 (C19), 26.21 (C19); IR (oil, cm$^{-1}$) 3215 (w), 2971 (w) 1738 (s), 1715 (s); MS (CI+) m/z (relative intensity): 435 ([M+H], 10), 379 (30), 335 (100); Exact Mass Calcd for [C$_{21}$H$_{27}$N$_2$O$_6$S]+H requires m/z 435.1590 Found 435.1576 (CI+).

Reference Example 91: Preparation of 1-(p-Methoxy)phenyl-4-Hexylsulfanyl-1,7-dihydro-2H-azepine-3,6-dione, (4RS, 5RS, 7RS) 2-Aza-4-Hexylsulfanyl-5-(p-methoxy)phenyl-bicyclo[3.2.0] heptan-1,3-dione and (4RS, 5SR, 7RS) 2-Aza-4-Hexylsulfanyl-5-(p-methoxy)phenyl-bicyclo[3.2.0] heptan-1,3-dione

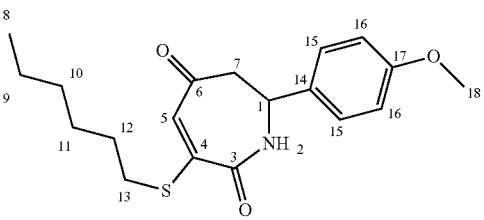

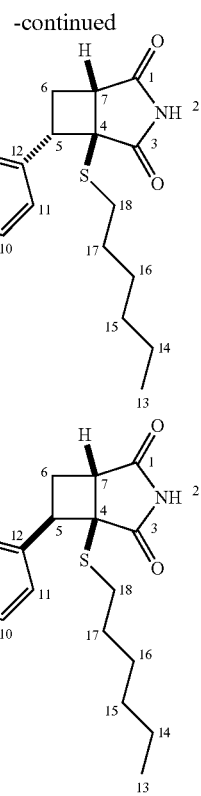

Hexylsulfanylmaleimide (25 mg, 0.12 mmol) was dissolved in acetonitrile (25 mL) to provide a 0.005M solution. The resulting solution was degassed for 30 minutes, 4-methoxy styrene (154 μL, 1.20 mmol) added and irradiated in pyrex glassware for 5 minutes with stirring. Solvent was removed in vacuo and purification by flash chromatography (gradient elution in petroleum ether to 30% ethyl acetate in petroleum ether) afforded 1-(p-methoxy)phenyl-4-Hexylsulfanyl-1,7-dihydro-2H-azepine-3,6-dione as a colourless oil (10 mg, 0.037 mmol) in 25% yield and (4RS, 5RS, 7RS) 2-aza-4-hexylsulfanyl-5-(p-methoxy)phenyl-bicyclo[3.2.0]heptan-1,3-dione (major) and (4RS, 5SR, 7RS) 2-aza-4-hexylsulfanyl-5-(p-methoxy)phenyl-bicyclo[3.2.0]heptan-1,3-dione (minor) as a colourless oil (27 mg, 0.77 mmol) in 67% yield as a mixture of diastereomers (10:1).

4-Hexylsulfanyl-1-(p-methoxy)phenyl-1,7-dihydro-2H-azepine-3,6-dione $\delta_H$ (600 MHz, CDCl$_3$) 7.21 (d, 2H, J=8.5, 2×Ar-H), 7.18 (s, 1H, NH), 6.84 (d, 2H, J=9.0, 2×Ar—H), 6.13 (s, 1H, H-5), 4.08 (t, 1H, J=7.9, H-1), 3.80 (s, 3H, H$_3$-18), 2.99 (dd, 1H, J=7.2 and 15.7, HH-7), 2.91 (dd, 1H, J=8.7 and 15.7, HH-7), 2.35-2.26 (m, 2H, H$_2$-13), 1.51-1.43 (m, 2H, H$_2$-12), 1.33-1.16 (m, 6H, H$_2$-9H$_2$-10 and H$_2$-11), 0.85 (t, 3H, J=7.0, H$_3$-8); $\delta_C$ (150 MHz, CDCl$_3$) 171.03 (C=O), 170.05 (C=O), 159.06 (C17), 147.37 (C4), 132.92 (C14), 129.37 (C5), 128.79 (2×Ar-H), 114.18 (2×Ar-H), 55.38 (C18), 46.61 (C1), 32.59 (C7), 31.45 (C13), 31.38 (CH$_2$), 29.22 (CH$_2$), 28.64 (CH$_2$), 22.61 (CH$_2$), 14.14 (C8); IR (oil, cm$^{-1}$) 3275 (w), 2927 (m) 1774 (w), 1717 (s); MS (CI+) m/z (relative intensity): 347 ([M+], 15), 237 (70), 230 (100), 202 (60); Exact Mass Calcd for [C$_{19}$H$_{25}$NO$_3$S]+ requires m/z 347.1550 Found 363.1553 (CI+).

(4RS, 5RS, 7RS) 2-Aza-4-hexylsulfanyl-5-(p-methoxy)phenyl-bicyclo[3.2.0]heptan-1,3-dione (in bold) and (4RS, 5SR, 7RS) 2-Aza-4-hexylsulfanyl-5-(p-methoxy)phenyl-bicyclo[3.2.0]heptan-1,3-dione $\delta_H$ (600 MHz, CDCl$_3$) 8.71 (s, 1H, NH), 8.45 (s, 0.1H, NH), 7.24 (d, 2H, J=7.86 2×Ar-H), 7.15 (d, 0.2H, J=8.7, 2×Ar-H), 6.90 (d, 1H, J=8.6, 2×Ar-H), 6.86 (d, 0.2H, J=8.6, 2×Ar—H), 3.99 (t, 1H, J=8.8, H-5), 3.94 (dd, 0.1H, J=8.4 and 10.1, H-5), 3.81 (s, 3H, H$_3$-8), 3.77 (s, 0.3H, H$_3$-8), 3.20 (dd, 0.1H, J=4.5 and 11.9, H-7), 3.13 (dd, 1H, J=3.4 and 11.0, H-7), 3.09 (dt, 0.1H, J=10.6 and 13.2, HH-6), 2.98 (ddd, 1H, J=8.7, 11.2 and 12.9, HH-6), 2.67 (dt, 0.1H, J=7.3 and 11.5, HH-18), 2.63-2.53 (m, 1.1H, HH-6 and HH-18), 2.54 (ddd, 1H, J=4.5, 8.4 and 11.9, HH-6), 2.43 (ddd, 1H, J=6.7, 8.2 and 11.3, HH-18), 2.15 (ddd, 1H, J=6.7, 8.4 and 11.4, HH-18), 1.56-1.52 (m, 0.2H, H$_2$-17), 1.39-1.33 (m, 0.2H, CH$_2$), 1.31-1.09 (m, 8.4H, H$_2$-14, H$_2$-15, H$_2$-16, H$_2$-17 and 2×CH$_2$) 0.87 (t, 0.3H, J=7.1, H$_3$-13), 0.83 (t, 3H, J=7.1, H$_3$-13); Only signals of major diastereoisomer shown $\delta_C$ (150 MHz, CDCl$_3$) 177.81 (C=O), 175.48 (C=O), 159.39 (C9), 129.94 (2×Ar-H), 128.56 (C12), 113.65 (2×Ar-H), 57.63 (C4), 55.38 (C8), 45.25 (C5), 43.78 (C7), 31.33 (CH$_2$), 29.23 (CH$_2$), 29.01 (CH$_2$), 28.62 (CH$_2$), 26.53 (C18), 22.52 (C6), 14.10 (C13); IR (oil, cm$^{-1}$) 3216 (w), 2928 (m) 1771 (m), 1707 (s); MS (CI+) m/z (relative intensity): 348 ([M+H], 20), 135 (20), 134 (100); Exact Mass Calcd for [C$_{19}$H$_{25}$NO$_3$S]+H requires m/z 348.1633 Found 363.1642 (CI+).

Reference Example 92: Preparation of (4RS, 5SR, 7RS) 2-Aza-4-(N-Ac-L-Cys-Benzylamine)-5-phenyl-bicyclo[3.2.0]heptan-1,3-dione

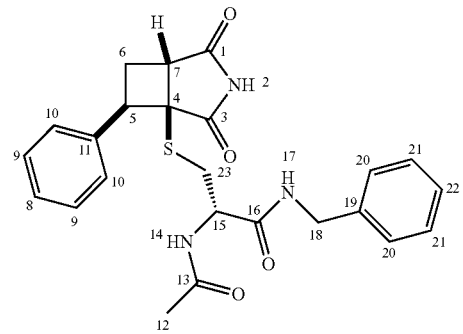 [SMILES: CC(=O)N[C@H](CS[C@]12C(=O)NC(=O)[C@H]1C[C@@H]2c1ccccc1)C(=O)NCc1ccccc1]

N—Ac-Cys(Mal)-Benzylamine (29 mg, 0.084 mmol) was dissolved in acetonitrile (50 mL) to provide a 0.002M solution. The resulting solution was degassed for 30 minutes, styrene (10 μL, 0.084 mmol) added and irradiated in pyrex glassware for 5 minutes with stirring. Solvent was removed in vacuo and purification by flash chromatography (gradient elution in 30% ethyl acetate in petroleum ether to 10% methanol in ethyl acetate) afforded the desired compound as a colourless oil (33 mg, 0.073 mmol) in 87% as a mixture of diastereomers of the [2+2] reaction. Reanalysis of the crude suggests the reaction was successful in around 70%.

N—Ac-Cys(Mal)-Benzylamine (58 mg, 0.17 mmol) was dissolved in acetonitrile (80 mL) to provide a 0.002M solution. The resulting solution was degassed for 30 minutes, styrene (191 μL, 1.70 mmol) added and irradiated in pyrex glassware for 5 minutes with stirring. Solvent was removed in vacuo and purification by flash chromatography (gradient elution in 30% ethyl acetate in petroleum ether to 10% methanol in ethyl acetate) afforded the desired compound as a colourless oil (14 mg, 0.031 mmol) in 19% yield. Reanalysis of the crude suggests the reaction was successful in at least 75%.

$\delta_H$ (600 MHz, CDCl$_3$) 8.69 (s, 1H, H-2), 7.36-7.26 (m, 8H, 8×Ar-H), 7.18 (d, 2H, J=7.0, 2×Ar-H), 6.65 (t, 1H, J=5.6, H-17), 6.51 (d, 1H, J=7.4, H-14), 4.33 (d, 2H, J=6.0, H$_2$-18), 4.30 (td, 1H, J=1.2 and 5.4, H-15), 4.05 (t, 1H, J=8.9, H-5), 3.16 (dd, 1H, J=3.1 and 11.1, H-7), 3.04 (ddd, 1H, J=8.9, 11.1 and 12.8, HH-23), 2.94 (dd, 1H, J=6.6 and 13.3, HH-6), 2.59 (ddd, 1H, J=3.4, 8.9 and 12.5, HH-23), 2.31 (dd, 1H, J=5.3 and 13.6, HH-6), 1.98 (s, 3H, H$_3$-12); $\delta_C$ (150 MHz, CDCl$_3$) 179.07 (C=O), 176.97 (C=O), 171.10 (C=O), 169.67 (C=O), 137.67 (Ar), 136.16 (Ar), 129.02 (2×Ar-H), 128.80 (2×Ar-H), 128.55 (2×Ar-H), 128.35 (Ar—H), 128.78 (2×Ar-H), 127.66 (Ar—H), 57.44 (C4), 52.61 (C15), 46.09 (C5), 43.68 (C7), 43.66 (C18), 30.58 (C6), 26.15 (C23), 23.17 (C12); IR (oil, cm$^{-1}$) 3437 (w), 1726 (s); MS (FAB+) m/z (relative intensity): 695 ([M+H], 10), 439 (10), 286 (100); Exact Mass Calcd for [C$_{32}$H$_{34}$N$_6$O$_8$S$_2$]+H requires m/z 695.1958 Found 695.1964 (FAB+).

Reference Example 93: Preparation of (4RS, 5RS, 7RS) 2-Aza-2-methyl-4-hexylsulfanyl-5-phenyl-bicyclo[3.2.0]heptan-1,3-dione and (4RS, 5SR, 7RS) 2-Aza-2-methyl-4-hexylsulfanyl-5-phenyl-bicyclo[3.2.0]heptan-1,3-dione

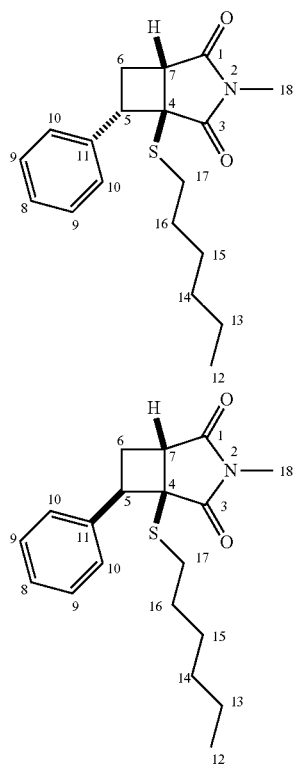

N-Methyl hexylsulfanylmaleimide (27 mg, 0.119 mmol) was dissolved in acetonitrile (25 mL) to provide a 0.005M solution. The resulting solution was degassed for 30 minutes, styrene (136 µL, 1.19 mmol) added and irradiated in pyrex glassware for 5 minutes with stirring. Solvent was removed in vacuo and purification by flash chromatography (gradient elution in petroleum ether to 30% ethyl acetate in petroleum ether) afforded (4RS, 5RS, 7RS) 2-aza-2-methyl-4-hexylsulfanyl-5-phenyl-bicyclo[3.2.0]heptan-1,3-dione as a colourless oil (5 mg, 0.015 mmol) in 13% and (4RS, 5SR, 7RS) 2-aza-2-methyl-4-hexylsulfanyl-5-phenyl-bicyclo[3.2.0]heptan-1,3-dione as a colourless oil (23 mg, 0.069 mmol) in 58% yield.

(4RS, 5RS, 7RS) 2-Aza-2-methyl-4-hexylsulfanyl-5-phenyl-bicyclo[3.2.0]heptan-1,3-dione $\delta_H$ (600 MHz, CDCl$_3$) 7.32-7.30 (m, 3H, 3×Ar-H), 7.13 (d, 2H, J=7.9, 2×H-10), 3.99 (dd, 1H, J=7.8 and 10.2, H-5), 3.20 (dd, 1H, J=4.8 and 10.3, H-7), 3.13-3.07 (m, 1H, HH-6), 2.93 (s, 3H, H$_3$-18), 2.65 (td, 1H, J=7.5 and 11.4, HH-17), 2.58 (td, 1H, J=7.5 and 11.8, HH-17), 2.46 (ddd, 1H, J=4.9, 7.7 and 12.0, HH-6), 1.55-1.25 (m, 8H, H$_2$-13, H$_2$-14, H$_2$-15 and H$_2$-16), 0.87 (t, 3H, J=7.0, H$_3$-12); $\delta_C$ (150 MHz, CDCl$_3$) 177.78 (C=O), 175.17 (C=O), 137.21 (C11), 128.71 (2×Ar-H), 127.93 (C8), 127.24 (2×Ar-H), 48.23 (C5), 42.71 (C7), 31.42 (CH$_2$), 30.07 (C17), 29.33 (CH$_2$), 28.69 (CH$_2$), 25.71 (CH$_2$), 25.25 (C18), 22.58 (CH$_2$), 14.12 (C12); IR (oil, cm$^{-1}$) 2927 (w) 1715 (s); MS (CI+) m/z (relative intensity): 332 ([M+H], 40), 228 (40), 86 (70), 84 (100); Exact Mass Calcd for [C$_{19}$H$_{25}$NO$_2$S]+H requires m/z 332.1684 Found 333.1697 (CI+).

(4RS, 5SR, 7RS) 2-Aza-2-methyl-4-hexylsulfanyl-5-phenyl-bicyclo[3.2.0]heptan-1,3-dione $\delta_H$ (600 MHz, CDCl$_3$) 7.39-7.30 (m, 5H, 5×Ar-H), 3.90 (t, 1H, J=8.7, H-5) 3.13-3.11 (m, 4H, H$_3$-18 and H-7), 3.00 (ddd, 1H, J=8.5, 11.0 and 12.8, HH-6), 2.53 (ddd, 1H, J=3.7, 9.1 and 12.8, HH-6), 2.40 (ddd, 1H, J=6.4, 8.1 and 11.3, HH-17), 2.06 (ddd, 1H, J=6.5, 8.3 and 11.3, HH-17), 1.25-1.08 (m, 8H, H$_2$-13, H$_2$-14, H$_2$-15 and H$_2$-16), 0.82 (t, 3H, J=7.4, H$_3$-12); $\delta_C$ (150 MHz, CDCl$_3$) 178.73 (C=O), 177.70 (C=O), 136.77 (C11), 128.89 (2×Ar-H), 128.27 (2×Ar-H), 127.99 (C8), 55.69 (C4), 45.62 (C5), 42.61 (C7), 31.29 (CH$_2$), 28.94 (CH$_2$), 28.68 (CH$_2$), 28.55 (C17), 26.26 (C6), 25.70 (C18), 22.58 (CH$_2$), 14.09 (C12); IR (oil, cm$^{-1}$) 2927 (w) 1703 (s); MS (CI+) m/z (relative intensity): 332 ([M+H], 100); Exact Mass Calcd for [C$_{19}$H$_{25}$NO$_2$S]+H requires m/z 332.1684 Found 332.1680 (CI+).

Reference Example 94: Preparation of (4RS, 5RS, 7RS) 2-Aza-2-phenyl-4-hexylsulfanyl-5-phenyl-bicyclo[3.2.0]heptan-1,3-dione, (4RS, 5SR, 7RS) 2-Aza-2-phenyl-4-hexylsulfanyl-5-phenyl-bicyclo[3.2.0]heptan-1,3-dione and 1-Phenyl-3-phenyl-4-hexylsulfanyl-1,7-dihydro-2H-azepine-3,6-dione

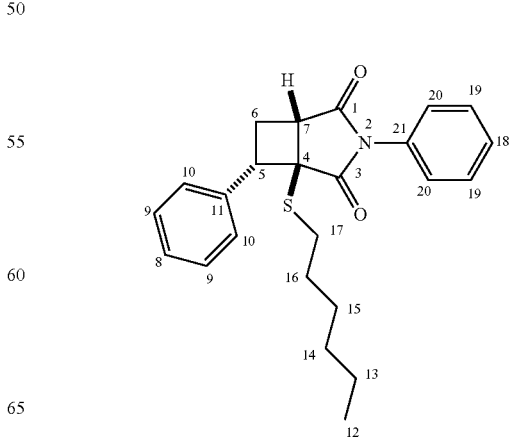

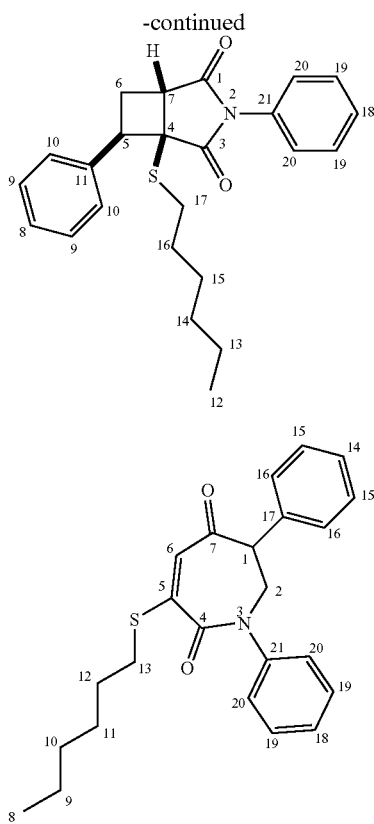

N-Phenyl hexylsulfanylmaleimide (34 mg, 0.12 mmol) was dissolved in acetonitrile (25 mL) to provide a 0.005M solution. The resulting solution was degassed for 30 minutes, styrene (135 µL, 1.18 mmol) added and irradiated in pyrex glassware for 5 minutes with stirring. Solvent was removed in vacuo and purification by flash chromatography (gradient elution in petroleum ether to 30% ethyl acetate in petroleum ether) afforded (4RS, 5RS, 7RS) 2-aza-2-phenyl-4-hexylsulfanyl-5-phenyl-bicyclo[3.2.0]heptan-1,3-dione and (4RS, 5SR, 7RS) 2-aza-2-phenyl-4-hexylsulfanyl-5-phenyl-bicyclo[3.2.0]heptan-1,3-dione as a colourless oil (37 mg, 0.94 mmol) in 80% yield as a mixture of diastereoisomers (11:2) and 1-phenyl-3-phenyl-4-hexylsulfanyl-1,7-dihydro-2H-azepine-3,6-dione as a colourless oil (0.5 mg, 0.001 mmol) in 1% yield (4RS, 5RS, 7RS) 2-aza-2-phenyl-4-hexylsulfanyl-5-phenyl-bicyclo[3.2.0]heptan-1,3-dione and (4RS, 5SR, 7RS) 2-aza-2-phenyl-4-hexylsulfanyl-5-phenyl-bicyclo[3.2.0]heptan-1,3-dione (4RS, 5RS, 7RS) 2-Aza-2-phenyl-4-hexylsulfanyl-5-phenyl-bicyclo[3.2.0]heptan-1,3-dione in bold $\delta_H$ (600 MHz, CDCl$_3$) 7.54-7.52 (m, 11H, 2×Ar-H), 7.46-7.42 (m, 4H, 4×Ar-H), 7.41-7.37 (m, 46H, 8×Ar-H and 2×Ar-H), 7.27-7.26 (m, 2H, 2×Ar-H), 7.06-7.05 (m, 2H, 2×Ar-H), 4.09 (t, 1H, J=8.5, H-5), 4.08 (t, 5.5H, J=8.5, H-5), 3.35 (dd, 1H, J=4.7 and 10.5, H-7), 3.29 (dd, 5.5H, J=4.0 and 10.9, H-7), 3.20 (td, 1H, J=10.3 and 13.3, HH-6), 3.09 (ddd, 5.5H, J=8.2, 11.0 and 13.0, HH-6), 2.78 (td, 1H, J=7.4 and 11.7, HH-17), 2.72-2.68 (m, 6.5H, HH-6 and HH-6), 2.66 (dd, 1H, J=4.8 and 7.4, HH-17), 2.52 (ddd, 5.5H, J=6.5, 8.2 and 11.4, HH-17), 2.16 (ddd, 5.5H, J=6.6, 8.4 and 11.4, HH-17), 1.63-1.58 (m, 2H, H$_2$-16), 1.42-1.37 (m, 2H, H$_2$-15), 1.36-1.09 (m, 24H, 4×CH$_2$ and 2×CH$_2$), 0.88 (t, 3H, J=6.7, H$_3$-12), 0.83 (t, 16.5H, J=7.3, H$_3$-12); $\delta_C$ (150 MHz, CDCl$_3$) 177.65 (C=O), 176.82 (C=O), 176.67 (C=O), 174.08 (C=O), 136.96 (C11), 136.82 (C11), 132.06 (C21), 131.86 (C21), 129.40 (2×Ar-H), 129.22 (Ar—H), 128.96 (2×Ar-H), 128.84 (Ar—H), 128.79 (Ar—H), 128.34 (2×Ar-H), 128.08 (Ar—H), 127.51 (Ar—H), 126.56 (2×Ar-H), 126.34 (Ar—H), 55.57 (C4), 55.47 (C4), 48.78 (C5), 45.87 (C5), 44.88 (C7), 42.79 (C7), 31.45 (C17), 31.31 (C17), 30.27 (CH$_2$), 29.46 (CH$_2$), 29.08 (CH$_2$), 28.75 (CH$_2$), 28.56 (CH$_2$), 26.95 (CH$_2$), 22.60 (CH$_2$), 22.52 (CH$_2$), 14.14 (C12), 14.10 (C12) Several carbon signals are missing due to overlap of the diastereomers; IR (oil, cm$^{-1}$) 2926 (w) 1709 (s); MS (CI+) m/z (relative intensity): 394 ([M+H], 70), 290 (100), 105 (100); Exact Mass Calcd for [C$_{24}$H$_{27}$NO$_2$S]+H requires m/z 394.1841 Found 394.1834 (CI+).

1-Phenyl-3-phenyl-4-hexylsulfanyl-1,7-dihydro-2H-azepine-3,6-dione $\delta_H$ (600 MHz, CDCl$_3$) 7.54-7.27 (m, 10H, 10×Ar-H), 6.32 (s, 1H, H-6), 4.19 (t, 1H, J=88.0, H-1), 3.14-3.03 (m, 2H, H$_2$-2), 2.39-2.29 (m, 2H, H$_2$-13), 1.61-1.10 (m, 8H, 4×CH$_2$), 0.89-0.81 (m, 3H, H$_3$-8); $\delta_C$ (150 MHz, CDCl$_3$) 146.31 (C=O), 141.19 (C=O), 130.19 (Ar), 129.41 (Ar), 129.20 (Ar—H), 128.93 (2×Ar-H), 128.49 (2×Ar-H), 127.90 (Ar—H), 127.76 (2×Ar-H), 126.03 (2×Ar-H), 47.19 (C1), 32.70 (CH$_2$), 31.43 (CH$_2$), 29.83 (CH$_2$), 29.20 (CH$_2$), 28.63 (CH$_2$), 22.61 (CH$_2$), 14.13 (C8); IR (oil, cm$^{-1}$) 2926 (m) 1715 (s); MS (CI+) m/z (relative intensity): 394 ([M+H], 40), 278 (100); Exact Mass Calcd for [C$_{24}$H$_{27}$NO$_2$S]+H requires m/z 394.1841 Found 394.1829 (CI+).

Reference Example 95: Preparation of (4RS, 5SR, 7RS) 2-Aza-4-phenylthio-5-phenyl-bicyclo[3.2.0]heptan-1,3-dione and (4RS, 5RS, 7RS) 2-Aza-4-phenylthio-5-phenyl-bicyclo[3.2.0]heptan-1,3-dione

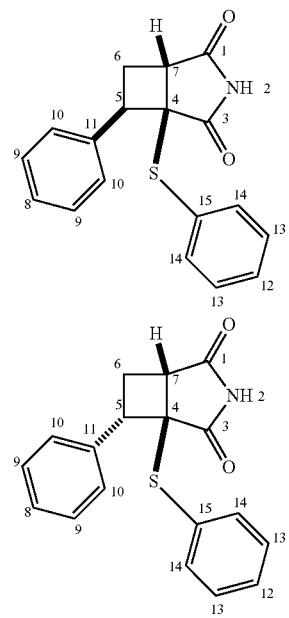

Phenylthiomaleimide (17 mg, 0.082 mmol) was dissolved in acetonitrile (25 mL) to provide a 0.003M solution. The resulting solution was degassed for 30 minutes, styrene (111 µL, 0.82 mmol) added and irradiated in pyrex glassware for 5 minutes with stirring. Solvent was removed in vacuo and purification by flash chromatography (gradient elution in petroleum ether to 30% ethyl acetate in petroleum ether) afforded (4RS, 5SR, 7RS) 2-aza-4-phenylthio-5-phenyl-bicyclo[3.2.0]heptan-1,3-dione as a colourless oil (1.5 mg, 0.005 mmol) in 6% yield and (4RS, 5RS, 7RS) 2-aza-4-phenylthio-5-phenyl-bicyclo[3.2.0]heptan-1,3-dione as a colourless oil (17.5 mg, 0.056 mmol) in 69% yield.

(4RS, 5SR, 7RS) 2-Aza-4-phenylthio-5-phenyl-bicyclo[3.2.0]heptan-1,3-dione $\delta_H$ (600 MHz, CDCl$_3$) 8.05 (s, 1H, NH), 7.42-7.41 (m, 2H, 2×Ar-H), 7.35-7.17 (m, $\delta_H$, 8×Ar-H), 4.05 (t, 1H, J=10.1, H-5), 3.29 (dd, 1H, J=5.5 and 13.0, H-7), 3.01 (dt, 1H, J=10.3 and 13.0, HH-6), 2.56 (ddd, 1H, J=5.6, 10.1 and 13.4, HH-6); $\delta_C$ (150 MHz, CDCl$_3$) 176.69 (C=O), 174.10 (C=O), 136.56 (C11), 136.01 (2×Ar-H), 130.13 (Ar—H), 129.66 (2×Ar-H), 129.28 (C15), 128.72 (2×Ar-H), 128.01 (Ar—H), 127.32 (2×Ar-H), 60.59 (C4), 46.32 (C5), 43.70 (C7), 25.51 (C6); IR (oil, cm$^{-1}$) 3226 (w), 2925 (w) 1715 (s); MS (CI+) m/z (relative intensity): 310 ([M+H], 10), 206 (30), 111 (100); Exact Mass Calcd for [C$_{18}$H$_{15}$NO$_2$S]+H requires m/z 310.0902 Found 310.0901 (CI+).

(4RS, 5RS, 7RS) 2-Aza-4-phenylthio-5-phenyl-bicyclo[3.2.0]heptan-1,3-dione $\delta_H$ (600 MHz, CDCl$_3$) 8.24 (s, 1H, NH), 7.43-7.30 (m, 6H, 8×Ar-H), 7.27-7.24 (m, 2H, 2×Ar-H), 4.13 (t, 1H, J=9.0, H-5), 3.20-3.13 (m, 2H, HH-6 and H-7), 2.55 (ddd, 1H, J=5.6, 8.3 and 13.4, HH-6); $\delta_C$ (150 MHz, CDCl$_3$) 177.99 (C=O), 177.17 (C=O), 135.80 (C11), 135.80 (2×Ar-H), 129.64 (Ar—H), 129.54 (2×Ar-H), 128.95 (C15), 128.51 (2×Ar-H), 128.45 (2×Ar-H), 128.22 (Ar—H), 60.72 (C4), 45.80 (C5), 43.39 (C7), 25.20 (C6); IR (oil, cm$^{-1}$) 3211 (w), 1772 (w) 1707 (s); MS (CI+) m/z (relative intensity): 310 ([M+H], 50), 206 (100), 104 (40); Exact Mass Calcd for [C$_{18}$H$_{15}$NO$_2$S]+H requires m/z 310.0902 Found 310.0905 (CI+).

Reference Example 96: Preparation of (4RS, 7RS) 2-Aza-4-hexylsulfanyl-bicyclo[3.2.0]hept-5-ene-1,3-dione

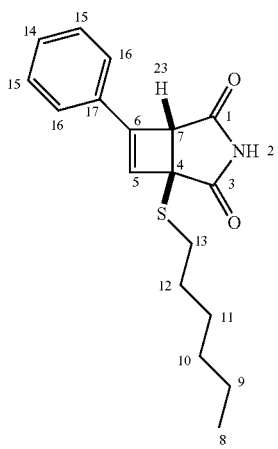 [SMILES: CCCCCCS[C@@]12C=C(c3ccccc3)[C@@H]1C(=O)NC2=O]

Hexylsulfanylmaleimide (25 mg, 0.12 mmol) was dissolved in acetonitrile (25 mL) to provide a 0.005M solution. The resulting solution was degassed for 30 minutes, phenyl acetylene (128 µL, 1.16 mmol) added and irradiated in pyrex glassware for 30 minutes with stirring. Solvent was removed in vacuo and purification by flash chromatography (gradient elution in petroleum ether to 30% ethyl acetate in petroleum ether) afforded the desired compound as a colourless oil (4.5 mg, 0.014 mmol) in 18% yield (based on recovered SM) alongside SM (1.5 mg, 0.007 mmol) in 6% yield. $\delta_H$ (600 MHz, CDCl$_3$) 7.86 (s, 1H, NH), 7.68 (d, 2H, J=7.86, 2×Ar-H), 7.40-7.34 (m, 3H, 3×Ar-H), 6.58 (s, 1H, H-5), 3.73 (s, 1H, H-7), 2.57 (dt, 1H, J=2.3 and 7.4, H$_2$-13), 1.77-1.19 (m, 8H, 4×CH$_2$), 0.85 (t, 3H, J=7.3, H$_3$-8); $\delta_C$ (150 MHz, CDCl$_3$) 173.46 (C=O), 173.28 (C=O), 149.72 (C17), 130.25 (C6), 130.02 (C14), 128.85 (2×Ar-H), 126.32 (2×Ar-H), 125.76 (C5), 53.78 (C7), 31.33 (CH$_2$), 29.70 (CH$_2$), 29.32 (CH$_2$), 28.61 (CH$_2$), 22.55 (CH$_2$), 14.11 (C8); IR (oil, cm$^{-1}$) 3228 (w), 2925 (m), 1770 (w) 1709 (s); MS (CI+) m/z (relative intensity): 316 ([M+H], 100), 214 (30); Exact Mass Calcd for [C$_{18}$H$_{22}$NO$_2$S]+H requires m/z 316.0371 Found 316.1365 (CI+).

Reference Example 97: Preparation of 1-Butyl-4-hexylsulfanyl-1,7-dihydro-2H-azepine-3,6-dione and (4RS, 5SR, 7RS) 2-Aza-4-hexylsulfanyl-5-butyl-bicyclo[3.2.0]heptan-1,3-dione

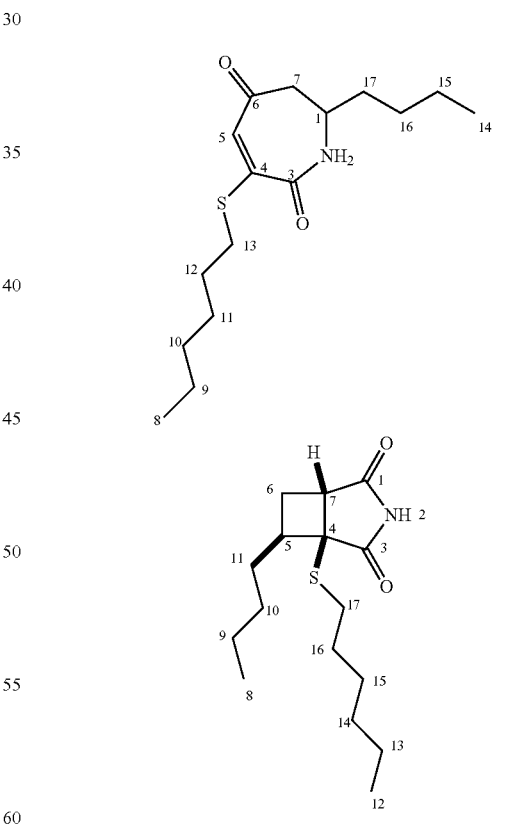

Hexylsulfanylmaleimide (25 mg, 0.116 mmol) was dissolved in acetonitrile (20.7 mL) and hex-1-ene (4.3 mL, 11.6 mmol) to provide a 0.005M solution. The resulting solution was degassed for 30 minutes and irradiated in pyrex glassware for 5 minutes with stirring. Solvent was removed in vacuo and purification by flash chromatography (gradient elution in petroleum ether to 30% ethyl acetate in petroleum ether) afforded 1-butyl-4-hexylsulfanyl-1,7-dihydro-2H-azepine-3,6-dione as a colourless oil (4 mg, 0.013 mmol) in 12% yield (alongside (4RS, 5SR, 7RS) 2-aza-4-hexylsulfanyl-5-butyl-bicyclo[3.2.0]heptan-1,3-dione) and (4RS, 5SR, 7RS) 2-aza-4-hexylsulfanyl-5-butyl-bicyclo[3.2.0]heptan-1,3-dione as a colourless oil (16 mg, 0.054 mmol) in 47% yield.

1-Butyl-4-hexylsulfanyl-1,7-dihydro-2H-azepine-3,6-dione $\delta_H$ (600 MHz, CDCl$_3$) 7.29 (s, 1H, NH), 6.43 (s, 1H, H-5), 2.91-2.76 (m, 3H, H-1 and H$_2$-17), 2.70 (dd, 1H, J=1.4 and 5.8, HH-7), 2.64 (dd, 1H, J=1.4 and 7.9, HH-7), 2.49 (t, 1H, J=7.4, H$_2$-13), 1.81-1.25 (m, 12H, 6×CH$_2$), 0.93-0.85 (m, 6H, H$_3$-8 and H$_3$-14); $\delta_C$ (150 MHz, CDCl$_3$) 174.39 (C=O), 171.40 (C=O), 148.19 (C4), 129.28 (C5), 43.90 (C1), 34.97 (CH$_2$), 31.53 (CH$_2$), 30.60 (CH$_2$), 29.70 (CH$_2$), 29.07 (CH$_2$), 28.76 (CH$_2$), 28.51 (CH$_2$), 22.66 (CH$_2$), 22.65 (CH$_2$), 14.16 (CH$_3$), 14.13 (CH$_3$); IR (oil, cm$^{-1}$) 3226 (w), 2927 (m) 1715 (s); MS (CI+) m/z (relative intensity): 298 ([M+H], 80), 187 (100); Exact Mass Calcd for [C$_{16}$H$_{27}$NO$_2$S]+H requires m/z 298.1841 Found 298.1841 (CI+).

(4RS, 5SR, 7RS) 2-Aza-4-hexylsulfanyl-5-butyl-bicyclo[3.2.0]heptan-1,3-dione $\delta_H$ (600 MHz, CDCl$_3$) 8.19 (s, 1H, NH), 3.09 (dd, 1H, J=4.5 and 10.2, H-7), 2.70-2.64 (m, 1H, H-5), 2.53-2.45 (m, 2H, H$_2$-17), 2.37-2.28 (m, 2H, H$_2$-6), 1.80-1.73 (m, 1H, HH-11), 1.59-1.50 (m, 2H, HH-11 and HH-10), 1.38-1.20 (m, 11H, HH-10 and 5×CH$_2$), 0.90 (t, 3H, J=7.1, CH$_3$), 0.87 (t, 3H, J=7.3, CH$_3$); $\delta_C$ (150 MHz, CDCl$_3$) 178.73 (C=O), 177.81 (C=O), 56.10 (C4), 44.29 (C7), 40.99 (C5), 31.42 (C17), 29.24 (CH$_2$), 28.99 (CH$_2$), 28.90 (CH$_2$), 28.74 (CH$_2$), 28.73 (CH$_2$), 27.92 (CH$_2$), 22.59 (CH$_2$), 22.58 (CH$_2$), 14.12 (CH$_3$), 14.09 (CH$_3$); IR (oil, cm$^{-1}$) 3209 (w), 2927 (m) 1774 (w), 1711 (s); MS (CI+) m/z (relative intensity): 298 ([M+H], 100); Exact Mass Calcd for [C$_{16}$H$_{27}$NO$_2$S]+H requires m/z 298.1841 Found 298.1845 (CI+).

Reference Example 98: Preparation of (4RS, 7RS) 2-Aza-4-hexylsulfanyl-5-ethyl-6-ethyl-bicyclo[3.2.0]hept-5-ene-1,3-dione

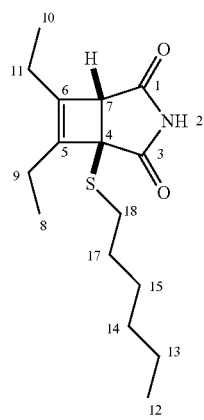 [SMILES: CCCCCCS[C@]12C(=O)NC(=O)[C@H]1C(CC)=C2CC]

Hexylsulfanylmaleimide (25 mg, 0.116 mmol) was dissolved in acetonitrile (21.1 mL) and hex-3-yne (3.9 mL, 11.6 mmol) to provide a 0.005M solution. The resulting solution was degassed for 30 minutes and irradiated in pyrex glassware for 5 minutes with stirring. Solvent was removed in vacuo and purification by flash chromatography (gradient elution in petroleum ether to 30% ethyl acetate in petroleum ether) afforded the desired compound as a colourless oil (17 mg, 0.057 mmol) in 49% yield. $\delta_H$ (600 MHz, CDCl$_3$) 8.26 (s, 1H, NH), 3.88 (s, 1H, H-7), 2.99 (ddd, 1H, J=7.5, 9.1 and 12.8, HH-18), 2.87 (ddd, 1H, J=5.1, 8.7 and 12.9, HH-18), 2.39-2.20 (m, 2H, HH-9 and HH-11), 1.95-1.75 (m, 2H, HH-9 and HH-11), 1.56-1.10 (m, 8H, 4×CH$_2$), 0.90-0.86 (m, 9H, H$_3$-8, H$_3$-10 and H$_3$-12); $\delta_C$ (150 MHz, CDCl$_3$) 172.66 (C=O), 171.34 (C=O), 148.84 (C=C), 142.53 (C=C), 70.45 (C4), 48.86 (C18), 48.09 (C7), 31.45 (CH$_2$), 28.51 (CH$_2$), 23.53 (CH$_2$), 22.50 (CH$_2$), 21.89 (CH$_2$), 21.62 (CH$_2$) 14.09 (C12), 12.03 (CH$_3$), 11.84 (CH$_3$); IR (oil, cm$^{-1}$) 2931 (m) 1717 (s); MS (CI+) m/z (relative intensity): 312 ([M+OH], 100), 178 (100); Exact Mass Calcd for [C$_{16}$H$_{25}$NO$_2$S]+OH requires m/z 312.1633 Found 312.1648 (CI+).

Reference Example 99: Preparation of 1-Ethyl-2-ethyl-6-hexylsulfanyl-1,2-dihydro-3H-azepine-4,7-dione

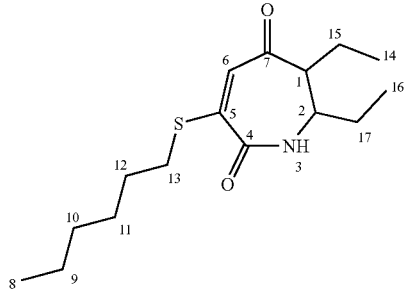 [SMILES: CCCCCCSC1=CC(=O)C(CC)C(CC)NC1=O]

Hexylsulfanylmaleimide (25 mg, 0.116 mmol) was dissolved in acetonitrile (21.1 mL) and trans-hex-3-ene (3.9 mL, 11.6 mmol) to provide a 0.005M solution. The resulting solution was degassed for 30 minutes and irradiated in pyrex glassware for 5 minutes with stirring. Solvent was removed in vacuo and purification by flash chromatography (gradient elution in petroleum ether to 30% ethyl acetate in petroleum ether) afforded the desired compound as a colourless oil (2 mg, 0.007 mmol) in 6% yield. $\delta_H$ (600 MHz, CDCl$_3$) 7.32 (s, 1H, NH), 6.49 (s, 1H, H-6), 2.92 (ddd, 1H, J=4.6, 6.3 and 10.8, H-1), 2.83 (ddd, 1H, J=5.2, 9.4 and 12.8, HH-13), 2.75 (dd, 1H, J=5.9 and 10.9, H-2), 2.62 (ddd, 1H, J=6.7, 9.6 and 12.7 HH-13), 2.07-2.00 (m, 1H, HH-17), 1.89-1.83 (m, 1H, HH-15), 1.79-1.40 (m, 6H, HH-15, HH-17 and 2×CH$_2$), 1.33-1.30 (m, 4H, 2×CH$_2$), 1.10 (t, 3H, J=7.5, H$_3$-16), 0.92 (t, 3H, J=7.4, CH$_3$), 0.89 (t, 3H, J=7.0, CH$_3$); $\delta_C$ (150 MHz, CDCl$_3$) 171.00 (C=O), 169.53 (C=O), 149.76 (C5), 129.27 (C6), 62.54 (C2), 51.16 (C13), 40.42 (C1), 31.48 (CH$_2$), 28.65 (CH$_2$), 23.65 (CH$_2$), 23.32 (CH$_2$), 22.52 (CH$_2$), 17.23 (C17) 14.11 (CH$_3$), 13.96 (CH$_3$), 12.33 (CH$_3$); IR (oil, cm$^{-1}$) 2962 (m) 1717 (s); MS (CI+) m/z (relative intensity): 314 ([M+OH], 75), 180 (100); Exact Mass Calcd for [C$_{16}$H$_{26}$NO$_2$S]+OH requires m/z 314.1790 Found 314.1799 (CI+).

Reference Example 100: Preparation of (4RS, 7RS) 2-Aza-4-hexylsulfanyl-5,5-diphenyl-bicyclo[3.2.0]heptan-1,3-dione

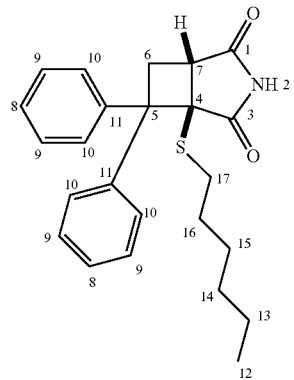 [SMILES: CCCCCCS[C@]12C(=O)NC(=O)[C@H]1CC2(c1ccccc1)c1ccccc1]

Hexylsulfanylmaleimide (25 mg, 0.116 mmol) was dissolved in acetonitrile (21 mL) and 1,1-diphenylethyene (203 μL, 1.16 mmol) to provide a 0.005M solution. The resulting solution was degassed for 30 minutes and irradiated in pyrex glassware for 5 minutes with stirring. Solvent was removed in vacuo and purification by flash chromatography (gradient elution in petroleum ether to 30% ethyl acetate in petroleum ether) afforded the desired compound as a colourless oil (30 mg, 0.075 mmol) in 64% yield. $\delta_H$ (600 MHz, CDCl$_3$) 8.15 (s, 1H, NH), 7.42 (m, 2H, 2×H-8), 7.36-7.21 (m, 8H, 8×Ar-H), 3.54 (dd, 1H, J=10.3 and 12.9, HH-6), 3.34 (dd, 1H, J=5.7 and 10.3, H-7), 3.18 (dd, 1H, J=5.8 and 12.9, HH-6), 2.43 (dt, 1H, J=7.3 and 11.0, HH-17), 2.34 (dt, 1H, J=7.4 and 11.0, HH-17), 1.40-1.34 (m, 2H, H$_2$-16), 1.26-1.20 (m, 4H, H$_2$-14 and H$_2$-15), 1.18-1.13 (m, 2H, H$_2$-13), 0.84 (t, 3H, J=7.5, H$_3$-12); $\delta_C$ (150 MHz, CDCl$_3$) 177.16 (C=O), 175.87 (C=O), 142.09 (2×Ar), 141.80 (2×Ar), 128.17 (2×Ar-H), 128.13 (2×Ar-H), 128.10 (2×Ar-H), 128.06 (2×Ar-H), 127.44 (Ar—H), 127.32 (Ar—H), 63.03 (C5), 57.20 (C4), 44.38 (C7), 35.17 (C6), 31.35 (CH$_2$), 30.07 (C17), 28.77 (CH$_2$), 28.71 (CH$_2$) 22.53 (CH$_2$), 14.11 (C12); IR (oil, cm$^{-1}$) 2927 (m) 1772 (w), 1709 (s); MS (ES−) m/z (relative intensity): 392 ([M], 10), 212 (100); Exact Mass Calcd for [C$_{24}$H$_{26}$NO$_2$S] requires m/z 392.1684 Found 392.1674 (ES−)

Reference Example 101: Preparation of (4RS, 5RS, 7RS) 2-Aza-2-methylenecyclohexane-4-hexylsulfanyl-5-phenyl-bicyclo[3.2.0]heptan-1,3-dione and (4RS, 5SR, 7RS) 2-Aza-2-methylenecyclohexane-4-hexylsulfanyl-5-phenyl-bicyclo[3.2.0]heptan-1,3-dione

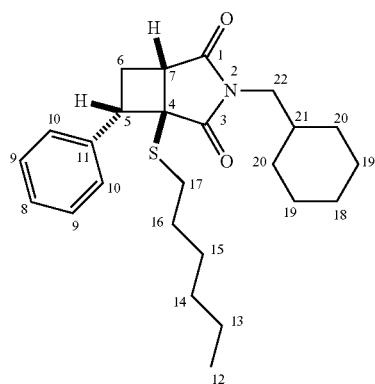

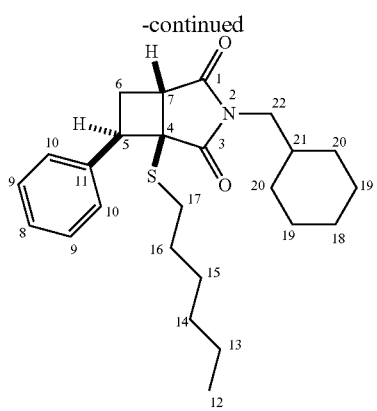

N-Methylene hexylsulfanylmaleimide (25 mg, 0.116 mmol) was dissolved in acetonitrile (21 mL) and 1,1-diphenylethyene (203 μL, 1.16 mmol) to provide a 0.005M solution. The resulting solution was degassed for 30 minutes and irradiated in pyrex glassware for 5 minutes with stirring. Solvent was removed in vacuo and purification by flash chromatography (gradient elution in petroleum ether to 30% ethyl acetate in petroleum ether) afforded (4RS, 5RS, 7RS) 2-aza-2-methylenecyclohexane-4-hexylsulfanyl-5-phenyl-bicyclo[3.2.0]heptan-1,3-dione and (4RS, 5SR, 7RS) 2-aza-2-methylenecyclohexane-4-hexylsulfanyl-5-phenyl-bicyclo[3.2.0]heptan-1,3-dione as a colourless oil (30 mg, 0.075 mmol) as a mix of diastereoisomers (10:1) in 64% yield.

(4RS, 5RS, 7RS) 2-aza-2-methylenecyclohexane-4-hexylsulfanyl-5-phenyl-bicyclo[3.2.0]heptan-1,3-dione in Bold $\delta_H$ (600 MHz, CDCl$_3$) 7.39-7.29 (m, 5.2H, 5×Ar-H and 0.2×Ar-H), 7.24 (d, 0.1H, J=7.4, H-8), 7.16 (d, 2H, J=7.4, 0.2×H-10), 4.00 (dd, 0.1H, J=8.2 and 9.9, H-5), 3.89 (t, 1H, J=8.7, H-5), 3.46 (d, 2.2H, J=7.5, H$_2$-22 and H$_2$-22), 3.19 (dd, 0.1H, J=5.1 and 10.5, H-7), 3.12 (dd, 1H, J=3.5 and 10.9, H-7), 3.07 (td, 0.1H, J=10.5 and 13.1, HH-6), 3.00 (ddd, 1H, J=8.5, 11.5 and 12.6, HH-6), 2.64 (ddd, 0.1H, J=6.9, 11.4 and 14.8, HH-17), 2.56 (td, 0.1H, J=6.9 and 11.6, HH-6), 2.53 (ddd, 1H, J=3.3, 9.1 and 12.9, HH-6), 2.48 (ddd, 0.1H, J=5.4, 8.0 and 13.2, HH-17), 2.39 (td, 1H, J=7.4 and 11.4, HH-17), 2.08 (td, 1H, J=7.7 and 11.4, HH-17), 1.83-0.99 (m, 2H, 20.9H), 0.87 (t, 3H, J=7.0, H$_3$-12), 0.82 (t, 3H, J=7.5, H$_3$-12); $\delta_C$ (150 MHz, CDCl$_3$) 179.12 (C=O), 178.35 (C=O), 178.15 (C=O), 175.41 (C=O), 137.23 (C11), 137.12 (C11), 129.08 (2×Ar-H), 128.76 (2×Ar-H), 128.47 (2×Ar-H), 128.16 (C8), 127.99 (C8), 127.51 (2×Ar-H), 55.84 (C4), 55.69 (C4), 48.06 (C5), 45.97 (C5), 45.63 (C22), 45.48 (C22), 42.94 (C7), 42.83 (C7), 36.67 (C21), 36.58 (C21), 31.64 (CH$_2$), 31.49 (CH$_2$), 31.08 (CH$_2$), 31.01 (CH$_2$), 30.96 (CH$_2$), 30.34 (CH$_2$), 30.04 (CH$_2$), 29.67 (CH$_2$), 29.28 (CH$_2$), 28.98 (CH$_2$), 28.82 (CH$_2$), 26.76 (CH$_2$), 26.63 (CH$_2$), 26.52 (CH$_2$), 26.45 (CH$_2$), 25.96 (CH$_2$), 25.94 (CH$_2$), 25.82 (CH$_2$), 14.34 (C12), 14.31 (C12) Several carbon signals are missing due to overlap of the diastereomers; IR (oil, cm$^{-1}$) 2925 (m) 1703 (s); MS (CI+) m/z (relative intensity): 414 ([M+H], 100), 309 (20); Exact Mass Calcd for [C$_{25}$H$_{35}$NO$_2$S]+H requires m/z 414.2461 Found 414.2452 (CI+).

Reference Example 102: Preparation of (4RS, 5SR, 7SR) 2-Aza-4-hexylsulfanyl-5-phenyl-7-hexylsulfanyl-bicyclo[3.2.0]heptan-1,3-dione and (4RS, 5RS, 7SR) 2-Aza-4-hexylsulfanyl-5-phenyl-7-hexylsulfanyl-bicyclo[3.2.0]heptan-1,3-dione

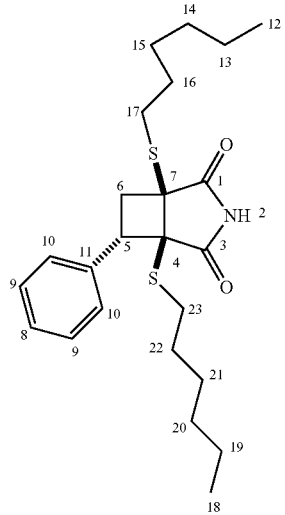

2,3 Dihexylsulfanylmaleimide (38 mg, 0.115 mmol) was dissolved in acetonitrile (25 mL) to provide a 0.005M solution. The resulting solution was degassed for 30 minutes, styrene (133 μL, 1.2 mmol) added and irradiated in pyrex glassware for 20 minutes with stirring. Solvent was removed in vacuo and purification by flash chromatography (gradient elution in petroleum ether to 30% ethyl acetate in petroleum ether) afforded (4RS, 5SR, 7SR) 2-aza-4-hexylsulfanyl-5-phenyl-7-hexylsulfanyl-bicyclo[3.2.0]heptan-1,3-dione as a colourless oil (3 mg, 0.007 mmol) in 6% yield and (4RS, 5RS, 7SR) 2-aza-4-hexylsulfanyl-5-phenyl-7-hexylsulfanyl-bicyclo[3.2.0]heptan-1,3-dione as a colourless oil (3 mg, 0.007 mmol) in 6% yield.

(4RS, 5SR, 7SR) 2-Aza-4-hexylsulfanyl-5-phenyl-7-hexylsulfanyl-bicyclo[3.2.0]heptan-1,3-dione $\delta_H$ (600 MHz, $CDCl_3$) 7.96 (s, 1H, NH), 7.33 (d, 2H, J=7.0, 2×Ar-H), 7.28 (t, 1H, J=7.0, H-8), 7.21 (d, 2H, J=7.5, 2×Ar-H), 4.02 (t, 1H, J=10.0, H-5), 2.98-2.92 (m, 2H, HH-6 and —S—CHH—), 2.87 (dd, 1H, J=10.8 and 13.6, HH-6), 2.83-2.72 (m, 2H, —S—CHH— and —S—CHH—), 2.69 (dt, 1H, J=7.4 and 10.8, —S—CHH—) 1.68-1.57 (m, 4H, $H_2$-16 and $H_2$-22), 1.45-1.31 (m, 4H, $H_2$-15 and $H_2$-21), 1.31-1.25 (m, 8H, $H_2$-13, $H_2$-14, $H_2$-19 and $H_2$-20), 0.86 (t, 6H, J=7.0, $H_3$-12 and $H_3$-18); $\delta_C$ (150 MHz, $CDCl_3$) 176.91 (C=O), 172.96 (C=O), 136.09 (C11), 128.83 (2×Ar-H), 128.13 (C8), 127.41 (2×Ar-H), 62.86 (C4), 54.36 (C7), 46.49 (C5), 33.28 (C6), 31.51 ($CH_2$), 31.47 ($CH_2$), 30.65 ($SCH_2$), 30.09 ($SCH_2$), 29.22 ($CH_2$), 28.96 ($CH_2$), 28.80 ($CH_2$), 28.74 ($CH_2$), 22.63 ($CH_2$), 22.60 ($CH_2$), 14.17 ($CH_3$), 14.15 ($CH_3$); IR (oil, $cm^{-1}$) 3194 (w), 2928 (m) 1774 (w), 1722 (s); MS (CI+) m/z (relative intensity): 432 ([M−H], 5), 332 (50), 316 (95), 207 (100); Exact Mass Calcd for [$C_{24}H_{35}NO_2S_2$]—H requires m/z 432.2026 Found 432.2029 (CI+).

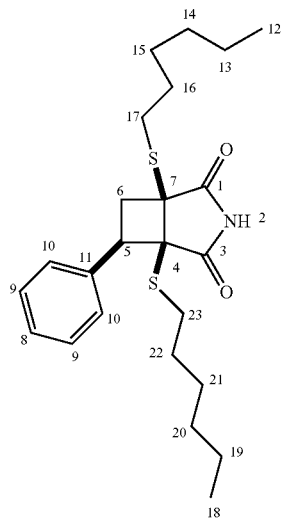

(4RS, 5RS, 7SR) 2-Aza-4-hexylsulfanyl-5-phenyl-7-hexylsulfanyl-bicyclo[3.2.0]heptan-1,3-dione $\delta_H$ (600 MHz, $CDCl_3$) 8.10 (s, 1H, NH), 7.41 (d, 2H, J=6.9, 2×Ar-H), 7.37 (t, 1H, J=6.9, H-8), 7.33 (d, 2H, J=6.9, 2×Ar-H), 3.92 (t, 1H, J=8.9, H-5), 2.95 (dd, 1H, J=8.9 and 12.9, HH-6), 2.86 (dt, 1H, J=6.9 and 14.2, —S—CHH—), 2.78-2.66 (m, 2H, HH-6 and —S—CHH—), 2.60 (ddd, 1H, J=6.3, 8.3 and 10.9, —S—CHH—) 2.00 (ddd, 1H, J=5.6, 8.6 and 10.7, —S—CHH—), 1.65-1.60 (m, 2H, HH-16 and HH-22), 1.43-1.06 (m, 14H, HH-16, HH-22, $H_2$-13, $H_2$-14, $H_2$-15, $H_2$-19, $H_2$-20 and $H_2$-21), 0.88 (t, 3H, J=6.7, $CH_3$), 0.82 (t, 3H, J=7.1, $CH_3$); $\delta_C$ (150 MHz, $CDCl_3$) 176.59 (C=O), 176.44 (C=O), 136.03 (C11), 129.50 (2×Ar-H), 128.83 (C8), 128.29 (2×Ar-H), 62.32 (C4), 54.58 (C7), 45.33 (C5), 34.85 (C6), 31.48 ($CH_2$), 31.33 ($CH_2$), 30.51 ($CH_2$), 29.21 ($CH_2$), 29.06 ($CH_2$), 28.90 ($CH_2$), 28.76 ($CH_2$), 28.53 ($CH_2$), 22.62 ($CH_2$), 22.50 ($CH_2$), 14.16 ($CH_3$), 14.11 ($CH_3$); IR (oil, $cm^{-1}$) 3215 (w), 2926 (m) 1774 (w), 1715 (s); MS (CI+) m/z (relative intensity): 432 ([M−H], 5), 329 (60), 207 (100), 161 (60); Exact Mass Calcd for [$C_{24}H_{35}NO_2S_2$]—H requires m/z 432.2026 Found 432.2034 (CI+).

Example 40: Preparation of (4RS, 5RS, 7SR) 2-Aza-4-(N-Boc-Cys-OMe)-5-phenyl-7-(N-Boc-Cys-OMe)-bicyclo[3.2.0]heptan-1,3-dione

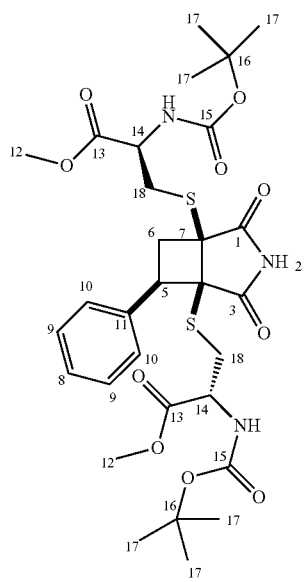 [SMILES: COC(=O)[C@H](CS[C@]12C[C@H](c3ccccc3)[C@@]1(SC[C@H](NC(=O)OC(C)(C)C)C(=O)OC)C(=O)NC2=O)NC(=O)OC(C)(C)C]

2,3-Di-(N-Boc-Cys-OMe)-maleimide (76 mg, 0.135 mmol) was dissolved in acetonitrile (29 mL) to provide a 0.005M solution. The resulting solution was degassed for 30 minutes, styrene (148 µL, 1.35 mmol) added and irradiated in pyrex glassware for 30 minutes with stirring. Solvent was removed in vacuo and purification by flash chromatography (gradient elution in 10% ethyl acetate in petroleum ether to 30% ethyl acetate in petroleum ether) afforded a mixture of (4RS, 5RS, 7SR) 2-aza-4-(N-Boc-Cys-OMe)-5-phenyl-7-(N-Boc-Cys-OMe)-bicyclo[3.2.0]heptan-1,3-diones and (4RS, 5SR, 7SR) 2-aza-4-(N-Boc-Cys-OMe)-5-phenyl-7-(N-Boc-Cys-OMe)-bicyclo[3.2.0]heptan-1,3-diones as a colourless oil (28 mg, 0.042 mmol) in 36% yield. The spectra from this mixture was very complex but MS confirmed the identity of the compounds as all having the same mass. 4RS, 5RS, 7SR) 2-aza-4-(N-Boc-Cys-OMe)-5-phenyl-7-(N-Boc-Cys-OMe)-bicyclo[3.2.0]heptan-1,3-diones and (4RS, 5SR, 7SR) 2-aza-4-(N-Boc-Cys-OMe)-5-phenyl-7-(N-Boc-Cys-OMe)-bicyclo[3.2.0]heptan-1,3-diones was also isolated alongside a [5+2] product as a colourless oil (46 mg) $^1$H NMR and MS data suggest 40% of this (by mass) is the desired conjugation products (18 mg, 0.028 mmol) in 20% yield. $\delta_H$ (600 MHz, CDCl$_3$) 8.32 (d, 4.7H, J=8.7, N—H), 8.05 (s, 1.2H, N—H), 7.79 (s, 1H, N—H), 7.40-7.20 (m, 60H, Ar—H), 5.65 (d, 1H, J=7.2, H—N), 5.57 (d, 5.2H, J=8.2, H—N), 5.45 (d, 4.9H, J=7.3, H—N), 5.40 (d, 1.9H, J=7.8, H—N), 4.92 (d, 2.5H, J=7.3, H-14), 4.74 (d, 3.7H, J=7.8, H-14), 4.62-4.54 (m, 8H, H-14), 4.16-4.11 (m, 2.7H), 4.09-4.06 (m, 3.9H), 3.97-3.9 (m, 7.8H), 3.80-3.75 (m, 50.5H, H$_3$-12), 3.66 (s, 22.6H, H$_3$-12) 3.47-3.04 (m, 41.4, H$_2$-18), 2.99-2.94 (m, 9.5H, H$_2$-18), 2.82-2.73 (m, 9.5H, H$_2$-18), 1.46-1.42 (m, 240H, H$_3$-17); $\delta_C$ (150 MHz, CDCl$_3$) 175.94 (C=O), 175.84 (C=O), 175.82 (C=O), 171.10 (C=O), 171.04 (C=O), 170.95 (C=O), 155.28 (Ar), 129.63 (Ar—H), 129.50 (Ar—H), 128.96 (Ar—H), 128.88 (Ar—H), 128.80 (Ar—H), 128.75 (Ar—H), 128.59 (Ar—H), 128.53 (Ar—H), 128.41 (Ar—H), 80.51 (C16), 80.22 (C16), 52.97 (C12), 52.93 (C12), 52.71 (C14), 52.61 (C14), 45.25 (C5), 32.92 (C18), 32.86 (C18), 31.19 (C18), 31.08 (C18), 29.83 (C6), 28.42 (C17) Several carbon signals are missing due to overlap of the diastereomers; IR (oil, cm$^{-1}$) 2924 (m), 1712 (s); MS (CI+) m/z (relative intensity): 666 ([M−H], 100); Exact Mass Calcd for [C$_{30}$H$_{41}$N$_3$O$_{10}$S$_2$]—H requires m/z 666.2155 Found 666.2188 (CI+).

---

The invention claimed is:

1. A compound of formula (IIIa)

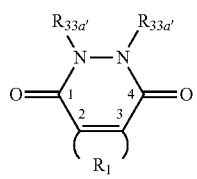

wherein:
  $R_1$ is a peptide or protein containing a first cysteine residue and a second cysteine residue, $R_1$ is attached at the 2-position in the compound of formula (IIIa) by a thiol bond —S— which is derived from the thiol group in said first cysteine residue, and $R_1$ is attached at the 3-position in the compound of formula (IIIa) by a thiol bond —S— which is derived from the thiol group in said second cysteine residue;
  each $R_{33a'}$ is the same or different and represents a hydrogen atom or a group of formula Y, Nu, -L(Z)$_n$, IG, $F_2$ or -L(F$_2$)$_m$(Z)$_{n-m}$;
  $F_2$ is a functional moiety;
  each group of formula Y is the same or different and represents an electrophilic leaving group;
  each group of formula Nu is the same or different and represents a nucleophile selected from —OH, —SH, —NH$_2$ and —NH(C$_{1-6}$ alkyl);
  each group of formula L is the same or different and represents a linker group;
  each group of formula Z is the same or different and represents a reactive group attached to a group of formula L which is capable of reacting with a compound containing a functional moiety $F_2$ such that said functional moiety $F_2$ becomes linked to said group of formula L;
  n is 1, 2 or 3;
  each group of formula IG is the same or different and represents a moiety which is a C$_{1-20}$ alkyl group, a C$_{2-20}$ alkenyl group or a C$_{2-20}$ alkynyl group, which is unsubstituted or substituted by one or more substituents selected from halogen atoms and sulfonic acid groups, and in which (a) 0, 1 or 2 carbon atoms are replaced by groups selected from C$_{6-10}$ arylene, 5- to 10-membered heteroarylene, C$_{3-7}$ carbocyclylene and 5- to 10-membered heterocyclylene groups, and (b) 0, 1 or 2 —CH$_2$— groups are replaced by groups selected from —O—, —S—, —S—S—, —C(O)— and —N(C$_{1-6}$ alkyl)- groups, wherein:
    (i) said arylene, heteroarylene, carbocyclylene and heterocyclylene groups are unsubstituted or substituted by one or more substituents selected from halogen atoms and C$_{1-6}$ alkyl, C$_{1-6}$ alkoxy, C$_{1-6}$ alkylthiol, —N(C$_{1-6}$ alkyl)(C$_{1-6}$ alkyl), nitro and sulfonic acid groups; and
    (ii) 0, 1 or 2 carbon atoms in said carbocyclylene and heterocyclylene groups are replaced by —C(O)— groups; and
  m is an integer having a value of from zero to n.

2. A compound according to claim 1, which comprises at least one group of formula $F_2$.

3. A compound according to claim 1, wherein the first cysteine residue of $R_1$ and the second cysteine residue of $R_1$ in the compound of formula (IIIa) are derived from an internal disulfide bridge formed in the peptide or protein.

4. A compound according to claim 1, wherein $R_1$ is an antibody or an antibody fragment that is capable of binding to a specific antigen via an epitope on the antigen.

5. A compound according to claim 2, wherein $F_2$ is a drug.

6. A compound according to claim 5, wherein the drug is a cytotoxic agent.

7. A compound according to claim 1, wherein at least one of the groups $R_{33a''}$ represents a group of formula $F_2$ or -L(F$_2$).

8. A compound according to claim 7, wherein one of the groups $R_{33a'}$ represents a group of formula $F_2$ or -L(F$_2$) and the other group $R_{33a'}$ represents a hydrogen atom or a group of formula IG.

9. A compound according to claim 5, wherein at least one of the groups $R_{33a'}$ represents a group of formula $F_2$ or -L(F$_2$).

10. A compound according to claim 9, wherein one of the groups $R_{33a'}$ represents a group of formula $F_2$ or -L(F$_2$) and the other group $R_{33a'}$ represents a hydrogen atom or a group of formula IG.

* * * * *